(12) United States Patent
Achard et al.

(10) Patent No.: US 7,741,316 B2
(45) Date of Patent: *Jun. 22, 2010

(54) PHARMACOLOGICAL USES OF AZETIDINE DERIVATIVES

(75) Inventors: Daniel Achard, Thiais (FR); Herve Bouchard, Thiais (FR); Jean Bouquerel, Drancy (FR); Bruno Filoche, Creteil (FR); Serge Grisoni, Choisy le Roi (FR); Augustin Hittinger, Choisy le Roi (FR); Michael R. Myers, Saint Nom la Breteche (FR)

(73) Assignee: Aventis Pharma S.A., Antony (FR)

(*) Notice: Subject to any disclaimer, the term of this patent is extended or adjusted under 35 U.S.C. 154(b) by 1545 days.

This patent is subject to a terminal disclaimer.

(21) Appl. No.: 10/988,337

(22) Filed: Nov. 12, 2004

(65) Prior Publication Data

US 2005/0130953 A1  Jun. 16, 2005

Related U.S. Application Data

(63) Continuation of application No. 10/242,575, filed on Sep. 12, 2002, now Pat. No. 6,872,717, which is a continuation of application No. 09/798,072, filed on Mar. 2, 2001, now Pat. No. 6,479,479.

(60) Provisional application No. 60/200,399, filed on Apr. 27, 2000.

(30) Foreign Application Priority Data

Mar. 3, 2000 (FR) .................................. 00 02775

(51) Int. Cl.
| | | |
|---|---|---|
| A01N 43/00 | (2006.01) | |
| A61K 31/397 | (2006.01) | |
| A61K 31/00 | (2006.01) | |
| C07D 217/00 | (2006.01) | |
| C07D 215/12 | (2006.01) | |
| C07D 421/00 | (2006.01) | |
| C07D 401/00 | (2006.01) | |
| C07D 403/00 | (2006.01) | |
| C07D 205/00 | (2006.01) | |
| C07D 263/60 | (2006.01) | |
| C07D 277/60 | (2006.01) | |
| C07D 295/00 | (2006.01) | |
| C07D 277/62 | (2006.01) | |
| C07D 277/20 | (2006.01) | |
| C07D 413/00 | (2006.01) | |
| C07D 263/52 | (2006.01) | |

(52) U.S. Cl. ............................. 514/210.01; 514/210.17; 514/210.18; 514/210.19; 514/210.2; 514/210.21; 548/950; 548/152; 548/202; 548/217; 548/364.1; 548/518; 544/60; 544/111; 544/242; 544/359; 546/139; 546/150; 546/176; 546/268.1

(58) Field of Classification Search ............ 514/210.01, 514/210.17, 210.18, 210.19, 210.2, 210.21; 548/950, 152, 202, 217, 364.1, 518; 544/60, 544/111, 242, 359; 546/176, 286.1, 139, 546/150

See application file for complete search history.

(56) References Cited

U.S. PATENT DOCUMENTS

| 4,260,606 A | 4/1981 | Cale, Jr. et al. |
| 5,073,646 A | 12/1991 | Pinol et al. |
| 6,022,868 A | 2/2000 | Olesen et al. |
| 6,379,666 B1 * | 4/2002 | Tobinick ................. 424/134.1 |
| 2002/0081584 A1 * | 6/2002 | Blumenfeld et al. ........... 435/6 |

OTHER PUBLICATIONS

DiMarzo et al. 2000, Enhanced levels of endogenous cannabinoids in the globus pallidus are associated with a reduction in movement in an animal model of Parkinson's disease. FASEB J., vol. 14, pp. 1432-1438.*

Poncelet et al. 1999, Blockade of cannabinoid (CB1) receptors by SR 141716 selectively antagonizes drug-induced reinstatement of exploratory behaviour in gerbils. Psychopharmacology, vol. 144, pp. 144-150.*

Arnone et al. 1997, Selective inhibition of sucrose and ethanol intake by SR 141716, an antagonist of central cannabinoid (CB1) receptors. Psychopharmacology, vol. 132, pp. 104-106.*

Barth F et al, The development of cannabinoid antagonists, Curr. Med. Chem., vol. 6(8), Aug. 1999, pp. 745-755.

Brotchie JM, CB1 cannabinoid receptor signalling in Parkinson's disease, Curr. Opin. Pharmacol., vol. 3(1), Feb. 2003, pp. 54-61.

Ruiu S et al, Synthesis and Characterization of NESS 0327: A Novel Putative Antagonist of the CB1 Cannabinoid Receptor, J. Pharmacol. Exp. ther., vol. 306(1), Jul. 2003, pp. 363-370.

(Continued)

Primary Examiner—Sreeni Padmanabhan
Assistant Examiner—Kara R McMillian
(74) Attorney, Agent, or Firm—Balaram Gupta

(57) ABSTRACT

A method of treating or preventing Alzheimer's disease, Parkinson's Disease and/or schizophrenia, this method comprising administering to a patient in need of such treatment a compound of formula:

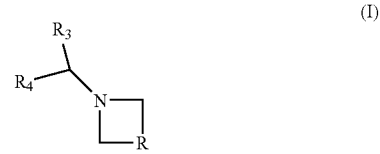

(I)

in which R, $R_3$ and $R_4$ are as defined in the specification.

13 Claims, No Drawings

OTHER PUBLICATIONS

Tzavara ET et al, The CB1 receptor antagonist SR141716A selectively increases monoaminergic neurotransmission in the medial prefrontal cortax: implications for therapeutic actions, J. Pharmacol., vol. 138(4), Feb. 2003, pp. 544-553.

W. E. Bachmann; *Journal of the American Chemical Society*; "The Relative Stability of Penta-Arylethanes I. The Preparation of Penta-Arylethanes"; May 1933; vol. 56; pp. 2135-2139.

A. L. Plasz et al.; *Journal of the Chemical Society, Chemical Communications*; "Photolytic Reduction of Phenyl Quinolin-3-yl Ketone to 3-Benzylquinoline"; 1972; pp. 527.

M. Hudlicky; *ACS Monograph Series #186*; "Oxidations in Organic Chemistry"; 1990; pp. 252-263.

G.A. Brine et al.; *Journal of Heterocyclic Chemistry*; "Carbon-13 Nuclear Magnetic Resonance Spectra of Fentanyl Analogs"; May-Jun. 1989; vol. 26; pp. 677-686.

D. Nagarathnam; *Synthesis*; "A Simple Synthesis of 2-Substituted Indoles"; Aug. 1992; pp. 743-745.

A. R. Katritzky et al.; *Journal of Heterocyclic Chemistry*; "Novel Syntheses of 1,3,3-Trinitroazetidine"; Mar.-Apr. 1994; vol. 31; pp. 271-275.

P. R. Dave; *Journal of Organic Chemistry*; "Acylative Dealkylation of N-tert-Butyl-3-substituted Azetidines: Facile Access to [1.1.0] Azabicyclobutane, 3-Hydroxyazetidinium Hydrochloride, and 3-Azetidinones"; 1996; vol. 61; pp. 5453-5455.

M. Grisar et al.; *Journal of Medicinal Chemistry*; "Benzhydryl and Fluorenyl Lactamimides with Hypoglycemic, Diuretic, Blood Platelet Aggregation Inhibitory, and Antiinflammatory Activities"; 1973; vol. 16, No. 8; pp. 885-893.

N. G. Kundu et al.; *Journal of the Chemical Society, Perkin Transactions 1*; "Palladium-catalysed heteroannulation with acetylenic compounds: synthesis of benzofurnas"; 1997; pp. 2815-2820.

M. Moreno-Mañas et al.; *European Journal of Medicinal Chemistry*; "New imidazole anti-fungal agents derived from benzo[b]thiophene. Part II"; 1988; vol. 23; pp. 477-482.

Skinner et al.; *Journal of Medicinal Chemistry*; "Antiviral Agents. 1. Benzothiazol and Benzoxazole Analogs of 2-($\alpha$-Hydroxybenzyl)benzimidazole"; 1971; vol. 14, No. 6; pp. 546-549.

N. K. Harn; *Tetrahedron Letters*; "Acylation of Oxazoles by the Copper-Mediated Reaction of Oxazol-2-ylzinc Chloride Derivatives"; 1955; vol. 36, No. 52; pp. 9453-9456.

A. Medici et al.; *Tetrahedron Letters*; "Reactions of 2-Trimethylsilylthiazole with Acyl Chlorides and Aldehydes Synthesis of New Thiazol-2-YL Derivatives"; 1983; vol. 24, No. 28; pp. 2901-2904.

R. D. Riecke et al.; *Journal of Organic Chemistry*; "Direct Preparation of 3-Thienyl Organometallic Reagents: 3-Thienylzinc and 3-Thienylmagnesium Iodides and 3-Thienylmanganese Bromides and Their Coupling Reactions"; 1997; vol. 62, No. 20; pp. 6921-6927.

J. Knabe et al.; *Archives of Pharmacology*; "Synthese von 1-Acylisochinolinen über Reissert-Verbindungen"; 1973; vol. 306(9), pp. 648-658.

R. Consonni et al.; *Journal of the Chemical Society—Perkin Transactions 1*; "Diels-Alder reactions of N-sulfonyl substituted aza-ortho-xylylenes generated from the corresponding 1,4-dihydro-2H-3,1-benzoxazin-2-one derivatives"; 1996; pp. 1809-1814.

L. Brandsma et al.; *Synthetic Communications*; "A Large-Scale Procedure for the Preparation of 3-Bromothiophene From 2-Bromothiophene and Sodamide in Liquid Ammonia"; 1990, vol. 20(11); pp. 1697-1700.

M. Lemaire et al.; *Synthetic Communications*; "A Convenient Synthesis of 3-Fluorothiophene"; 1994; vol. 24(11); pp. 95-101.

H. Goda et al.; *Synthesis*; "Facile Synthesis of 5-Substituted 2-Acetylthiophenes"; 1992; vol. 9; pp. 849-851.

P. Baeuerle et al.; *Journal of the Chemical Society-Perken Transactions 2*; "Synthesis and Structural Characterization of Alkyl Oligothiophenes—The First Isomerically Pure Dialkylsexithiophene"; 1993; pp. 489-494.

P. Bouyssou et al.; *Journal of Heterocyclic Chemistry*; "Synthesis of 7- and 5,7-Substituted-6-fluoro-2-methyl-1,2,3,4-tetrahydroquinolines: Convenient Precursors of Quinolone Antibacterial Agents"; 1992; vol. 29(4); pp. 895-898.

N. Suzuki et al.; *Journal of the Chemical Society, Chemical Communications*; "Synthetic Reactions in Polyethylene Glycol. Diazotization and Sandmeyer Reactions of Anilines in Polyethylene Glycol-Methylene Dichloride"; 1984; pp. 1523-1524.

S. Marburg et al.; *Journal of Heterocyclic Chemistry*; "A Short Efficient Synthesis of 4-Amino-2,3-dihydrobenzofuran"; 1980; vol. 17; pp. 1333-1335.

V. Percec et al.; *Journal of Organic Chemistry*; "Aryl Mesylates in Metal Catalyzed Homo- and Cross-Coupling Reactions. 4. Scope and Limitations of Aryl Mesylates in Nickel Catalyzed Cross-Coupling Reactions"; 1995; vol. 60(21); pp. 6895-6903.

J. F. Hansen et al.; *Journal of Heterocyclic Chemistry*; "Synthetic Studies Leading to DE-Ring Analogs of Camptothecin (1)"; 1973; vol. 10; pp. 711-714.

L. E. Hollister; *Pharmacological Reviews*; "Health Aspects of Cannabis"; 1986; vol. 38; pp. 1-20.

S. Renu; *Progress in Drug Research*; "Chemistry and Pharmacology of Cannabis"; 1991; vol. 36; pp. 71-115.

S. Consroe; *Marijuana/Cannabinoids: Neurobiology and Neurophysiology* (Eds. Murphy, L.; Barthe. A.); "Potential Role of Cannabinoids for Therapy of Neurological Disorders"; 1992; pp. 459-524.

J. E. Kuster; J. I. Stevenson et al.; *Journal of Pharmacology and Experimental Therapeutics*; "Aminoalkylindole Binding in Rat Cerebellum: Selective Displacement by Natural and Synthetic Cannabinoids"; 1993; vol. 264; pp. 1352-1363.

T. Hayashi et al; *Journal of the American Chemicl Society*; "Dichloro[1,1'-bis(diphenylphosphino)ferrocene]palladium-(II): An Effective Catalyst for Cross-Coupling of Secondary and Primary Alkyl Grignard and Alkylzinc Reagents with Organic Halides"; 1984; vol. 106; pp. 158-163.

J. Wityak et al.; *Bioorganic and Medicinal Chemistry Letters*; "Synthesis and Antiplatelet Activity of DMP 757 Analogs"; 1995; vol. 5(18); pp. 2097-2100.

M. Desai; L. Stramiello; *Tetrahedron Letters*; "Polymer Bound EDC (P-EDC): A Convenient Reagent for Formation of an Amide Bond"; 1993; vol. 34(48); pp. 7685-7688.

G. Pandey; T. D. Bagul et al.; *Journal of Organic Chemistry*; "[3+2] Cycloaddition of Nonstabilized Azomethine Ylides. 7. Stereoselective Synthesis of Epibatidine and Analogues"; 1998; vol. 63; pp. 760-768.

A. G. Anderson; R. Lok; *Journal of Organic Chemistry*; "The Synthesis of Azetidine-3-carboxylic Acid"; 1972; vol. 37; pp. 3953-3955.

* cited by examiner

PHARMACOLOGICAL USES OF AZETIDINE DERIVATIVES

CROSS-REFERENCE TO RELATED APPLICATION

This application is a continuation of copending application Ser. No. 10/242,575, filed Sep. 12, 2002, which application is, in turn, a continuation of application Ser. No. 09/798,072, filed Mar. 2, 2001, now U.S. Pat. No. 6,479,479, which claims the benefit of U.S. Provisional Application No. 60/200,399, filed Apr. 27, 2000 and French Application No. 002775, filed Mar. 3, 2000.

The present invention relates to derivatives of formula:

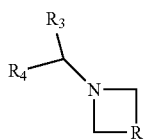

(I)

their salts, their preparation and the medicaments containing them.

In formula (I),

R represents a radical $CR_1R_2$, $C=C(R_5)SO_2R_6$ or $C=C(R_7)SO_2alk$, or $R_1$ represents a hydrogen atom and $R_2$ represents a radical —$C(R_8)(R_9)(R_{10})$, —$C(R_8)(R_{11})(R_{12})$, —CO—$NR_{13}R_{14}$, —$CH_2$—CO—$NR_{13}R_{14}$, —$CH_2$—CO—$R_6$, —CO—$R_6$, —CO-cycloalkyl, —SO—$R_6$, —$SO_2$—$R_6$, —$C(OH)(R_{12})(R_6)$, —$C(OH)(R_6)$(alkyl), —$C(=NOalk)R_6$, —$C(=NO-CH_2$—CH=$CH_2)R_6$, —$CH_2$—$CH(R_6)NR_{31}R_{32}$, —$CH_2$—$C(=NOalk)R_6$, —$CH(R_6)NR_{31}R_{32}$, —$CH(R_6)NHSO_2alk$, —$CH(R_6)NHCONHalk$ or —$CH(R_6)NHCOalk$, or $R_1$ represents an alkyl, NH—$R_{15}$, cyano, —S-alk-$NR_{16}R_{17}$, —$CH_2$—$NR_{18}R_{19}$, or —$NR_{20}R_{21}$ radical and $R_2$ represents a radical —$C(R_8)(R_{11})(R_{12})$, $R_3$ and $R_4$, which are identical or different, represent either an alkyl or cycloalkyl radical, or an aromatic chosen from phenyl, naphthyl or indenyl, these aromatics being unsubstituted or substituted with one or more halogen atoms or alkyl, alkoxy, formyl, hydroxyl, trifluoromethyl, trifluoromethoxy, —CO-alk, cyano, —COOH, —COOalk, —$CONR_{22}R_{23}$, —CO—NH—$NR_{24}R_{25}$, alkylsulfanyl, alkylsulfinyl, alkylsulfonyl, alkylsulfanylalkyl, alkylsulfinylalkyl, alkylsulfonylalkyl, hydroxyalkyl or -alk-$NR_{24}R_{25}$ radicals; or a heteroaromatic chosen from the benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidinyl, quinolyl, 1,2,3,4-tetrahydroisoquinolyl, thiazolyl and thienyl rings, it being possible for these heteroaromatics to be unsubstituted or substituted with one or more halogen atoms or alkyl, alkoxy, hydroxyl, trifluoromethyl, trifluoromethoxy, cyano, —COOH, —COOalk, —CO—NH—$NR_{24}R_{25}$, —$CONR_{22}R_{23}$, -alk-$NR_{24}R_{25}$, alkylsulfanyl, alkylsulfinyl, alkylsulfonyl, alkylsulfanylalkyl, alkylsulfinylalkyl, alkylsulfonylalkyl or hydroxyalkyl radicals, $R_5$ represents a hydrogen atom or an alkyl radical, $R_6$ represents a radical Ar or Het, $R_7$ represents a cycloalkyl, heterocycloalkyl or heterocyclenyl radical optionally substituted by a —CSO-phenyl radical, $R_8$ represents a hydrogen atom or an alkyl radical, $R_9$ represents a radical —CO—$NR_{26}R_{27}$, —COOH, —COOalk, —$CH_2OH$, —NH—CO—NH-alk, —$CH_2$—$NHR_{28}$ or —NHCOOalk, $R_{10}$ represents a radical Ar or Het, $R_{11}$ represents a radical —$SO_2$-alk, —$SO_2$—Ar or —$SO_2$-Het, $R_{12}$ represents a hydrogen atom or a radical Ar or Het, $R_{13}$ represents a hydrogen atom or an alkyl radical, $R_{14}$ represents a radical Ar, Het, -alk-Ar or -alk-Het, $R_{15}$ represents an alkyl, cycloalkyl or -alk-$NR_{29}R_{30}$ radical, $R_{16}$ and $R_{17}$, which are identical or different, represent a hydrogen atom or an alkyl radical or alternatively $R_{16}$ and $R_{17}$ together form with the nitrogen atom to which they are attached a 3- to 10-membered unsaturated or saturated mono- or bicyclic heterocycle optionally containing one or more other heteroatoms chosen from oxygen, sulfur and nitrogen and optionally substituted with one or more alkyl radicals, $R_{18}$ represents a hydrogen atom or an alkyl radical, $R_{19}$ represents a hydrogen atom or an alkyl, cycloalkyl, cycloalkylalkyl, cycloalkylcarbonyl, —$SO_2$alk, —CO—NHalk or —COOalk radical, or alternatively $R_{18}$ and $R_{19}$ form with the nitrogen atom to which they are attached a 3- to 10-membered unsaturated or saturated mono- or bicyclic heterocycle optionally containing one or more heteroatoms chosen from oxygen, sulfur and nitrogen and optionally substituted with one or more alkyl radicals, —$NR_{20}R_{21}$ represents a 3- to 8-membered saturated or unsaturated monocyclic heterocycle optionally containing another heteroatom chosen from oxygen, nitrogen and sulfur, $R_{22}$ and $R_{23}$, which are identical or different, represent a hydrogen atom or an alkyl radical or alternatively $R_{22}$ and $R_{23}$ together form with the nitrogen atom to which they are attached a 3- to 10-membered saturated mono- or bicyclic heterocycle optionally containing another heteroatom chosen from oxygen, sulfur and nitrogen and being optionally substituted with one or more alkyl radicals, $R_{24}$ and $R_{25}$, which are identical or different, represent a hydrogen atom or an alkyl, —COOalk, cycloalkyl, alkylcycloalkyl, -alk-O-alk or hydroxyalkyl radical or alternatively $R_{24}$ and $R_{25}$ together form with the nitrogen atom to which they are attached a 3- to 10-membered saturated or unsaturated mono- or bicyclic heterocycle, optionally containing another heteroatom chosen from oxygen, sulfur and nitrogen and being optionally substituted with one or more alkyl, —COalk, —COOalk, —CO—NHalk, —CS—NHalk, oxo, hydroxyalkyl, -alk-O-alk or —CO—$NH_2$ radicals, $R_{26}$ and $R_{27}$, which are identical or different, represent a hydrogen atom or an alkyl, hydroxyalkyl, cycloalkyl, cycloalkylalkyl, -alk-COOalk, -alk-Ar, -alk-Het, Het or -alk-$N(alk)_2$ radical, $R_{26}$ and $R_{27}$ may also form with the nitrogen atom to which they are attached a 3- to 10-membered unsaturated or saturated mono- or bicyclic heterocycle optionally containing one or more other heteroatoms chosen from oxygen, sulfur and nitrogen and optionally substituted with one or more alkyl or alkoxy radicals or halogen atoms, $R_{28}$ represents a —$CH_2$-alk, benzyl, —$SO_2$alk, —CONHalk, —COalk, cycloalkylalkylcarbonyl, cycloalkylcarbonyl or —CO—$(CH_2)_n$OH radical, n is equal to 1, 2 or 3, $R_{29}$ and $R_{30}$, which are identical or different, represent a hydrogen atom or an alkyl radical or alternatively $R_{29}$ and $R_{30}$ together form with the nitrogen atom to which they are attached a 3- to 10-membered saturated mono- or bicyclic heterocycle optionally containing another heteroatom chosen from oxygen, sulfur and nitrogen and being optionally substituted with one or more alkyl radicals, $R_{31}$ and $R_{32}$, which are identical or different, represent a hydrogen atom or an alkyl, Ar or -alk-Ar radical or alternatively $R_{31}$ and $R_{32}$ together form with the nitrogen atom to which they are attached a heterocycle chosen from aziridinyl, azetidinyl, pyrrolidinyl and piperidinyl, alk represents an alkyl or alkylene radical, Ar represents a phenyl or naphthyl radical optionally substituted with one or more substituents chosen from a halogen atom or an alkyl, alkoxy, —CO-alk, cyano, —COOH, —COOalk, —$CONR_{22}R_{23}$, —CO—NH—$NR_{24}R_{25}$, alkylsulfanyl, alkylsulfinyl, alkylsulfonyl, alkylsulfanylalkyl, alkylsulfinylalkyl, alkylsulfonylalkyl, hydroxyalkyl, -alk-$NR_{24}R_{25}$, —$NR_{24}R_{25}$, alkylthioalkyl, formyl, hydroxyl, $CF_3$, $OCF_3$, Het, —O-alk-NH-cycloalkyl or $SO_2NH_2$ radical, Het represents a 3- to 10-membered unsaturated or saturated mono- or bicyclic heterocycle containing one or more heteroatoms chosen from oxygen, sulfur and nitrogen and optionally substituted with one or more halogen atoms or alkyl, alkoxy, alkoxycarbonyl, —$CONR_{22}R_{23}$, hydroxyl, hydroxyalkyl, oxo or $SO_2NH_2$ radicals.

In the preceding definitions and in those which follow, unless otherwise stated, the alkyl and alkylene radicals and portions and the alkoxy radicals and portions are in the form of a straight or branched chain and contain 1 to 6 carbon atoms, the cycloalkyl radicals contain 3 to 10 carbon atoms and the heterocycloalkyl and heterocyclenyl radicals contain 3 to 10 carbon atoms.

Among the alkyl radicals, there may be mentioned the methyl, ethyl, n-propyl, isopropyl, n-butyl, sec-butyl, isobutyl, tert-butyl, pentyl and hexyl radicals. Among the alkoxy radicals, there may be mentioned the methoxy, ethoxy, n-propoxy, iso-propoxy, n-butoxy, iso-butoxy, sec-butoxy, tert-butoxy and pentyloxy radicals.

Among the cycloalkyl radicals, there may be mentioned the cyclopropyl, cyclobutyl, cyclopentyl and cyclohexyl radicals.

The heterocycloalkyl radicals are cycloalkyl radicals in which at least one of the carbon atoms is replaced with a heteroatom chosen from nitrogen, sulfur and oxygen. Among these, there may be mentioned the pyrrolidinyl, imidazolidinyl, pyrazolidinyl, piperidyl, piperazinyl and morpholinyl rings.

The heterocyclenyl radicals are cycloalkyl radicals in which at least one carbon atom is replaced with a heteroatom chosen from oxygen, sulfur and nitrogen and which contain at least one carbon-carbon or carbon-nitrogen double bond. Among the heterocyclenyl radicals, there may be mentioned the 1,2,3,4-tetrahydrohydropyridinyl, 3,6-dihydropyridyl, 1,2-dihydropyridyl, 1,4-dihydropyridyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, 3,4-dihydro-2H-pyrane, dihydrofuranyl and fluorodihydrofuranyl rings. Those preferred are the 3,6-dihydropyridyl rings.

The term halogen comprises chlorine, fluorine, bromine and iodine.

Among the heterocycles representing Het, the following heterocycles may be mentioned: benzofuryl, benzothiazolyl, benzothienyl, benzoxazolyl, chromanyl, 2,3-dihydrobenzofuryl, 2,3-dihydrobenzothienyl, furyl, indolinyl, indolyl, isochromanyl, isoquinolyl, piperidyl, pyrrolyl, pyridyl, pyrimidinyl, quinolyl, 1,2,3,4-tetrahydroisoquinolyl, 1,2,3,4-tetrahydroquinolyl, thiazolyl and thienyl.

When $R_3$ and/or $R_4$ represent independently a substituted phenyl, the latter is preferably mono-, di- or trisubstituted.

When $R_{16}$ and $R_{17}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

When $R_{18}$ and $R_{19}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

The heterocycle formed by $NR_{20}R_{21}$ is preferably azetidinyl, pyrrolidinyl, piperidinyl, morpholinyl, thiamorpholinyl, piperazinyl or imidazolyl.

When $R_{22}$ and $R_{23}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

When $R_{24}$ and $R_{25}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

When $R_{26}$ and $R_{27}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

When $R_{29}$ and $R_{30}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

When $R_{31}$ and $R_{32}$ together form with the nitrogen atom to which they are attached a 3- to 10-membered saturated or unsaturated mono- or bicyclic heterocycle, the latter is preferably an azetidinyl, pyrrolidinyl, piperidinyl, morpholinyl, thiamorpholinyl or piperazinyl ring.

Preferably,

R represents a radical $CR_1R_2$, either $R_1$ represents a hydrogen atom, and $R_2$ represents a radical —$C(R_8)(R_{11})(R_{12})$ or $C(R_8)(R_9)(R_{10})$, or $R_1$ represents an alkyl radical and $R_2$ represents a radical —$C(R_8)(R_{11})(R_{12})$, $R_3$ and $R_4$, which are identical or different, represent either a phenyl which is unsubstituted or substituted with one or more halogen atoms or alkyl, alkoxy, trifluoromethyl, trifluoromethoxy, cyano, —$CONR_{22}R_{23}$, hydroxyalkyl or -alk-$NR_{24}R_{25}$ radicals; or a heteroaromatic chosen from the pyridyl, pyrimidinyl, thiazolyl and thienyl rings, it being possible for these heteroaromatics to be unsubstituted or substituted with one or more halogen atoms or alkyl, alkoxy, hydroxyl, trifluoromethyl, trifluoromethoxy, cyano, —CONR$_{22}$R$_{23}$, -alk-NR$_{24}$R$_{25}$ or hydroxyalkyl radicals, R$_8$ represents a hydrogen atom, R$_9$ represents a —CO—NR$_{26}$R$_{27}$, —COOalk, —CH$_2$OH, —NH—CO—NH-alk, —CH$_2$—NHR$_{28}$ or —NHCOOalk radical, R$_{10}$ represents a radical Ar or Het, R$_{11}$ represents a radical —SO$_2$-alk, —SO$_2$—Ar or —SO$_2$-Het, R$_{12}$ represents represents a hydrogen atom or a radical Ar or Het, R$_{22}$ and R$_{23}$, which are identical or different, represent a hydrogen atom or an alkyl radical or alternatively R$_{22}$ and R$_{23}$ together form with the nitrogen atom to which they are attached a 3- to 10-membered saturated mono- or bicyclic heterocycle, optionally containing another heteroatom chosen from oxygen, sulfur and nitrogen and being optionally substituted with one or more alkyl radicals, R$_{24}$ and R$_{25}$, which are identical or different, represent a hydrogen atom or an alkyl, cycloalkyl, alkylcycloalkyl or hydroxyalkyl radical or alternatively R$_{24}$ and R$_{25}$ together form with the nitrogen atom to which they are attached a 3- to 10-membered saturated or unsaturated mono- or bicyclic heterocycle optionally containing another heteroatom chosen from oxygen, sulfur and nitrogen and being optionally substituted with one or more alkyl, —COalk, —COOalk, —CO—NHalk, —CS—NHalk, oxo or —CO—NH$_2$ radicals, Ar represents a phenyl or naphthyl radical optionally substituted with 1 or 2 subtituents chosen from a halogen atom or an alkyl, alkoxy, —CO-alk, cyano, —COOalk, —CONR$_{22}$R$_{23}$, alkylsulfonyl, hydroxyalkyl, -alk-NR$_{24}$R$_{25}$, —NR$_{24}$R$_{25}$, hydroxyl, CF$_3$, OCF$_3$, —O-alk-NH-cycloalkyl or SO$_2$NH$_2$ radical, Het represents a benzofuryl, benzothiazolyl, benzothienyl, benzoxazolyl, furyl, isoquinolyl, pyrrolyl, pyridyl, quinolyl, 1,2,3,4-tetrahydroisoquinolyl, 1,2,3,4-tetrahydroquinolyl, thiazolyl or thienyl ring.

The compounds of formula (I) may be provided in the form of enantiomers and diastereoisomers. These optical isomers and mixtures thereof form part of the invention.

The compounds of formula (I) for which R represents a radical CR$_1$R$_2$, in which R$_1$ represents a hydrogen atom and R$_2$ represents a radical C(R$_8$)(R$_{11}$)(R$_{12}$) in which R$_8$ represents a hydrogen atom, R$_{11}$ represents a radical —SO$_2$—Ar, —SO$_2$-Het or —SO$_2$alk and R$_{12}$ represents a hydrogen atom or a radical Ar or Het, and the compounds of formula (I) for which R represents a radical C=C(R$_5$)SO$_2$R$_6$ or C=C(R$_7$)SO$_2$alk may be prepared according to the following reaction scheme:

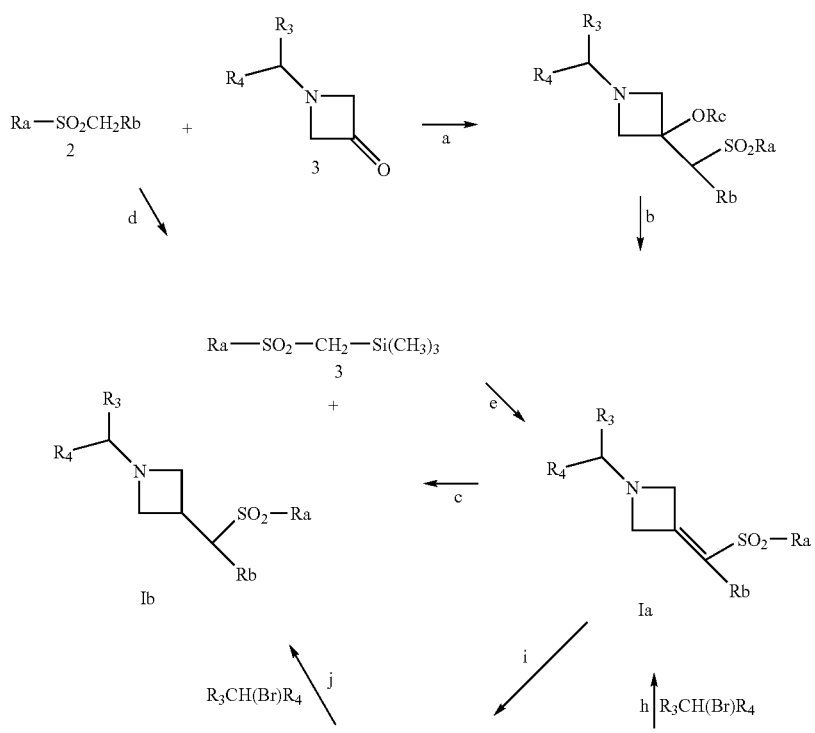

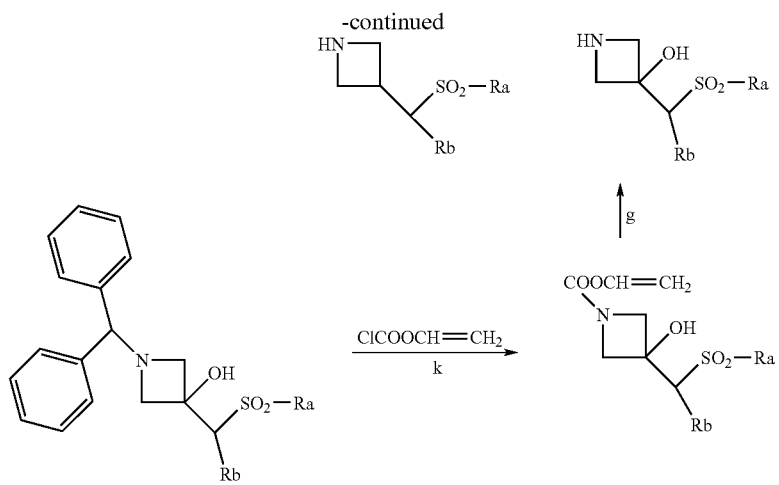

in these formulae, either Ra represents an alkyl, Het or Ar radical and Rb represents a hydrogen atom or a radical Ar or Het, or Ra represents a radical Ar or Het and Rb represents a hydrogen atom or an alkyl radical, or Ra represents an alkyl radical and Rb represents a cycloalkyl, heterocycloalkyl or heterocyclenyl radical optionally substituted with a radical —CSO-phenyl, Rc represents a hydrogen atom or an acetyl radical, $R_3$, $R_4$, Ar and Het have the same meanings as in formula (I).

Reactions d and e can only be used when Rb is a hydrogen atom.

The reaction is generally carried out in an inert solvent such as an ether (for example tetrahydrofuran), in the presence of a strong base such as tert-butyllithium, n-butyllithium, lithium diisopropylamide or potassium tert-butoxide, at a temperature of between −70° C. and −15° C.

The dehydration reaction b is generally carried out by any dehydration method known to a person skilled in the art which makes it possible to dehydrate an alcohol in order to obtain the corresponding alkene. Preferably, the acetyloxy derivative is prepared by the action of acetyl chloride, in an inert solvent such as pyridine, tetrahydrofuran, dioxane, a chlorinated solvent (for example dichloromethane or chloroform), at a temperature of between 5° C. and 20° C. and then the medium is treated with a base such as an alkali metal hydroxide (for example sodium hydroxide), an alkali metal carbonate (for example sodium or potassium carbonate), an amine such as a trialkylamine (for example triethylamine, 4-dimethylaminopyridine, 1,8-diazabicyclo[5.4.0]undec-7-ene, at a temperature of between 0° C. and the boiling point of the reaction medium. The acetyloxy intermediate may be isolated or otherwise. The acetyloxy may also be prepared directly in the reaction medium of reaction a.

Reduction c is generally carried out in an inert solvent such as a (1-4C) aliphatic alcohol (for example methanol), a chlorinated solvent (for example chloroform or dichloromethane) or a mixture of these solvents, in the presence of $NaBH_4$, at a temperature of between 0° C. and the boiling point of the reaction medium.

Reaction d is carried out by the action of trimethylsilyl chloride, in an inert solvent such as an ether (for example tetrahydrofuran), in the presence of n-butyllithium, at a temperature of −70° C.

Reaction e is generally carried out in an inert solvent such as an ether (for example tetrahydrofuran), in the presence of a strong base such as tert-butyllithium, n-butyllithium, lithium diisopropylamide or potassium tert-butoxide, at a temperature of between −70° C. and −15° C.

Reaction f is generally carried out in a chlorinated solvent (for example dichloromethane or chloroform), at a temperature of 0° C. at the boiling point of the reaction medium.

The hydrolysis g is carried out in an inert solvent such as an ether (for example dioxane), by means of hydrochloric acid, at a temperature in the region of 20° C.

The reactions h and j are preferably carried out in an inert solvent such as acetonitrile, in the presence of a base such as an alkali metal carbonate (for example potassium carbonate), at the boiling point of the reaction medium.

Reaction i is carried out under a hydrogen atmosphere, in the presence of a catalyst such as palladium or one of its derivatives, in an inert solvent such as methanol or ethanol, at a temperature of between 15° C. and 60° C.

Reaction k is carried out in an inert solvent such as a chlorinated solvent (for example dichloromethane or chloroform) at a temperature of between 0° C. and the boiling point of the reaction mixture.

The derivatives $R_3CH(Br)R_4$ are commercially available or may be obtained by application or adaptation of the method described by BACHMANN W. E., J. Am. Chem. Soc., 2135 (1933). Generally, the corresponding alcohol $R_3CHOHR_4$ is brominated by means of hydrobromic acid, in acetic acid, at a temperature of between 0° C. and the boiling point of the reaction medium.

The corresponding alcohols $R_3CHOHR_4$ are commercially available or may be obtained by application or adaptation of the methods described by PLASZ A. C. et al., J. Chem. Soc. Chem. Comm., 527 (1972).

The intermediates of formula 2 may be obtained by application or adaptation of the methods described in the examples. In particular, the procedure is carried out according to the following reaction schemes:

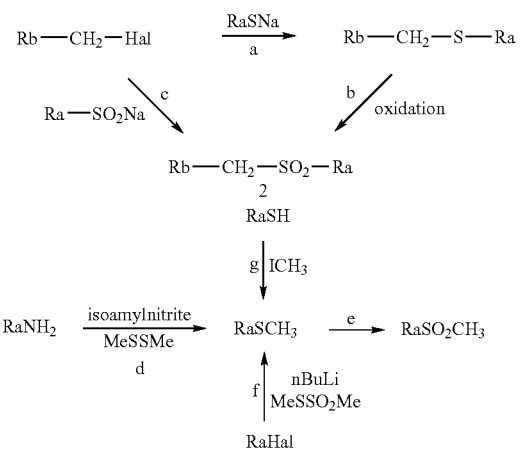

in these formulae Hal represents a halogen atom and, preferably, chlorine, bromine or iodine, Ra and Rb have the same meanings as previously mentioned for derivative 2.

Reaction a is generally carried out in an inert solvent such as dimethylformamide or a 1-4C aliphatic alcohol, at a temperature of between 20° C. and 30° C.

Reactions b and e are carried out by any known method which makes it possible to oxidize a sulfur-containing derivative without affecting the rest of the molecule such as those described by M. HUDLICKY, Oxidations in Organic Chemistry, ACS Monograph, 186, 252-263 (1990). For example, the procedure is carried out by the action of an organic peroxy acid or a salt of such a peroxy acid (peroxycarboxylic or peroxysulfonic acids, in particular peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or inorganic peracids or a salt of such an acid (for example periodic or persulfuric acid), in an inert solvent such as a chlorinated solvent (for example chloroform or dichloromethane), at a temperature of between 0 and 25° C. It is also possible to use hydrogen peroxide, optionally in the presence of a metal oxide (sodium tungstate) or a periodate (for example sodium periodate), in an inert solvent such as a 1-4C aliphatic alcohol (for example methanol or ethanol), acetic acid, water or a mixture of these solvents, at a temperature of between 0 and 60° C. It is also possible to carry out the procedure by means of tert-butyl hydroperoxide in the presence of titanium tetraisopropoxide in a 1-4C aliphatic alcohol (for example methanol or ethanol) or a water-alcohol mixture, at a temperature in the region of 25° C. or by means of oxone$^R$ (potassium peroxymonosulfate), in a 1-4C aliphatic alcohol (for example methanol or ethanol), in the presence of water, acetic acid or sulfuric acid, at a temperature in the region of 20° C.

Reaction c is preferably carried out in an inert solvent such as a 1-4C aliphatic alcohol (for example methanol or ethanol), at a temperature of between 20° C. and the boiling point of the reaction medium.

Reaction d is carried out under an inert atmosphere (argon), at a temperature of between 50° C. and the boiling point of the reaction medium.

Reaction f is generally carried out in an inert solvent such as tetrahydrofuran or an aliphatic ether (for example ethyl ether), at a temperature in the region of −70° C.

Reaction g is generally carried out in an inert solvent such as dimethylformamide, an aliphatic ether (for example ethyl ether) or a 1-4C aliphatic alcohol in the presence of a base (for example sodium hydride), at a temperature of between 0° C. and 60°.

The derivatives of formula Rb—CH$_2$-Hal are commercially available or may be obtained by application or adaptation of the methods described in the examples. In particular, the methylated derivative or the corresponding alcohol is halogenated using a halogenating agent such as hydrobromic acid, in acetic acid, at a temperature close to 20° C. or N-bromo- or N-chlorosuccinimide in the presence of benzoyl peroxide, in an inert solvent such as tetrachloromethane, at the boiling point of the reaction medium. The methylated derivatives or the corresponding alcohols are commercially available or may be obtained according to the methods described by BRINE G. A. et al., J. Heterocyl. Chem, 26, 677 (1989) and NAGARATHNAM D., Synthesis, 8, 743 (1992) and in the examples.

The azetidinones of formula 3 may be obtained by application or adaptation of the methods described by KATRITZKY A. R. et al., J. Heterocycl. Chem., 271 (1994), or DAVE P. R., J. Org. Chem., 61, 5453 (1996) and in the examples. The procedure is generally carried out according to the following reaction scheme:

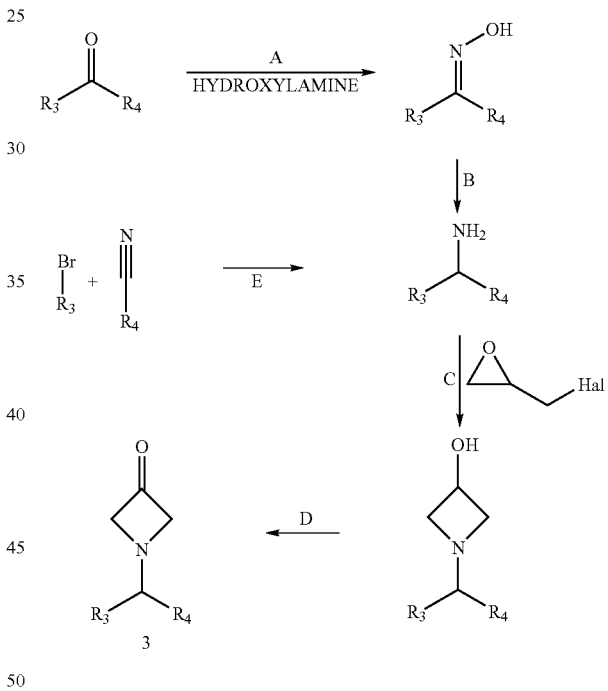

In these formulae, R$_3$ and R$_4$ have the same meanings as in formula (I) and HAL represents a chlorine or bromine atom.

In step A, the procedure is preferably carried out in an inert solvent such as a 1-4C aliphatic alcohol (ethanol or methanol for example), optionally in the presence of an alkali metal hydroxide, at the boiling point of the reaction medium.

In step B, the reduction is generally carried out using lithium aluminum hydride, in tetrahydrofuran at the boiling point of the reaction medium.

In step C, the procedure is preferably carried out in an inert solvent such as a 1-4C aliphatic alcohol (ethanol or methanol for example) in the presence of sodium hydrogen carbonate, at a temperature of between 20° C. and the boiling point of the reaction medium.

In step D, the oxidation is preferably carried out in DMSO, using the sulfurtrioxide-pyridine complex, at a temperature close to 20° C. or using dimethyl sulfoxide, in the presence of oxalyl chloride and triethylamine, at a temperature of between −70 and −50° C.

In step E, the procedure is carried out according to the method described by GRISAR M. et al., in J. Med. Chem., 885 (1973). The magnesium compound of the brominated derivative is formed and then the nitrile is reacted, in an ether such as ethyl ether, at a temperature of between 0° C. and the boiling point of the reaction medium. After hydrolysis with an alcohol, the intermediate imine is reduced in situ with sodium borohydride at a temperature of between 0° C. and the boiling point of the reaction medium.

The $R_3$—CO—$R_4$ derivatives are commercially available or may be obtained by application or adaptation of the methods described by KUNDER N. G. et al. J. Chem. Soc. Perkin Trans 1, 2815 (1997); MORENO-MARRAS M., Eur. J. Med. Chem., 23 (5) 477 (1988); SKINNER et al., J. Med. Chem., 14 (6) 546 (1971); HURN N. K., Tet. Lett., 36 (52) 9453 (1995); MEDICI A. et al., Tet. Lett., 24 (28) 2901 (1983); RIECKE R. D. et al., J. Org. Chem., 62 (20) 6921 (1997); KNABE J. et al., Arch. Pharm., 306 (9) 648 (1973); CON- SONNI R. et al., J. Chem. Soc. Perkin Trans 1, 1809 (1996); FR-96-2481 and JP-94-261393.

The $R_3$Br derivatives are commercially available or may be obtained by application or adaptation of the methods described by BRANDSMA L. et al., Synth. Comm., 20 (11) 1697 and 3153 (1990); LEMAIRE M. et al., Synth. Comm., 24 (1) 95 (1994); GODA H. et al., Synthesis, 9 849 (1992); BAEUERLE P. et al., J. Chem. Soc. Perkin Trans 2, 489 (1993).

The $R_4$CN derivatives are commercially available or may be obtained by application or adaptation of the methods described by BOUYSSOU P. et al., J. Het. Chem., 29 (4) 895 (1992); SUZUKI N. et al., J. Chem. Soc. Chem. Comm., 1523 (1984); MARBURG S. et al., J. Het. Chem., 17 1333 (1980); PERCC V. et al., J. Org. Chem., 60 (21) 6895 (1995).

The compounds of formula (I) for which R represents a radical $CR_1R_2$ in which $R_1$ represents a hydrogen atom and $R_2$ represents a radical $C(R_8)(R_9)(R_{10})$ in which $R_8$ represents a hydrogen atom, $R_9$ represents a radical —CO—$NR_{26}R_{27}$, —COOH, —COOalk, —$CH_2OH$, —NHCOOalk or —NH—CO—NH-alk and $R_{10}$ represents a radical Ar or Het may be prepared according to the following reaction scheme:

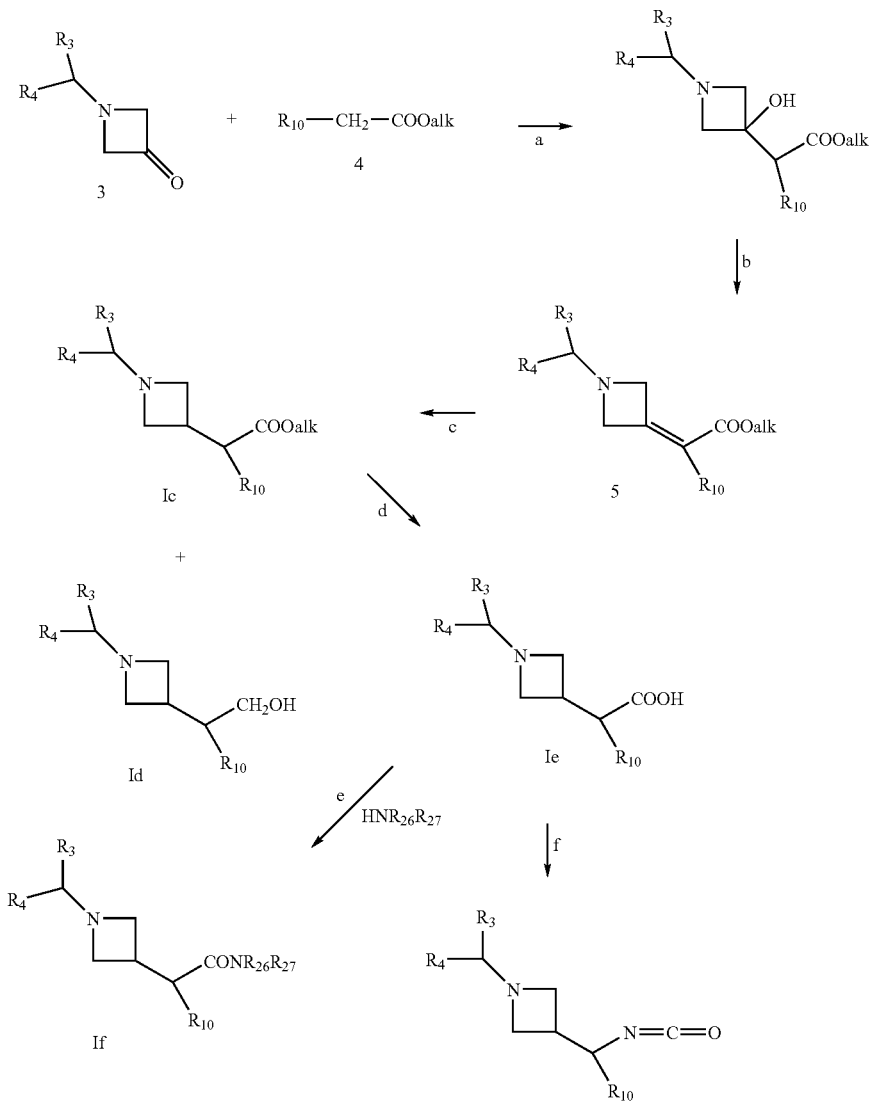

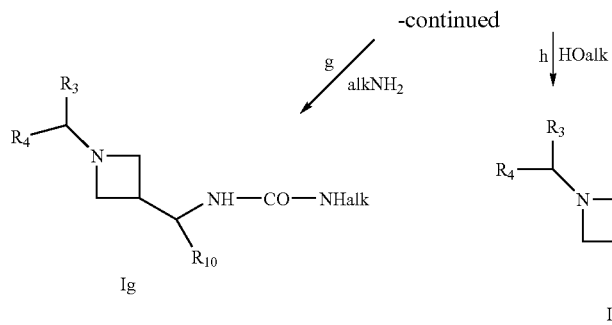
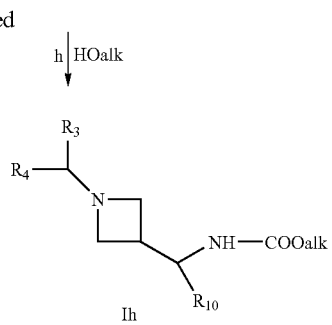

in these formulae $R_3$, $R_4$, $R_{10}$, $R_{26}$ and $R_{27}$ have the same meanings as in formula (I) and alk represents an alkyl radical.

The derivatives of formula 4 are commercially available or may be obtained by esterification of the corresponding acids, optionally in an activated form such as the acid chloride. The acids are commercially available or may be obtained from the corresponding methylated derivatives according to the method described by J P. HANSEN et al., J. Heteocycl., 10, 711 (1973).

Reaction a is generally carried out in an inert solvent such as an ether (for example tetrahydrofuran), in the presence of a strong base such as tert-butyllithium, n-butyllithium, lithium diisopropylamide or potassium tert-butoxide, at a temperature of between −70° C. and −15° C.

Reaction b is generally carried out by any dehydration method known to a person skilled in the art which makes it possible to dehydrate an alcohol in order to obtain the corresponding alkene and in particular the methods previously described.

The reduction c is generally carried out in an inert solvent such as an aliphatic alcohol (1-4C) such as methanol, a chlorinated solvent such as chloroform, dichloromethane or a mixture of these solvents, in the presence of $NaBH_4$, at a temperature of between 0° C. and the boiling point of the reaction medium.

Reaction d is carried out by any method known to a person skilled in the art which makes it possible to pass from an ester to the corresponding acid without affecting the rest of the molecule. The procedure is preferably carried out in an inert solvent such as dioxane, in the presence of hydrochloric acid, at the boiling point of the reaction medium.

Reaction e is carried out by any method known to a person skilled in the art which makes it possible to pass from an acid or a reactive derivative of this acid to a carboxamide without affecting the rest of the molecule. Preferably, when the acid is used, the procedure is carried out in the presence of a condensing agent which is used in peptide chemistry such as a carbodiimide (for example N,N'-dicyclohexylcarbodiimide) or N,N'-carbonyldiimidazole, in an inert solvent such as an ether (for example tetrahydrofuran or dioxane), an amide (dimethylformamide) or a chlorinated solvent (for example methylene chloride, 1,2-dichloroethane or chloroform) at a temperature of between 0° C. and the reflux temperature of the reaction mixture. When a reactive derivative of the acid is used, it is possible to cause the anhydride, a mixed anhydride or an ester (which may be chosen from the activated or non-activated esters of the acid) to react; the procedure is then carried out either in an organic medium, optionally in the presence of an acid acceptor such as a nitrogen-containing organic base (for example trialkylamine, pyridine, 1,8-diazabicyclo[5.4.0]undec-7-ene or 1,5-diazabicyclo[4.3.0]non-5-ene), in a solvent as cited above, or a mixture of these solvents, at a temperature of between 0° C. and the reflux temperature of the reaction mixture, or in a biphasic aqueous-organic medium in the presence of an alkaline or alkaline-earth base (sodium hydroxide or potassium hydroxide) or an alkali or alkaline-earth metal carbonate or bicarbonate at a temperature of between 0 and 40° C.

Reaction f is carried out by CURTIUS arrangement, in the presence of diphenylphosphorazide azide and triethylamine, in toluene, at a temperature in the region of 50° C.

For reactions g and h, the procedure is carried out directly in the reaction medium of step g at a temperature in the region of 20° C.

The compounds of formula (I) for which R represents a radical $CR_1R_2$ in which $R_1$ is a hydrogen atom and $R_2$ represents a radical $—C(R_8)(R_9)(R_{10})$ for which $R_8$ is a hydrogen atom, $R_9$ is a radical $—CH_2—NHR_{28}$ and $R_{10}$ represents a radical Ar or Het, may be prepared according to the following reaction scheme:

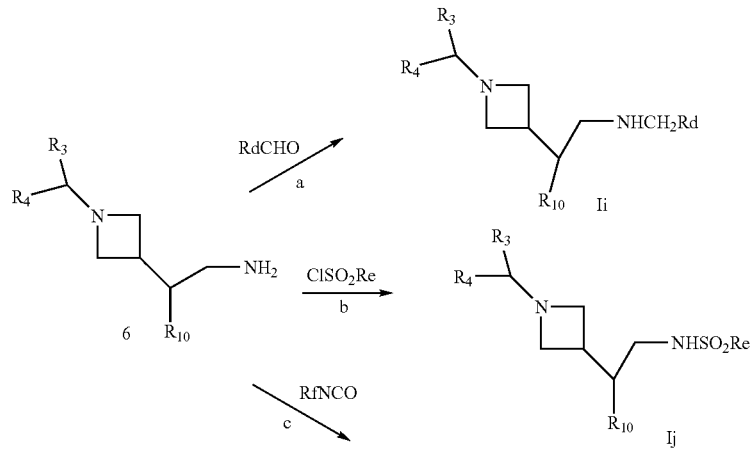

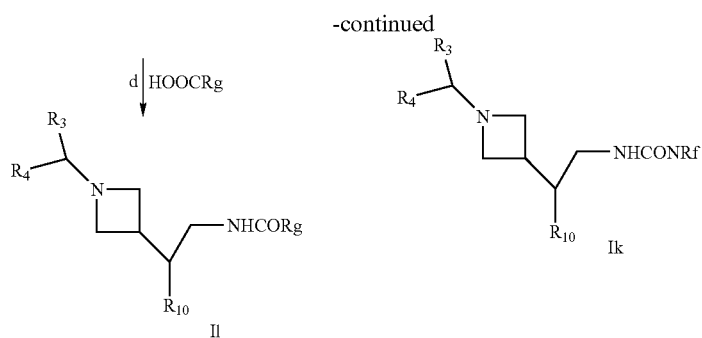

In these formulae, $R_3$, $R_4$ and $R_{10}$ have the same meanings as in formula (I), Rd represents an alkyl or phenyl radical, Re represents an alkyl radical, Rf represents an alkyl radical, Rg represents an alkyl, cycloalkylalkyl, cycloalkyl, —(CH$_2$)$_n$OH radical, n is equal to 1, 2 or 3.

Step a is generally carried out in an inert solvent such as an aliphatic alcohol (1-4C) (for example methanol), in a chlorinated solvent (for example dichloromethane or dichloroethane) or tetrahydrofuran, in the presence of a base such as NaBH(OCOCH$_3$)$_3$, at a temperature in the region of 20° C.

Step b is generally carried out in an inert solvent such as a halogenated solvent (for example dichloromethane), in the presence of an organic base such as triethylamine or dimethylaminopyridine, at a temperature of between 0° C. and the boiling point of the reaction medium.

Step c is generally carried out in an inert solvent such as tetrahydrofuran, dimethylformamide, a chlorinated solvent (for example chloroform or 1,2-dichloroethane), an aromatic solvent (for example benzene or toluene), at a temperature of between 10° C. and the boiling point of the reaction medium.

Step d is carried out by any method known to a person skilled in the art which makes it possible to pass from an acid or a reactive derivative of this acid to a carboxamide without affecting the rest of the molecule and in particular the preferred methods previously described.

The derivatives 6 may be obtained according to the following reaction scheme:

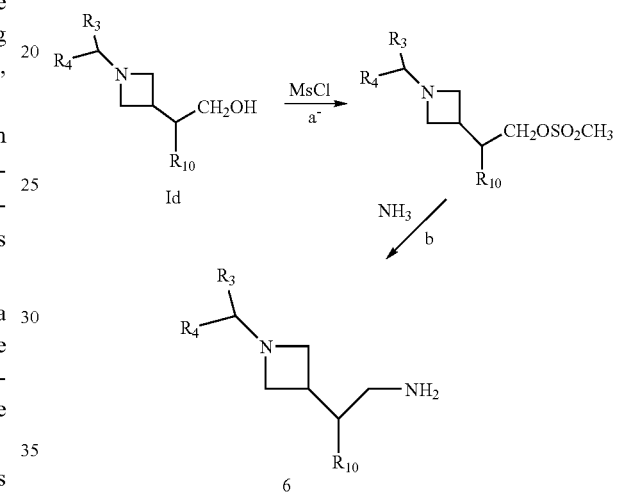

In these formulae, $R_3$, $R_4$ and $R_{10}$ have the same meanings as in formula (I) and Ms is a methylsulfonyloxy radical.

Step a is generally carried out in an inert solvent such as tetrahydrofuran, in the presence of triethylamine, at a temperature of between 10 and 20° C.

Step b is generally carried out with liquid aqueous ammonia in methanol, in an autoclave, at a temperature in the region of 60° C.

The compounds of formula (I) in which R represents a radical $CR_1R_2$ in which $R_1$ is a hydrogen atom and $R_2$ is a radical —CONR$_{13}$R$_{14}$ may be prepared according to the following reaction scheme:

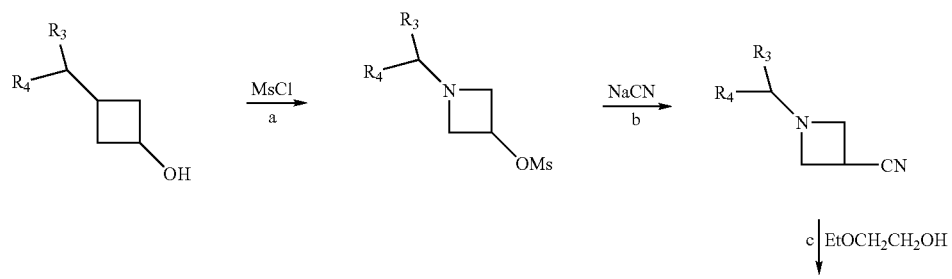

-continued

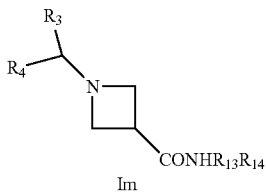 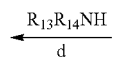 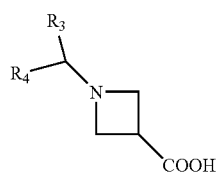

In these formulae, $R_3$, $R_4$, $R_{13}$ and $R_{14}$ have the same meanings as in formula (I), Ms represents a methylsulfonyloxy radical and Et represents ethyl.

Step a is carried out in the presence of triethylamine, in an inert solvent such as an ether (for example tetrahydrofuran), at a temperature in the region of 0° C.

Step b is generally carried out in an inert solvent such as a mixture of water and dimethylformamide, at a temperature of between 30 and 75° C.

Step c is carried out by any method known to a person skilled in the art which makes it possible to pass from a cyanated compound to the corresponding acid without affecting the rest of the molecule. Preferably, the procedure is carried out by means of potassium hydroxide in an aliphatic alcohol (1-4C) (for example ethanol) or in an aqueous medium, at the boiling point of the reaction medium.

Step d is carried out by any method known to a person skilled in the art which makes it possible to pass from an acid or a reactive derivative of this acid to a carboxamide without affecting the rest of the molecule molecule and in particular the preferred methods previously described.

The compounds of formula (I) for which R represents a radical $CR_1R_2$ in which $R_1$ is a hydrogen atom and $R_2$ is a radical $—CH_2—CONR_{13}R_{14}$ may be prepared according to the following reaction scheme:

In these formulae, $R_3$, $R_4$, $R_{13}$ and $R_{14}$ have the same meanings as in formula (I) and Et represents an ethyl radical.

Reaction a is generally carried out in an inert solvent such as tetrahydrofuran, in the presence of a base such as sodium hydride, or an alkali metal carbonate (for example potassium carbonate), at a temperature of between 20° C. and the boiling point of the reaction medium.

Reaction b is generally carried out by means of $NaBH_4$, in ethanol, at a temperature in the region of 0° C.

Reaction c is carried out by any method known to a person skilled in the art which makes it possible to pass from an ester to the corresponding acid without affecting the rest of the molecule. The procedure is preferably carried out in an inert solvent such as dioxane, in the presence of hydrochloric acid, at the boiling point of the reaction medium.

Reaction d is carried out by any method known to a person skilled in the art which makes it possible to pass from an acid or a reactive derivative of this acid to a carboxamide without affecting the rest of the molecule molecule and in particular the preferred methods previously described.

The intermediates 7 may also be obtained by malonic synthesis according to the following reaction scheme:

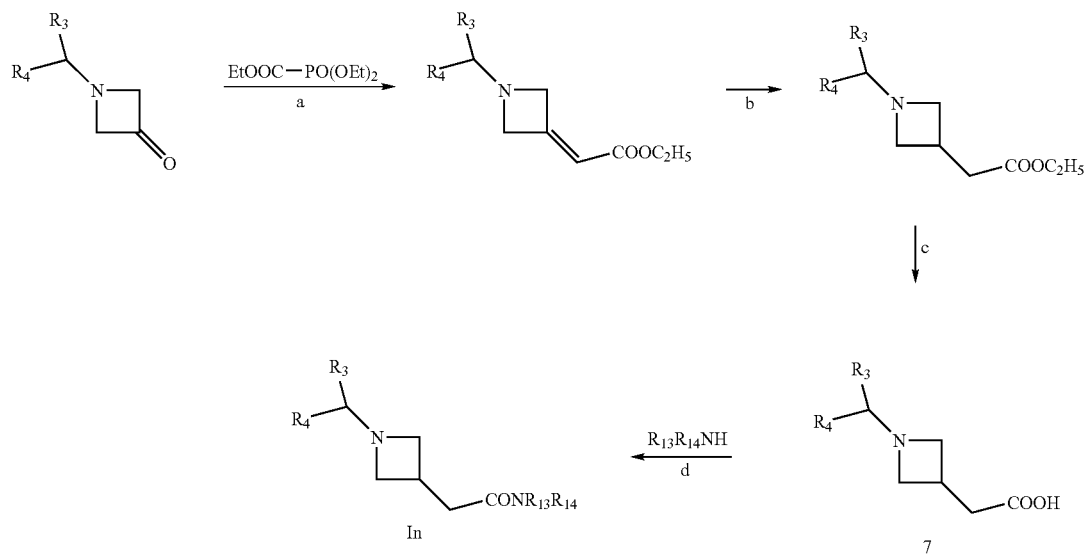

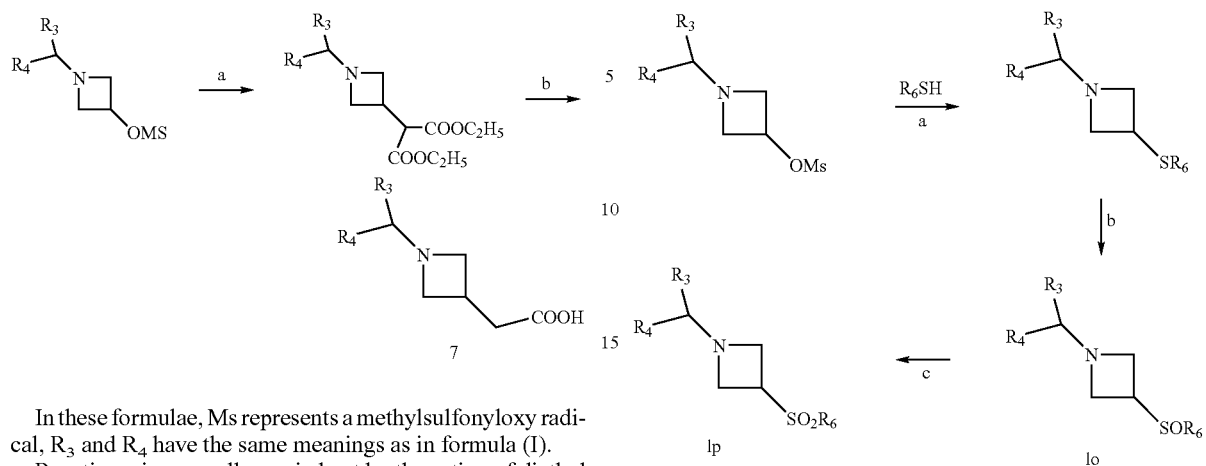

In these formulae, Ms represents a methylsulfonyloxy radical, $R_3$ and $R_4$ have the same meanings as in formula (I).

Reaction a is generally carried out by the action of diethyl malonate, in an inert solvent such as tetrahydrofuran, in the presence of freshly prepared sodium ethoxide, at the boiling point of the reaction medium.

Reaction b is generally carried out in an aqueous solution of hydrochloric acid at the boiling point of the reaction medium.

The compounds In may also be obtained according to the following reaction scheme:

In these formulae, $R_3$, $R_4$ and $R_6$ have the same meanings as in formula (I) and Ms is a methylsulfonyloxy radical.

Step a is generally carried out in an inert solvent such as tetrahydrofuran, in the presence of an inorganic base such as sodium hydride, at a temperature of between 0° C. and the boiling point of the reaction medium.

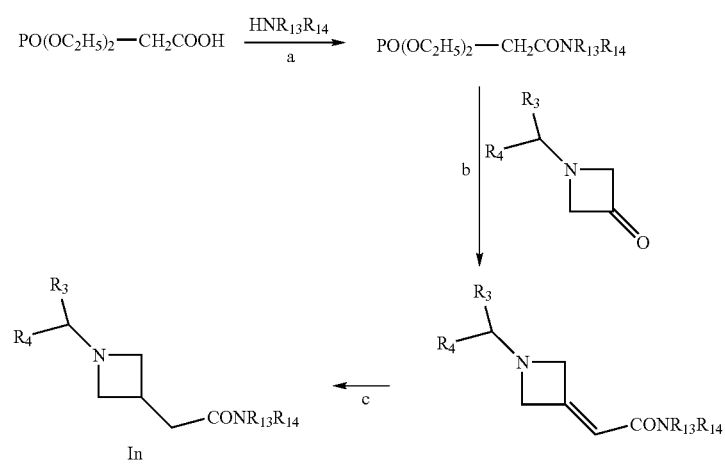

In these formulae, $R_3$, $R_4$, $R_{13}$ and $R_{14}$ have the same meanings as in formula (I).

Step a is carried out by any method known to a person skilled in the art which makes it possible to pass from an acid or a reactive derivative of this acid to a carboxamide without affecting the rest of the molecule molecule and in particular the preferred methods previously described.

Step b is generally carried out in an inert solvent such as tetrahydrofuran, in the presence of a base such as sodium hydride or potassium carbonate, at a temperature of between 20° C. and the boiling point of the reaction medium.

The reduction of step c is generally carried out by means of $NaBH_4$, in ethanol, at a temperature in the region of 20° C.

The compounds of formula (I) for which R represents a radical $CR_1R_2$ in which $R_1$ is a hydrogen atom and $R_2$ represents a radical —$SOR_6$ or —$SO_2R_6$ may be prepared according to the following reaction scheme:

Step b is generally carried out by any method of persons skilled in the art for oxidizing a sulfur-containing derivative, such as those described by M. HUDLICKY, Oxidations in Organic Chemistry, ACS Monograph, 186, 252-263 (1990). For example, the procedure is carried out by the action of an organic peroxy acid or a salt of such a peroxy acid (peroxycarboxylic or peroxysulfonic acids, in particular peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or inorganic peracids or a salt of such an acid (for example periodic or persulfuric acid), in an inert solvent such as a chlorinated solvent (for example chloroform or dichloromethane), at a temperature of between 0 and 25° C. or alternatively by means of oxone in a water-alcohol (methanol or ethanol) mixture.

Step c is generally carried out by any method of persons skilled in the art for oxidizing a sulfinyl derivative. Preferably, the procedure is carried out by the action of an organic peroxy acid or a salt of such a peroxy acid (peroxycarboxylic or peroxysulfonic acids, in particular peroxybenzoic acid, 3-chloroperoxybenzoic acid, 4-nitroperoxybenzoic acid, peroxyacetic acid, trifluoroperoxyacetic acid, peroxyformic acid or monoperoxyphthalic acid) or alternatively by means of oxone, in a water-alcohol (methanol or ethanol) mixture.

The compounds of formula (I) for which R represents a radical $CR_1R_2$ in which $R_1$ is a hydrogen atom and $R_2$ represents a radical —$COR_6$ or —CO-cycloalkyl may be prepared according to the following reaction scheme:

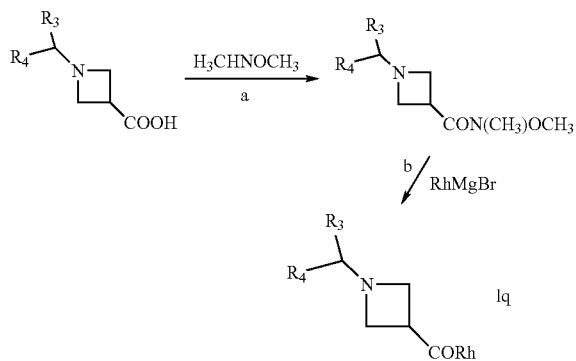

In these formulae, $R_3$ and $R_4$ have the same meanings as in formula (I) and Rh has the same meanings as $R_6$ or represents a cycloalkyl radical (3 to 10 carbon atoms).

Step a is carried out by any method known to a person skilled in the art which makes it possible to pass from an acid or a reactive derivative of this acid to a carboxamide without affecting the rest of the molecule and in particular the preferred methods previously described.

Step b is generally carried out in an inert solvent such as an ether such as tetrahydrofuran, at a temperature in the region of 0° C. The organomagnesium compounds are prepared according to methods known to a person skilled in the art, such as those described in the examples.

The compounds of formula (I) for which $R_1$ is a hydrogen atom and $R_2$ is a radical —$C(OH)(R_6)(R_{12})$, —$C(OH)(R_6)$(alkyl), —$C(=NO—CH_2—CH=CH_2)R_6$ or —$C(=NOalk)R_6$ may be prepared according to the following reaction scheme:

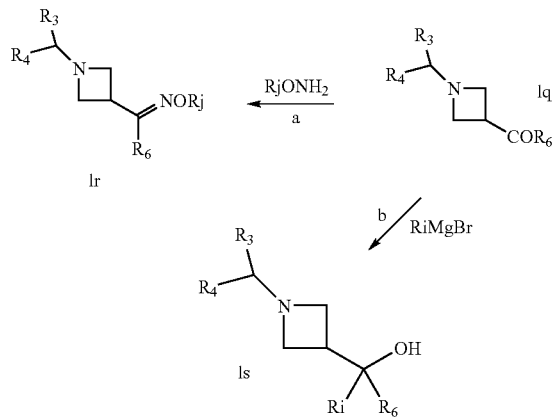

In these formulae, $R_3$, $R_4$ and $R_6$ have the same meanings as in formula (I), Ri has the same meanings as $R_{12}$ or represents an alkyl radical (1 to 6 carbon atoms in a straight or branched chain) and Rj represents an alkyl radical (1 to 6 carbon atoms in a straight or branched chain) or —$CH_2$—$CH=CH_2$.

Step a is generally carried out in an inert solvent such as an aliphatic alcohol (for example ethanol), in the presence of sodium acetate, at a temperature of between 20° C. and the boiling point of the reaction medium.

Step b is generally carried out in an inert solvent such as an ether such as tetrahydrofuran, at a temperature in the region of 0° C. The organomagnesium compounds are prepared according to methods known to a person skilled in the art, such as those described in the examples.

The compounds of formula (I) for which R represents a radical $CR_1R_2$ in which $R_1$ is a hydrogen atom and $R_2$ represents a radical —$CH(R_6)NR_{31}R_{32}$, in which $R_{31}$ and $R_{32}$ are hydrogen atoms or radicals —$CH(R_6)NHSO_2alk$, —$CH(R_6)NHCONHalk$ or —$CH(R_6)NHCOR_{31}$, may be prepared according to the following reaction scheme:

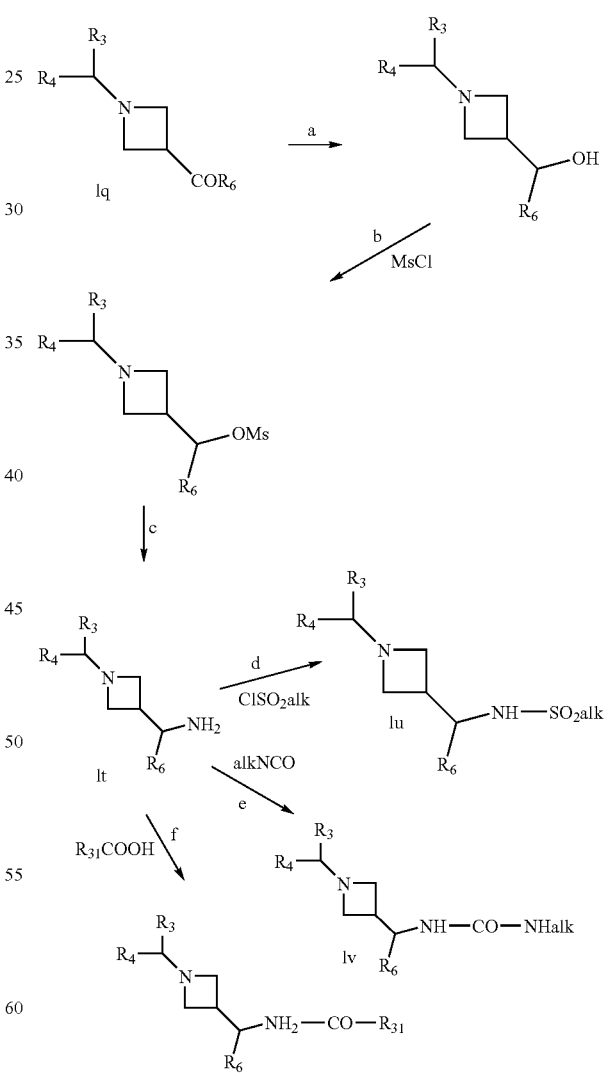

In these formulae, $R_3$, $R_4$, $R_6$ and $R_{31}$ have the same meanings as in formula (I), Ms represents a methylsulfonyloxy radical and alk represents an alkyl radical.

Reaction a is generally carried out by means of $NaBH_4$ in ethanol, at a temperature in the region of 20° C.

Step b is carried out in the presence of triethylamine, in an inert solvent such as an ether (for example tetrahydrofuran), at a temperature in the region of 0° C.

Step c is carried out by means of liquid aqueous ammonia in methanol, in an autoclave at a temperature in the region of 60°.

Step d is generally carried out in an inert solvent such as a halogenated solvent (for example dichloromethane) or tetrahydrofuran, in the presence of an organic base such as triethylamine, dimethylaminopyridine, at a temperature in the region of 20° C.

Step e is carried out by any method known to a person skilled in the art which makes it possible to pass from an acid or a reactive derivative of this acid to a carboxamide without affecting the rest of the molecule and in particular the preferred methods previously described.

Step f is generally carried out by means of an inert solvent such as tetrahydrofuran, dimethylformamide, a chlorinated solvent (for example chloroform or dichloroethane), an aromatic solvent (for example benzene or toluene), at a temperature of between 10° C. and the boiling point of the reaction medium.

The compounds of formula (I) for which R represents a radical $CR_1R_2$ in which $R_1$ is a hydrogen atom and $R_2$ represents a radical $—CH(R_6)NR_{31}R_{32}$, $R_{31}$ is a hydrogen atom and $R_{32}$ is an alkyl, Ar or -alk-Ar radical may be prepared by the action of a halide $HalR_{31}$ on a compound of formula (I) for which R represents a radical $CR_1R_2$ in which $R_1$ is a hydrogen atom and $R_2$ represents a radical $—CH(R_6)NR_{31}R_{32}$, $R_{31}$ and $R_{32}$ are hydrogen atoms.

This reaction is carried out in an inert polar solvent such as acetonitrile, tetrahydrofuran or dimethylformamide, in the presence of an organic or inorganic base (alkali metal (for example sodium or potassium) carbonate, trialkylamine (for example triethylamine or dimethylaminopyridine)), at a temperature of between 0° C. and the boiling point of the solvent, optionally in the presence of palladium or one of its salts or complexes.

The compounds of formula (I) for which R represents a radical $CR_1R_2$ in which $R_1$ is a hydrogen atom and $R_2$ represents a radical $—CH(R_6)NR_{31}R_{32}$, $R_{31}$ is a hydrogen atom and $R_{32}$ is an alkyl radical may also be prepared by the action of a corresponding compound of formula (I) for which R represents a radical $CR_1R_2$ in which $R_1$ is a hydrogen atom and $R_2$ represents a radical $—CO—R_6$ on an amine $HNR_{31}R_{32}$ for which $R_{31}$ is a hydrogen atom and $R_{32}$ is an alkyl radical.

This reaction is generally carried out in an inert solvent such as a chlorinated solvent (for example dichloromethane or dichloroethane), in the presence of a reducing agent such as sodium triacetoxy-borohydride, at a temperature of between 0° C. and 70° C.

The compounds of formula (I) for which R represents a radical $CR_1R_2$ in which $R_1$ is a hydrogen atom and $R_2$ represents a radical $—CH(R_6)NR_{31}R_{32}$, $R_{31}$ and $R_{32}$ are alkyl, Ar or -alk-Ar radicals may be prepared by the action of a halide $HalR_{32}$ on a compound of formula (I) for which R represents a radical $CR_1R_2$ in which $R_1$ is a hydrogen atom and $R_2$ represents a radical $—CH(R_6)NR_{31}R_{32}$, $R_{31}$ is a hydrogen atom and $R_{32}$ is an alkyl, Ar or -alk-Ar radical.

This reaction is carried out in an inert polar solvent such as acetonitrile, tetrahydrofuran or dimethylformamide, in the presence of an organic or inorganic base (alkali metal (for example sodium or potassium) carbonate, trialkylamine (for example triethylamine or dimethylaminopyridine)), at a temperature of between 0° C. and the boiling point of the solvent, optionally in the presence of palladium or one of its salts or complexes.

The compounds of formula (I) for which R represents a radical $CR_1R_2$ in which $R_1$ is a hydrogen atom and $R_2$ represents a radical $—CH(R_6)NR_{31}R_{32}$, $R_{31}$ is a hydrogen atom and $R_{32}$ is a (2-6C) alkyl or -(2-6C)alk-Ar radical may be prepared by the action of an aldehyde RaCHO for which Ra is an alkyl or -alk-Ar radical on a compound of formula (I) for which R represents a radical $CR_1R_2$ in which $R_1$ is a hydrogen atom and $R_2$ represents a radical $—CH(R_6)NR_{31}R_{32}$, $R_{31}$ and $R_{32}$ are hydrogen atoms.

This reaction is carried out in an inert solvent such as dichloromethane, dichloroethane, toluene or tetrahydrofuran, at a temperature of between 0° C. and 50° C. in the presence of a reducing agent such as sodium triacetoxyborohydride or sodium cyanoborohydride.

The compounds of formula (I) for which R represents a radical $CR_1R_2$ in which $R_1$ is a hydrogen atom and $R_2$ represents a radical $—CH(R_6)NR_{31}R_{32}$, $R_{31}$ is an alkyl, Ar or -alk-Ar radical and $R_{32}$ is a (2-6C) alkyl or -(2-6C)alk-Ar radical may be prepared by the action of an aldehyde RaCHO for which Ra is an alkyl or -alk-Ar radical on a compound of formula (I) for which R represents a radical $CR_1R_2$ in which $R_1$ is a hydrogen atom and $R_2$ represents a radical $—CH(R_6)NR_{31}R_{32}$, $R_{31}$ is a hydrogen atom and $R_{32}$ is an alkyl, Ar or -alk-Ar radical.

This reaction is carried out in an inert solvent such as dichloromethane, dichloroethane, toluene or tetrahydrofuran, at a temperature of between 0° C. and 50° C. in the presence of a reducing agent such as sodium triacetoxyborohydride or sodium cyanoborohydride.

The compounds of formula (I) for which R represents a radical $CR_1R_2$ in which $R_1$ is a hydrogen atom and $R_2$ represents a radical $—CH(R_6)NR_{31}R_{32}$, $R_{31}$ and $R_{32}$ form with the nitrogen atom to which they are attached a heterocycle chosen from aziridinyl, azetidinyl, pyrrolidinyl or piperidinyl may be prepared by the action of a dihalide Hal-(2-5C)alk-Hal on a compound of formula (I) for which R represents a radical $CR_1R_2$ in which $R_1$ is a hydrogen atom and $R_2$ represents a radical $—CH(R_6)NR_{31}R_{32}$, $R_{31}$ and $R_{32}$ are hydrogen atoms.

This reaction is carried out in an inert polar solvent such as acetonitrile, tetrahydrofuran or dimethylformamide, in the presence of an organic or inorganic base (alkali metal (for example sodium or potassium) carbonate, trialkylamine (for example triethylamine or dimethylaminopyridine)), at a temperature of between 0° C. and the boiling point of the solvent, optionally in the presence of palladium or one of its salts or complexes.

The compounds of formula (I) for which R represents a radical $CR_1R_2$ in which $R_1$ is a hydrogen atom and $R_2$ represents a radical $—CH_2—COR_6$, $—CH_2—CH(R_6)—NR_{31}R_{32}$ or $—CH_2—C(=NOalk)R_6$ may be prepared according to the following reaction scheme:

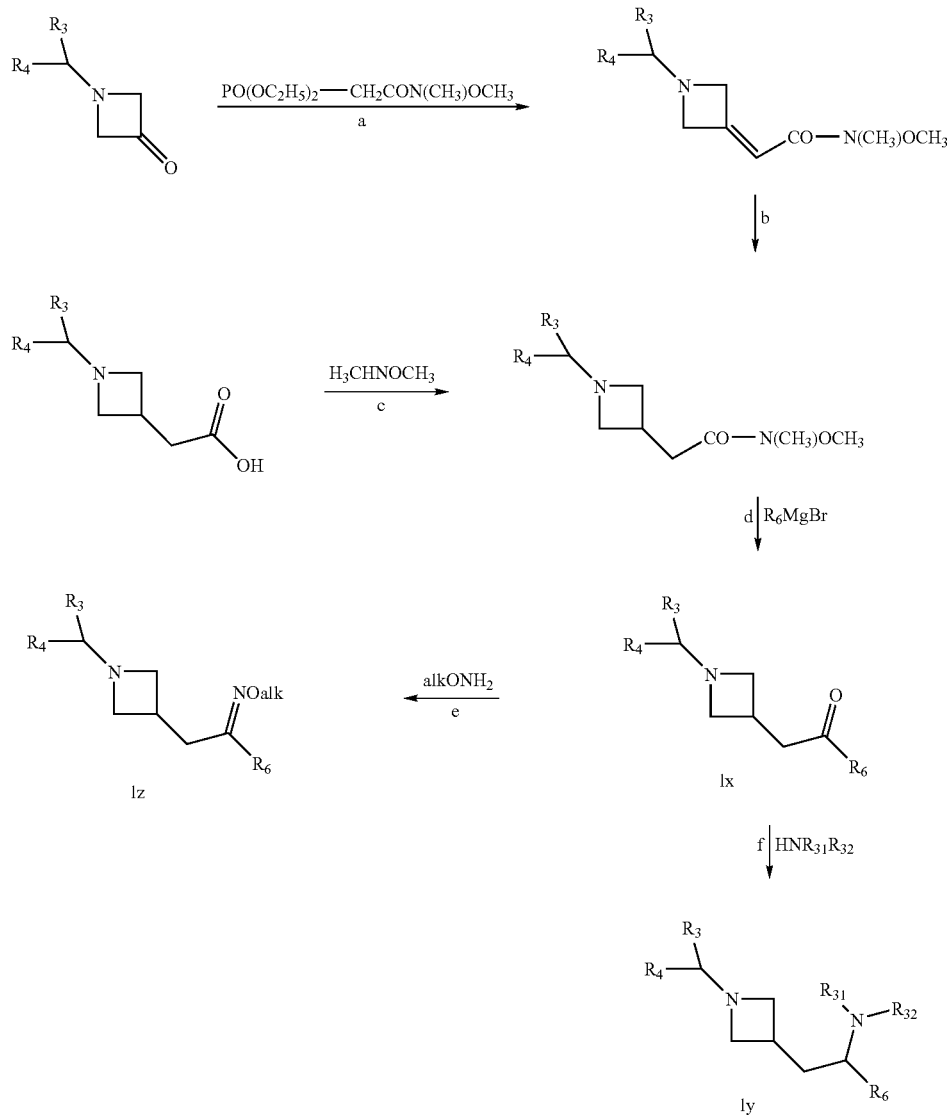

In these formulae, $R_3$, $R_4$, $R_6$, $R_{31}$ and $R_{32}$ have the same meanings as in formula (I) and alk represents an alkyl radical.

Step a is generally carried out in a solvent such as tetrahydrofuran, at a temperature of between 20° C. and the boiling point of the reaction medium.

Step b is generally carried out in an inert solvent such as an aliphatic alcohol (for example methanol), a chlorinated solvent (chloroform or dichloromethane) or a mixture of these solvents, in the presence of a reducing agent such as $NaBH_4$, at a temperature of between 0° C. and the boiling point of the reaction medium.

Step c is carried out by any method known to a person skilled in the art which makes it possible to pass from an acid or a reactive derivative of this acid to a carboxamide without affecting the rest of the molecule and in particular the preferred methods previously described.

Step d is generally carried out in an inert solvent such as an ether such as tetrahydrofuran, at a temperature in the region of 0° C. The organomagnesium compounds are prepared according to the m'yhodes known to a person skilled in the art such as those described in the examples.

Step e is generally carried out in an inert solvent such as a 1-4C aliphatic alcohol such as methanol, in the presence of sodium acetate, at a temperature of between 20° C. and the boiling point of the reaction medium.

Step f is carried out in an inert solvent such as a chlorinated solvent (for example dichloromethane or dichloroethane), in the presence of a reducing agent such as sodium triacetoxyborohydride, at a temperature of between 0° C. and 70° C.

The compounds of formula (I) for which R represents a radical $CR_1R_2$ in which $R_1$ represents a cyano, —S-alk-$NR_{16}R_{17}$, —$NHR_{15}$, alkyl or —$NR_{20}R_{21}$ radical and $R_2$ represents a radical —$C(R_8)(R_{11})(R_{12})$ in which $R_8$ is a hydrogen atom may be prepared according to the following reaction scheme:

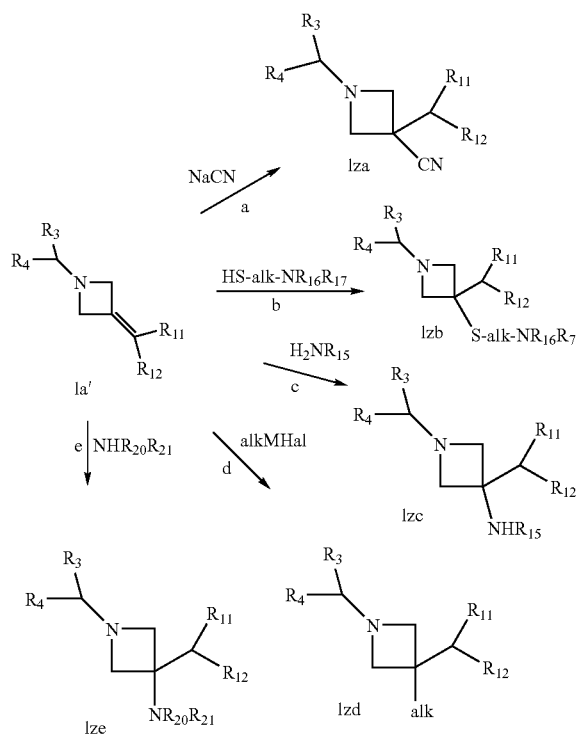

In these formulae, $R_3$, $R_4$, $R_{11}$, $R_{12}$, $R_{15}$, $R_{16}$ and $R_{17}$ have the same meanings as in formula (I), alk represents an alkyl radical, Hal represents a halogen atom and M represents a metal and preferably copper.

Step a is preferably carried out in a polar solvent such as dimethyl sulfoxide, at a temperature of between 20 and 50° C.

Step b is preferably carried out in an inert solvent such as dimethyl sulfoxide, tetrahydrofuran or acetonitrile, in the presence of a base such as an alkali metal carbonate (for example potassium carbonate) or ammonium hydroxide, at a temperature of between 20° C. and the boiling point of the reaction medium.

Step c is preferably carried out in an inert solvent such as dimethyl sulfoxide, tetrahydrofuran or acetonitrile, in the presence of a base such as an alkali metal carbonate (for example potassium carbonate) or ammonium hydroxide, at a temperature of between 20° C. and the boiling point of the reaction medium.

Step d is preferably carried out in an inert solvent such as an ether (ethyl ether) or tetrahydrofuran, at a temperature of between −78° C. and 20° C.

Step e is preferably carried out in an inert solvent such as dimethyl sulfoxide, tetrahydrofuran, acetonitrile, dichloromethane or dichloroethane in the presence of a base such as an alkali metal carbonate (for example potassium carbonate) or ammonium hydroxide, at a temperature of between 20° C. and the boiling point of the reaction medium.

The compounds of formula (I) for which R represents a radical $CR_1R_2$ in which $R_1$ represents a radical -alk-$NR_{18}R_{19}$, $R_{18}$ and $R_{19}$ represent a hydrogen atom may be prepared by reducing the corresponding compound of formula (I) for which R represents a radical $CR_1R_2$ in which $R_1$ represents a cyano radical.

This reaction is generally carried out in an inert solvent such as tetrahydrofuran, ethyl ether or toluene, at a temperature of between 0° C. and the boiling point of the reaction medium, in the presence of a reducing agent such as aluminum hydride.

The compounds of formula (I) for which R represents a radical $CR_1R_2$ in which $R_1$ represents a radical -alk-$NR_{18}R_{19}$, $R_{18}$ represents a hydrogen atom and $R_{19}$ represents an alkyl, cycloalkyl, cycloalkylalkyl, cycloalkylcarbonyl, —$SO_2$alk, —CO—NHalk or —COOalk radical may be prepared by the action of a halide Hal$R_{19}$, Hal represents a halogen, on a compound of formula (I) for which R represents a radical $CR_1R_2$ in which $R_1$ represents a radical -alk-$NR_{18}R_{19}$, $R_{18}$ and $R_{19}$ represent a hydrogen atom.

This reaction is carried out in an inert polar solvent such as acetonitrile, tetrahydrofuran or dimethylformamide, in the presence of an organic or inorganic base (alkali metal (for example sodium or potassium) carbonate, trialkylamine (for example triethylamine or dimethylaminopyridine)), at a temperature of between 0° C. and the boiling point of the solvent, optionally in the presence of palladium or one of its salts or complexes.

The compounds of formula (I) for which R represents a radical $CR_1R_2$ in which $R_1$ represents a radical -alk-$NR_{18}R_{19}$, $R_{18}$ represents an alkyl radical and $R_{19}$ represents an alkyl, cycloalkyl, cycloalkylalkyl, cycloalkylcarbonyl, —$SO_2$alk, —CO—NHalk or —COOalk radical may be prepared by the action of an alkyl halide on a compound of formula (I) for which R represents a radical $CR_1R_2$ in which $R_1$ represents a radical -alk-$NR_{18}R_{19}$, $R_{18}$ represents a hydrogen atom and $R_{19}$ represents an alkyl, cycloalkyl, cycloalkylalkyl, cycloalkylcarbonyl, —$SO_2$alk, —CO—NHalk or —COOalk radical.

This reaction is carried out in an inert polar solvent such as acetonitrile, tetrahydrofuran or dimethylformamide, in the presence of an organic or inorganic base (alkali metal (for example sodium or potassium) carbonate, trialkylamine (for example triethylamine or dimethylaminopyridine)), at a temperature of between 0° C. and the boiling point of the solvent, optionally in the presence of palladium or one of its salts or complexes.

The compounds of formula (I) for which R represents a radical $CR_1R_2$ in which either $R_1$ represents a hydrogen atom and $R_2$ represents a radical —$C(R_8)(R_9)(R_{10})$ or —$C(R_8)(R_{11})(R_{12})$, or $R_1$ represents an alkyl, NH—$R_{15}$, cyano, —S-alk-$NR_{16}R_{17}$, -alk-$NR_{18}R_{19}$ or —$NR_{20}R_{21}$ radical and $R_2$ represents a radical —$C(R_8)(R_{11})(R_{12})$ and $R_8$ represents an alkyl radical may be prepared by alkylation of a corresponding compound of formula (I) for which $R_8$ is a hydrogen atom.

This reaction is preferably carried out by means of a base such as an alkali metal hydride (for example sodium hydride), an alkali metal amide (for example sodium amide) or an organometallic derivative, in an inert solvent such as an aliphatic ether (ethyl ether) or tetrahydrofuran, at a temperature of between −78° C. and 30° C., by means of an alkylating agent such as an alkyl halide or an alkyl sulfonate.

The compounds of formula (I) for which R represents a radical C═$C(R_7)SO_2$alk may also be prepared according to the following reaction scheme:

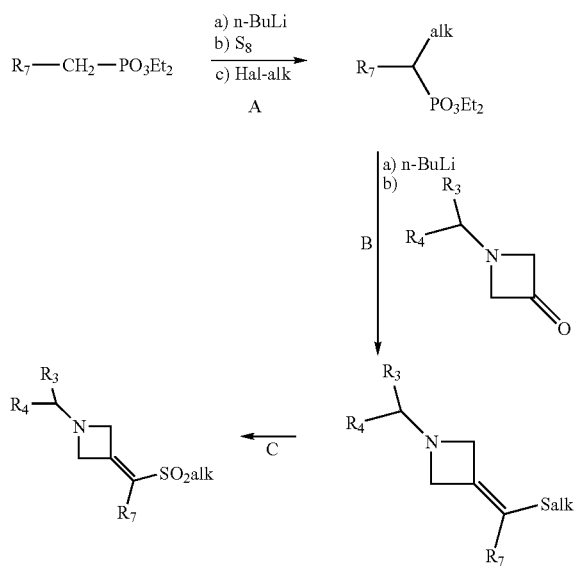

In these formulae, $R_3$, $R_4$ and $R_7$ have the same meanings as in formula (I), alk represents an alkyl radical and Hal represents a halogen atom.

Reaction A is generally carried out in an inert solvent such as an ether (for example ethyl ether), in the presence of a strong base such as tert-butyllithium or n-butyllithium, at a temperature of between −70° C. and −50° C., followed by the addition of sulfur and then an alkyl halide (for example iodide or bromide).

Reaction B is generally carried out in an inert solvent such as an ether (for example tetrahydrofuran), in the presence of a strong base such as tert-butyllithium or n-butyllithium, at a temperature of between −70° C. and −50° C., followed by the addition of azeditin-3-one, a return to room temperature and hydrolysis.

Reaction C is carried out by any known method which makes it possible to oxidize a sulfur-containing derivative without affecting the rest of the molecule, such as those previously described.

It is understood for persons skilled in the art that, to carry out the processes according to the invention which are described above, it may be necessary to introduce groups protecting amino, hydroxyl and carboxyl functions in order to avoid side reactions. These groups are those which allow removal without affecting the rest of the molecule. As examples of groups protecting the amino function, there may be mentioned tert-butyl or methyl carbamates which may be regenerated using iodotrimethylsilane or allyl using palladium catalysts. As examples of groups protecting the hydroxyl function, there may be mentioned triethylsilyl and tert-butyldimethylsilyl which may be regenerated using tetrabutylammonium fluoride or alternatively asymmetric acetals (methoxymethyl or tetrahydropyranyl for example) with regeneration using hydrochloric acid. As groups protecting carboxyl functions, there may be mentioned esters (allyl or benzyl for example), oxazoles and 2-alkyl-1,3-oxazolines. Other protecting groups which can be used are described by GREENE T. W. et al., Protecting Groups in Organic Synthesis, second edition, 1991, John Wiley & Sons.

The compounds of formula (I) may be purified by the customary known methods, for example by crystallization, chromatography or extraction.

The enantiomers of the compounds of formula (I) may be obtained by resolution of the racemates for example by chromatography on a chiral column according to PIRCKLE W. H. et al., Asymmetric synthesis, Vol. 1, Academic Press (1983) or by formation of salts or by synthesis from chiral precursors. The diastereoisomers may be prepared according to known-conventional methods (crystallization, chromatography or from chiral precursors).

The compounds of formula (I) may be optionally converted to addition salts with an inorganic or organic acid by the action of such an acid in an organic solvent such as an alcohol, a ketone, an ether or a chlorinated solvent. These salts also form part of the invention.

As examples of pharmaceutically acceptable salts, the following salts may be mentioned: benzenesulfonate, hydrobromide, hydrochloride, citrate, ethanesulfonate, fumarate, gluconate, iodate, isethionate, maleate, methane sulfonate, methylene-bis-β-oxynaphthoate, nitrate, oxalate, pamoate, phosphate, salicylate, succinate, sulfate, tartrate, theophyllineacetate and p-toluenesulfonate.

The compounds of formula (I) exhibit advantageous pharmacological properties. These compounds possess a high affinity for the cannabinoid receptors and particularly those of the CB1 type. They are CB1 receptor antagonists and are therefore useful in the treatment and prevention of disorders affecting the central nervous system, the immune system, the cardiovascular or endocrine system, the respiratory system, the gastrointestinal apparatus and reproductive disorders (Hollister, Pharm. Rev.; 38, 1986, 1-20, Reny and Sinha, Prog. Drug Res., 36, 71-114 (1991), Consroe and Sandyk, in Marijuana/Cannabinoids, Neurobiology and Neurophysiology, 459, Murphy L. and Barthe A. Eds, CRC Press; 1992).

Accordingly, these compounds may be used for the treatment or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, in weaning from chronic treatments and alcohol or drug abuse (opioids, barbiturates, cannabis, cocaine, amphetamine, phencyclide, hallucinogens, benzodiazepines for example), as analgesics or potentiators of the analgesic activity of the narcotic and nonnarcotic drugs. They may also be used for the treatment or prevention of intestinal transit.

The affinity of the compounds of formula (I) for the cannabis receptors has been determined according to the method described by KUSTER J. E., STEVENSON J. I., WARD S. J., D'AMBRA T. E., HAYCOCK D. A. in J. Pharmacol. Exp. Ther., 264 1352-1363 (1993).

In this test, the $IC_{50}$ of the compounds of formula (I) is less than or equal to 1000 nM.

Their antagonist activity has been shown by means of the model of hypothermia induced by an agonist of the cannabis receptors (CP-55940) in mice, according to the method described by Pertwee R. G. in Marijuana, Harvey D. J. eds, 84 Oxford IRL Press, 263-277 (1985). (In summary, as described particularly at pages 265 of this paper, this model simply involves administering the test compound to the mouse and then measuring and recording internal temperature changes in the test animal for a predetermined time period.)

In this test, the DE50 of the compounds of formula (I) is less than or equal to 50 mg/kg.

The compounds of formula (I) exhibit low toxicity. Their $LD_{50}$ is greater than 40 mg/kg by the subcutaneous route in mice.

The preferred compounds of formula (I) are the following:
(RS)-1-[bis(4-chlorophenyl)methyl)]-3-[(3,5-difluoro-phenyl)(methylsulfonyl)methyl]azetidine,
(R)-1-[bis(4-chlorophenyl)methyl)]-3-[(3,5-difluoro-phenyl)(methylsulfonyl)methyl]azetidine,
(S)-1-[bis(4-chlorophenyl)methyl)]-3-[(3,5-difluoro-phenyl)(methylsulfonyl)methyl]azetidine,
(RS)-1-[bis(4-chlorophenyl)methyl)]-3-[(pyrid-3-yl)-(methylsulfonyl)methyl]azetidine,
(R)-1-[bis(4-chlorophenyl)methyl)]-3-[(pyrid-3-yl)-(methylsulfonyl)methyl]azetidine,
(S)-1-[bis(4-chlorophenyl)methyl)]-3-[(pyrid-3-yl)-(methylsulfonyl)methyl]azetidine,
(RS)-1-[bis(3-fluorophenyl)methyl]-3-[(3,5-difluoro-phenyl)methylsulfonylmethyl]azetidine,
(R)-1-[bis(3-fluorophenyl)methyl]-3-[(3,5-difluoro-phenyl)methylsulfonylmethyl]azetidine,
(S)-1-[bis(3-fluorophenyl)methyl]-3-[(3,5-difluoro-phenyl)methylsulfonylmethyl]azetidine,
1-[bis(4-chlorophenyl)methyl]-3-(RS)-{[3-azetidin-1-yl-phenyl]methylsulfonylmethyl}azetidine,
1-[bis(4-chlorophenyl)methyl]-3-(R)-{[3-azetidin-1-yl-phenyl]methylsulfonylmethyl}azetidine,
1-[bis(4-chlorophenyl)methyl]-3-(S)-{[3-azetidin-1-yl-phenyl]methylsulfonylmethyl}azetidine,
(RS)-1-[3-({1-[bis(4-chlorophenyl)methyl]azetidin-3-yl}-methylsulfonylmethyl)phenyl]pyrrolidine,
(R)-1-[3-({1-[bis(4-chlorophenyl)methyl]azetidin-3-yl}-methylsulfonylmethyl)phenyl]pyrrolidine,
(S)-1-[3-({1-[bis(4-chlorophenyl)methyl]azetidin-3-yl)-methylsulfonylmethyl)phenyl]pyrrolidine,
(RS)-N-[3-({1-[bis(4-chlorophenyl)methyl]azetidin-3-yl}methylsulfonylmethyl)phenyl]-N-methylamine,
(R)-N-[3-({1-[bis(4-chlorophenyl)methyl]azetidin-3-yl}methylsulfonylmethyl)phenyl]-N-methylamine,
(S)-N-[3-({1-[bis(4-chlorophenyl)methyl]azetidin-3-yl}methylsulfonylmethyl)phenyl]-N-methylamine,
(RS)-1-[bis(4-chlorophenyl)methyl]-3-[(3,5-bistri-fluoromethylphenyl)methylsulfonylmethyl]azetidine,
(R)-1-[bis(4-chlorophenyl)methyl]-3-[(3,5-bistrifluoro-methylphenyl)methylsulfonylmethyl]azetidine,
(S)-1-[bis(4-chlorophenyl)methyl]-3-[(3,5-bistri-fluoromethylphenyl)methylsulfonylmethyl]azetidine,
1-[bis(4-chlorophenyl)methyl]-3-(phenylsulfonylmethyl)-azetidine,
(RS)-1-[bis(4-chlorophenyl)methyl]-3-[(3,5-difluoro-phenyl)methylsulfonylmethyl]-3-methylazetidine,
(R)-1-[bis(4-chlorophenyl)methyl]-3-[(3,5-difluoro-phenyl)methylsulfonylmethyl]-3-methylazetidine,
(S)-1-[bis(4-chlorophenyl)methyl]-3-[(3,5-difluoro-phenyl)methylsulfonylmethyl]-3-methyl-azetidine,
(RS)-2-{1-[bis(4-chlorophenyl)methyl]azetidin-3-yl}-2-(3,5-difluorophenyl)-N-cyclohexylacetamide,
(R)-2-{1-[bis(4-chlorophenyl)methyl]azeditin-3-yl}-2-(3,5-difluorophenyl)-N-cyclohexylacetamide,
(S)-2-{1-[bis(4-chlorophenyl)methyl]azetidin-3-yl)-2-(3,5-difluorophenyl)-N-cyclohexylacetamide,
(RS)-2-{1-[bis(4-chlorophenyl)methyl]azetidin-3-yl}-2-(3,5-difluorophenyl)-N-isobutylacetamide,
(R)-2-{1-[bis(4-chlorophenyl)methyl]azetidin-3-yl}-2-(3,5-difluorophenyl)-N-isobutylacetamide,
(S)-2-{1-[bis(4-chlorophenyl)methyl]azetidin-3-yl}-2-(3,5-difluorophenyl)-N-isobutylacetamide,
(RS)-2-{1-[bis(4-chlorophenyl)methyl]azetidin-3-yl}-2-(3,5-difluorophenyl)-N-cyclopropylmethylacetamide,
(R)-2-{1-[bis(4-chlorophenyl)methyl]azetidin-3-yl}-2-(3,5-difluorophenyl)-N-cyclopropylmethylacetamide,
(S)-2-{1-bis(4-chlorophenyl)methyl]azetidin-3-yl}-2-(3,5-difluorophenyl)-N-cyclopropylmethylacetamide,
(RS)-2-{1-[bis(4-chlorophenyl)methyl]azetidin-3-yl}-2-(3,5-difluorophenyl)-N-isopropylacetamide,
(R)-2-{1-[bis(4-chlorophenyl)methyl]azetidin-3-yl}-2-(3,5-difluorophenyl)-N-isopropylacetamide,
(S)-2-{1-[bis(4-chlorophenyl)methyl]azetidin-3-yl}-2-(3,5-difluorophenyl)-N-isopropylacetamide,
(RS)-1-[bis(4-chlorophenyl)methyl]-3-[1-(3,5-difluoro-phenyl)-1-methylsulfonylethyl]azetidine,
(R)-1-[bis(4-chlorophenyl)methyl]-3-[1-(3,5-difluoro-phenyl)-1-methylsulfonylethyl]azetidine,
(S)-1-[bis(4-chlorophenyl)methyl]-3-[1-(3,5-difluoro-phenyl)-1-methylsulfonylethyl]azetidine,
(RS)-1-[bis(4-fluorophenyl)methyl]-3-[(3,5-difluoro-phenyl)methylsulfonylmethyl]azetidine,
(R)-1-[bis(4-fluorophenyl)methyl]-3-[(3,5-difluoro-phenyl)methylsulfonylmethyl]azetidine,
(S)-1-[bis(4-fluorophenyl)methyl]-3-[(3,5-difluoro-phenyl)methylsulfonylmethyl]azetidine,
(RS)-{1-[(3-pyridyl)-(4-chlorophenyl)methyl]-3-[(3,5-difluorophenyl)methylsulfonylmethyl]azetidine,
(SS)-{1-[(3-pyridyl)-(4-chlorophenyl)methyl]-3-[(3,5-difluorophenyl)methylsulfonylmethyl]azetidine,
(RR)-{1-[(3-pyridyl)-(4-chlorophenyl)methyl]-3-[(3,5-difluorophenyl)methylsulfonylmethyl]azetidine,
(SR)-{1-[(3-pyridyl)-(4-chlorophenyl)methyl]-3-[(3,5-difluorophenyl)methylsulfonylmethyl]azetidine,
(RS)-{1-[(4-pyridyl)-(4-chlorophenyl)methyl]-3-[(3,5-difluorophenyl)methylsulfonylmethyl]azetidine,
(SS)-{1-[(4-pyridyl)-(4-chlorophenyl)methyl]-3-[(3,5-difluorophenyl)methylsulfonylmethyl]azetidine,
(RR)-{1-[(4-pyridyl)-(4-chlorophenyl)methyl]-3-[(3,5-difluorophenyl)methylsulfonylmethyl]azetidine,
(SR)-{1-[(4-pyridyl)-(4-chlorophenyl)methyl]-3-[(3,5-difluorophenyl)methylsulfonylmethyl]azetidine,
(RS)-5-((4-chlorophenyl)-{3-[(3,5-difluorophenyl)-methylsulfonylmethyl]azetidin-1-yl}methyl)pyrimidine,
(SR)-5-((4-chlorophenyl)-{3-[(3,5-difluorophenyl)-methylsulfonylmethyl]azetidin-1-yl}methyl)pyrimidine,
(RR)-5-((4-chlorophenyl)-{3-[(3,5-difluorophenyl)-methylsulfonylmethyl]azetidin-1-yl}methyl)pyrimidine,
(SS)-5-((4-chlorophenyl)-{3-[(3,5-difluorophenyl)-methylsulfonylmethyl]azetidin-1-yl}methyl)pyrimidine,
(SS)-{1-[(2-chloropyrid-5-yl)-(4-chlorophenyl)methyl]-3-[(3,5-difluorophenyl)methylsulfonylmethyl]azetidine,
(RR)-{1-[(2-chloropyrid-5-yl)-(4-chlorophenyl)methyl]-3-[(3,5-difluorophenyl)methylsulfonylmethyl]azetidine,
(RS)-{1-[(2-chloropyrid-5-yl)-(4-chlorophenyl)methyl]-3-[(3,5-difluorophenyl)methylsulfonylmethyl]azetidine,
(SR)-{1-[(2-chloropyrid-5-yl)-(4-chlorophenyl)methyl]-3-[(3,5-difluorophenyl)methylsulfonylmethyl]azetidine, their optical isomers and their pharmaceutically acceptable salts.

The following examples illustrate the invention.

EXAMPLE 1

(RS)-1-[Bis(4-chlorophenyl)methyl]-3-[(3,5-di-fluorophenyl)(methylsulfonylmethyl]azetidin may be prepared from 1.0 g of 1-[bis(4-chlorophenyl)methyl)]-3-[(3,5-difluorophenyl)(methylsulfonyl)methylene]-azetidine in 40 cm$^3$ of methanol, 96 mg of sodium borohydride are added and the mixture is stirred for 3 hours at 20° C. After addition of 100 cm$^3$ of dichloromethane, the reaction mixture is washed twice with 50 cm$^3$ of water and dried over magnesium sulfate, filtered and concentrated to dryness under reduced pressure (2.7 kPa). The crude product is chromatographed on a silica gel column (particle size 0.063-0.200 mm, height 6 cm, diameter 3 cm), eluting under an argon pressure of 0.8 bar with dichloromethane and then the mixture dichloromethane+1% methanol and collecting 80-cm$^3$ fractions. Fractions 13 to 15 are combined and concentrated to dryness under reduced pressure (2.7 kPa). 0.55 g of a white solid is obtained which is taken up in 50 cm$^3$ of diisopropyl ether, filtered and dried to give 0.47 g of (RS)-1-[bis(4-chlorophenyl)methyl)]-3-[(3,5-difluorophenyl)(methyl-sulfonyl)methyl]azetidine in the form of a white solid [$^1$H NMR spectrum (400 MHz, (CD$_3$)$_2$SO d4 with addition of a few drops of CD$_3$COOD d4, at a temperature of 353 K, δ in ppm): 2.46 (t, J=7.5 Hz: 1H); 2.77 (s: 3H); 3.15 (mt: 2H); 3.40 (mt: 1H); 3.49 (broad t, J=7.5 Hz: 1H); 4.46 (s: 1H); 4.81 (d, J=9 Hz: 1H); from 7.05 to 7.20 (mt: 3H); from 7.15 to 7.45 (mt: 8H)].

1-[Bis(4-chlorophenyl)methyl)]-3-[(3,5-difluoro-phenyl)(methylsulfonyl)methylene]azetidine may be prepared according to two methods:

Method 1

0.65 cm$^3$ of methylsulfonyl chloride is added to a solution of 2.94 g of 1-[bis(4-chloro-phenyl)methyl]-3-[(3,5-difluorophenyl)-(methylsulfonyl)methyl-(RS)]azetidin-3-ol in 250 cm$^3$ of dichloromethane at 22° C., followed, in small portions over 15 minutes by 2.42 g of 4-dimethylaminopyridine; the orange-colored solution is stirred for 2 hours at room temperature. The reaction mixture is washed 3 times with 150 cm$^3$ of distilled water and once with 150 cm$^3$ of a saturated sodium chloride solution, then dried with magnesium sulfate, filtered and concentrated to dryness under reduced pressure (2.7 kPa). The residue obtained is chromatographed on a silica gel column (particle size 0.04-0.06 mm, diameter 5.5 cm, height 15 cm), under an argon pressure of 0.5 bar with a mixture of ethyl acetate and cyclohexane (1/9 by volume) as eluent and collecting 70-cm$^3$ fractions. Fractions 15 to 36 are combined and then concentrated to dryness under reduced pressure (2.7 kPa). 1.86 g of a white foam are obtained, which foam is crystallized from isopropyl ether to give a solid melting at 190° C. Recrystallization from 45 cm$^3$ of ethanol gives 1.08 g of 1-[Bis(4-chlorophenyl)methyl]-3-[(3,5-difluorophenyl)(methylsulfonyl)methylene]azetidine melting at 206° C. [NMR spectrum in DMSO-d6, T=300K, δ in ppm (300 MHz): 3.00 (3H, s, SCH$_3$), 3.87 (2H, s, NCH$_2$), 4.20 (2H, s, NCH$_2$), 4.75 (1H, s, NCH), 7.15 (2H, d, J=8 Hz, 2CH arom.), 7.30 (5H, m, 5CH arom.), 7.45 (4H, d, J=7 Hz, 4CH arom.)].

6.75 g of 3-[(3,5-difluorophenyl)(methyl-sulfonyl)methyl-(RS)]azetidin-3-ol hydrochloride are added to a solution of 6.8 g of bis(4-chlorophenyl)-bromomethane in 300 cm$^3$ of acetonitrile, followed by 2.97 g of potassium carbonate. The reaction mixture is heated for 1 hour under reflux, cooled to room temperature, filtered and concentrated to dryness under reduced pressure (2.7 kPa). The residue obtained is chromatographed on a silica gel column (particle size 0.04-0.06 mm, diameter 8.5 cm, height 22 cm), under an argon pressure of 0.5 bar with a mixture of ethyl acetate and cyclohexane (25/75 by volume) as eluent and collecting 250-cm$^3$ fractions. Fractions 11 to 48 are combined and then concentrated to dryness under reduced pressure (2.7 kPa). 5.3 g of 1-[bis(4-chlorophenyl)-methyl]-3-[(3,5-difluorophenyl)methylsulfonyl) methyl-(RS)]azetidin-3-ol are obtained. [$^1$H NMR spectrum (300 MHz, (CD$_3$)$_2$SO d6, δ in ppm): 2.00 (s: 3H); 2.94 (s: 3H); 3.25 (mt: 2H); 3.48 (d, J=9 Hz: 1H); 3.80 (d, J=9 Hz: 1H); 4.54 (s: 1H); 5.34 (s: 1H); 7.15 (d, J=8.5 Hz: 2H); from 7.20 to 7.40 (mt: 8H); 7.50 (broad t, J=9 Hz: 1H)].

Bis(4-chlorophenyl)bromomethane may be prepared according to the procedure described by BACHMANN W. E., J. Am. Chem. Soc., 2135 (1933).

3-[(3,5-Difluorophenyl)methylsulfonyl)methyl-(RS)]azetidin-3-ol hydrochloride may be obtained in the following manner: 160 cm$^3$ of a 6.2 N hydrochloric acid solution in dioxane are added to a solution of 37 g of 3-[(3,5-difluorophenyl)(methylsulfonyl)methyl-(RS)]-1-(vinyloxycarbonyl) azetidin-3-ol in 160 cm$^3$ of dioxane. After 16 hours at room temperature, the reaction mixture is concentrated to dryness under reduced pressure (2.7 kPa). The residue obtained is taken up in 320 cm$^3$ of ethanol, heated for 1 hour under reflux and cooled on an ice-cold bath. The solid which appears is filtered, washed with ethyl ether and dried at 40° C. under reduced pressure (2.7 kPa). 29.85 g of white crystals are obtained whose melting point is greater than 260° C.

3-[(3,5-Difluorophenyl)(methyl-sulfonyl)methyl-(RS)]-1-(vinyloxycarbonyl)azetidin-3-ol may be obtained in the following manner: a solution of 14 cm$^3$ of vinyl chloroformate in 35 cm$^3$ of dichloromethane is added at 5° C. to a solution of 60.18 g of 1-benzhydryl-3-[(3,5-difluorophenyl)-(methylsulfonyl)methyl-(RS)]azetidin-3-ol in 100 cm$^3$ of dichloromethane. After 20 hours at room temperature, the reaction mixture is concentrated to dryness under reduced pressure (2.7 kPa). The residue obtained is chromatographed on a silica gel column (particle size 0.04-0.06 mm, diameter 11 cm, height 32 cm), under an argon pressure of 0.5 bar with a mixture of ethyl acetate and cyclohexane (3/7 by volume) as eluent and collecting 1000-cm$^3$ fractions. Fractions 8 to 18 are combined and then concentrated to dryness under reduced pressure (2.7 kPa). 37 g of 3-[(3,5-difluorophenyl)-(methylsulfonyl)methyl-(RS)]-1-(vinyloxycarbonyl)-azetidin-3-ol are obtained in the form of white crystals melting at 195° C.

1-Benzhydryl-3-[(3,5-difluorophenyl)(methyl-sulfonyl) methyl-(RS)]azetidin-3-ol may be obtained in the following manner: 29.5 cm$^3$ of 1.6 N n-butyllithium in solution in hexane are added to a solution of 6.73 cm$^3$ of diisopropylamine in 110 cm$^3$ of tetrahydrofuran, under an argon atmosphere, cooled to −70° C. After 30 minutes, a mixture of 8.7 g of 3,5-difluorobenzyl methyl sulfone in 200 cm$^3$ of tetrahydrofuran is then added and the stirring is maintained for 45 minutes at −70° C. 10 g of 1-benzhydrylazetidin-3-one dissolved in 60 cm$^3$ of tetrahydrofuran are added and then the medium is stirred for 20 minutes while allowing the mixture to return to room temperature. The reaction mixture is hydrolyzed with 400 cm$^3$ of a saturated ammonium chloride solution, extracted with dichloromethane, washed 3 times with 500 cm$^3$ of water and then a saturated sodium chloride solution. The organic phase is dried over magnesium sulfate, filtered and then concentrated to dryness under reduced pressure (2.7 kPa). The residue (19 g) is taken up in isopropyl ether from which it crystallizes. After filtration and drying, 15.35 g of 1-benzhydryl-3-[(3,5-difluorophenyl)(methylsulfonyl)-methyl-(RS)]azetidin-3-ol are obtained in the form of white crystals.

1-Benzhydrylazetidin-3-one may be prepared according to the procedure described by KATRITZKY A. R. et al. in J. Heterocycl. Chem., 271 (1994).

3,5-Difluorobenzyl methyl sulfone may be prepared in the following manner: starting with 33.46 g of 3,5-difluorobenzyl methyl sulfide in 318 cm$^3$ of water, 318 cm$^3$ of acetic acid and 318 cm$^3$ of ethanol, 129.9 g of oxone$^R$ are added at 5° C. After 16 hours at room temperature, the reaction mixture is diluted with dichloromethane, washed with water and with a saturated sodium chloride solution, dried, filtered and concentrated to dryness under reduced pressure (2.7 kPa). 35.57 g of 3,5-difluorobenzyl methyl sulfone are obtained in the form of white crystals, m.p.=135° C.

3,5-Difluorobenzyl methyl sulfide may be prepared in the following manner: starting with 40 g of 3,5-difluorobenzyl bromide and 16.25 g of sodium methyl thiolate in DMF at 60° C., 33.46 g of 3,5-difluorobenzyl methyl sulfide are obtained after treatment in the form of a yellow oil.

Method 2

0.80 g of crushed sodium hydroxide is added to a solution of 2.2 g of 3-acetoxy-1-[bis(4-chloro-phenyl)methyl]-3-[(3,5-difluorophenyl)(methyl-sulfonyl)methyl-(RS)]azetidine in 25 cm$^3$ of dioxane at room temperature. After 16 hours at room temperature, 50 cm$^3$ of water and 100 cm$^3$ of ethyl acetate are added. The mixture is separated after settling, the organic phase washed again with 100 cm$^3$ of water, dried over magnesium sulfate, filtered and concentrated to dryness under reduced pressure (2.7 kPa). A white foam is obtained which is crystallized from isopropyl ether to give 0.85 g of a solid melting at 190° C. Crystallization from 20 cm$^3$ of ethanol gives 0.70 g of 1-[bis(4-chlorophenyl)methyl]-3-[(3,5-difluorophenyl)-(methylsulfonyl)methylene]azetidine melting at 205° C.

14 cm$^3$ of a 1.6 N solution of n-butyllithium in hexane are added at −70° C. to a solution of 4.77 g of (3,5-difluorobenzyl)methyl sulfone in 70 cm$^3$ of tetrahydrofuran under an argon atmosphere. After 1 hour at −70° C., a solution of 6.8 g of 1-[bis(4-chloro-phenyl)methyl]azetidin-3-one in 30 cm$^3$ of tetrahydrofuran is added, followed 1 hour later by a solution of 2.34 cm$^3$ of acetyl chloride in 20 cm$^3$ of tetrahydrofuran and the temperature of the reaction mixture is increased to 20° C. for 1 hour. 50 cm$^3$ of water and 200 cm$^3$ of ethyl acetate are added. The mixture is separated after settling, the organic phase is washed with 100 cm$^3$ of water, 100 cm$^3$ of a saturated sodium chloride solution, dried over magnesium sulfate, filtered and concentrated to dryness under reduced pressure (2.7 kPa). 14.4 g of 3-acetoxy-1-[bis(4-chlorophenyl)methyl]-3-[(3,5-difluorophenyl)(methyl-sulfonyl)methylsulfonylmethyl-(RS)]azetidine are obtained in the form of a yellow oil [$^1$H NMR spectrum (400 MHz, CDCl$_3$, δ in ppm) 2.79 (s: 3H); 3.04 (AB, J=9 Hz: 2H); 3.27 (d, J=9 Hz: 1H) 3.45 (s: 1H); 3.81 (d, J=9 Hz: 1H); 4.32 (s: 1H); 4.49 (s: 1H); 6.88 (tt, J=9 and 2.5 Hz); from 7.20 to 7.35 (mt: 10H)].

1-[Bis(4-chlorophenyl)methyl]azetidin-3-one may be prepared according to the following procedure: a solution of 8.1 cm$^3$ dimethylsulfoxide in 17.6 cm$^3$ of dichloromethane is added to a solution of 5.0 cm$^3$ of oxalyl chloride in 73 cm$^3$ of dichloromethane cooled to −78° C. After 0.5 hour at −78° C., a solution of 16.0 g of 1-[bis(4-chlorophenyl)methyl]azetidin-3-ol dissolved in 50 cm$^3$ of dichloromethane is poured in. After 5 hours at −78° C., 26.6 cm$^3$ of triethylamine are added dropwise and the reaction mixture is allowed to return to room temperature. After 16 hours, the reaction mixture is washed with 4 times 200 cm$^3$ of water and then with 200 cm$^3$ of a saturated sodium chloride solution, dried over magnesium sulfate, filtered and concentrated to dryness under reduced pressure (2.7 kPa). The residue obtained is chromatographed on a silica gel column (particle size 0.04-0.06 mm, diameter 9.2 cm, height 21 cm), under an argon pressure of 0.5 bar with a mixture of ethyl acetate and cyclohexane (40/60 by volume) as eluent and collecting 200-cm$^3$ fractions. Fractions 15 to 25 are combined and concentrated to dryness under reduced pressure (2.7 kPa). 8.9 g of 1-bis(4-chlorophenyl)methyl]azetidin-3-one are obtained in the form of pale yellow crystals melting at 111° C.

1-[Bis(4-chlorophenyl)methyl]azetidin-3-ol may be prepared according to the procedure described by KATRITZKY A. R. et al., J. Heterocycl. Chem., (1994), 271 starting with 35.5 g of [bis(4-chlorophenyl)-methyl]amine hydrochloride and 11.0 cm$^3$ of epichlorohydrin. 9.0 g of 1-[bis(4-chlorophenyl)-methyl]azetidin-3-ol are isolated.

[Bis(4-chlorophenyl)methyl]amine hydrochloride may be prepared according to the method described by GRISAR M. et al., J. Med. Chem., 885 (1973).

EXAMPLE 2

(−)-1-[Bis(4-chlorophenyl)methyl)]-3-[(3,5-difluorophenyl)(methylsulfonyl)methyl]azetidine and (+)-1-[bis(4-chlorophenyl)methyl)]-3-[(3,5-difluoro-phenyl)(methylsulfonyl)methyl]azetidine may be prepared by CLHP separation on a CHIRALPAK AS chiral column (particle size 20 μm, height 23 cm, diameter 6 cm) of 0.52 g of the racemate prepared in Example 1. By eluting with the heptane/ethanol (90/10) mixture at a flow rate of 80 cm$^3$/min and after having concentrated the collected fractions to dryness under reduced pressure (2.7 kPa), there are obtained 110 mg of (−)-1-[bis(4-chlorophenyl)methyl)]-3-[(3,5-difluoro-phenyl)(methylsulfonyl)methyl]azetidine [α$_D$]=6.30 (C=0.5 M in methanol) in the form of a white solid melting at 178° C. and 134 mg of (+)-1-[bis(4-chloro-phenyl)methyl)]-3-[(3,5-difluorophenyl)(methyl-sulfonyl)methyl]azetidine [α$_D$]=+5.80 (C=0.5 M in methanol) in the form of a white solid melting at 178° C.

EXAMPLE 3

The mixture of the 2 A diastereoisomer forms 1-[4-[(R*)-(4-chlorophenyl)-{3-[3,5-difluorophenyl)-methylsulfonyl-methyl-(R)]azetidin-1-yl}methyl]benzyl]-pyrrolidine and 1-[4-[(R*)-(4-chlorophenyl)-{3-[(3,5-difluorophenyl)methylsulfonylmethyl-(S)]azetidin-1-yl}methyl]benzyl]pyrrolidone may be prepared by carrying out the procedure in the following manner: 20 mg of sodium borohydride are added to a solution of 60 mg of 1-(R*)-[4-(4-chlorophenyl)-{3-[(3,5-difluoro-phenyl)methylsulfonylmethylene]azetidin-1-yl}methyl)-benzyl]pyrrolidone, A isomer form, in 2 cm$^3$ of ethanol and 2 cm$^3$ of dichloromethane. After stirring for 20 hours at 20° C., 0.25 cm$^3$ of water and 20 cm$^3$ of dichloromethane are added and the mixture is stirred and dried over magnesium sulfate and then filtered and concentrated to dryness under reduced pressure (2.7 kPa). The residue is chromatographed on a silica gel column (particle size 0.063-0.200 mm, height 7 cm, diameter 1 cm), eluting under an argon pressure of 0.1 bar with dichloromethane and then with a mixture of dichloromethane and methanol (95/5 by volume) and collecting 5-cm$^3$ fractions. Fractions 13 to 18 are combined and concentrated to dryness under reduced pressure (2.7 kPa). 38 mg of the mixture of the 2 A diastereoisomer forms 1-[4-[(R*)-(4-chlorophenyl)-{3-[(3,5-difluorophenyl)methylsulfonylmethyl-(R)]azetidin-1-yl}methyl]benzyl]pyrrolidine and 1-[4-[(R*)-(4-chlorophenyl)-{3-[(3,5-difluorophenyl)methylsulfonyl-methyl-(S)]azetidin-1-yl}methyl]benzyl]pyrrolidine are obtained in the form of a white foam [¹H NMR spectrum (400 MHz, CDCl₃, δ in ppm): 1.77 (mt: 4H); from 2.40 to 2.60 (mt: 5H); 2.67 (s: 3H); from 3.10 to 3.25 (mt: 2H); 3.38 (mt: 1H); from 3.50 to 3.70 (mt: 3H); 4.24 (s: 1H); 4.25 (d, J=11 Hz: 1H); 6.83 (broad t, J=9 Hz: 1H); 6.94 (mt: 2H) from 7.10 to 7.35 (mt: 8H)].

1-(R*)-[4-(4-Chlorophenyl)-{3-[(3,5-difluoro-phenyl)methylsulfonylmethylene]azetidin-1-yl}methyl)-benzyl]pyrrolidine, A isomer form, may be prepared by carrying out the procedure in the following manner: 50 mm³ of pyrrolidine are added to a solution of 0.32 g of 1-{(R*)-[4-(chloromethyl)phenyl]-(4-chlorophenyl)-methyl}-3-[(3,5-difluorophenyl)methylsulfonyl-methylene]azetidine, A isomer form, and 5 mg of sodium iodide in 10 cm³ of dichloromethane. After stirring for 20 hours at 20° C., 50 mm³ of pyrrolidine are added to the mixture, the mixture is stirred for 8 hours and then 50 mm³ of pyrrolidine are again added and the mixture is stirred for 20 hours at 20° C. The reaction mixture is washed with water and then the organic phase is dried over magnesium sulfate and concentrated to dryness under vacuum (2.7 kPa). The residue obtained is chromatographed on a silica gel column (particle size 0.06-0.200 mm, diameter 1.2 cm, height 30 cm), under an argon pressure of 0.1 bar, eluting with dichloromethane and then with a dichloromethane and methanol (97.5/2.5 by volume) mixture and collecting 3-cm³ fractions. Fractions 12 to 40 are combined and then concentrated to dryness under reduced pressure (2.7 kPa). 0.18 g of 1-(R*)-[4-(4-Chlorophenyl)-{3-[(3,5-difluorophenyl)-methylsulfonylmethylene]azetidin-1-yl}methyl)benzyl]-pyrrolidine, A isomer form, is obtained in the form of a white foam [α]²⁰ 365 nm=−22.50±0.7 (c=0.5%; dichloromethane) [¹H NMR spectrum (300 MHz, CDCl₃, δ in ppm): 1.78 (mt: 4H); 2.51 (mt: 4H); 2.81 (s: 3H); 3.58 (s: 2H); 3.84 (mt: 2H); 4.33 (mt: 2H); 4.50 (2: 1H); 6.84 (tt, J=9 and 2.5 Hz: 1H); 6.98 (mt: 2H); from 7.20 to 7.40 (mt: 8H)].

1-{(R*)-[(4-Chloromethyl)phenyl]-(4-chloro-phenyl)methyl}-3-[(3,5-difluorophenyl)methylsulfonyl-methylene]azetidine, A isomer form, may be prepared by carrying out the procedure in the following manner: 12.4 cm³ of methylsulfonyl chloride are added to a solution of 28.0 g of the mixture of the 2 diastereoisomers (A forms) 1-{(R*)-[(4-chloromethyl)-phenyl]-(4-chlorophenyl)methyl}-3-[(R)-(3,5-difluoro-phenyl)methylsulfonylmethyl)]azetidin-3-ol and 1-{(R*)-[(4-chloromethyl)phenyl]-(4-chlorophenyl)methyl}-3-[(S)-(3,5-difluorophenyl)methylsulfonylmethyl]azetidin-3-ol and 32 g of 4-dimethylaminopyridine in 500 cm³ of dichloromethane. After stirring for one hour at 10° C. and then one hour at 20° C., the reaction mixture is washed with 500 cm³ of water, the organic phase is dried over magnesium sulfate and concentrated to dryness under reduced pressure (2.7 kPa). The residue is chromatographed on a silica gel column (particle size 0.06-0.200 mm, diameter 6 cm, height 30 cm), under an argon pressure of 0.2 bar, eluting with dichloromethane and collecting 250-cm³ fractions. Fractions 9 to 25 are combined and then concentrated to dryness under reduced pressure (2.7 kPa). 6.3 g of 1-{(R*)-[4-(chloromethyl)phenyl]-(4-chlorophenyl)methyl}-3-[(3,5-difluorophenyl)methylsulfonylmethylene]azetidine, A isomer form, are obtained in the form of a white foam.

The mixture of the 2 diastereoisomers (A forms) 1-{(R*)-[4-(chloromethyl)phenyl]-(4-chloro-phenyl)methyl}-3-[(R)-(3,5-difluorophenyl)-methylsulfonylmethyl)]azetidin-3-ol and 1-{(R*)-[4-(chloromethyl)phenyl](4-chlorophenyl)methyl}-3-[(S)-(3,5-difluorophenyl)methylsulfonylmethyl)]azetidin-3-ol may be prepared by carrying out the procedure in the following manner: 6 cm³ of thionyl chloride are added to a solution of 0.20 g of the mixture of the 2 diastereoisomers (A forms) 1-{(R*)-(4-chlorophenyl)[4-(hydroxymethyl)phenyl]methyl}-3.-[(R)-(3,5-difluoro-phenyl)methylsulfonylmethyl)]azetidin-3-ol, and 1-{(R*)-(4-chlorophenyl)[4-(hydroxymethyl)phenyl]-methyl}-3-[(S)-(3,5-difluorophenyl)methylsulfonyl-methyl)]azetidin-3-ol in 10 cm³ of dichloromethane. After stirring for 20 hours at 20° C., 5 cm³ of a saturated aqueous sodium hydrogencarbonate solution are added to the reaction mixture and then stirred for 15 minutes. The mixture is separated after settling, the organic phase is washed with water, dried over magnesium sulfate and then concentrated to dryness under reduced pressure (2.7 kPa). The residue is chromatographed on a silica gel column (particle size 0.04-0.06 mm, diameter 1.0 cm, height 20 cm), under an argon pressure of 0.2 bar, eluting with a cyclohexane and ethyl acetate (75/25 by volume) mixture and collecting 20-cm³ fractions. Fractions 4 to 7 are combined and concentrated to dryness under reduced pressure (2.7 kPa). 0.17 g of the mixture of the 2 diastereoisomers (A forms) 1-{(R*)-[4-(chloromethyl)-phenyl]-(4-chlorophenyl)methyl}-3-[(R)-(3,5-difluoro-phenyl)methylsulfonylmethyl)]azetidin-3-ol and 1-{(R*)-(4-chloromethyl)phenyl]-(4-chlorophenyl)methyl}-3-[(S)-(3,5-difluorophenyl)methylsulfonylmethyl]azetidin-3-ol, are obtained in the form of a white foam.

The mixture of the 2 diastereoisomers (A forms) 1-{(R*)-(4-chlorophenyl)[4-(hydroxymethyl)-phenyl]methyl}-3-[(R)-(3,5-difluorophenyl)-methylsulfonylmethyl)]azetidin-3-ol, and 1-{(R*)-(4-chlorophenyl)[4-(hydroxymethyl)phenyl]methyl}-3-[(S)-(3,5-difluorophenyl)methylsulfonylmethyl)]azetidin-3-ol may be prepared by carrying out the procedure in the following manner: 1.6 cm³ of a 1.5 M solution of diisobutylaluminum hydride in toluene are added to a solution, kept under argon and cooled to −30° C., of 0.58 g of the mixture of the 2 diastereoisomers (A forms) 3-acetoxy-1-{(R*)-(4-chlorophenyl)[4-(methoxycarbonyl)phenyl]methyl}-3-[(R)-(3,5-difluorophenyl)-methylsulfonylmethyl)]azetidine and 3-acetoxy-1-{(R*)-(4-chlorophenyl)[4-(methoxycarbonyl)phenyl]methyl}-3-[(S)-(3,5-difluorophenyl)methylsulfonylmethyl)]-azetidine, in 10 cm³ of anhydrous toluene. After stirring for 15 minutes at −30° C., 1.0 cm³ of the same hydride solution is again added and the mixture is allowed to return to 0° C. After stirring for 30 minutes, the stirred mixture is supplemented with 3 cm³ of water and 6 cm³ of 1 N sodium hydroxide and then extracted with 25 cm³ of dichloromethane. The organic phase is washed with 5 cm³ of water, 5 cm³ of brine and then dried over magnesium sulfate and concentrated to dryness under reduced pressure (2.7 kPa). The residue is chromatographed on a silica gel column (particle size 0.06-0.200 mm, diameter 1.2 cm, height 30 cm), under an argon pressure of 0.1 bar, eluting with a cyclohexane and ethyl acetate (50/50 by volume) mixture and collecting 30-cm³ fractions. Fractions 4 to 12 are combined and then concentrated to dryness under reduced pressure (2.7 kPa). 0.42 g of the mixture of the 2 diastereoisomers (A forms) 1-{(R*)-(4-chlorophenyl)-[4-(hydroxymethyl)phenyl]methyl}-3-[(R)-(3,5-difluoro-phenyl)methylsulfonylmethyl)]azetidin-3-ol and 1-{(R*)-(4-chlorophenyl)[4-(hydroxymethylphenyl)methyl}-3-[(S)-(3,5-difluorophenyl)methylsulfonylmethyl)]azetidin-3-ol, are obtained in the form of a white lacquer.

The mixture of the 2 diastereoisomers (A forms) 3-acetoxy-1-{(R*)-(4-chlorophenyl)[4-(methoxy-carbonyl)phenyl]methyl}-3-[(R)-(3,5-difluorophenyl)-methylsulfonylmethyl)]azetidine and 3-acetoxy-1-{(R*)-(4-chlorophenyl)[4-(methoxycarbonyl)phenyl]methyl}-3-[(S)-(3,5-difluorophenyl)methylsulfonylmethyl)]azetidine may be prepared by carrying out the procedure in the following manner: 3 cm³ of a 1.6 N solution of n-butyllithium in hexane are poured under argon over 5 minutes, into a solution, cooled to −60° C., of 1.0 g of (3,5-difluorobenzyl)methyl sulfone in 30 cm³ of tetrahydrofuran. After stirring for 1 hour at −60° C. and then for 30 minutes at −30° C., a solution, previously cooled to −60° C., of 1.45 g of 1-{(R*)-(4-chloro-phenyl)[4-(methoxycarbonyl)phenyl]-methyl}azetidin-3-one, A isomer form, in 15 cm³ of tetrahydrofuran is added dropwise to this mixture. After stirring for 30 minutes at −60° C. and then for 30 minutes at −30° C., 0.43 cm³ of acetyl chloride is added and the reaction mixture is allowed to return to 0° C. 40 cm³ of water and 40 cm³ of dichloromethane are then added to the medium, with stirring, and then the medium is allowed to return to room temperature and it is separated after settling. The organic phase is washed with 20 cm³ of water and is then dried over magnesium sulfate, filtered and concentrated to dryness under reduced pressure (2.7 kPa). The residue is chromatographed on a silica gel column (particle size 0.040-0.063 mm, diameter 3 cm, height 30 cm), eluting under an argon pressure of 0.5 bar with a cyclohexane and ethyl acetate (75/25 by volume) mixture and collecting 30-cm³ fractions. Fractions 21 to 35 are combined and then concentrated to dryness under reduced pressure (2.7 kPa). 1.28 g of the mixture of the 2 diasterisomers (A forms) 3-acetoxy-1-{(R*)-(4-chlorophenyl)[4-(methoxy-carbonyl)phenyl]methyl}-3-[(R)-(3,5-difluorophenyl)methylsulfonylmethyl)]azetidine and 3-acetoxy-1-{(R*)-(4-chlorophenyl)[4-(methoxycarbonyl)-phenyl]methyl}-3-[(S)-(3,5-difluorophenyl)methylsulfonylmethyl)]azetidine are obtained in the form of a cream-colored foam.

1-{(R*)-(4-Chlorophenyl)[4-methoxycarbonyl)-phenyl]methyl}azetidin-3-one, A isomer form, may be prepared by carrying out the procedure in the following manner: 0.90 cm³ of dimethyl sulfoxide is poured over 10 minutes into a solution, cooled to −60° C., of 0.55 cm³ of oxalyl chloride in 5 cm³ of dichloromethane. After stirring for 30 minutes at −60° C., a solution of 1.75 g of 1-{(R*)-(4-chlorophenyl)[4-(methoxycarbonyl)-phenyl]methyl}azetidin-3-ol, A isomer form, in 20 cm³ of dichloromethane is added to the mixture over 15 minutes. After stirring for 3 hours at −60° C., 2.7 cm³ of triethylamine are poured in and then the reaction medium is allowed to return to 0° C. 20 cm³ of water are then added, the mixture is stirred and then separated after settling. The organic phase is dried over magnesium sulfate, filtered and then concentrated to dryness at 50° C. under reduced pressure (2.7 kPa). The orange-colored oil obtained is chromatographed on a silica gel column (particle size 0.06-0.200 mm, diameter 2 cm, height 30 cm), under an argon pressure of 0.5 bar, eluting with a cyclohexane and ethyl acetate (75/25 by volume) mixture and collecting 30-cm³ fractions. Fractions 2 to 15 are combined and then concentrated to dryness under reduced pressure (2.7 kPa). 1.45 g of 1-{(R*)-(4-chlorophenyl)[4-(methoxycarbonyl)phenyl]methyl}azetidin-3-one, A isomer form, are obtained in the form of a yellow foam.

1-{(R*)-(4-Chlorophenyl)[4-methoxycarbonyl)-phenyl]methyl}azetidin-3-ol, A isomer form, may be prepared by carrying out the procedure in the following manner: 0.605 g of sodium hydrogen carbonate is added to a suspension of 2.0 g of methyl (+)-4-[(R*)-amino-(4-chlorophenyl)methyl]benzoate in 30 cm³ of ethanol followed by 0.60 cm³ of epibromohydrin. After stirring for 20 hours at 60° C., the reaction mixture is concentrated to dryness under reduced pressure (2.7 kPa). The residue is chromatographed on a silica gel column (particle size 0.06-0.200 mm, diameter 3 cm, height 35 cm), eluting under an argon pressure of 0.5 bar with a mixture of cyclohexane and ethyl acetate (70/30 by volume for fractions 6 to 10 and then 60/40 for fractions 18 to 27, and then 50/50) and collecting 60-cm³ fractions. Fractions 15 to 40 are combined and then concentrated to dryness under reduced pressure (2.7 kPa). The residue is taken up in 30 cm³ of ethanol and is then supplemented with 0.20 g of sodium hydrogen carbonate and 0.2 cm³ of epibromohydrin. After stirring for 48 hours at 20° C. and then 24 hours at 35° C., the mixture is filtered and the filtrate is concentrated to dryness at 60° C. under reduced pressure (2.7 kPa). 1.76 g of 1-{(R*)-(4-chlorophenyl)[4-(methoxycarbonyl)-phenyl]methyl}azetidin-3-ol, A isomer form, are obtained in the form of a pasty solid.

Methyl (+)-4-[(R*)-amino-(4-chlorophenyl)-methyl]benzoate may be prepared by carrying out the procedure in the following manner: 2.51 g of D-(−)-tartaric acid are added to a solution of 9.2 g of methyl 4-[(RS)-amino-(4-chlorophenyl) methyl]benzoate in 10 cm³ of methanol. The solution is concentrated to dryness under reduced pressure (2.7 kPa). The cream-colored foam obtained is dissolved in 50 cm³ of ethanol containing 5% of water and the resulting solution is allowed to crystallize for 20 hours at 20° C. The crystals are filtered, washed with ethanol containing 5% of water, drained and then dried under reduced pressure (2.7 kPa). 3.4 g of white crystals are obtained, which crystals are named "A crystals" [and which are stored for the subsequent preparation of the second enantiomer methyl (−)-4-[(R*)-amino-(4-chloro-phenyl)methyl]benzoate)]. The mother liquors are concentrated to dryness and a white foam is obtained (8.1 g) which is dissolved in 100 cm³ of ethyl acetate. The solution obtained is supplemented with 50 cm³ of 1 N sodium hydroxide, stirred and separated after settling. The organic phase is washed with 50 cm³ of water and then dried over magnesium sulfate and concentrated to dryness under reduced pressure (2.7 kPa). A yellow solid is obtained which is dissolved in 100 cm³ of methanol. The solution obtained is supplemented with 1.85 g of L-(+)-tartaric acid and the resulting solution is concentrated to dryness under reduced pressure (2.7 kPa). A cream-colored foam is obtained which, once dissolved in 27 cm³ of ethanol containing 4% of water, is allowed to crystallize for 20 hours at 20° C. The crystals are filtered, washed with ethanol containing 4% of water, drained and then dried under reduced pressure (2.7 kPa). 3.4 g of crystals of methyl (+)-4-[(R*)-amino-(4-chlorophenyl)methyl]benzoate L-(+)-tartrate are obtained which are recrystallized from 60 cm³ of ethanol containing 5% of water. After draining and then drying, 2.78 g of white crystals are obtained which are dissolved in 50 cm³ of ethyl acetate. The solution obtained is supplemented with 100 cm³ of 1 N sodium hydroxide, stirred and separated after settling. The organic phase is washed with 50 cm³ of water and then dried over magnesium sulfate and concentrated to dryness under reduced pressure (2.7 kPa). 2.1 g of methyl (+)-4-[(R*)-amino-(4-chlorophenyl)methyl]-benzoate are obtained in the form of a white solid.

Methyl 4-[(RS)-amino-(4-chlorophenyl)methyl]-benzoate may be prepared by carrying out the procedure in the following manner: 3.9 cm³ of hydrazine hydrate are added to a suspension of 16.3 g of methyl 4-[(RS)-phthalimido-(4-chlorophenyl)methyl]benzoate in 200 cm³ of methanol. After stirring for 5 hours at the reflux temperature and then for 20 hours at 20° C., the reaction mixture is filtered and the filtrate is concentrated to dryness under reduced pressure (2.7 kPa). The residue obtained is taken up in a mixture of 200 cm³ of water and 200 cm³ of ethyl acetate. After stirring for 15 minutes, the resulting suspension is filtered, the filtrate separated after settling in a separating funnel and the organic phase is washed with 50 cm³ of water, dried over magnesium sulfate and concentrated to dryness under reduced pressure (2.7 kPa). 8.4 g of methyl 4-[(RS)-amino-(4-chlorophenyl) methyl]benzoate are obtained in the form of a pale yellow oil.

Methyl 4-[(RS)-phthalimido-(4-chlorophenyl)-methyl]benzoate may be prepared by carrying out the procedure in the following manner: 12.6 g of potassium phthalimide are added to a solution of 11.6 g of methyl 4-[(RS)-bromo-(4-chlorophenyl)methyl]benzoate in 70 cm³ of N,N-dimethylformamide. After stirring for 3 hours at the reflux temperature, the reaction mixture is cooled to 20° C. and then supplemented with 300 cm³ of ethyl acetate and 300 cm³ of water. After stirring, the mixture is separated after settling, the aqueous phase reextracted with twice 100 cm³ of ethyl acetate, the combined organic phases are washed with twice 400 cm³ of water and then dried over magnesium sulfate and concentrated to dryness under reduced pressure (2.7 kPa). 16.3 g of methyl 4-[(RS)-phthalimido-(4-chlorophenyl)methyl]benzoate are obtained in the form of a pasty yellow solid.

Methyl 4-[(RS)-bromo-(4-chlorophenyl)methyl]-benzoate may be prepared by carrying out the procedure in the following manner: 10.18 g of N,N'-carbonyl-diimidazole and 54.3 cm³ of allyl bromide are added to a solution of 17.4 g of methyl 4-[(RS)-(4-chlorophenyl)-(hydroxy)methyl]benzoate in 200 cm³ of acetonitrile. After stirring for 30 minutes at 20° C., the reaction mixture is heated under reflux for 2 hours, stirred for 20 hours at 20° C. and concentrated almost to dryness under reduced pressure (2.7 kPa). The mixture, taken up in dichloromethane, is chromatographed on a silica gel column (particle size 0.06-0.200 mm, diameter 7 cm, height 30 cm), under an argon pressure of 0.5 bar, eluting with dichloromethane, and collecting 500-cm³ fractions. Fractions 3 to 6 are combined and then concentrated to dryness under reduced pressure (2.7 kPa). 11.6 g of methyl 4-[(RS)-bromo-(4-chloro-phenyl)methyl]benzoate are obtained in the form of an oil which will be used as it is in the next step.

Methyl 4-[(RS)-(4-chlorophenyl)(hydroxy)-methyl]benzoate may be prepared by carrying out the procedure in the following manner: 1.21 g of sodium borohydride are added slowly in small fractions (the medium becomes slightly-warm up to 50° C.) to a suspension of 2.75 g of methyl 4-(4-chloro-benzoyl)benzoate in 200 cm³ of methanol at 20° C. After stirring for 20 hours at 20° C., the reaction mixture is concentrated to a reduced volume and then supplemented with 150 cm³ of dichloromethane and, with stirring, with 100 cm³ of 0.5 N hydrochloric acid. After decantation, the organic phase is dried over magnesium sulfate, concentrated to dryness under reduced pressure (2.7 kPa). 2.5 g of methyl 4-[(RS)-(4-chlorophenyl)-(hydroxy)methyl]benzoate are obtained in the form of a colorless oil which crystallizes slowly at 20° C. and which will be used as it is in the next step.

Methyl 4-(4-chlorobenzoyl)benzoate may be prepared by carrying out the procedure in the following manner: 27.4 cm³ of tri-n-butylphosphine are added, under argon, to a solution, cooled to −22° C. of 19.3 g of terephthalic acid chloride monomethyl ester in 200 cm³ of tetrahydrofuran. After stirring for 20 minutes at −22° C., a solution of 4-chlorophenylmagnesium bromide (prepared from 19.15 g of 4-bromochlorobenzene, 2.43 g of magnesium and one iodine crystal in 100 cm³ of diethyl ether under reflux) is poured in while maintaining this temperature. After stirring for 30 minutes at −22° C., 150 cm³ of 1 N hydrochloric acid are added slowly, the mixture is allowed to return to 20° C. and then the medium is diluted with 200 cm³ of diethyl ether. The white suspension obtained is filtered, the solid is washed with twice 50 cm³ of water and then with twice 50 cm³ of diethyl ether. After draining and then drying under reduced pressure (2.7 kPa), 16.2 g of methyl 4-(4-chlorobenzoyl)benzoate are obtained in the form of a white solid melting at 170° C.

EXAMPLE 4

The mixture of the 2 B diastereoisomer forms 1-[4-[(R*)-(4-chlorophenyl)-(3-[(3,5-difluorophenyl)-methylsulfonyl-methyl-(R)]azetidin-1-yl}methyl]benzyl]-pyrrolidine and 1-[4-[(R*)-(4-chlorophenyl)-{3-[(3,5-difluorophenyl)methylsulfonylmethyl-(S)]azetidin-1-yl}methyl]benzylpyrrolidine may be prepared by carrying out the procedure as described in Example 3, starting with 50 mg of (+)-1-[4-(R*)-(4-chlorophenyl)-{3-[(3,5-difluorophenyl)methylsulfonylmethylene]azetidin-1-yl}-methyl)benzyl]pyrrolidine, B isomer form, 1.5 cm³ of ethanol, 1.5 cm³ of dichloromethane and 18 mg of sodium borohydride, with stirring for 8 hours at 50° C. and then for 48 hours at 20° C. 50 mg of the mixture of the 2 B diastereoisomer forms 1-[4-[(R*)-(4-chlorophenyl)-{3-[(3,5-difluorophenyl)methylsulfonylmethyl-(R)]azetidin-1-yl}methyl]benzyl]pyrrolidine and 1-[4-[(R*)-(4-chlorophenyl)-{3-[(3,5-difluorophenyl)methylsulfonyl-methyl-(S)]azetidin-1-yl}methyl]benzylpyrrolidine are obtained in the form of a white foam [¹H NMR spectrum (300 MHz, CDCl₃, δ in ppm). A 60/40 mixture of diastereoisomers is observed, *1.79 (mt: 4H); from 2.45 to 2.60 (mt: 5H); 2.67 (s: 3H); from 3.10 to 3.30 (mt: 2H); 3.40 (mt: 1H); 3.57 and 3.60 (2s: 2H in total); 3.65 (broad t, J=7.5 Hz: 1H); 4.26 and 4.30 (2s: 2H in total); 6.84 (tt, J=9 and 2 Hz: 1H); 6.96 (mt: 2H); from 7.25 to 7.40 (mt: 8H).

(+)-1-[4-(R*)-(4-Chlorophenyl)-{3-[(3,5-difluorophenyl)methylsulfonylmethylene]azetidin-1-yl}methyl)benzyl]pyrrolidine, B isomer form, may be prepared by carrying out the procedure as is described in Example 3, starting with 0.50 g of 1-{(R*)-[4-(chloromethyl)phenyl]-(4-chlorophenyl)methyl}-3-[(3,5-difluorophenyl)(methylsulfonyl)methylene] azetidine, B isomer form, 5 mg of sodium iodide, 15 cm³ of dichloromethane and 0.190 g of pyrrolidine. The crude product is chromatographed on a silica gel column (particle size 0.06-0.200 mm, diameter 1.5 cm, height 20 cm), under an argon pressure of 0.1 bar, eluting with dichloromethane and then with a dichloromethane and methanol (95/5 by volume) mixture and collecting 25-cm³ fractions. Fractions 20 to 40 are combined and then concentrated to dryness under reduced pressure (2.7 kPa). 0.28 g of (+)-1-[4-(R*)-(4-chlorophenyl)-(3-[(3,5-difluorophenyl)methylsulfonylmethylene]azetidin-1-yl}methyl)benzyl]pyrrolidine, B isomer form, is obtained in the form of a white foam. $[\alpha]^{20}_{365}$ nm=+26.8+/−0.8 (c=0.5%; dichloromethane) [−¹H NMR spectrum (300 MHZ, CDCl₃, δ in ppm): 1.78 (mt: 4H); 2.50 (mt: 4H); 2.80 (s: 3H); 3.57 (s: 2H); 3.84 (mt: 2H); 4.34 (mt: 2H); 4.50 (s: 1H); 6.84 (tt, J=9 and 2.5 Hz: 1H); 6.98 (mt: 2H); from 7.20 to 7.40 (mt: 8H)].

1-{(R*)-[4-(Chloromethyl)phenyl]-(4-chloro-phenyl)methyl}-3-[(3,5-difluorophenyl)(methylsulfonyl)-methylene] azetidine, B isomer form, may be prepared by carrying out the procedure as described in Example 3, starting with 7.3 g of the mixture of the 2 B diastereoisomer forms 1-{(R*)-[4-(chloromethyl)phenyl]-(4-chlorophenyl)methyl}-3-[(R)-(3,5-difluorophenyl)(methylsulfonyl)methyl)]azetidin-3-ol and 1-{(R*)-[4-(chloromethyl)phenyl]-(4-chlorophenyl)methyl}-3-[(S)-(3,5-difluoro-phenyl)(methylsulfonyl)methyl)]azetidin-3-ol, 8.2 g of 4-dimethylaminopyridine, 150 cm³ of dichloromethane and 3.2 cm³ of methylsulfonyl chloride. The crude product is chromatographed on a silica gel column (particle size 0.04-0.06 mm, diameter 3 cm, height 30 cm) under an argon pressure of 0.2 bar, eluting with dichloromethane and collecting 100-cm³ fractions. Fractions 15 to 30 are combined and then concentrated to dryness under reduced pressure (2.7 kPa). 2.50 g of 1-{(R*)-[4-(chloromethyl)phenyl]-(4-chlorophenyl)methyl}-3-[(3,5-difluorophenylmethylsulfonyl)methylene]azetidine, B isomer form, are obtained in the form of a white foam.

The mixture of the 2 B diastereoisomer forms 1-{(R*)-[4-(chloromethyl)phenyl[4-chlorophenyl)methyl}-3-[(R)-(3,5-difluorophenyl)(methylsulfonyl)methyl)]-azetidin-3-ol and 1-{(R*)-[4-(chloromethyl)phenyl]-(4-chlorophenyl)methyl}-3-[(S)-(3,5-difluorophenyl)-(methylsulfonyl)methyl)] azetidin-3-ol may be prepared by carrying out the procedure as described in Example 3, starting with 11.0 g of the mixture of the 2 B diastereoisomer forms 1-{(R*)-4-chlorophenyl)[4-(hydroxymethyl)phenyl]methyl}-3-[(R)-(3,5-difluoro-phenyl))(methylsulfonyl)methyl)]azetidin-3-ol and 1-{(R*)-(4-chlorophenyl)[4-(hydroxymethyl)phenyl]methyl}-3-[(S)-(3,5-difluorophenyl)(methylsulfonyl)methyl)]-azetidin-3-ol, 250 cm³ of dichloromethane and 3.1 cm³ of thionyl chloride. The crude product is chromatographed on a silica gel column (particle size 0.04-0.06 mm, diameter 3 cm, height 30 cm), under an argon pressure of 0.2 bar, eluting with a cyclohexane and ethyl acetate (70/30 by volume) mixture and collecting 50-cm³ fractions. Fractions 9 to 25 are combined and then concentrated to dryness under reduced pressure (2.7 kPa). 7.3 g of the mixture of the 2 B diastereoisomer forms 1-{(R*)-[4-(chloromethyl)phenyl]-(4-chlorophenyl)methyl}-3-[(R)-(3,5-difluorophenyl)-(methylsulfonyl)methyl)]azetidin-3-ol and 1-{(R*)-[4-(chloromethyl)phenyl]-(4-chlorophenyl)methyl}-3-[(S)-(3,5-difluorophenyl)(methylsulfonyl)methyl)] azetidin-3-ol are obtained in the form of a white foam.

The mixture of the 2 B diastereoisomer forms 1-{(R*)-(4-chlorophenyl)[4-(hydroxymethyl)-phenyl]methyl}-3-[(R)-(3,5-difluorophenyl)-(methylsulfonyl)methyl)]azetidin-3-ol and 1-{(R*)-[4-(chlorophenyl)[4-(hydroxymethyl)phenyl]methyl}-3-[(R)-3,5-difluorophenyl)(methylsulfonyl)methyl)]azetidin-3-ol may be prepared by carrying out the procedure as described in Example 3, starting with 18.0 g of the mixture of the 2 B diastereoisomer forms 3-acetoxy-1-{(R*)-(4-chlorophenyl)(4-(methoxycarbonyl)-phenyl]methyl}-3-[(R)-(3,5-difluorophenyl)-(methylsulfonyl)methyl]azetidine and 3-acetoxy-1-{(R*)-(4-chlorophenyl)[4-(methyloxycarbonyl)phenyl]methyl}-3-[(S)-(3,5-difluorophenyl)(methylsulfonyl)-methyl]azetidine, 150 cm³ of anhydrous toluene and 100 cm³ of a 20% solution of diisobutylaluminum hydride in toluene. The crude product is chromatographed on a silica gel column (particle size 0.06-0.200 mm, diameter 3 cm, height 30 cm), under an argon pressure of 0.1 bar, eluting with a cyclohexane and ethyl acetate (50/50 by volume) mixture and collecting 50-cm³ fractions. Fractions 15 to 30 are combined and concentrated to dryness under reduced pressure (2.7 kPa). 11.0 g of the mixture of the 2 B diastereoisomer forms 1-{(R*)-(4-chlorophenyl)[4-(hydroxymethyl)phenyl]methyl}-3-[(R)-(3,5-difluoro-phenyl)(methylsulfonyl)methyl]azetidin-3-ol and 1-{(R*)-[(4-chlorophenyl)[4-(hydroxymethyl)phenyl]-methyl}-3-[(S)-3,5-difluorophenyl)(methylsulfonyl)-methyl]azetidin-3-ol are obtained in the form of a white foam.

The mixture of the 2 B diastereoisomer forms 3-acetoxy-1-{(R*)-(4-chlorophenyl)[4-(methoxycarbonyl)-phenyl]methyl}-3-[(R)-(3,5-difluorophenyl)(methyl-sulfonyl)methyl] azetidine and 3-acetoxy-1-{(R*)-(4-chlorophenyl)(4-(methoxycarbonyl)phenyl]methyl}-3-[(S)-(3,5-difluorophenyl)methylsulfonyl)methyl]azetidine may be prepared by carrying out the procedure as described in Example 3, starting with 11.2 g of (3,5-difluoro-benzyl)methyl sulfone, 350 cm³ of tetrahydrofuran, 34 cm³ of a 1.6 N solution of n-butyllithium in hexane, 11.2 g of 1-{(R*)-(4-chlorophenyl)[4-(methoxycarbonyl)-phenyl]methyl}azetidin-3-one, B isomer form, and 5.5 cm³ of acetyl chloride. The crude product is chromatographed on a silica gel column (particle size 0.06-0.200 mm, diameter 4 cm, height 40 cm), eluting with a cyclohexane and ethyl acetate (70/30 by volume) mixture and collecting 100-cm³ fractions. Fractions 10 to 30 are combined and then concentrated to dryness under reduced pressure (2.7 kPa). 21 g of a still impure cream-colored foam are obtained, which foam is chromatographed on a silica gel column (particle size 0.06-0.200 mm, diameter 4 cm, height 40 cm), eluting with dichloromethane and collecting 100-cm³ fractions. Fractions 11 to 30 are combined and then concentrated to dryness under reduced pressure (2.7 kPa). 20.0 g of the mixture of the 2 B diastereoisomer forms 3-acetoxy-1-{(R*)-(4-chlorophenyl)[4-(methoxycarbonyl)phenyl]-methyl}-3-[(R)-(3,5-difluorophenyl)(methylsulfonyl)-methyl]azetidine and 3-acetoxy-{(R*)-(4-chlorophenyl)-[4-(methoxycarbonyl)phenyl]methyl}-3-[(S)-(3,5-difluorophenyl)(methylsulfonyl)methyl]azetidine are obtained in the form of a white foam.

1-{(R*)-(4-Chlorophenyl)[4-methoxycarbonyl)-phenyl]methyl}azetidin-3-one, B isomer form, may be prepared by carrying out the procedure as described in Example 3, starting with 8.7 cm³ of oxalyl chloride, 350 cm³ of dichloromethane, 14.2 cm³ of dimethyl sulfoxide, 29.0 g of 1-{(R*)-(4-chlorophenyl)[4-(methoxycarbonyl)phenyl]methyl}azeditin-3-ol, B isomer form, and 43 cm³ of triethylamine. The crude product is chromatographed on a silica gel column (particle size 0.06-0.200 mm, diameter 4 cm, height 40 cm, eluting with dichloromethane and collecting 250-cm³ fractions. Fractions 7 to 25 are combined and then concentrated to dryness under reduced pressure (2.7 kPa). 15.5 g of 1-{-(R*)-(4-chlorophenyl)[4-(methoxycarbonyl)phenyl]-methyl}azetidin-3-one, B isomer form, are obtained in the form of an orange-colored oil.

1-{(R*)-(4-Chlorophenyl)[4-(methoxycarbonyl)-phenyl]methyl}azeditin-3-ol, B isomer form, may be prepared as described in Example 3, starting with 25.5 g of methyl (−)-4-[1-(R*)-amino-1-(4-chlorophenyl)methyl]benzoate, 250 cm³ of ethanol, 7.9 g of sodium hydrogen carbonate and 7.7 cm³ of epibromohydrin. 29 g of 1-{(R*)-(4-chlorophenyl)[4-(methoxycarbonyl)phenyl]methyl}azeditin-3-ol, B isomer form, are obtained in the form of a yellow oil.

Methyl (−)-4-[(R*)-amino-(4-chlorophenyl)-methyl]benzoate may be prepared by carrying out two successive recrystallizations of the white crystals (3.4 g) named "A crystals" of Example 3, from 68 cm³ of ethanol containing 5% of water under reflux. The crystals obtained are filtered, drained and then dried under reduced pressure (2.7 kPa). 2.2 g of methyl (−)-4-[1-(R*)-amino-(4-chlorophenyl)methyl]benzoate D-(−)-tartrate are obtained in the form of white crystals which are dissolved in 50 cm³ of ethyl acetate. The solution obtained is supplemented with 50 cm³ of 1 N sodium hydroxide, stirred and then separated after settling. The organic phase is washed with 50 cm³ of water and then dried over magnesium sulfate and concentrated to dryness under reduced pressure (2.7 kPa). 1.9 g of methyl (−)-4-[(R*)-amino-(4-chlorophenyl)methyl]benzoate are obtained in the form of a white solid. [a]20° C., 365 nm=−58.1°+/−1 (c=0.5%)

EXAMPLE 5

1-[Bis(thien-2-yl)methyl]-3-((RS)-(3,5-difluorophenyl) methylsulfonylmethyl]azetidine may be prepared by carrying out the procedure as described in Example 3, starting with 0.10 g of 1-[bis(thien-2-yl)methyl]-3-[(3,5-difluorophenyl) methylsulfonyl-methylene]azetidine, 2 cm³ of methanol, 2 cm³ of dichloromethane and 25 mg of sodium borohydride, with stirring for 3 hours at 20° C. The crude product is chromatographed on a silica gel column (particle size 0.063-0.200 mm, height 7 cm, diameter 1 cm) eluting under an argon pressure of 0.1 bar with dichloromethane and collecting 4-cm³ fractions. Fractions 2 to 5 are combined and concentrated to dryness under reduced pressure (2.7 kPa). 83 mg of 1-[bis(thien-2-yl)methyl]-3-[(RS)-(3,5-difluorophenyl)methylsulfonylmethyl]-azetidine are obtained in the form of a white solid [$^1$H NMR spectrum (400 MHz, CDCl$_3$, δ in ppm): from 2.60 to 2.70 (mt: 1H); 2.66 (s: 3H); 3.31 (mt: 2H); 3.40 (mt: 1H); 3.73 (broad t, J=7.5 Hz: 1H); 4.27 (d, J=11 Hz: 1H); 4.92 (s: 1H); 6.83 (tt, J=9 and 2.5 Hz); from 6.85 to 7.00 (mt: 6H); 7.21 (mt: 2H)].

1-[Bis(thien-2-yl)methyl]-3-[(3,5-difluoro-phenyl)methylsulfonylmethylene]azetidine may be prepared by carrying out the operation according to the procedure described in Example 6, starting with 2.2 g of 1-[bis(thien-2-yl)methyl]-3-[(3,5-difluorophenyl)-methylsulfonylmethyl-(RS)]azetidin-3-ol, 0.64 cm³ of methylsulfonyl chloride, 2.3 g of 4-dimethylamino-pyridine and 75 cm³ of dichloromethane; after purification by chromatography and crystallization from diisopropyl ether, 1.3 g of 1-[bis(thien-2-yl)methyl]-3-[(3,5-difluorophenyl)methylsulfonylmethylene]-azetidine are obtained in the form of white crystals melting at 165° C.

1-[Bis(thien-2-yl)methyl]-3-[(3,5-difluorophenyl)methylsulfonylmethyl-(RS)]azetidin-3-ol may be prepared by carrying out the procedure in the following manner: 4 cm³ of 1.6 N n-butyllithium in hexane are added, under argon over 10 minutes, to a solution, cooled to −60° C., of 1.3 g of (3,5-difluoro-benzyl)methyl sulfone in 20 cm³ of tetrahydrofuran. After stirring for 45 minutes at −70° C., a solution of 1.5 g of 1-[bis(thien-2-yl)methyl]azetidin-3-one in 20 cm³ of tetrahydrofuran is poured in over 10 minutes. After stirring for 3 hours at −70° C., the reaction mixture is allowed to return to room temperature and then is supplemented with 10 cm³ of a saturated aqueous ammonium chloride solution. The mixture is separated after settling, the organic phase is dried over magnesium sulfate, filtered and then concentrated to dryness under reduced pressure (2.7 kPa). The residue is taken up in 20 cm³ of a mixture of cyclohexane and ethyl acetate (60/40 by volume) the suspension obtained is filtered, the solid is drained and then air-dried. 2.2 g of 1-[bis(thien-2-yl)methyl)-3-[(3,5-difluoro-phenyl)methylsulfonylmethyl-(RS)]azetidin-3-ol are obtained in the form of white crystals melting at 145° C.

1-[Bis(thien-2-yl)methyl]azetidin-3-one may be prepared by carrying out the procedure as described in Example 1 (method 2) starting with 4 g of 1-[bis(thien-2-yl)methyl]azetidin-3-ol, 2.6 cm³ of dimethyl sulfoxide, 7.7 cm³ of triethylamine, 7.7 cm³ of oxalyl chloride and 100 cm³ of dichloromethane. The residue obtained is purified by chromatography on a silica gel column (particle size 0.04-0.06 mm, diameter 3 cm, height 30 cm) with, as eluent, a cyclohexane and ethyl acetate (1/1 by volume mixture). The fractions obtained are evaporated to dryness under reduced pressure (2.7 kPa). 3.2 g of 1-[bis(thien-2-yl)methyl]azetidin-3-one are obtained in the form of cream-colored crystals melting at 70° C.

1-[Bis(thien-2-yl)methyl]azetidin-3-ol may be prepared by carrying out the procedure as described in Example 3, starting with 6 g of 1-[bis(thien-2-yl)methyl]amine, 2.5 cm³ of epibromohydrin, 2.6 g of sodium bicarbonate and 50 cm³ of ethanol. 4 g of 1-[bis(thien-2-yl)methyl]azetidin-3-ol are obtained in the form of beige crystals melting at 115° C.

1-[Bis(thien-2-yl)methyl]amine may be prepared in the following manner: a solution of 5 cm³ of 2-thiopheninecarbonitrile in 50 cm³ of diethyl ether is poured, dropwise, into a solution, cooled under argon to 10° C., of thien-2-ylmagnesium bromide (prepared from 1.29 g of magnesium and 3.22 cm³ of 2-bromothiophene in 75 cm³ of diethyl ether). After refluxing for 1 hour and 30 minutes, the reaction medium is cooled to 5° C. and then twice 20 cm³ of methanol are poured in dropwise, the suspension is filtered and the solid is washed with methanol. The filtrate obtained [lacuna] a brown solution. 2.45 g of sodium borohydride are added to this solution in several portions, under argon. The mixture is stirred at room temperature for 16 hours and is then diluted with ethyl acetate and slowly supplemented with water. The organic phase is extracted, washed with water, dried over magnesium sulfate and evaporated to dryness under reduced pressure (2.5 kPa) at 55° C. A brown-oil is obtained which is chromatographed on a silica gel column (particle size 0.2-0.063 mm, diameter 8 cm, height 23 cm) and eluted with a cyclohexane and ethyl acetate (90/10 and then 85/15 by volume) mixture. Fractions 21 to 30 are combined and evaporated to dryness under reduced pressure (2.7 kPa). 11 g of 1-[bis(thien-2-yl)methyl]amine are obtained in the form of a crystallized solid.

EXAMPLE 6

1-[Bis(p-tolyl)methyl]-3-[(RS)methylsulfonyl-phenylmethyl]azetidine may be prepared by carrying out the procedure as described in Example 3, starting with 0.10 g of 1-[bis(p-tolyl)methyl]-3-(methylsulfonyl-phenylmethylene) azetidine, 2 cm³ of methanol, 2 cm³ of dichloromethane and 25 mg of sodium borohydride. The crude product is chromatographed on a silica gel column (particle size 0.063-0.200 mm, height 7 cm, diameter 1 cm), eluting under an argon pressure of 0.1 bar with dichloromethane and collecting 4-cm³ fractions. Fractions 5 to 10 are combined and concentrated to dryness under reduced pressure (2.7 kPa). 35 mg of 1-[bis(p-tolyl)methyl]-3-[(RS)methylsulfonylphenyl-methyl]azetidine are obtained in the form of a white solid [$^1$H NMR spectrum (300 MHz, CDCl$_3$, δ in ppm): 2.24 (s: 3H); 2.27 (s 3H); 2.53 (t, J=7.5 Hz: 1H); 2.58 (s: 3H); 3.19 (mt: 2H); 3.49 (mt: 1H); 3.69 (broad t, J=7.5 Hz: 1H); 4.22 (s: 1H); 4.28 (d, J=11.5 Hz: 1H); from 6.95 to 7.45 (mts: 13H)].

1-[Bis(p-tolyl)methyl]-3-(methylsulfonyl-phenylmethylene)azetidine may be prepared by carrying out the procedure in the following manner: 0.125 cm³ of methylsulfonyl chloride is added to a solution of 0.48 g of 1-[bis(p-tolyl)methyl]-3-[methylsulfonyl-phenylmethyl-(RS)]azetidin-3-ol in 25 cm³ of anhydrous dichloromethane followed in small fractions by 0.465 g of 4-dimethylaminopyridine. After stirring for 20 hours at 20° C., the reaction mixture is washed with twice 80 cm³ of water, with 80 cm³ of brine, dried over magnesium sulfate and then concentrated to dryness under reduced pressure (2.7 kPa). The residue is chromatographed on a silica gel column (particle size 0.040-0.063 mm, height 17 cm, diameter 3.2 cm), eluting under an argon pressure of 0.5 bar with a mixture of cyclohexane and ethyl acetate (80/20 by volume) and collecting 40-cm³ fractions. Fractions 5 to 8 are combined and concentrated to dryness under reduced pressure (2.7 kPa). The residue is stirred with diisopropyl ether, the solid is filtered, drained and then dried under reduced pressure (2.7 kPa). 0.25 g of 1-[bis(p-tolyl)methyl]-3-(methylsulfonylphenyl-methylene)azetidine is obtained in the form of a white solid [NMR spectrum in DMSO-d6, T=300K, δ in ppm (250 MHz): 2.23 (6H, s, 2Ph—CH$_3$), 2.98 (3H, s, SCH$_3$), 3.76 (2H, s, NCH$_2$), 4.20 (2H, s, NCH$_2$), 5.55 (1H, s, NCH), 7.10 (4H, d, J=7 Hz, 4 CH arom.), 7.32 (4H, d, J=7 Hz, 4CH arom.), 7.43 (5H, s, phenyl)].

1-[Bis(p-tolyl)methyl]-3-[(methylsulfonyl)-phenylmethyl-(RS)]azetidin-3-ol may be prepared by carrying out the procedure in the following manner: 0.6 g of 3-((methylsulfonyl)(phenyl)methyl-(RS)]-azetidin-3-ol hydrochloride is added to a solution of 0.59 g of bromo(bis-p-tolyl)methane in 20 cm³ of acetonitrile followed by 0.3 g of potassium carbonate. After heating for 1 hour and 15 minutes at the reflux temperature, the reaction mixture is cooled to 20° C. and filtered. The filtrate is concentrated to dryness under reduced pressure (2.7 kPa) and the residue is chromatographed on a silica gel column (particle size 0.04-0.06 mm, diameter 4 cm, height 16 cm), eluting with a mixture of cyclohexane and ethyl acetate (70/30 by volume) and collecting 50-cm³ fractions. Fractions 8 to 13 are concentrated to dryness under reduced pressure (2.7 kPa). 0.48 g of 1-[bis(p-tolyl)methyl]-3-[(methylsulfonyl)(phenyl)methyl-(RS)]azetidin-3-ol is obtained in the form of a white solid.

Bromo(bis-p-tolyl)methane may be prepared according to the procedure described by BACHMANN W. E., J. Am. Chem. Soc., 2135, (1933).

3-[(Methylsulfonyl)phenylmethyl-(RS)]azeditin-3-ol hydrochloride may be prepared by carrying out the procedure in the following manner: 12.6 cm³ of a 6.2 N hydrochloric acid solution in dioxane are added to a solution of 2.62 g of 3-[(methylsulfonyl)(phenyl)methyl-(RS)]-1-(vinyloxy-carbonyl)azetidin-3-ol in 12.6 cm³ of dioxane. After stirring for 20 hours at 20° C., the mixture is concentrated to dryness at 50° C. under reduced pressure (2.7 kPa). The residue is taken up in 25 cm³ of ethanol, heated under reflux for 1 hour and then allowed to return to 20° C. and filtered. The solid is rinsed with diethyl ether and then drained and dried under reduced pressure (2.7 kPa). 1.89 g of 3-[(methyl-sulfonyl)phenylmethyl-(RS)]azeditin-3-ol hydrochloride are obtained in the form of white crystals.

3-[(Methylsulfonyl)(phenyl)methyl-(RS)]-1-(vinyloxycarbonyl)-azetidin-3-ol may be prepared by carrying out the procedure in the following manner: a solution of 0.99 cm³ of vinyl chloroformate in 4 cm³ of anhydrous dichloromethane is poured dropwise into a mixture, cooled to +5° C., of 3.92 g of 1-benzhydryl-3-[(methylsulfonyl)(phenyl)methyl-(RS)] azetidin-3-ol in 500 cm³ of anhydrous dichloromethane. After stirring for 48 hours at 20° C., the reaction mixture is concentrated to dryness under reduced pressure (2.7 kPa). The residue is chromatographed on a silica gel column (particle size 0.04-0.06 mm, diameter 5.6 cm, height 15.5 cm), eluting with a mixture of cyclohexane and ethyl acetate (70/30 by volume) and collecting 50-cm³ fractions. Fractions 17 to 36 are concentrated to dryness under reduced pressure (2.7 kPa). 0.9 g of 3-[(methylsulfonyl)(phenyl)methyl-(RS)]-1-(vinyloxycarbonyl)azetidin-3-ol is obtained in the form of a white solid.

1-Benzhydryl-3-[(methylsulfonyl)-(phenyl)methyl-(RS)] azetidin-3-ol may be prepared by carrying out the procedure as described in Example 1 (method 1), starting with 47 cm³ of diisopropylamine, 205.6 cm³ of a 1.6 M solution of n-butyl-lithium in hexane, 2.2 liters of tetrahydrofuran, 50 g of benzylmethyl sulfone and 69.6 g of 1-benzhydryl-azetidin-3-one. 94.3 g of 1-benzhydryl-3-[(methylsulfonyl)(phenyl) methyl-(RS)]azetidin-3-ol are obtained in the form of white crystals.

EXAMPLE 7

1-[Bis(3-fluorophenyl)methyl]-3-(RS)-[(3,5-difluorophenyl)methylsulfonylmethyl]azetidine may be prepared by carrying out the procedure as described in Example 3, starting with 0.10 g of 1-[bis(3-fluorophenyl)methyl]-3-[(3,5-difluorophenyl)methyl-sulfonylmethylene]azetidine, 2 cm³ of methanol, 2 cm³ of dichloromethane and 20 mg of sodium borohydride, with stirring for 48 hours at 20° C. The crude product is chromatographed on a silica gel column (particle size 0.063-0.200 mm, height 7 cm, diameter 1 cm), eluting under an argon pressure of 0.1 bar with dichloromethane and collecting 4-cm³ fractions. Fractions 3 to 7 are combined and concentrated to dryness under reduced pressure (2.7 kPa). 95 mg of 1-[bis(3-fluorophenyl)-methyl]-3-(RS)-[(3,5-difluorophenyl)methylsulfonyl-methyl]azetidine are obtained in the form of white crystals [$^1$H NMR spectrum (300 MHz, CDCl$_3$, δ in ppm) 2.57 (t, J=7.5 Hz: 1H); 2.66 (s: 3H); from 3.15 to 3.30 (mt: 2H); from 3.30 to 3.50 (mt: 1H); 3.66 (broad t, J=7.5 Hz: 1H); 4.27 (d, J=11.5 Hz: 1H); 4.28 (s: 1H); from 6.75 to 7.35 (mt: 11H)].

1-[Bis(3-fluorophenyl)methyl]-3-[(3,5-difluorophenyl) methylsulfonylmethylene]azetidine may be prepared by carrying out the procedure as described in Example 6, starting with 1.15 g of 1-[bis(3-fluoro-phenyl)methyl]-3-[(3,5-difluorophenyl)(methylsulfonyl)-methyl-(RS)]azetidin-3-ol, 30 cm³ of dichloromethane, 0.264 cm³ of methylsulfonyl chloride and 0.98 g of 4-dimethylaminopyridine. After chromatography on a silica gel column (particle size 0.06-0.200 mm, diameter 2.8 cm, height 25 cm), under an argon pressure of 1 bar with a mixture of ethyl acetate and cyclohexane (15/85 by volume) as eluent and collecting 60-cm³ fractions, 0.55 g of 1-[bis(3-fluorophenyl)methyl]-3-[(3,5-difluorophenyl)(methylsulfonyl)methylene]azetidine is obtained in the form of a white solid melting at 178° C.

1-[Bis(3-fluorophenyl)methyl]-3-[(3,5-difluorophenyl) (methylsulfonyl)methyl-(RS)]azetidin-3-ol may be prepared according to the following procedure: 3.65 cm³ of a 1.6 M solution of n-butyllithium in hexane are poured over 10 minutes into a mixture, cooled to −60° C., of diisopropylamine and 10 cm³ of tetrahydrofuran, the mixture is stirred for 10 minutes at −30° C. and then cooled to −70° C. A solution of 1.2 g of (3,5-difluorobenzyl)methyl sulfone in 30 cm³ of tetrahydrofuran is then added over 20 minutes. After stirring for 30 minutes at −70° C., the mixture is supplemented over 30 minutes with a solution of 1.5 g of 1-[bis(3-fluorophenyl) methyl]azetidin-3-one in 10 cm³ of tetrahydrofuran. After stirring for 2 hours at −70° C., the reaction mixture is brought to room temperature and then supplemented with 20 cm³ of a saturated aqueous ammonium chloride solution and 100 cm³ of dichloromethane. The mixture is separated after settling, the organic phase is washed with water and then dried over magnesium sulfate, filtered and concentrated to dryness under reduced pressure (2.7 kPa). The residue is chromatographed on a silica gel column (particle size 0.06-0.200 mm, diameter 3.2 cm, height 30 cm), eluting under an argon pressure of 1 bar with a mixture of ethyl acetate and cyclohexane (20/80 by volume) and collecting 60-cm³ fractions. Fractions 9 to 20 are combined and concentrated to dryness under reduced pressure (2.7 kPa). 1.95 g of 1-[bis(3-fluorophenyl) methyl]-3-[(3,5-difluorophenyl)(methylsulfonyl)methyl-(RS)]-azetidin-3-ol are obtained in the form of a white solid melting at 170° C. (decomposition).

1-[Bis(3-fluorophenyl)methyl]azetidin-3-one may be prepared by carrying out the procedure as described in Example 1 (method 2) starting with 0.7 cm³ of oxalyl chloride, 16 cm³ of dichloromethane, 1.12 cm³ of dimethylsulfoxide, 2 g of 1-[bis(3-fluorophenyl)-methyl]azetidin-3-ol and 3.7 cm³ of triethylamine. 1.55 g of 1-[bis(3-fluorophenyl)methyl]azetidin-3-one are obtained in the form of an oil which crystallizes at 20° C.

1-[Bis(3-fluorophenyl)methyl]azetidin-3-ol may be prepared by carrying out the procedure as described by KATRITSKY A. R. in J. Heterocycl. Chem, 31, 271 (1994) starting with 4.9 g of [bis(3-fluorophenyl)-methyl]amine and 1.78 cm³ of epichlorohydrin.

[Bis(3-fluorophenyl)methyl]amine may be prepared in the following manner: a solution of 5.17 g of 3,3'-difluorobenzophenone oxime in 30 cm³ of tetrahydrofuran is poured, under an argon atmosphere over 30 minutes, into a suspension of 1.27 g of lithium aluminum hydride in 80 cm³ of tetrahydrofuran. After stirring for 5 hours under reflux, 1.3 cm³ of water, 1.3 cm³ of 4 N sodium hydroxide, 2.6 cm³ of water and then 50 cm³ of ethyl acetate are added successively. After drying over magnesium sulfate and concentrating to dryness under reduced pressure (2.7 kPa), 4.9 g of [bis(3-fluorophenyl)methyl]amine are obtained in the form of a yellow oil.

3,3'-Difluorobenzophenone oxime may be prepared according to the following procedure: a solution of 1.6 g of hydroxylamine hydrochloride in 8 cm³ of water is poured dropwise into a solution of 5.0 g of 3,3'-difluorobenzophenone in 10 cm³ of ethanol and then 1.2 g of sodium hydroxide pellets are added in small fractions. The reaction mixture, heated under reflux for 10 minutes, is cooled to 20° C. and then acidified with 7.5 cm³ of 4 N hydrochloric acid. The oily precipitate obtained, once it has been triturated, becomes a white solid which is filtered, washed with water and then dried at 35° C. under reduced pressure (2.7 kPa). 5.17 g of 3,3'-difluorobenzophenone oxime are obtained in the form of a white solid.

EXAMPLE 8

1-[Bis(4-chlorophenyl)methyl]-3-(RS)-{[3-azetidin-1-yl-phenyl]methylsulfonylmethyl}azetidine may be prepared by carrying out the procedure as described in Example 3, starting with 0.10 g of 1-[bis(4-chloro-phenyl)methyl]-3-[(azetidin-1-yl-phenyl)methyl-sulfonylmethylene]azetidine, 2 cm³ of methanol, 2 cm³ of dichloromethane and 30 mg of sodium borohydride, stirring for 24 hours at 20° C. The crude product is chromatographed on a silica gel column (particle size 0.063-0.200 mm, height 7 cm, diameter 1 cm), eluting under an argon pressure of 0.1 bar with dichloromethane and collecting 4-cm³ fractions. Fractions 5 to 10 are combined and concentrated to dryness under reduced pressure (2.7 kPa). 20 mg of 1-[bis(4-chlorophenyl)-methyl]-3-(RS)-{[3-azetidin-1-yl-phenyl-]methylsulfonyl-methyl}azetidine are obtained in the form of an off-white lacquer [$^1$H NMR spectrum (300 MHz, CDCl$_3$, $\delta$ in ppm): 2.39 (mt; 2H); from 2.50 to 2.65 (mt: 1H); 2.60 (s: 3H); 3.20 (mt: 2H); 3.47 (mt: 1H); 3.66 (broad t, J=7 Hz: 1H); 3.89 (broad t, J=7.5 Hz 4H); 4.20 (d, J=11 Hz: 1H); 4.26 (s: 1H); from 6.35 to 6.50 (mt: 2H); 6.67 (broad d, J=7.5 Hz: 1H); from 7.10 to 7.40 (mt: 9H)].

1-[Bis(4-chlorophenyl)methyl]-3-[(azetidin-1-yl-phenyl)methylsulfonylmethylene]azetidine may be prepared by carrying out the procedure by carrying out the procedure as described in Example 6, starting with 0.83 g of 1-[bis(4-chlorophenyl)methyl]-3-[(azetidin-1-yl-phenyl)methylsulfonylmethyl-(RS)]azetidin-3-ol, 20 cm³ of dichloromethane, 0.18 cm³ of methylsulfonyl chloride and 0.75 g of 4-dimethylaminopyridine. 0.40 g of 1-[bis(4-chlorophenyl)methyl]-3-[(azetidin-1-yl-phenyl)methylsulfonylmethylene]azetidine is obtained in the form of a white foam.

1-[Bis(4-chlorophenyl)methyl]-3-[(azetidin-1-yl-phenyl)methylsulfonylmethyl-(RS)]azetidin-3-ol may be prepared by carrying out the procedure as described in Example 5, starting with 1.55 g of 1-(3-methyl-sulfonylmethylphenyl) azetidine, 5.2 cm³ of a 1.6 M solution of n-butyllithium in hexane, 30 cm³ of tetrahydrofuran and 2.11 g of 1-[bis(4-chlorophenyl)-methyl]azetidin-3-one. 0.83 g of 1-[bis(4-chloro-phenyl)methyl]-3-[(azetidin-1-yl-phenyl)methyl-sulfonylmethyl-(RS)]azetidin-3-ol is obtained in the form of an ochre-colored solid melting at 172° C.

1-(3-Methylsulfonylmethylphenyl)azetidine may be prepared by carrying out the procedure in the following manner: a solution of 1.9 g of 1-(3-methylsulfanylmethylphenyl)azetidine in 10 cm³ of ethanol is added to a mixture, cooled to 0° C., of 10 cm³ of water, 5 cm³ of acetic acid, 1.5 cm³ of 36 N sulfuric acid and 6.15 g of oxone. After stirring for 20 hours at 20° C., the reaction mixture is supplemented with 100 cm³ of water, 100 cm³ of ethyl acetate and is then neutralized by stirring with sodium hydrogen carbonate. The mixture obtained is separated after settling, the organic phase is dried over magnesium sulfate and then filtered and concentrated to dryness under reduced pressure (2.7 kPa). 1.55 g of 1-(3-methylsulfonyl-methylphenyl)azetidine are obtained in the form of a light brown gum.

1-[3-(Methylsulfonylmethyl)phenyl]azetidine may be prepared by carrying out a procedure in the following manner: 2.57 g of potassium tert-butoxide, 0.64 g of 1,1'-bis(diphenylphosphino)ferrocenyl-palladium chloride, 1.49 g of 1,1'-bis(diphenyl-phosphino)ferrocene, 0.12 g of copper iodide and 2.0 g of azetidine are added, under argon, to a solution of 4.6 g of 1-iodo-3-(methylsulfanylmethyl)benzene in 60 cm³ of tetrahydrofuran. After heating for 3 hours at the reflux temperature, the reaction mixture is cooled to room temperature and filtered on celite and then washing the latter with 150 cm³ of ethyl acetate. The combined filtrate and washings is acidified with 120 cm³ of 1 N hydrochloric acid and then separated after settling. The aqueous phase is supplemented with 60 cm³ of ethyl acetate and is then alkalinized with sodium hydrogen carbonate and the mixture is separated after settling. The organic phase is dried over magnesium sulfate, filtered and concentrated to dryness under reduced pressure (2.7 kPa). The residue is is chromatographed on a silica gel column (particle size 0.06-0.200 mm, diameter 3.5 cm, height 50 cm), eluting under an argon pressure of 0.5 bar with a mixture of ethyl acetate and cyclohexane (20/80 by volume) and collecting 100-cm³ fractions. Fractions 1 to 3 are combined and concentrated to dryness under reduced pressure (2.7 kPa). 1.9 g of 1-[3-(methylsulfonyl-methyl)phenyl]azetidine are obtained in the form of an oil.

1,1'-Bis(diphenylphosphino)-ferrocenylpalladium chloride may be prepared by carrying out the procedure according to Hayashi T. et al., in J. Am. Chem. Soc, 106, 158 (1984).

1-Iodo-3-(methylsulfanylmethyl)benzene may be prepared by carrying out the procedure in the following manner: 6.4 g of sodium methylthiolate are added to a solution of 25 g of 3-iodobenzyl bromide in 80 cm³ of N,N-dimethylformamide. After stirring for 20 hours at 20° C., the reaction mixture is supplemented with 250 cm³ of water, 200 cm³ of ethyl acetate and is stirred and then separated after settling. The organic phase is washed with four times 200 cm³ of water, dried over magnesium sulfate, filtered and then concentrated to dryness at 50° C. under reduced pressure (2.7 kPa). 22 g of 1-iodo-3-(methylsulfanylmethyl)benzene are obtained in the form of a gum.

EXAMPLE 9

The mixture of the 2 A form diastereoisomers 1-(R*)-{4-[(4-chlorophenyl)-{3-[(3,5-difluorophenyl)-methylsulfonyl-methyl-(R)]-3-imidazolyl-azetidin-1-yl}methyl]benzyl}-1H-imidazole and 1-(R*)-{4(4-chlorophenyl)-{3-[(3,5-difluorophenyl)methylsulfonyl-methyl-(S))}-3-imidazolyl-azetidin-1-yl}methyl]benzyl]-1H-imidazole may be prepared by carrying out the procedure in the following manner: 13.6 mg of imidazole are added to a solution of 50 mg of 1-{(R*)-[4-(chloromethyl)phenyl]-(4-chlorophenyl)methyl}-3-[(3,5-difluorophenyl)methylsulfonylmethylene]azetidine, A isomer form, in 1 cm³ of dichloromethane. After stirring for 20 hours at 20° C., the reaction mixture is directly chromatographed on a silica gel column: (particle size 0.063-0.200 mm, height 7 cm, diameter 1 cm), eluting under an argon pressure of 0.1 bar with a mixture of dichloromethane and methanol (98/2 by volume) and collecting 4-cm³ fractions. Fractions 4 to 9 are combined and concentrated to dryness under reduced pressure (2.7 kPa). 20 mg of the mixture of the 2 A form diastereoisomers 1-(R*)-{4-[(4-chlorophenyl)-{3-[(3,5-difluorophenyl)methylsulfonylmethyl-(R)]-3-imidazolyl-azetidin-1-yl}methyl]benzyl}-1H-imidazole and 1-(R*)-{4-[(4-chlorophenyl)-{3-[3-[(3,5-difluorophenyl)methylsulfonylmethyl-(S)]}-3-imidazolyl-azetidin-1-yl}methyl]benzyl]-1H-imidazole are obtained in the form of a white lacquer [¹H NMR spectrum (300 MHz, CDCl₃, δ in ppm): a mixture of diastoero-isomers is observed, * 2.64 (s: 3H); 3.42 (d, J=8 Hz: 1H); 3.50 (d, J=8 Hz: 1H); 3.75 (mt: 1H); 4.31 (broad d, J=8 Hz: 1H); 4.40 (s: 1H); 4.54 and 4.55 (2s: 2H in total); 4.72 (s: 1H); 6.84 (mt: 2H); 6.87 (s: 1H); 6.95 (mt: 1H); 7.11 (s: 1H); from 7.20 to 7.40 (mt 12)].

EXAMPLE 10

(1-Benzhydrylazetidin-3-yl)phenylmethanone O-methyloxime, a mixture of the 2 isomers Z and E, may be prepared by carrying out the procedure in the following manner: 0.286 g of O-methylhydroxylamine and 0.32 g of sodium acetate are added to a suspension of 0.80 g of 1-benzhydryl-3-benzoylazetidine in 30 cm³ of ethanol. After stirring for 24 hours at reflux temperature, the reaction mixture is allowed to cool at room temperature and filtered. The filtrate is concentrated to dryness at 50° C. under reduced pressure (2.7 kPa). The residue is taken up in 100 cm³ of dichloromethane and the solution is supplemented with 20 cm³ of water and 1 N hydrochloric acid, stirring until an acidic pH is obtained. The organic phase is separated after settling, dried over magnesium sulfate and then filtered and concentrated to dryness under reduced pressure (2.7 kPa).

The residue is chromatographed on a silica gel column (particle size 0.063-0.200 mm, height 36 cm, diameter 3.8 cm), eluting under an argon pressure of 0.5 bar with a mixture of cyclohexane and ethyl acetate (95/5, 92/8 and then 80/20 by volume) and collecting 30-cm³ fractions. Fractions 8 to 14 are combined and concentrated to dryness under reduced pressure (2.7 kPa). 0.20 g of (1-benzhydrylazetidin-3-yl)phenyl-methanone O-methyloxime, a mixture of the 2 isomers Z and E, is obtained in the form of a white solid [¹H NMR spectrum (250 MHz, (CD₃)₂SO d6, d in ppm). A 65/35 mixture of isomers is observed, * 2.68-3.02 and from 3.25 to 3.90 (mts: 5H in total); 3.76 and 3.80 (2s: 3H in total); 4.26 and 4.38 (2s: 1H in total); from 7.10 to 7.50 (mt: 15H)].

1-Benzhydryl-3-benzoylazetidine may be prepared by carrying out the procedure in the following manner: 112 cm³ of a 1 M solution of phenylmagnesium bromide in tetrahydrofuran are poured dropwise, under argon, into a solution, cooled to 0° C., of 11.5 g of (1-benzhydrylazetidin-3-yl) carboxylic-N-methoxy-N-methylamide acid in 350 cm³ of tetrahydrofuran, and then the mixture is allowed to return to room temperature. After stirring for 20 hours at 20° C., the reaction mixture is supplemented with 400 cm³ of a saturated ammonium chloride solution and then with 250 cm³ of ethyl acetate. After stirring, the mixture is separated after settling, the aqueous phase reextracted with 250 cm³ of ethyl acetate and the combined two organic phases are washed with twice 250 cm³ of water, dried over magnesium sulfate, filtered and concentrated to dryness at 50° C. under reduced pressure (2.7 kPa). The residue is stirred with 50 cm³ of diisopropyl ether, the suspension is filtered, the solid is drained and then dried under reduced pressure (2.7 kPa). 1-benzhydryl-3-benzoylazetidine are obtained in the form of a cream-colored solid.

(1-Benzhydrylazetidin-3-yl)carboxylic-N-methoxy-N-methylamide may be prepared by carrying out the procedure in the following manner: 13.35 g of (1-benzhydrylazetidin-3-yl)carboxylic acid and 1.0 g of hydroxybenzotriazole hydrate are added, with stirring, to a suspension of 4.0 g of N,O-dimethylhydroxylamine hydrochloride in 250 cm³ of dichloromethane. 6.92 g of 1-(3-dimethylaminopropyl)3-ethylcarbodiimide hydrochloride and 8.8 cm³ of N,N-diisopropylethylamine are added to this mixture, placed under argon and cooled to +5° C. After stirring for 3 hours at +5° C. and then for 20 hours at 20° C., the reaction mixture is supplemented with 200 cm³ of water and then separated after settling. The organic phase is washed with 300 cm³ of water, dried over magnesium sulfate, filtered and then concentrated to dryness under reduced pressure (2.7 kPa). The residue is stirred with 100 cm³ of diisopropyl ether, the suspension is filtered and the solid is drained and then dried under reduced pressure (2.7 kPa). 10.76 g of (1-benzhydrylazetidin-3-yl) carboxylic-N-methoxy-N-methylamide are obtained in the form of a cream-colored solid.

(1-Benzhydrylazetidin-3-yl)carboxylic acid may be prepared by carrying out the procedure in the following manner: a solution of 11 g of potassium hydroxide in 9 cm³ of water is added dropwise to a suspension, cooled to +5° C., of 14 g of (1-benzhydryl-azetidin-3-yl)carbonitrile in 140 cm³ of 2-ethoxyethanol and then the mixture is heated to 95° C. After stirring for 16 hours at this temperature, the reaction mixture is poured slowly, with stirring, over ice and left at 0° C. for 68 hours and then concentrated to dryness to dryness at 50° C. under reduced pressure (2.7 kPa). The residue is taken up in 400 cm³ of water, the solution is acidified to pH 4 with 6 N hydrochloric acid and then supplemented with 400 cm³ of ethyl acetate. The resulting suspension is filtered, the solid is drained and then dried at 50° C. under reduced pressure (2.7 kPa). 13.55 g of (1-benzhydrylazetidin-3-yl)carboxylic acid are obtained in the form of a cream-colored solid.

(1-Benzhydrylazetidin-3-yl)carbonitrile may be prepared by carrying out the procedure in the following manner: a solution of 18.54 g of sodium cyanide in 25 cm³ of water is added dropwise to a solution of 40 g of 1-benzhydrylazetidine-3-yl methylsulfonate in 350 cm³ of N,N-dimethylformamide. After stirring for 24 hours at 65° C., the reaction mixture, allowed to return to room temperature, is then poured, with stirring, into a mixture of 550 cm³ of water and 300 g of ice. The suspension obtained is filtered, the solid is washed with three times 110 cm³ of water and then dissolved in 350 cm³ of dichloromethane. The solution is dried over magnesium sulfate, filtered and concentrated to dryness under reduced pressure (2.7 kPa). The residue is stirred with 200 cm³ of diisopropyl ether, the suspension filtered, the solid drained and then dried under reduced pressure (2.7 kPa). 28.4 g of (1-benzhydrylazetidin-3-yl)-carbonitrile are obtained in the form of a pinkish cream-colored solid.

1-Benzhydrylazetidin-3-yl methylsulfonate may be prepared by carrying out the procedure starting with 100 g of 1-benzhydrylazetidin-3-ol, 800 cm³ of dichloromethane, 31 cm³ of methylsulfonyl chloride and 35 cm³ of pyridine. The crude product obtained is chromatographed on a silica gel column (particle size 0.063-0.200 mm, height 50 cm, diameter 11 cm), eluting under an argon pressure of 0.5 bar with a mixture of cyclohexane and ethyl acetate (80/20, 75/25, and then 70/30 and 60/40 by volume) and collecting 1-liter fractions. Fractions 12 to 31 are combined and concentrated to dryness under reduced pressure (2.7 kPa). 66 g of 1-benzhydrylazetidine-3-yl methylsulfonate are obtained in the form of a yellowish white solid.

1-Benzhydrylazetidin-3-ol may be prepared by carrying out the procedure as described by Alan R. KATRITZKY et al., in J. Heterocyclic Chem.; 31, 271 (1994).

EXAMPLE 11

(RS)-1-[3-({1-Bis(4-chlorophenyl)methyl]-azetidin-3-yl}methylsulfonylmethyl)phenyl]pyrrolidine may be prepared by carrying out the procedure as described in Example 3, starting with 0.10 g of 1-[3-({1-[bis(4-chlorophenyl)methyl]azetidin-3-yl}-methylsulfonylmethylene)phenyl]pyrrolidine, 1.5 cm$^3$ of anhydrous methanol, 1.5 cm$^3$ of anhydrous dichloromethane, and 30 mg of sodium borohydride, stirring for 3 hours at 20° C. and then 8 hours at 50° C. The crude product is chromatographed on a silica gel column (particle size 0.040-0.063 mm, height 8 cm, diameter 1 cm), eluting under an argon pressure of 0.8 bar with a mixture of cyclohexane and ethyl acetate (80/20 by volume) and collecting 5-cm$^3$ fractions. Fractions 22 to 28 are combined and concentrated to dryness under reduced pressure (2.7 kPa), the residue is stirred with 5 cm$^3$ of pentane, the solid is filtered, drained and dried. 18 mg of (RS)-1-[3-({1-[bis(4-chlorophenyl)methyl]azetidin-3-yl}methyl-sulfonylmethyl)phenyl]pyrrolidine are obtained in the form of white powder [$^1$H NMR spectrum (300 MHz, CDCl$_3$, δ in ppm): 2.01 (mt: 4H); 2.59 (mt: 1H); 2.61 (s: 3H); from 3.10 to 3.25 (mt: 2H); 3.27 (mt: 4H); from 3.40 to 3.55 (mt: 1H); 3.66 (mt: 1H); 4.20 (d, J=12 Hz: 1H); 4.25 (s: 1H); from 6.45 to 6.65 (mt 3H); from 7.10 to 7.35 (mt: 9H)].

1-[3-({1-[Bis(4-chlorophenyl)methyl]azetidin-3-yl}methylsulfonylmethylene)phenyl]pyrrolidine may be prepared by carrying out the procedure as described in Example 6, starting with 0.6 g of 1-[bis(4-chlorophenyl)methyl]-3-[(methylsulfonyl)(3-pyrrolidinylphenyl)methyl-(RS)]azetidin-3-ol, 0.1 cm$^3$ of methylsulfonyl chloride and 0.5 g of 4-dimethylaminopyridine, the residue obtained is purified by chromatography on a silica gel column (particle size 0.04-0.06 mm, diameter 2 cm, height 30 cm) under an argon pressure of 0.5 bar with a dichloromethane and ethanol mixture as eluent (98.5/1.5 by volume) and collecting 10-cm$^3$ fractions. Fraction 4 is concentrated to dryness under reduced pressure (2.7 kPa). After recrystallization from 5 cm$^3$ of diethyl ether, 0.5 g of 1-[3-({1-[bis(4-chlorophenyl)methyl]-azetidin-3-yl}methylsulfonylmethylene)phenyl]-pyrrolidine is obtained in the form of a solid melting at 133° C.

1-[Bis(4-chlorophenyl)methyl]-3-[(methyl-sulfonyl)(3-pyrrolidinylphenyl)methyl-(RS)]azetidin-3-ol may be obtained by carrying out the operation according to the procedure of Example 5, starting with 0.5 g of 1-[3-(methylsulfonylmethyl)phenyl]pyrrolidine, 0.6 g of 1-[bis(4-chlorophenyl)methyl]azetidin-3-one, 15 cm$^3$ of tetrahydrofuran and 1.4 cm$^3$ of a 1.6 N solution of n-butyllithium in hexane. 0.6 g of 1-[bis(4-chlorophenyl)methyl]-3-[(methylsulfonyl)(3-pyrrolidinylphenyl)methyl-(RS)]azetidin-3-ol is obtained in the form of a cream-colored solid.

1-[3-(Methylsulfonylmethyl)phenyl]pyrrolidine may be prepared by carrying out the procedure described in Example 8, starting with 6 cm$^3$ of water, 6 cm$^3$ of 100% acetic acid, 3.5 cm$^3$ of 36 N sulfuric acid, 3.11 g of oxone, 0.96 g of 1-[3-(methylsulfanylmethyl)phenyl]-pyrrolidine and 6 cm$^3$ of ethanol. 0.478 g of 1-[3-(methylsulfonylmethyl)phenyl]pyrrolidine is obtained in the form of a light brown gum.

1-[3-(Methylsulfanylmethyl)phenyl]pyrrolidine may be prepared by carrying out the procedure as described in Example 8, starting with 4.0 g of 1-iodo-3-(methylsulfanylmethyl)benzene, 120 cm$^3$ of tetrahydrofuran, 2.2 g of sodium tert-butoxide, 0.556 g of 1,1'-bis(diphenylphosphino)ferrocenylpalladium chloride, 1.26 g of 1,1'-bis(diphenylphosphino)-ferrocene and 2.6 g of pyrrolidine. 1.9 g of 1-[3-(methylsulfanylmethyl)phenyl]pyrrolidine are obtained in the form of an oil.

EXAMPLE 12

N-(RS)-[3-({1-[Bis(4-chlorophenyl)methyl]-azetidin-3-yl}methylsulfonylmethyl)phenyl]-N-methyl-carbamic acid tert-butyl ester may be prepared by carrying out the procedure as described in Example 3, starting with 0.10 g of N-[3-({1-[bis(4-chlorophenyl)-methyl]azetidin-3-yl}methylsulfonylmethylene)phenyl]-N-methylcarbamic acid tert-butyl ester, 1.5 cm$^3$ of anhydrous methanol, 1.5 cm$^3$ of anhydrous dichloromethane and 30 mg of sodium borohydride, with stirring for 3 hours at 20° C. The crude product is stirred with 10 cm$^3$ of diisopropyl ether, the solid is filtered, drained and then dried under reduced pressure (2.7 kPa). 94 mg of N-(RS)-[3-({1-[bis(4-chlorophenyl)methyl]azetidin-3-yl}methylsulfonylmethyl)phenyl]-N-methylcarbamic acid tert-butyl ester are obtained in the form of a white powder [$^1$H NMR spectrum (300 MHz, (CD$_3$)$_2$SO d6, δ in ppm): 1.36 (s: 9H); 2.46 (t, J=7.5 Hz: 1H); 2.75 (s 3H); from 3.00 to 3.55 (mt: 4H); 3.17 (s: 3H); 4.45 (s: 1H); 4.78 (d, J=11 Hz: 1H); from 7.20 to 7.50 (mt 12H)].

N-[3-({1-[Bis(4-chlorophenyl)methyl]azetidin-3-yl} methylsulfonylmethylene)phenyl]-N-methylcarbamic acid tert-butyl ester may be prepared by carrying out the procedure as described in Example 6, starting with 5.6 g of 1-[bis(4-chlorophenyl)methyl]-3-{[3-(N-tert-butyloxycarbonyl-N-methylamino)phenyl]methylsulfonyl-methyl-(RS)}azetidin-3-ol, 100 cm$^3$ of dichloromethane, 1.59 g of methylsulfonyl chloride and 4.5 g of 4-dimethylaminopyridine. The crude product obtained is purified by chromatography on a silica gel column (particle size 0.04-0.06 mm, diameter 4 cm and weight of silica 250 g), eluting under a nitrogen pressure of 0.5 bar with a mixture of ethyl acetate and cyclohexane (30/70 by volume) and collecting 100-cm$^3$ fractions. Fractions 12 to 18 are combined, concentrated to dryness under reduced pressure (2.7 kPa). 3.2 g of N-[3-({1-[bis(4-chlorophenyl)methyl]azetidin-3-yl}methylsulfonylmethylene)phenyl]-N-methylcarbamic acid tert-butyl ester are obtained in the form of a white foam.

1-[Bis(4-chlorophenyl)methyl]-3-{[3-(N-tert-butyloxycarbonyl-N-methylamino)phenyl]methylsulfonyl-methyl-(RS)}azetidin-3-ol, may be prepared by carrying out the procedure as described in Example 5, starting with 3.8 g of N-[3-(methylsulfonylmethyl)phenyl]-N-methylcarbamic acid tert-butyl ester, 50 cm$^3$ of tetrahydrofuran, 9.5 cm$^3$ of a 1.6 N solution of n-butyllithium in hexane, and 3.82 g of 1-[bis(4-chlorophenyl)methyl]azetidin-3-one. The crude product is purified by chromatography on a silica gel column (particle size 0.04-0.06 mm, diameter 4 cm, weight of silica 250 g), eluting under a nitrogen pressure of 0.5 bar with dichloromethane and then with a dichloromethane and ethanol (99/1 by volume) mixture and collecting 500-cm$^3$ fractions. Fractions 10 to 16 are combined, concentrated to dryness under reduced pressure (2.7 kPa). 5.6 g of 1-[bis(4-chlorophenyl)-methyl]-3-{[3-(N-tert-butyloxycarbonyl-N-methylamino)-phenyl]methylsulfonylmethyl-(RS)}azetidin-3-ol are obtained in the form of a foam.

N-[3-(Methylsulfonylmethyl)phenyl]-N-methylcarbamic acid tert-butyl ester may be prepared by carrying out the procedure in the following manner: 3.7 g of di-tert-butyl dicarbonate are added to a solution of 3 g of N-[3-(methylsulfonylmethyl)phenyl]N-methylamine in 80 cm³ of dichloromethane. After stirring for 20 hours at 20° C., the reaction mixture is supplemented with 100 cm³ of water and then separated after settling. The organic phase is dried over magnesium sulfate, filtered and then concentrated to dryness under reduced pressure (2.7 kPa). The residue is chromatographed on a silica gel column (particle size 0.04-0.06 mm, diameter 4 cm and weight of silica 300 g), eluting under a nitrogen pressure of 0.5 bar with a mixture of ethyl acetate and cyclohexane (45/55 by volume) and collecting 100-cm³ fractions. Fractions 11 to 16 are combined and concentrated to dryness under reduced pressure (2.7 kPa). 3.8 g of N-[3-(methyl-sulfonylmethyl)phenyl]-N-methylcarbamic acid tert-butyl ester are obtained in the form of a gum which crystallizes.

N-[3-(Methylsulfonylmethyl)phenyl]N-methylamine may be obtained by carrying out the procedure in the following manner: a mixture of 9.65 cm³ of formic acid and 19.63 cm³ of acetic anhydride is heated at 50° C. for 3 hours under argon, and then the solution obtained is allowed to return to room temperature. 40 cm³ of tetrahydrofuran are poured in and the medium is cooled to −20° C. After stirring for 2 hours at −20° C., a solution of 14.8 g of 3-(methylsulfonylmethyl)phenylamine is poured in while the temperature is maintained. After stirring for 2 hours at −20° C., and then for 48 hours at 20° C., the mixture is filtered, the solid is drained and then washed with three times 50 cm³ of diisopropyl ether and dried under reduced pressure (2.7 kPa). A solid A is obtained. The filtrate is concentrated to half the volume, the resulting suspension is filtered, the solid is drained, washed with diisopropyl ether and dried. A solid B is obtained. The two solids A and B are combined and taken up in 375 cm³ of tetrahydrofuran and the mixture, cooled to 0° C., is supplemented, over 20 minutes, with 80 cm³ of a 2 M solution of borane-dimethyl sulfide complex in tetrahydrofuran and then heated at reflux temperature for 3 hours. The reaction mixture, cooled to +5° C., is supplemented over 20 minutes with 60 cm³ of methanol, stirred for 1 hour at room temperature and then supplemented with gaseous hydrochloric acid to a pH of 1. The mixture is heated under reflux for one hour and then supplemented with 300 cm³ of water and with a 3 N solution of sodium hydroxide to pH 8. The resulting mixture is extracted with 500 cm³ of ethyl acetate, the organic phase is washed successively with a saturated aqueous sodium hydrogen carbonate solution, and with brine, and is then dried over magnesium sulfate and concentrated to dryness under reduced pressure (2.7 kPa). The residue is taken up in 100 cm³ of 4 N sulfuric acid, the solution obtained is washed with 100 cm³ of ethyl acetate, then alkalinized to pH 8 with 3 N sodium hydroxide and with a saturated aqueous sodium carbonate solution and is then extracted with twice 75 cm³ of ethyl acetate. The combined extracts are dried over magnesium sulfate and concentrated to dryness under reduced pressure (2.7 kPa). 8.98 g of N-[3-(methylsulfonylmethyl)phenyl]N-methylamine are obtained in the form of a pink solid.

3-(Methylsulfonylmethyl)phenylamine may be prepared by carrying out the procedure in the following manner: a suspension of 23.7 g of 1-(methylsulfonyl-methyl)-3-nitrobenzene in 150 cm³ of methanol and 65 cm³ of 36% hydrochloric acid is heated to reflux temperature and then 18.5 g of iron are carefully added over 10 minutes, in small fractions. After heating under reflux for 4 hours and then stirring at room temperature for 20 hours, the reaction mixture is supplemented with 5 g of iron and then again heated under reflux for one hour and then at room temperature for 20 hours. The mixture is then alkalinized to pH 9 with aqueous ammonia and with sodium hydrogen carbonate, and then extracted with 3 times 250 cm³ of ethyl acetate, dried over magnesium sulfate and concentrated to dryness under reduced pressure (2.7 kPa). 14.9 g of 3-(methylsulfonylmethyl)phenyl-amine are obtained in the form of a beige powder.

1-(Methylsulfonylmethyl)-3-nitrobenzene may be prepared by heating under reflux 23.8 g of 3-nitro-benzyl chloride, 20 g of sodium methyl sulfinate and 250 cm³ of absolute ethanol. 23.74 g of 1-(methyl-sulfonylmethyl)-3-nitrobenzene are obtained in the form of a white powder.

EXAMPLE 13

(RS)-N-[3-({1-[Bis(4-chlorophenyl)methyl]-azetidin-3-yl}methylsulfonylmethyl)phenyl]-N-methylamine may be prepared by carrying out the procedure as described in Example 3 starting with 0.10 g of N-[3-({1-[bis(4-chlorophenyl)methyl]azetidin-3-yl}methylsulfonylmethylene)phenyl]-N-methylamine, 1.5 cm³ of anhydrous methanol, 1.5 cm³ of anhydrous dichloromethane and 45 mg of sodium borohydride, with stirring for 20 hours at 20° C. and then for 5 hours at 50° C. The crude product is chromatographed on a silica gel column (particle size 0.040-0.063 mm, height 10 cm, diameter 1 cm), eluting under an argon pressure of 0.8 bar with a mixture of cyclohexane and ethyl acetate (80/20, and then 60/40 by volume) and collecting 5-cm³ fractions. Fractions 20 to 26 are combined and concentrated to dryness under reduced pressure (2.7 kPa), the residue is stirred with 5 cm³ of pentane, the solid is filtered, drained and dried. 20 mg of (RS)-N-[3-({1-[bis(4-chlorophenyl)methyl]azetidin-3-yl}methylsulfonylmethyl)phenyl]-N-methylamine are obtained in the form of a white powder [$^1$H NMR spectrum (300 MHz, CDCl$_3$, δ in ppm): from 2.50 to 2.65 (mt: 1H); 2.60 (s: 3H); 2.82 (d, J=5 Hz: 3H); 3.18 (mt: 2H); from 3.35 to 3.50 (mt: 1H); 3.64 (broad t, J=7.5 Hz: 1H); 3.80 (mt: 1H); 4.18 (d, J=11.5 Hz 1H); 4.24 (s: 1H); from 6.50 to 6.70 (mt: 3H); from 7.10 to 7.35 (mt: 9H].

N-[3-({1-[Bis(4-chlorophenyl)methyl]azetidin-3-yl}methylsulfonylmethylene)phenyl]-N-methylamine may be prepared by carrying out the procedure in the following manner: 2.7 g of 1-[bis(4-chlorophenyl)methyl]-3-{[3-(N-tertbutyloxycarbonyl-N-methylamino)phenyl]methylsulfonylmethylene}azetidine in 30 cm³ of dioxane and 30 cm³ of a 4.7 N solution of hydrochloric dioxane are stirred for 20 hours. The reaction medium is evaporated to dryness under reduced pressure (2.7 kPa), taken up in 50 cm³ of water and 50 cm³ of ethyl acetate, stirred and cautiously neutralized with a saturated aqueous sodium bicarbonate solution. The organic phase is separated, dried over magnesium sulfate, treated with animal charcoal and then concentrated under reduced pressure (2.7 kPa) to a volume of about 25 cm³, then filtered and concentrated to dryness under reduced pressure. 1.3 g of N-[3-({1-[bis(4-chlorophenyl)methyl]azetidin-3-yl}methylsulfonylmethylene)phenyl]-N-methylamine are obtained in the form of white crystals melting at 228° C.

EXAMPLE 14

(RS)-1-[Bis(4-chlorophenyl)methyl]-3-[(3,5-bis-trifluoromethylphenyl)methylsulfonylmethyl]azetidine may be prepared by carrying out the procedure as described in Example 3, starting with 0.10 g of 1-[bis(4-chlorophenyl)methyl]-3-[(3,5-bis-trifluoro-methylphenyl)methylsulfonylmethylene]azetidine, 1.5 cm³ of anhydrous methanol, 1.5 cm³ of anhydrous dichloromethane and 15 mg of sodium borohydride, with stirring for 3 hours at 20° C. The crude product is stirred with 5 cm³ of pentane, the solid is filtered, drained and dried. 82 mg of (RS)-1-[bis(4-chloro-phenyl) methyl]-3-[(3,5-bis-trifluoromethylphenyl)-methylsulfonyl-methyl]azetidine are obtained in the form of a white powder [$^1$H NMR spectrum (400 MHz, (CD$_3$)$_2$SO d6, δ in ppm): 2.84 (s: 3H); 3.08 (mt: 2H); from 3.25 to 3.40 (mt: 1H); from 3.45 to 3.65 (mt: 2H); 4.45 (s: 1H); 5.13 (d, J=10.5 Hz: 1H); from 7.25 to 7.50 (mt: 8H); 8.11 (broad s: 2H); 8.15 (broad s 1H)].

1-[Bis(4-chlorophenyl)methyl]-3-[(3,5-bis-trifluoromethylphenyl)methylsulfonylmethylene]azetidine may be prepared by carrying out the procedure in the following manner: 0.96 g of crushed sodium hydroxide is added in fractions to a solution of 3.16 g of 3-acetoxy-1-[bis(4-chlorophenyl)methyl]-3-{[3,5-bis(trifluoromethyl)phenyl]methylsulfonylmethyl-(RS)}-azetidine in 40 cm³ of dioxane. After stirring for 1 hour at room temperature, the reaction mixture is supplemented with 200 cm³ of ethyl acetate, 200 cm³ of water and is then separated after settling. The organic phase is washed with twice 80 cm³ of water, then with 80 cm³ of brine, dried over magnesium sulfate, then filtered and concentrated to dryness under reduced pressure (2.7 kPa). The residue is chromatographed on a silica gel column (particle size 0.040-0.063 mm, height 14.5 cm, diameter 4.8 cm), eluting under an argon pressure of 0.5 bar with a mixture of cyclohexane and ethyl acetate (85/15 by volume) and collecting 40-cm³ fractions. Fractions 8 to 15 are combined and concentrated to dryness under reduced pressure (2.7 kPa), 1.49 g of 1-[bis(4-chlorophenyl)methyl]-3-{[(3,5-bis-trifluoromethylphenyl] methylsulfonyl-methylene}azetidine are obtained in the form of a white foam.

3-Acetoxy-1-[bis(4-chlorophenyl)methyl]-3-{[3,5-bis (trifluoromethyl)phenyl]methylsulfonylmethyl-(RS)}-azetidine may be prepared by carrying out the procedure in the following manner: 4.1 cm³ of a 1.6 N solution of n-butyl-lithium in hexane are poured dropwise, under argon, into a solution, cooled to −78° C., of 2.0 g of [3,5-bis(trifluoromethyl)benzyl]-methyl sulfone in 35 cm³ of tetrahydrofuran. After stirring for one hour at −70° C., a solution of 2.0 g of 1-[bis(4-chlorophenyl)methyl]azetidin-3-one in 35 cm³ of tetrahydrofuran is added dropwise. After stirring for 2 hours at −78° C., a solution of 0.7 cm³ of acetyl chloride in 5 cm³ of anhydrous dietheyl ether is poured in and then the mixture is allowed to return to room temperature. After stirring for 2 hours and 30 minutes, the reaction mixture is supplemented with 100 cm³ of water and separated after settling. The organic phase is washed with 100 cm³ of water, then with 100 cm³ of brine and is then dried over magnesium sulfate and concentrated to dryness under reduced pressure (2.7 kPa). The residue is chromatographed on a silica gel column (particle size 0.04-0.06 mm, diameter 5.6 cm, height 16 cm), eluting under an argon pressure of 0.5 bar with a mixture of ethyl acetate and cyclohexane (10/90 and then 40/60 by volume) and collecting 100-cm³ fractions. Fractions 37 to 52 are combined and concentrated to dryness under reduced pressure (2.7 kPa). 3.56 g of 3-acetoxy-1-[bis(4-chlorophenyl) methyl]-3-{[3,5-bis(trifluoromethyl)-phenyl]methylsulfonylmethyl-(RS)}-azetidine are obtained in the form of a white foam.

[3,5-Bis(trifluoromethyl)benzyl]methyl sulfone may be prepared by heating under reflux 1.8 g of 3,5-bis(trifluoromethyl)benzyl chloride, 50 cm³ of absolute ethanol and 1.22 g of sodium methyl sulfinate. 1.86 g of [3,5-bis(trifluoromethyl)benzyl]methyl sulfone are obtained in the form of a white solid.

EXAMPLE 15

N-[4-((4-Chlorophenyl)-{3-[(3,5-difluorophenyl)methylsulfonylmethyl-(RS)]azetidin-1-yl}methyl-(RS))benzyl]-N,N-dimethylamine, a mixture of two diastereoisomers, may be prepared by carrying out the procedure as described in Example 3, starting with 0.10 g of N-[4-((4-chlorophenyl)-{3-[(3,5-difluorophenyl)methylsulfonylmethylene]azetidin-1-yl}methyl-(RS)-benzyl]-N,N-dimethylamine, 1.5 cm³ of anhydrous methanol, 1.5 cm³ of anhydrous dichloromethane and 45 mg of sodium borohydride, with stirring for 16 hours at 20° C. and then for 16 hours at 50° C. The crude product is chromatographed on a silica gel column (particle size 0.040-0.063 mm, height 22 cm, diameter 1 cm), eluting under an argon pressure of 0.8 bar with a mixture of ethyl acetate and methanol (97/3 by volume) and collecting 20-cm³ fractions. Fractions 17 to 25 are combined and concentrated to dryness under reduced pressure (2.7 kPa), the residue is stirred with 5 cm³ of pentane, the solid is filtered, drained and dried. 6 mg of N-[4-((4-chlorophenyl)-{3-[(3,5-difluorophenyl)methylsulfonylmethyl-(RS)]azetidin-1-yl}methyl-(RS))benzyl]-N,N-dimethylamine, a mixture of two diastereoisomers, are obtained in the form of a white powder [$^1$H NMR spectrum (300 MHz, CDCl$_3$, δ in ppm): 2.20 (s: 6H); 2.53 (t, J=7 Hz: 1H); 2.65 (s: 3H); from 3.10 to 3.25 (mt: 2H); from 3.30 to 3.45 (mt: 1H); 3.35 (broad s: 2H); 3.63 (broad t, J=7 Hz: 1H); 4.24 (s: 1H); 4.25 (d, J=11 Hz: 1H); 6.82 (tt, J=9 and 2 Hz: 1H); 6.94 (mt: 2H); from 7.15 to 7.35 (mt: 8H)].

N-[4-((4-Chlorophenyl)-{3-[(3,5-difluoro-phenyl)methylsulfonylmethylene]azetidin-1-yl}methyl-(RS))benzyl]-N,N-dimethylamine may be prepared by carrying out the procedure in the following manner: 1.0 g of (RS)-4-((4-chlorophenyl)-{3-[(3,5-difluorophenyl) methylsulfonylmethylene]azetidin-1-yl}methyl) benzaldehyde is added, under argon, to a solution of 0.93 cm³ of a 2 M solution of dimethylamine in methanol in 30 cm³ of anhydrous 1,2-dichloroethane. After stirring for 30 minutes at room temperature, 0.9 g of sodium triacetoxyborohydride is added in small fractions. After stirring for 48 hours, the reaction mixture is supplemented with 2.65 cm³ of 1 N sodium hydroxide, 100 cm³ of water and 100 cm³ of dichloromethane and is then separated after settling. The organic phase is washed with twice 80 cm³ of water and with 80 cm³ of brine and is then dried over magnesium sulfate and concentrated to dryness under reduced pressure (2.7 kPa). The residue is chromatographed on a silica gel column (particle size 0.04-0.06 mm, diameter 4 cm, height 17.5 cm), eluting under an argon pressure of 0.5 bar with a mixture of ethyl acetate and cyclohexane (30/70 by volume) and collecting 40-cm³ fractions. Fractions 48 to 53 are combined and concentrated to dryness under reduced pressure (2.7 kPa). 0.46 g of N-[4-((4-chlorophenyl)-{3-[(3,5-difluorophenyl)methylsulfonylmethylene]-azetidin-1-yl}methyl-(RS))benzyl]-N,N-dimethylamine is obtained in the form of a white solid.

(RS)-4-((4-Chlorophenyl)-{3-[(3,5-difluoro-phenyl)methylsulfonylmethylene]azetidin-1-yl}methyl)-benzaldehyde may be prepared by carrying out the procedure in the following manner: 75.6 cm³ of 5 N hydrochloric acid are added to a solution of 18.9 g of 1-[(4-chlorophenyl)-(4-[1,3]dioxolan-2-ylphenyl)-methyl]-(RS)-3-[(3,5-difluorophenyl)methylsulfonyl-methylene]azetidine in 80 cm³ of tetrahydrofuran. After 3 hours at room temperature, the mixture is taken up in dichloromethane and distilled water and then brought to pH 14 by addition of 30% sodium hydroxide and separated after settling. The organic phase is washed twice with 100 m³ of water and then 100 cm³ of a saturated aqueous sodium chloride solution, dried over magnesium sulfate, filtered and concentrated to dryness under reduced pressure (2.7 kPa). 16 g of (RS)-4-((4-chlorophenyl)-{3-[(3,5-difluorophenyl)methyl-sulfonylmethylene]-azetidin-1-yl}methyl)benzaldehyde are obtained in the form of a white foam.

1-[(4-Chlorophenyl)-(4-(1,3]dioxolan-2-ylphenyl)methyl]-(RS)-3-[(3,5-difluorophenyl)methyl-sulfonylmethylene]azetidine may be prepared according to the following method: 13.0 cm³ of 1,8-diazabicyclo-[5-4-0]undec-7-ene are added dropwise to a solution of 34.45 g of the mixture of the two diastereoisomers of 1-[(4-chlorophenyl)-(4-[1,3]dioxolan-2-ylphenyl)methyl-(RS)]-3-[(3,5-difluorophenyl) methylsulfonylmethyl-(RS)]azetidin-3-yl acetate in 400 cm³ of tetrahydrofuran under argon at 0° C., and after the usual treatment, the product is chromatographed on a silica gel column (particle size 0.04-0.06 mm, diameter 10.2 cm, height 23 cm), eluting under an argon pressure of 0.5 bar with a mixture of ethyl acetate and cyclohexane (20/80 by volume) and collecting 250-cm³ fractions; 16.6 g of 1-[(4-chlorophenyl)-(4-[1,3]dioxolan-2-ylphenyl)methyl]-(RS)-3-[(3,5-difluorophenyl)-methylsulfonylmethylene]azetidine are obtained in the form of a white solid.

The mixture of the two diastereoisomers 1-[(4-chlorophenyl)-(4-[1,3]dioxolan-2-ylphenyl)methyl-(RS)]-3-[(3,5-difluorophenyl)methylsulfonylmethyl-(RS)]azetidin-3-yl acetate diastereoisomers may be obtained in the following manner: by carrying out the procedure according to Example 1 (method 2), starting with 11.6 g of (3,5-difluorobenzyl) methyl sulfone, 35.1 cm³ of a 1.6 N solution of n-butyllithium in hexane, 19.3 g of 1-{(4-chlorophenyl)[4-([1,3]dioxolan-2-yl)phenyl]methyl-(RS)}azetidin-3-one and 8.8 cm³ of acetyl chloride in 500 cm³ of tetrahydrofuran, 37.8 g of the mixture of the two 1-[(4-chlorophenyl)-(4-[1,3]dioxolan-2-ylphenyl)methyl-(RS)]-3-[(3,5-difluorophenyl)methylsulfonylmethyl-(RS)]azetidin-3-yl acetate diastereoisomers are obtained in the form of a white foam.

1-{(4-Chlorophenyl)[4-([1,3]dioxolan-2-yl)-phenyl]methyl-(RS)}azetidin-3-one may be prepared in the following manner: 46 cm³ of triethylamine are added, at room temperature, to a solution of 28.32 g of 1-{(4-chlorophenyl)[4-([1,3] dioxolan-2-yl)phenyl]methyl-(RS)}azetidin-3-ol in 200 cm³ of dimethyl sulfoxide, followed by the dropwise addition of a solution of 34 g of sulfur trioxide-pyridine complex in 100 cm³ of dimethyl sulfoxide. After 0.25 hour at room temperature, the reaction mixture is poured over ice, extracted with ethyl acetate, washed with 3 times 400 cm³ of water and then with 400 cm³ of a saturated sodium chloride solution, dried over magnesium sulfate, filtered and concentrated to dryness under reduced pressure (2.7 kPa). The residue obtained is chromatographed on a silica gel column (particle size 0.04-0.06 mm, diameter 9.2 cm, height 21 cm) under an argon pressure of 0.5 bar with a mixture of ethyl acetate and cyclohexane (20/80 by volume) as eluent and collecting 250-cm³ fractions. Fractions 9 to 18 are combined and then concentrated to dryness under reduced pressure (2.7 kPa). 20.4 g of 1-{(4-chlorophenyl)[4-([1,3]dioxolan-2-yl)phenyl]methyl-(RS)}azetidin-3-one are obtained in the form of a yellow oil.

1-{(4-Chlorophenyl)[4-([1,3]dioxolan-2-yl)phenyl]methyl-(RS)}azetidin-3-ol may be prepared as described in Example 3, starting with 35.0 g of {(4-chlorophenyl)[4-(1,3-dioxolan-2-yl)phenyl]methyl}amine, 8.3 g of epibromohydrin, 5.1 g of sodium hydrogen carbonate and 400 cm³ of ethanol. 30.3 g of 1-{(4-chlorophenyl)[4-([1,3]dioxolan-2-yl)phenyl]methyl-(RS)}azetidin-3-ol are isolated.

{(4-Chlorophenyl)[4-([1,3]-dioxolan-2-yl)phenyl]methyl-(RS)}amine hydrochloride may be prepared according to the method described by GRISAR M. et al., J. Med Chem., 885 (1973) starting with 67.2 g of 4-([1,3]-dioxolan-2-yl) benzonitrile, 88.2 g of 1-bromo-4-chlorobenzene, 11 g of magnesium and 600 cm³ of ethyl ether. 42.3 g of {(4-chlorophenyl)[4-([1,3]-dioxolan-2-yl)phenyl]methyl-(RS) }amine are obtained in the form of a yellow oil.

EXAMPLE 16

1-[(4-Chlorophenyl)(thien-2-yl)methyl-(RS)]-3-[(3,5-difluorophenyl)methylsulfonylmethyl-(RS)]azetidine, a mixture of two diastereoisomers, may be prepared by carrying out the procedure as described in Example 3, starting with 0.10 g of 1-[(4-chlorophenyl)(thien-2-yl)methyl-(RS)]-3-[(3,5-difluorophenyl)methylsulfonylmethylene]azetidine, 1.5 cm³ of anhydrous methanol, 1.5 cm³ of anhydrous dichloromethane and 45 mg of sodium borohydride, with stirring for 16 hours at 20° C. and then for 16 hours at 50° C. The crude product is chromatographed on a silica gel column (particle size 0.040-0.063 mm, height 25 cm, diameter 1 cm), eluting under an argon pressure of 1 bar with a mixture of cyclohexane and ethyl acetate (90/10 by volume), and collecting 20-cm³ fractions. Fractions 37 to 42 are combined and concentrated to dryness under reduced pressure (2.7 kPa), the residue is stirred with 5 cm³ of pentane, the solid is filtered, drained and dried. 8 mg of 1-[(4-chlorophenyl)(thien-2-yl)methyl-(RS)]-3-[(3,5-difluorophenyl)-methylsulfonylmethyl-(RS)]azetidine, a mixture of two diastereoisomers, are obtained in the form of a white powder [$^1$H NMR spectrum (300 MHz, CDCl$_3$, δ in ppm). A mixture of diastereoisomers is observed, from 2.50 to 2.70 (mt: 1H); 2.66 and 2.68 (2s: 3H in total); from 3.15 to 3.80 (mt: 4H); from 4.20 to 4.30 (mt: 1H); 4.31 and 4.57 (2s: 1H in total); from 6.80 to 7.00 and from 7.10 to 7.40 (mts: 10H in total)].

1-[(4-Chlorophenyl)(thien-2-yl)methyl-(RS)]-3-[(3,5-difluorophenyl)methylsulfonylmethylene]-azetidine may be prepared by carrying out the procedure as described in Example 6, starting with 0.52 g of a mixture of the two 1-[(4-chlorophenyl)(thien-2-yl)-methyl-(RS)]-3-[(3,5-difluorophenyl)methylsulfonyl-methyl-(RS)]azetidin-3-ol diastereoisomers, 0.14 cm³ of methylsulfonyl chloride and 0.49 g of 4-dimethylamino-pyridine. After chromatography on a silica gel column (particle size 0.06-0.200 mm, diameter 2.4 cm, height 20 cm), eluting under an argon pressure of 0.5 bar with a mixture of ethyl acetate and cyclohexane (20/80 by volume) and collecting 30-cm³ fractions, 0.32 g of (RS)-1-[(4-chlorophenyl(thien-2-yl)methyl]-3-[(3,5-difluorophenyl)methylsulfonylmethylene]azetidine is obtained in the form of a white solid melting at 176° C.

The mixture of the two 1-[(4-chlorophenyl)-(thien-2-yl) methyl-(RS)]-3-[(3,5-difluorophenyl)methyl-sulfonylmethyl-(RS)]azetidin-3-ol diastereoisomers may be prepared by carrying out the procedure as described in Example O, starting with 1.60 cm³ of 1.6 N n-butyllithium in solution in hexane, 0.83 g of (3,5-difluorobenzyl)methyl sulfone and 1.06 g of 1-[(4-chlorophenyl)(thien-2-yl)methyl-(RS)]azetidin-3-one. After purification on a silica gel column (particle size 0.06-0.200 mm, diameter 2.8 cm, height 30 cm), eluting under an argon pressure of 0.5 bar with a mixture of ethyl acetate and cyclohexane (25/75 by volume) and collecting 40-cm³ fractions, 0.55 g of the mixture of the 1-[(4-chlorophenyl)(thien-2-yl)methyl-(RS)]-3-[(3,5-difluorophenyl) methylsulfonylmethyl-(RS)]azetidin-3-ol diastereoisomers is obtained in the form of an off-white solid.

1-[(4-Chlorophenyl)(thien-2-yl)methyl-(RS)]azetidin-3-one may be prepared by carrying out the procedure as described in Example 1 (method 2), starting with 1.83 cm³ of oxalyl chloride, 20 cm³ of dichloromethane, 3.04 cm³ of dimethyl sulfoxide, 5.2 g of 1-[(4-chlorophenyl)(thien-2-yl)methyl-(RS)]azetidin-3-ol, 80 cm³ of dichloromethane and 9.12 cm³ of triethylamine. 3.3 g of 1-[(4-chlorophenyl)(thien-2-yl)methyl-(RS)]azetidin-3-one are obtained in the form of a yellow oil which crystallizes at room temperature.

1-[(4-Chlorophenyl)(thien-2-yl)methyl-(RS)]azetidin-3-ol may be prepared by carrying out a procedure in the following manner: 4.12 g of sodium bicarbonate are added to a solution of 11.0 g of [(4-chlorophenyl)(thien-2-yl)methyl-(RS)]amine in 80 cm³ of ethanol. The mixture, heated to 65° C., is supplemented with 4.03 cm³ of epibromohydrin. After stirring for 20 hours at 65° C., the crude mixture is filtered and the filtrate concentrated to dryness under reduced pressure (2.7 kPa). The residue is chromatographed on a silica gel column (particle size 0.06-0.200 mm, diameter 3.6 cm, height 32 cm), eluting under an argon pressure of 0.5 bar with a mixture of ethyl acetate and cyclohexane (25/75 by volume) and collecting 60-cm³ fractions. 6.3 g of 1-[(4-chlorophenyl)(thien-2-yl)methyl-(RS)]azetidin-3-ol are obtained in the form of a pale yellow oil.

[(4-Chlorophenyl)(thien-2-yl)methyl-(RS)]amine may be prepared in the following manner: a solution of 10.92 g of 2-thiophenecarbonitrile in 80 cm³ of diethyl ether is poured slowly into a suspension, cooled to 10° C. of 4-chlorophenylmagnesium bromide (prepared from 19.15 g of 4-bromochlorobenzene and 2.43 g of magnesium) in 120 cm³ of anhydrous ethyl ether. After refluxing for one hour, the mixture is cooled to 10° C., supplemented slowly with 40 cm³ of methanol and then filtered on supercel. 4.54 g of sodium borohydride are added under argon and in small fractions over 15 minutes and then the reaction medium is stirred for 20 hours at 20° C. The mixture obtained is diluted with ethyl acetate and then washed with water. The organic phase is dried over magnesium sulfate, concentrated to dryness at 50° C. under reduced pressure (2.7 kPa). The residue is chromatographed on a silica gel column (particle size 0.06-0.200 mm, diameter 5 cm, height 42 cm), eluting under an argon pressure of 0.5 bar with a mixture of ethyl acetate and cyclohexane (4/6 by volume) and collecting 100-cm³ fractions. Fractions 6 to 12, concentrated to dryness, correspond to 13 g of imine in the form of a yellow oil which is taken up in 100 cm³ of methanol. The solution obtained is supplemented with 2.4 g of sodium borohydride and stirred for one hour at 5° C. The mixture obtained is diluted with ethyl acetate and then washed with water. The organic phase is dried over magnesium sulfate, concentrated to dryness at 50° C. under reduced pressure (2.7 kPa). The residue is chromatographed on a silica gel column (particle size 0.06-0.200 mm, diameter 3.2 cm, height 40 cm), eluting under an argon pressure of 0.5 bar with a mixture of ethyl acetate and cyclohexane (4/6 by volume) and collecting 60-cm³ fractions. 11.0 g of [(4-chlorophenyl)(thien-2-yl)methyl-(RS)]amine are obtained in the form of a yellow oil.

EXAMPLE 17

(RS)-[3-({1-[Bis(4-chlorophenyl)methyl]-azetidin-3-yl}methylsulfonylmethyl)phenyl]methanol may be prepared by carrying out the procedure as described in Example 3, starting with 0.050 g of [3-({1-[bis(4-chlorophenyl)methyl]azetidin-3-yl}methylsulfonyl-methylene)phenyl]methanol, 1.0 cm³ of anhydrous methanol, 1.0 cm³ of anhydrous dichloromethane and 20 mg of sodium borohydride, with stirring for 3 hours at 20° C. The crude product is chromatographed on a silica gel column (particle size 0.040-0.063 mm, height 20 cm, diameter 1 cm), eluting under an argon pressure of 0.8 bar with a mixture of cyclohexane and ethyl acetate (90/10 by volume) and collecting 10-cm³ fractions. Fractions 30 to 38 are combined and concentrated to dryness under reduced pressure (2.7 kPa), the residue is stirred with 5 cm³ of pentane, the solid is filtered, drained and dried. 13 mg of (RS)-[3-({1-[bis(4-chlorophenyl)methyl]azetidin-3-yl}methylsulfonylmethyl)phenyl]methanol are obtained in the form of a white powder [¹H NMR spectrum (300 MHz, CDCl₃, δ in ppm): 1.75 (t, J=6 Hz: 1H); 2.52 (t, J=7.5 Hz: 1H); 2.59 (s: 3H); 3.17 (broad t, J=7.5 Hz 2H); 3.48 (mt: 1H); 3.65 (mt: 1H); 4.23 (s: 1H); 4.28 (d, J=11.5 Hz: 1H); 4.70 (d, J=6 Hz: 2H); from 7.15 to 7.40 (mt: 12H)].

[3-({1-[Bis(4-chlorophenyl)methyl]azetidin-3-yl}methylsulfonylmethylene)phenyl]methanol may be prepared by carrying out the procedure in the following manner: 17 cm³ of a 1 M solution of tetrabutylammonium fluoride in tetrahydrofuran are poured into a solution, cooled to +5° C., of 5.1 g of 1-[bis(4-chlorophenyl)-methyl]-3-{[3-(tertbutyldimethylsilyloxymethyl)phenyl]-methylsulfonyl-methylene}azetidine in 51 cm³ of tetrahydrofuran. After stirring for 20 minutes at cooled temperature and then for 3 hours at 20° C., the reaction mixture is poured into a mixture of 200 cm³ of water and 100 cm³ of ethyl acetate and then separated after settling. The organic phase is washed with water, dried over magnesium sulfate and then filtered and concentrated to dryness under reduced pressure (2.7 kPa). The residue obtained is purified by chromatography on a silica gel column (particle size 0.04-0.06 mm, diameter 2 cm, height 30 cm), eluting under a nitrogen pressure of 0.5 bar with a dichloromethane and ethanol (97/3 by volume) mixture and collecting 100-cm³ fractions. Fractions 10 to 14 are combined and concentrated to dryness under reduced pressure (2.7 kPa). The yellow solid obtained is taken up in 2 cm³ of dichloromethane and 10 cm³ of ethyl acetate and then filtered on sintered glass and washed with 2 cm³ of ethyl acetate. 1.6 g of [3-({1-[bis(4-chlorophenyl)methyl]azetidin-3-yl}methylsulfonyl-methylene)phenyl]methanol are obtained in the form of a white solid melting at 214° C.

1-[Bis(4-chlorophenyl)methyl]-3-{[3-(tert-butyldimethylsilyloxymethyl)phenyl]methylsulfonyl-methylene}azetidine may be prepared by carrying out the operation according to the procedure of Example 1, starting with 10.8 g of 1-(bis(4-chlorophenyl)methyl]-3-{[3-(tert-butyldimethylsilyloxymethyl)phenyl]-methylsulfonylmethyl-(RS)}azetidin-3-ol, 2 cm³ of methylsulfonyl chloride and 8.5 g of 4-dimethylamino-pyridine, the residue obtained is purified by chromatography on a silica gel column (particle size 0.04-0.06 mm, diameter 4 cm, height 40 cm) under a nitrogen pressure of 0.5 bar with dichloromethane as eluent and collecting 100-cm³ fractions. Fractions 12 to 29 are combined and concentrated to dryness under reduced pressure (2.7 kPa). 5.2 g of 1-[bis(4-chloro-phenyl)methyl]-3-{[3-(tert-butyldimethylsilyloxy-methyl)phenyl]methylsulfonyl-methylene}azetidine are obtained in the form of a gum.

1-[Bis(4-chlorophenyl)methyl]-3-{[3-(tert-butyldimethylsilyloxymethyl)phenyl]methylsulfonyl-methyl-(RS)}azetidin-3-ol may be prepared by carrying out the operation according to the procedure of Example 5, starting with 5.8 g of tert-butyl-(3-methylsulfonyl-methylbenzyloxy)dimethyl-silane and 5.6 g of 1-[bis(4-chlorophenyl)methyl]azetidin-3-one, 10.8 g of 1-[bis(4-chlorophenyl)methyl]-3-{[3-(tert-butyldimethylsilyloxy-methyl)phenyl]methylsulfonylmethyl-(RS)}azetidin-3-ol are obtained in the form of a gum.

tert-Butyl-(3-methylsulfonylmethylbenzyloxy)-dimethylsilane may be prepared by carrying out the procedure in the following manner: 4.87 g of imidazole are added to a solution of 5.73 g of (3-methylsulfonyl-methylphenyl)methanol in 50 cm³ of N,N-dimethylformamide, followed by 10.3 cm³ of tert-butylchlorodimethyl-silane. After stirring for 20 hours at room temperature, the reaction mixture is concentrated to dryness under reduced pressure (2.7 kPa). The residue is chromatographed on a silica gel column (particle size 0.06-0.200 mm, diameter 3.5 cm, weight of silica 100 g), eluting under a nitrogen pressure of 0.5 bar with dichloromethane, and collecting 100-cm³ fractions. Fractions 2 to 7 are combined, concentrated to dryness under reduced pressure (2.7 kPa). 5.8 g of an oil are obtained, which oil crystallizes at room temperature (m.p.=75° C.)

(3-Methylsulfonylmethylphenyl)methanol may be prepared by carrying out the procedure in the following manner: a mixture of 26 g of 3-(methylsulfonylmethyl)-benzoic acid and 4.6 g of lithium aluminum hydride in 600 cm³ of tetrahydrofuran is stirred for 18 hours at a temperature close to 20° C. The solution is cooled to 0° C. and then 15 cm³ of ethyl acetate, 30 cm³ of water, 5 cm³ of a 15% aqueous solution of sodium hydroxide and finally 30 cm³ of water are added-successively. The mixture is filtered on celite and the filtrate taken up in 600 cm³ of ethyl acetate. The organic phase is taken up in 500 cm³ of water and then 200 cm³ of a saturated aqueous sodium chloride solution, separated after settling, dried over anhydrous magnesium sulfate, filtered and concentrated to dryness under reduced pressure (2.7 kPa). 10.4 g of (3-methylsulfonyl-methylphenyl)methanol are obtained in the form of a gum.

3-(Methylsulfonylmethyl)benzoic acid may be prepared in the following manner: by carrying out the operation according to the procedure of Example 14, starting with 23.3 g of 3-chloromethylbenzoic acid. 23.3 g of sodium methane sulfinate, 26 g of 3-(methylsulfonylmethyl) benzoic acid are obtained in the form of a white solid melting at 210° C.

EXAMPLE 18

1-[Bis(4-chlorophenyl)methyl]-3-(phenylsulfonylmethyl) azetidine may be prepared by carrying out the procedure in the following manner: 13 mg of sodium borohydride are added, under argon, to a solution of 0.15 g of 1-[bis(4-chlorophenyl)methyl)]-3-(phenylsulfonylmethylene)azetidine in 3 cm³ of anhydrous ethanol and 3.5 cm³ of anhydrous dichloromethane. After stirring for 1 hour and 45 minutes, 14 mg of sodium borohydride are again added and then the mixture is kept stirring for 20 hours at 20° C. The reaction mixture is then heated to 50° C., supplemented with 9.5 mg of sodium borohydride and kept stirred for 2 hours and 30 minutes at 50° C. and then cooled to room temperature. 0.5 cm³ of water, 10 cm³ of dichloromethane and then 50 mg of magnesium sulfate are then added to the mixture, filtered and then evaporated to dryness under reduced pressure (2.7 kPa). The residue is chromatographed on a silica gel column (particle size 0.063-0.200 mm, height 15 cm, diameter 1 cm), eluting under an argon pressure of 0.5 bar with a mixture of cyclohexane and ethyl acetate (80/20 by volume) and collecting 5-cm³ fractions. Fractions 12 to 19 are combined and concentrated to dryness under reduced pressure (2.7 kPa). 29 mg of 1-[bis (4-chlorophenyl)methyl)]-3-(phenylsulfonylmethyl)azetidine are obtained in the form of a white solid [¹H NMR spectrum (300 MHz, CDCl₃, δ in ppm): from 2.75 to 8.90 (mt: 3H); 3.32 (mt: 2H); 3.37 (d, J=7 Hz: 2H); 4.22 (s: 1H); from 7.20 to 7.30 (mt: 8H); 7.57 (broad t, J=7.5 Hz: 2H); 7.67 (tt, J=7.5 and 1.5 Hz 1H); 7.88 (broad d, J=7.5 Hz: 2H)].

EXAMPLE 19

1-[Bis(4-chlorophenyl)methyl)]-3-(phenylsulfonylmethylene)azetidine may be prepared by carrying out the procedure in the following manner: 12 cm³ of a 1.6 M solution of n-butyllithium in hexane are poured, over 5 minutes, into a solution, cooled to −70° C., under argon, of 4.34 g of (phenylsulfonyl-methyl)trimethylsilane in 40 cm³ of dimethyl ether. After stirring the mixture for 30 minutes at −60° C., a solution of 1-[bis(4-chlorophenyl)methyl]azetidin-3-one in 30 cm³ of dimethyl ether [produced in the form of a base prepared by treating 7.35 g of 1-[bis(4-chloro-phenyl)methyl]azetidin-3-one hydrobromide dissolved in 30 cm³ of water, with 25 cm³ of 1 N sodium hydroxide and extracting the base obtained with 30 cm³ of diethyl ether, then drying and concentrating to dryness under reduced pressure (2.7 kPa)] is poured in over 10 minutes. After stirring for 45 minutes at −70° C. and then for 2 hours at 20° C., the reaction mixture is supplemented with 12 cm³ of a saturated aqueous ammonium chloride solution, 20 cm³ of water and then extracted with 12 40 cm³ of ethyl acetate. The combined organic phases are [lacuna] with 40 cm³ of water, dried over magnesium sulfate and then concentrated to dryness under reduced pressure (2.7 kPa). The oil obtained is chromatographed on a silica gel column (particle size 0.063-0.200 mm, height 40 cm, diameter 5 cm), eluting under an argon pressure of 0.5 bar with a mixture of cyclohexane and ethyl acetate (90/10 and then 85/15 by volume) and collecting 100-cm³ fractions. Fractions 10 to 16 are combined and concentrated to dryness under reduced pressure (2.7 kPa). The oil obtained is triturated in 10 cm³ of diethyl ether, the suspension filtered and the solid dried. 1.17 g of 1-[bis(4-chlorophenyl)methyl)]-3-(phenylsulfonylmethylene)-azetidine are obtained in the form of a white solid [¹H NMR spectrum (300 MHz, CDCl₃ d in ppm): 3.88 (mt: 2H); 4.29 (mt: 2H); 4.50 (s: 1H); 6.17 (mt: 1H); from 7.20 to 7.40 (mt 8H); 7.56 (broad t, J=7.5 Hz: 2H); 7.64 (tt, J=7.5 and 1.5 Hz: 1H); 7.87 (broad d, J=7.5 Hz: 2H)].

(Phenylsulfonylmethyl)trimethylsilane may be prepared by carrying out the procedure in the following manner: 13 cm³ of a 1.6 M solution of n-butyllithium in hexane are poured, with stirring under argon over 20 minutes, into a solution, cooled to −70° C., of 3 g of methyl phenyl sulfone in 40 cm³ of anhydrous tetrahydrofuran. After stirring for 30 minutes at −70° C., 2.66 cm³ of trimethylchlorosilane are added to the mixture, and the heating is stopped. After stirring for 4 hours at room temperature, the reaction mixture is supplemented with 30 cm³ of water and extracted with 30 cm³ of ethyl acetate. The organic phase is washed with 30 cm³ of water, dried over magnesium sulfate, filtered and then concentrated to dryness under reduced pressure (2.7 kPa). 4.34 g of (phenylsulfonylmethyl)-trimethylsilane are obtained in the form of a yellow liquid.

EXAMPLE 20

2-{1-[Bis(4-chlorophenyl)methyl]azetidin-3-ylmethylsulfonyl}pyridine may be prepared by carrying out the procedure in the following manner: 0.125 g of sodium borohydride is added to a solution of 0.25 g of 2-{1-[bis(4-chlorophenyl)methyl)]azetidin-3-ylidenemethylsulfonyl} pyridine in 20 cm³ of a 50/50 mixture of dichloromethane and ethanol. After stirring for 1 hour at 50° C., the reaction mixture is cooled to 20° C., supplemented with 20 cm³ of dichloromethane, 1 cm³ of water and 0.1 g of magnesium sulfate. The mixture is filtered and the filtrate is concentrated at 50° C. under reduced pressure (2.7 kPa). The residue is chromatographed on a silica gel column (particle size 0.040-0.063 mm, height 15 cm, diameter 1 cm), eluting under an argon pressure of 0.5 bar with a mixture of cyclohexane and ethyl acetate (40/60 by volume) and collecting 10-cm³ fractions. Fractions 5 to 10 are combined and concentrated to dryness under reduced pressure (2.7 kPa). 0.18 g of 2-{1-[bis(4-chlorophenyl)methyl]azetidin-3-ylmethylsulfonyl}-pyridine is obtained in the form of a white powder (¹H NMR spectrum (300 MHz, CDCl₃, δ in ppm): from 2.80 to 3.00 (mt: 3H); 3.34 (mt: 2H); 3.70 (d, J=7 Hz 2H); 4.25 (s: 1H); from 7.20 to 7.40 (mt: 8H); 7.57 (ddd, J=8-5 and 1 Hz: 1H); 7.97 (split t, J=8 and 1.5 Hz: 1H); 8.07 (broad d, J=8 Hz: 1H); 8.75 (broad d, J=5 Hz: 1H)].

2-{1-[Bis(4-chlorophenyl)methyl)]azetidin-3-ylidenemethylsulfonyl}pyridine may be prepared by carrying out the procedure in the following manner: 0.25 cm³ of methylsulfonyl chloride is added to a solution of 0.9 g of 1-[bis(4-chlorophenyl)methyl)]-3-(pyrid-2-ylsulfonylmethyl)azetidin-3-ol in 50 cm³ of dichloromethane, the mixture is stirred for 15 minutes and 0.9 g of 4-dimethylaminopyridine is added. After stirring for 3 hours at 20° C., 30 cm³ of water and 30 cm³ of dichloromethane are added to the mixture and then the organic phase is separated after settling, dried over magnesium sulfate, filtered and concentrated to dryness under reduced pressure (2.7 kPa). The residue is chromatographed on a silica gel column (particle size 0.04-0.063 mm, height 25 cm, diameter 2 cm), eluting under an argon pressure of 0.5 bar with a mixture of cyclohexane and ethyl acetate (40/60 by volume) and collecting 20-cm³ fractions. Fractions 4 to 8 are combined and concentrated to dryness under reduced pressure (2.7 kPa). 0.50 g of 2-{1-[bis(4-chlorophenyl)methyl)]azetidin-3-ylidenemethylsulfonyl}-pyridine is obtained in the form of a yellow powder.

1-[Bis(4-chlorophenyl)methyl)]-3-(pyrid-2-ylsulfonylmethyl)azetidin-3-ol may be prepared by carrying out the procedure in the following manner: 2.13 g of potassium tert-butoxide are added to a solution, cooled to −78° C. under argon, of 2.92 g of 1-[bis(4-chlorophenyl)methyl)]azetidin-3-one and 3 g of 2-methylsulfonylpyridine in 50 cm³ of tetrahydrofuran. After stirring for 3 hours at −78° C., the reaction mixture is allowed to return to 0° C. and then 50 cm³ of diethyl ether, 10 cm³ of water and 10 cm³ of a saturated aqueous ammonium chloride solution are added. The organic phase is separated after settling, dried over magnesium sulfate, filtered and concentrated to dryness under reduced pressure (2.7 kPa). The residue is chromatographed on a silica gel column (particle size 0.063-0.200 mm, height 30 cm, diameter 3 cm), eluting under an argon pressure of 0.5 bar, first with dichloromethane and then with a mixture of dichloromethane and methanol (97/3 by volume) and collecting 20-cm³ fractions. Fractions 8 to 15 are combined and concentrated to dryness under reduced pressure (2.7 kPa). A still impure brown oil is obtained which is chromatographed on a silica gel column (particle size 0.04-0.063 mm, height 20 cm, diameter 2 cm), eluting under an argon pressure of 0.5 bar, first with dichloromethane and then with a mixture of dichloromethane and methanol (97/3 by volume) and collecting 20-cm³ fractions. Fractions 5 to 25 are combined and concentrated to dryness and the residue obtained is again chromatographed on the same column and under the same conditions but eluting with dichloromethane. Fractions 12 to 20 are combined and concentrated to dryness under reduced pressure (2.7 kPa). 0.3 g of 1-[bis(4-chlorophenyl)methyl)]-3-(pyrid-2-ylsulfonylmethyl)azetidin-3-ol is obtained in the form of a white foam.

2-Methylsulfonylpyridine may be prepared by carrying out the procedure in the following manner: 0.25 cm³ of 100% acetic acid is added, with stirring under argon, to a solution of 20 g of sodium tungstate dihydrate in 10 cm³ of water, followed by 7.0 g of 2-methylsulfanylpyridine. This mixture is heated to 65° C., 10 cm³ of 30% hydrogen peroxide are slowly poured in over 15 minutes, then the mixture is stirred at 85° C. for 30 minutes and then cooled to +10° C. 1.0 cm³ of 32% aqueous ammonia and 5.0 cm³ of a 37.5% aqueous solution of sodium hydrogen sulfite are added to the medium, followed by 10 cm³ of water and 50 cm³ of dichloromethane. The mixture is separated after settling, the organic phase is dried over magnesium sulfate, filtered and concentrated to dryness under reduced pressure (2.7 kPa). The colorless oil obtained is disintegrated with 50 cm³ of petroleum ether and the insoluble gum is filtered and taken up in 30 cm³ of dichloromethane. The solution obtained is concentrated to dryness at 50° C. under reduced pressure (2.7 kPa). 3.5 g of 2-methylsulfonylpyridine are obtained in the form of a colorless oil.

2-Methylsulfanylpyridine may be prepared by carrying out the procedure in the following manner: 6.2 cm³ of methyl iodide are slowly added to a solution of 11.0 g of 2-mercaptopyridine in 105 cm³ of 1 N sodium hydroxide. The reaction mixture, whose temperature has risen to 30° C., is cooled to room temperature. After stirring for 2 hours, the mixture is extracted with 100 cm³ of dichloromethane, the organic phase is dried over magnesium sulfate and concentrated to dryness at 50° C. under reduced pressure (2.7 kPa). The oil obtained is purified by distillation under reduced pressure. 9.0 g of 2-methylsulfanylpyridine are obtained in the form of a colorless liquid, b.p.=84° C./45 mmHg.

EXAMPLE 21

3-{1-[Bis(4-chlorophenyl)methyl]azetidin-3-ylmethylsulfonyl}pyridine may be prepared by carrying out the procedure as described in Example 20, starting with 0.15 g of 3-{1-[bis(4-chlorophenyl)methyl)]-azetidin-3-ylidenemethylsulfonyl}pyridine, 20 cm³ of a 50/50 mixture of dichloromethane and ethanol, and 80 mg of sodium borohydride. 0.11 g of 3-{1-[bis(4-chloro-phenyl)methyl]azetidin-3-ylmethylsulfonyl}pyridine is obtained in the form of a white powder [¹H NMR spectrum (300 MHz, CDCl₃, δ in ppm): from 2.75 to 2.95 (mt: 3H); 3.35 (mt: 2H); 3.43 (d, J=6.5 Hz; 2H); 4.25 (s: 1H); from 7.20 to 7.40 (mt: 8H); 7.54 (ddd, J=8-5 and 1 Hz: 1H); 8.18 (ddd, J=8-2.5 and 1.5 Hz: 1H); 8.90 (dd, J=5 and 1.5 Hz: 1H); 9.11 (dd, J=2.5 and 1 Hz: 1H)].

3-{1-[Bis(4-chlorophenyl)methyl)]azetidin-3-ylidenemethylsulfonyl}pyridine may be prepared by carrying out the procedure as described in Example 20, starting with 0.8 g of 1-[bis(4-chlorophenyl)methyl)]-3-(pyrid-3-ylsulfonylmethyl)azetidin-3-ol, 50 cm³ of dichloromethane, 0.22 cm³ of methylsulfonyl chloride and 0.8 g of 4-dimethylaminopyridine. 0.50 g of 3-{1-[bis(4-chlorophenyl)methyl)] azetidin-3-ylidenemethylsulfonyl}pyridine is obtained in the form of a cream-colored powder.

1-[Bis(4-chlorophenyl)methyl)]-3-(pyrid-3-ylsulfonylmethyl)azetidin-3-ol may be prepared by carrying out the procedure as described in Example 20, starting with 3.3 g of 1-[bis(4-chlorophenyl)methyl)]-azetidin-3-one, 50 cm³ of tetrahydrofuran, 3.5 g of 3-methylsulfonylpyridine and 2.4 g of potassium tert-butoxide. 1.4 g of 1-[bis(4-chlorophenyl)

methyl)]-3-(pyrid-3-ylsulfonylmethyl)azetidin-3-ol are obtained in the form of a white powder.

3-Methylsulfonylpyridine may be prepared by carrying out the procedure as described in Example 20, starting with 33 g of sodium tungstate, 10 cm³ of water, 0.25 cm³ of 100% acetic acid, 9.5 g of 3-methylsulfanylpyridine, 15 cm³ of 30% hydrogen peroxide and then 2 cm³ of 32% aqueous ammonia and 2 cm³ of a 37.5% aqueous solution of sodium hydrogen sulfite. The crude oil obtained is crystallized with 20 cm³ of diisopropyl ether, the crystals are filtered, drained and dried under reduced pressure (2.7 kPa). 4.5 g of 3-methylsulfonylpyridine are obtained in the form of white crystals (m.p.=58° C.)

3-Methylsulfanylpyridine may be prepared by carrying out the procedure in the following manner: 20 cm³ of isoamyl nitrite are added to a mixture, heated to 80° C. under argon, of 9.4 g of 3-aminopyridine and 100 cm³ of dimethyl disulfide. After stirring for 2 hours at 90° C., the reaction mixture is cooled to 20° C. and then purified by fractional distillation under reduced pressure. 8.4 g of 3-methylsulfanylpyridine are obtained in the form of a pale yellow liquid, b.p.=90° C./30 mm of mercury.

EXAMPLE 22

4-{1-[Bis(4-chlorophenyl)methyl]azetidin-3-ylmethylsulfonyl}pyridine may be prepared by carrying out the procedure as described in Example 20, starting with 0.15 g of 4-{1-[bis(4-chlorophenyl)methyl]-azetidin-3-ylidenemethylsulfonyl}pyridine, 20 cm³ of a 50/50 mixture of dichloromethane and ethanol, and 80 mg of sodium borohydride. 0.13 g of 4-{1-[bis(4-chloro-phenyl)methyl]azetidin-3-ylmethylsulfonyl}pyridine is obtained in the form of a white powder [¹H NMR spectrum (300 MHz, CDCl₃, δ in ppm): from 2.75 to 2.90 (mt: 1H); 2.88 (t, J=7 Hz: 2H); 3.36 (t, J=7 Hz: 2H); 3.42 (d, J=7 Hz: 2H); 4.25 (s: 1H); from 7.20 to 7.35 (mt: 8H); 7.75 (broad d, J=6 Hz: 2H); 8.93 (broad d, J=6 Hz: 2H)].

4-{1-[Bis(4-chlorophenyl)methyl)]azetidin-3-ylidenemethylsulfonyl}pyridine may be prepared by carrying out the procedure as described in Example 20, starting with 0.8 g of 1-[bis(4-chlorophenyl)methyl)]-3-(pyrid-4-ylsulfonylmethyl)azetidin-3-ol, 50 cm³ of dichloromethane, 0.22 cm³ of methylsulfonyl chloride and 0.8 g of 4-dimethylaminopyridine. The crude product is purified by chromatography on a silica gel column (particle size 0.04-0.063 mm, height 20 cm, diameter 2 cm), eluting under an argon pressure of 0.5 bar with a mixture of cyclohexane and ethyl acetate (40/60 by volume) and collecting 20-cm³ fractions. Fractions 5 to 10 are combined and concentrated to dryness under reduced pressure (2.7 kPa). 0.42 g of 4-{1-[bis(4-chlorophenyl)methyl)]azetidin-3-ylidenemethylsulfonyl}-pyridine is obtained in the form of a white crystalline powder.

1-[Bis(4-chlorophenyl)methyl)]-3-(pyrid-4-ylsulfonylmethyl)azetidin-3-ol may be prepared by carrying out the procedure as described in Example 20, starting with 2.5 g of 1-[bis(4-chlorophenyl)methyl)]-azetidin-3-one, 50 cm³ of tetrahydrofuran, 2.6 g of 4-methylsulfonylpyridine and 1.8 g of potassium tert-butoxide. The crude product obtained is purified by chromatography on a silica gel column (particle size 0.04-0.063 mm, height 30 cm, diameter 3 cm), eluting under an argon pressure of 0.5 bar with dichloromethane and then with a mixture of dichloromethane and methanol (98/2 by volume) and collecting 20-cm³ fractions. Fractions 8 to 27 are combined and concentrated to dryness under reduced pressure (2.7 kPa). A cream-colored powder is obtained which is recrystallized from 5 cm³ of acetonitrile. The crystals are filtered, drained and dried under reduced pressure (2.7 kPa). 1.4 g of 1-[bis(4-chlorophenyl)methyl)]-3-(pyrid-4-ylsulfonylmethyl)azetidin-3-ol are obtained in the form of white crystals, m.p.=130° C.

4-Methylsulfonylpyridine may be prepared by carrying out the procedure as described in Example 20, starting with 14 g of sodium tungstate, 4 cm³ of water, 0.05 cm³ of 100% acetic acid, 3.3 g of 4-methylsulfanyl-pyridine, 6.5 cm³ of 30% hydrogen peroxide and then 0.25 cm³ of 32% aqueous ammonia and 1 cm³ of 37.5% aqueous solution of sodium hydrogen sulfite. The crude oil obtained is crystallized with 10 cm³ of diisopropyl ether, the crystals are filtered, drained and dried under reduced pressure (2.7 kPa). 2.6 g of 4-methyl-sulfonylpyridine are obtained in the form of white crystals.

4-Methylsulfanylpyridine may be prepared by carrying out the procedure as described in Example 20, starting with 11.0 g of 4-mercaptopyridine, 105 cm³ of 1 N sodium hydroxide and 6.2 cm³ of methyl iodide. The crude oil obtained is purified by distillation under reduced pressure. 4.0 g of 4-methylsulfanylpyridine are obtained in the form of a white paste, b.p.=120° C./45 mm of mercury.

EXAMPLE 23

1-[Bis(4-chlorophenyl)methyl]-3-[(3,5-difluorophenyl) sulfonylmethyl]azetidine may be prepared by carrying out the procedure in the following manner: 78 mg of sodium borohydride are added, under argon, to a solution of 0.50 g of 1-[bis(4-chlorophenyl)methyl]-3-[(3,5-difluorophenyl)sulfonylmethylene]azetidine dissolved in 25 cm³ of anhydrous methanol and 25 cm³ of anhydrous dichloromethane. After stirring for 24 hours, 80 cm³ of water and 50 cm³ of dichloromethane are added, the mixture is separated after settling, washed with 80 cm³ of water and then 80 cm³ of a saturated aqueous sodium chloride solution. The organic phase is dried with magnesium sulfate, filtered and then evaporated to dryness under reduced pressure (2.7 kPa). The residue is chromatographed on a silica gel column (particle size 0.02-0.04 mm, height 20 cm diameter 14 cm), eluting under an argon pressure of 0.7 bar with a mixture of cyclohexane and ethyl acetate (90/10 by volume) and collecting 5-cm³ fractions. Fractions 60 to 82 are combined and concentrated to dryness under reduced pressure (2.7 kPa). 0.29 g of 1-[bis(4-chlorophenyl)methyl]-3-[(3,5-difluorophenyl)sulfonyl-methyl] azetidine is obtained in the form of a white solid [¹H NMR spectrum (300 MHz, CDCl₃, δ in ppm): from 2.75 to 2.95 (mt: 1H); 2.88 (t, J=7 Hz: 2H); 3.36 (t, J=Hz: 2H); 3.41 (d, J=7 Hz: 2H); 4.26 (s: 1H); 7.13 (tt, J=9 and 2.5 Hz: 1H); from 7.20 to 7.35 (mt: 8H); 7.44 (mt: 2H)].

EXAMPLE 24

1-[Bis(4-chlorophenyl)methyl]-3-[(3,5-difluorophenyl) sulfonylmethylene]azetidine may be prepared by carrying out the procedure in the following manner: 4.3 cm³ of methylsulfonyl chloride are added to 18.8 g of 1-[bis(4-chlorophenyl)methyl]-3-[(3,5-difluorophenyl)sulfonylmethyl]azetidin-3-ol dissolved in 800 cm³ of dichloromethane at room temperature, followed, in small portions, by 16 g of 4-dimethylamino pyridine. After 22 hours, the reaction mixture is washed with 3 times 700 cm³ of water and then 700 cm³ of a saturated aqueous sodium chloride solution. The organic phase is dried with magnesium sulfate, filtered and then evaporated to dryness under reduced pressure (2.7 kPa). The residue (25 g) is chromatographed on a silica gel column (particle size 0.02-0.04 mm, height 36 cm, diameter 8.5 cm) eluting under an argon pressure of 0.7 bar with a mixture of cyclohexane and ethyl acetate (90/10 by volume) and collecting 250-cm³ fractions. Fractions 2 to 148 are combined and concentrated to dryness under reduced pressure (2.7 kPa). 2.79 g of 1-[bis(4-chlorophenyl)methyl]-3-[(3,5-difluorophenyl)sulfonylmethylene]azetidine are obtained in the form of a white solid [¹H NMR spectrum (300 MHz, CDCl₃, δ in ppm) 3.91 (mt: 2H); 4.28 (mt: 2H); 4.51 (s: 1H); 6.15 (mt: 1H); 7.08 (tt, J=9 and 2.5 Hz 1H); from 7.25 to 7.40 (mt: 8H); 7.40 (mt: 2H)].

1-[Bis(4-chlorophenyl)methyl]-3-[(3,5-difluorophenyl)sulfonylmethyl]azetidin-3-ol may be prepared by carrying out the procedure in the following manner: 42.9 cm³ of 1.6 M butyllithium in hexane are added dropwise to a solution of 13.2 g of (3,5-difluorophenyl)methyl sulfone in 800 cm³ of tetrahydrofuran. After 0.5 hour at −70° C. and 0.5 hour at −30° C., 14 g of 1-[bis(4-chlorophenyl)methyl]azetidin-3-one dissolved in 150 cm³ of tetrahydrofuran are added dropwise at −70° C. After 3 hours at −70° C., the reaction mixture is poured into a saturated ammonium chloride solution and extracted with ethyl acetate. The organic phase is washed twice with 400 cm³ of water and then 400 cm³ of a saturated aqueous sodium chloride solution, dried with magnesium sulfate, filtered and then evaporated to dryness under reduced pressure (2.7 kPa). The residue (25.14 g) is chromatographed on a silica gel column (particle size 0.06-0.04 mm, height 31 cm, diameter 7.5 cm), eluting under an argon pressure of 0.5 bar with a mixture of cyclohexane and ethyl acetate (85/15 by volume) and collecting 200-cm³ fractions. Fractions 13 to 16 are combined and concentrated to dryness under reduced pressure (2.7 kPa). After crystallization from ethyl ether, filtration and drying, 4.5 g of 1-[bis(4-chlorophenyl)methyl]-3-[(3,5-difluorophenyl)sulfonylmethyl]azetidin-3-ol are obtained in the form of a white solid.

(3,5-Difluorophenyl)methyl sulfone may be prepared by carrying out the procedure in the following manner: 225 cm³ of water and, in small quantities at 5° C., 56.3 g of oxone$^R$ are added to a solution of 13.3 g of (3,5-difluorophenyl)methylsulfide dissolved in 450 cm³ of methanol. After 20 hours at room temperature, the reaction mixture is diluted with dichloromethane and water and separated after settling. The organic phase is washed twice with 700 cm³ of water and then 700 cm³ of a saturated aqueous sodium chloride solution, dried with magnesium sulfate, filtered and then evaporated to dryness under reduced pressure (2.7 kPa). 13.2 g of (3,5-difluorophenyl)methyl sulfone are obtained in the form of a white solid.

(3,5-Difluorophenyl)methylsulfide may be prepared by carrying out the procedure in the following manner: 64 cm³ of 1.6 M n-butyllithium in hexane are added dropwise at −70° C. to 11.8 cm³ of 1-bromo-3,5-difluorobenzene diluted in 200 cm³ of ethyl ether. After 0.5 hour at −70° C., 14.2 g of S-methyl methylthiosulfonate dissolved in 60 cm³ of tetrahydrofuran are added dropwise at −70° C. After 3 hours at −70° C. and then 18 hours at room temperature, the reaction mixture is poured into a saturated ammonium chloride solution and extracted with ethyl acetate. The organic phase is washed twice with 200 cm³ of water and then 300 cm³ of a saturated aqueous sodium chloride solution, dried with magnesium sulfate, filtered and then evaporated to dryness under reduced pressure (2.7 kPa). 13.3 g of (3,5-difluorophenyl)-methylsulfide are obtained in the form of a yellow oil.

EXAMPLE 25

0.25 g of meta-chloroperbenzoic acid is added at room temperature to a solution of 0.40 g of 1-[bis(4-chlorophenyl)methyl]-3-(phenylsulfanyl)azetidine in 20 cm³ of dichloromethane. After stirring for 3 hours at room temperature, the reaction mixture is washed with 30 cm³ of a saturated sodium hydrogen carbonate solution, dried over magnesium sulfate, filtered and concentrated to dryness under reduced pressure (2.7 kPa). After chromatography on a silica gel column (particle size 0.06-0.200 mm, height 25 cm, diameter 2 cm), eluting under an argon pressure of 0.8 bar with an ethyl acetate/cyclohexane 20/80 by volume mixture and collecting 60-cm³ fractions, fractions 9 to 16 are combined and concentrated to dryness under reduced pressure (2.7 kPa), taken up in heptane in order to isolate 100 mg of 1-[bis(4-chlorophenyl)methyl]-3-[(RS)-phenylsulfinyl]azetidine in the form of a white solid [¹H NMR spectrum (300 MHz, CDCl₃, δ in ppm): 3.01 (broad t, J=7.5 Hz: 1H); 3.32 (broad t, J=7.5 Hz 1H); 3.45 (broad t, J=7.5 Hz: 2H); 3.59 (mt: 1H); 4.45 (broad s,: 1H); from 7.15 to 7.65 (mts: 13H)].

EXAMPLE 26

1.2 g of oxone$^R$ are added in several portions to a solution of 0.80 g of 1-[bis(4-chlorophenyl)methyl]-3-(phenylsulfanyl)azetidine in 3.4 cm³ of water, 3.4 cm³ of acetic acid, 3.4 cm³ of ethanol and 1.7 cm³ of sulfuric acid. After stirring for 20 hours at room temperature, the reaction mixture is diluted with 100 cm³ of dichloromethane, washed with 3 times 100 cm³ of water, dried over magnesium sulfate, filtered and concentrated to dryness under reduced pressure (2.7 kPa). After chromatography on a silica gel column (particle size 0.06-0.200 mm, height 40 cm, diameter 2 cm), eluting under an argon pressure of 0.8 bar with an ethyl acetate/cyclohexane (20/80 by volume) mixture and collecting 60-cm³ fractions, fractions 9 to 15 are combined and concentrated to dryness under reduced pressure (2.7 kPa), taken up in heptane, the solid filtered and dried in order to isolate 0.23 g of 1-[bis(4-chlorophenyl)methyl]-3-(phenylsulfonyl)azetidine in the form of a white solid [¹H NMR spectrum (300 MHz, CDCl₃, δ in ppm): from 3.35 to 3.50 (mt: 4H); 3.96 (mt: 1H); 4.44 (s: 1H); from 7.20 to 7.35 (mt: 8H); 7.57 (broad t, J=7.5 Hz 2H); 7.68 (tt, J=7.5 and 1.5 Hz: 1H); 7.88 (broad d, J=7.5 Hz: 2H)].

EXAMPLE 27

43.5 mg of sodium borohydride are added to a solution of 0.6 g of methyl 5-({1-[bis(4-chlorophenyl)-methyl]azetidin-3-ylidene}methylsulfonylmethyl)thien-2-ylcarboxylate in 70 cm³ of methanol cooled to around 0° C. The reaction medium is stirred for 15 minutes at this temperature, and then for 5 hours at 20° C. before again being cooled to around 0° C. and supplemented with 8.7 mg of sodium borohydride. After 18 hours at room temperature, the reaction mixture is concentrated to dryness under reduced pressure (2.7 kPa). The residue obtained is supplemented with 100 cm³ of dichloromethane and 20 cm³ of distilled water. The mixture is separated after settling, the organic phase washed with twice 20 cm³ of distilled water, dried over magnesium sulfate, filtered and concentrated to dryness under reduced pressure (2.7 kPa). The residue obtained is purified by flash chromatography on silica gel [eluent: cyclohexane/ethyl acetate (70/30 by volume)]. 0.18 g of methyl (RS)-5-({1-[bis(4-chlorophenyl)methyl]azetidin-3-yl}methylsulfonylmethyl)thien-2-ylcarboxylate is obtained in the form of a white powder [¹H NMR spectrum (400 MHz, (CD₃)₂SO d6, δ in ppm): 2.60 (t, J=7.5 Hz 1H); 2.86 (s: 3H); 3.14 (mt: 2H); from 3.20 to 3.35 (mt: 1H); 3.45 (broad t, J=7.5 Hz: 1H); 3.82 (s: 3H); 4.47 (s: 1H); 5.27 (d, J=11 Hz: 1H); 7.28 (d, J=4 Hz: 1H); from 7.30 to 7.50 (mt: 8H); 7.72 (d, J=4 Hz: 1H)].

Methyl 5-({1-[bis(4-chlorophenyl)methyl]-azetidin-3-ylidene}methylsulfonylmethyl)thien-2-yl-carboxylate may be obtained in the following manner: 5.15 g of methyl 5-(methylsulfonylmethyl)thien-2-ylcarboxylate are added, at room temperature under an argon atmosphere, to a solution of 6.12 g of 1-[bis(4-chlorophenyl)methyl]azetidin-3-one in 200 cm³ of tetrahydrofuran and then the suspension obtained is cooled to −70° C. There are successively added 2.47 g of potassium tert-butoxide, and then after 1 hour 30 min at this temperature a solution of 1.7 cm³ of methylsulfonylchloride in 8 cm³ of ethyl ether over 2 minutes. The reaction medium is maintained for 1 hour at −70° C. and then the temperature is allowed to rise to around 20° C. before pouring in 80 cm³ of distilled water. The tetrahydrofuran is expelled under reduced pressure and the aqueous residue obtained is extracted with 500 cm³ of dichloromethane. The mixture is separated after settling, the organic phase is washed with 3 times 80 cm³ of distilled water, dried over magnesium sulfate, filtered and concentrated to dryness under reduced pressure (2.7 kPa). The residue obtained is purified by flash chromatography on silica gel [eluent: cyclohexane/ethyl acetate (70/30 by volume)]. 1.6 g of methyl 5-({1-[bis(4-chlorophenyl)methyl] azetidin-3-ylidene}methylsulfonylmethyl)thien-2-ylcarboxylate are obtained in the form of a cream-colored foam.

Methyl 5-(methylsulfonylmethyl)thien-2-ylcarboxylate may be obtained in the following manner: 31.7 g of sodium methyl sulfinate are added to a solution of 73 g of methyl 5-(bromomethyl)thien-2-ylcarboxylate in 150 cm³ of ethanol and the suspension obtained is heated under reflux for 7 hours. The reaction medium is then concentrated to dryness under reduced pressure (2.7 kPa). The residue is extracted with four times 500 cm³ of ethyl acetate, the combined organic phases are washed successively with 250 cm³ of distilled water and 250 cm³ of a saturated sodium chloride solution, dried over magnesium sulfate, filtered and incompletely concentrated under reduced pressure. The solid which appears is isolated by filtration, rinsed with three times 25 cm³ of ice-cold ethyl acetate and provides 21.4 g of methyl 5-(methylsulfonylmethyl)thien-2-ylcarboxylate in the form of a cream-colored powder.

Methyl 5-(bromomethyl)thien-2-ylcarboxylate may be prepared according to the method described by Wityak J. et al., Bioorg. Med. Chem. Lett. (1995), 5(18), 2097-100.

EXAMPLE 28

(RS)-1-[Bis(4-chlorophenyl)methyl]-3-[(3,5-difluorophenyl)methylsulfonylmethyl]azetidin-3-ylcyclopropylamine may be prepared in the following manner: 2.52 cm³ of cyclopropylamine are added to a solution of 3 g of 1-[bis(4-chlorophenyl)methyl)]-3-[(3,5-difluorophenyl)(methylsulfonyl) methylene]-azetidine in 30 cm³ of dichloromethane, at a temperature in the region of 24° C., under an inert argon atmosphere. After 39 hours at a temperature in the region of 24° C., the reaction medium is concentrated under reduced pressure (3 mbar) at a temperature in the region of 40° C. 3.26 g of a pale yellow foam are thus obtained, which foam is taken up in 30 cm³ of dichloromethane and 2.52 cm³ of cyclopropylamine. The solution obtained is stirred at a temperature in the region of 21° C., under an inert argon atmosphere, for 87 hours and then concentrated under 3 mbar at a temperature in the region of 40° C. 3.64 g of (RS)-1-[bis(4-chlorophenyl) methyl]-3-[(3,5-difluorophenyl)-methylsulfonylmethyl]azetidin-3-ylcyclopropylamine are thus obtained in the form of a pale yellow foam. [¹H NMR spectrum (300 MHz, CDCl₃, δ in ppm): 0.29 (mt: 1H); from 0.40 to 0.75 (mt: 3H); 2.50 (mt: 1H); 2.73 (s 3H); 2.90 (unresolved complex: 1H); from 3.45 to 3.70 (mt: 3H); 4.36 (broad s: 1H); from 4.60 to 4.80 (broad unresolved complex: 1H); 6.87 (tt, J=9 and 2.5 Hz: 1H); from 7.20 to 7.40 (mt: 10H)].

EXAMPLE 29

(RS)-{1-[Bis(4-chlorophenyl)methyl]-3-[(3,5-difluorophenyl)methylsulfonylmethyl]azetidin-3-yl}-(2-pyrrolidin-1-ylethyl)amine may be prepared in the following manner: 0.076 cm³ of 1-(2-aminoethyl)-pyrrolidine is added to a solution of 50 mg of 1-[bis(4-chlorophenyl)methyl)]-3-[(3,5-difluorophenyl)-(methylsulfonyl)methylene]azetidine in 0.5 cm³ of dichloromethane, at a temperature in the region of 21° C., under an inert argon atmosphere. The solution-obtained is stirred at a temperature in the region of 21° C., under an argon atmosphere, for 22 hours, concentrated under an air stream at a temperature in the region of 42° C. and then the crude residue obtained is dried under reduced pressure (about 3 mbar) at a temperature in the region of 40° C. (RS)-{1-[bis (4-chlorophenyl)methyl]-3-[(3,5-difluorophenyl)methylsulfonylmethyl]azetidin-3-yl}-(2-pyrrolidin-1-yl-ethyl) amine is obtained in the form of an ochre-colored foam. (¹H NMR spectrum (300 MHz, CDCl₃, δ in ppm); from 1.75 to 1.95 (mt: 4H); from 2.55 to 2.85 (mt: 6H); 2.79 (s: 3H); 2.91 (t, J=6.5 Hz: 2H); 3.06 (d, J=8.5 Hz: 1H); 3.17 (d, J=8.5 Hz: 1H); 3.32 (d, J=8.5 Hz: 1H); 3.41 (d, J=8.5 Hz: 1H); 4.31 (s: 1H); 4.56 (s: 1H); 6.88 (tt, J=8.5 and 2.5 Hz: 1H); 7.22 (s: 4H); 7.25 (s: 4H; 7.34 (mt: 2H)].

EXAMPLE 30

(RS)-{1-[Bis(4-chlorophenyl)methyl]-3-[(3,5-difluorophenyl)methanesulfonylmethyl]azetidin-3-yl}methylamine may be prepared according to Example 29, starting with 50 mg of 1-[bis(4-chorophenyl)methyl)]-3-[(3,5-difluorophenyl)(methylsulfonyl)methylene]-azetidine, 0.5 cm³ of dichloromethane and 0.3 cm³ of a solution of methylamine in tetrahydrofuran (2 M solution). (RS)-{1-[bis(4-chlorophenyl)methyl]-3-[(3,5-difluorophenyl)methylsulfonylmethyl]azetidin-3-yl}methylamine is obtained in the form of a yellow gum. [¹H NMR spectrum (400 MHz, CDCl₃ δ in ppm): from 2.00 to 2.20 (broad unresolved complex: 1H); 2.62 (s: 3H); 2.76 (s: 3H); 3.04 (d, J=9 Hz: 1H); 3.18 (d, J=9 Hz: 1H); 3.37 (AB, J=9 Hz: 2H); 4.31 (s: 1H); 4.55 (s: 1H); 6.89 (tt, J=9 and 2.5 Hz: 1H); 7.22 (s 4H); 7.24 (s: 4H); 7.32 (mt: 2H)].

EXAMPLE 31

(RS)-{1-[Bis(4-chlorophenyl)methyl]-3-[(3,5-difluorophenyl)methylsulfonylmethyl]azetidin-3-yl}isobutylamine may be prepared according to Example 29, starting with 50 mg of 1-[bis(4-chlorophenyl)-methyl)]-3-[(3,5-difluorophenyl)(methylsulfonyl)-methylene]azetidine, 0.5 cm³ of dichloromethane and 0.0596 cm³ of isobutylamine. (RS)-{1-[bis(4-chloro-phenyl)methyl]-3-[(3,5-difluorophenyl)methylsulfonyl-methyl]azetidin-3-yl}isobutylamine is obtained in the form of a white foam [¹H NMR spectrum (300 MHz, CDCl₃ δ in ppm): 1.01 (2d, J=7 Hz: 6 H); from 1.70 to 2.15 (broad unresolved complex: 1H); 1.76 (mt: 1H); 2.51 (dd, J=10.5 and 7 Hz: 1H); 2.76 (s: 3H); 2.80 (dd, J=10.5 and 6 Hz: 1H); 3.01 (d, J=8.5 Hz: 1H); 3.14 (d, J=8.5 Hz: 1H); 3.32 (d, J=8.5 Hz: 1H); 3.44 (d, J=8.5 Hz:

1H); 4.31 (s: 1H); 4.58 (s: 1H); 6.88 (tt, J=8.5 and 2.5 Hz: 1H); from 7.15 to 7.30 (mt: 8H); 7.35 (mt: 2H)].

EXAMPLE 32

(RS)-{1-[Bis(4-chlorophenyl)methyl]-3-[(3,5-difluorophenyl)methylsulfonylmethyl]azetidin-3-yl}ethylamine may be prepared according to Example 29 starting with 50 mg of 1-[bis(4-chlorophenyl)methyl)]-3-[(3,5-difluorophenyl)(methylsulfonyl)methylene]-azetidine, 0.5 cm³ of dichloromethane and 0.3 cm³ of a solution of ethylamine in tetrahydrofuran (2 M solution). (RS)-{1-[bis(4-chlorophenyl)methyl]-3-[(3,5-difluorophenyl)methylsulfonylmethyl]azetidin-3-yl}ethylamine is obtained in the form of a yellow gum [¹H NMR spectrum(300 MHz, CDCl₃ δ in ppm): 1.22 (t, J=7 Hz: 3 H); from 2.70 to 2.85 (mt: 2H); 2.77 (s: 3H); from 2.95 to 3.10 (unresolved complex 1H); 3.05 (d, J=8.5 Hz: 1H); 3.17 (d, J=8.5 Hz: 1H); 3.33 (d, J=8.5 Hz: 1H); 3.40 (d, J=8.5 Hz: 1H); 4.30 (s: 1H); 4.54 (s: 1H); 6.89 (tt, J=9 and 2.5 Hz: 1H); from 7.15 to 7.30 (mt: 8H); 7.34 (mt: 2H)].

EXAMPLE 33

(RS)-N-{1-[Bis(4-chlorophenyl)methyl]-3-[(3,5-difluorophenyl)methylsulfonylmethyl]azetidin-3-yl}-N',N'-dimethylethane-1,2-diamine may be prepared according to Example 29, starting with 50 mg of 1-[bis(4-chlorophenyl)methyl)]-3-[(3,5-difluorophenyl)-(methylsulfonyl)methylene]azetidine, 0.5 cm³ of dichloromethane and 0.0659 cm³ of N,N-dimethylethylene-diamine. (RS)-N-{1-bis(4-chlorophenyl)methyl]-3-[(3,5-difluorophenyl)methylsulfonylmethyl]azetidin-3-yl}-N',N'-dimethylethane-1,2-diamine is obtained in the form of a white foam [¹H NMR spectrum (300 MHz, CDCl₃ δ in ppm): 2.32 (s: 6H); 2.53 (t, J=6 Hz: 2H); 2.79 (s: 3H); 2.94 (t, J=6 Hz 2H); 3.06 (d, J=8.5 Hz: 1H); 3.16 (d, J=8.5 Hz: 1H); 3.30 (d, J=8.5 Hz: 1H); 3.41 (d, J=8.5 Hz: 1H); 4.30 (s: 1H); 4.55 (s: 1H); 6.88 (tt, J=9 and 2.5 Hz: 1H); 7.21 (s: 4H); 7.24 (s: 4H); 7.34 (mt: 2H)].

EXAMPLE 34

(RS)-1-[Bis(4-chlorophenyl)methyl]-3-[(3,5-difluorophenyl)methanesulfonylmethyl]-3-methylazetidine may be prepared in the following manner: a few drops of pure methyl iodide are added, under an argon atmosphere at a temperature in the region of 24° C., to a suspension of 400 mg of magnesium turnings in 2.5 cm³ of anhydrous diethyl ether, followed by 1 cm³ of methyl iodide in solution in 22.5 cm³ of diethyl ether. The suspension obtained is stirred for 30 minutes at a temperature in the region of 24° C. and then cooled to a temperature in the region of 0° C. with an ice+water mixture. 1.65 g of CuBr.Me₂S complex, are added, at a temperature in the region of 0° C., and then the reaction mixture is stirred for 15 minutes at a temperature in the region of 0° C. The yellow suspension obtained is added, at a temperature in the region of 0° C., to a solution of 0.5 g of 1-[Bis(4-chlorophenyl)methyl)]-3-[(3,5-difluorophenyl)(methylsulfonyl)methylene]-azetidine in a mixture of 1 cm³ of tetrahydrofuran and 1 cm³ of diethyl ether. The suspension obtained is stirred for 4 hours at a temperature in the region of 0° C. and then at a temperature in the region of 25° C. for 16 hours. The black suspension obtained is diluted with 100 cm³ of ethyl acetate and 15 cm³ of saturated aqueous ammonium chloride solution. The reaction mixture is filtered on sintered glass covered with Celite, the solid residue is rinsed with ethyl acetate and then with water. After decantation of the filtrate, the organic phase is separated, washed with 10 cm³ of water, 10 cm³ of a saturated aqueous sodium chloride solution, dried over magnesium sulfate, filtered on sintered glass and concentrated under reduced pressure (20 mbar) at a temperature in the region of 43° C. 550 mg of an orange-colored foam are thus obtained, which foam is purified by preparative thin-layer chromatography on silica [14 preparative Merck Kieselgel 60F254 plates; 20×20 cm; thickness 0.5 mm; deposition in solution in dichloromethane], eluting with a methanol-dichloromethane mixture (0.5-99.5 by volume). After elution of the zone corresponding to the desired product with a methanol-dichloromethane (15-85 by volume) mixture, filtration on sintered glass and then evaporation of the solvents under reduced pressure at a temperature in the region of 40° C., 290 mg of a white foam are obtained, which foam is dissolved in 15 cm³ of anhydrous dichloromethane and reacted with 500 mg of thiophenol resin (supplier Argonaut, 1.45 mMol/g) and 1 g of ethylenediamine resin (0.8 mMol/g) for 38 hours at a temperature in the region of 20° C. The suspension is filtered on sintered glass, the resins are rinsed with dichloromethane and the filtrate is concentrated under reduced pressure (5 mbar) at a temperature in the region of 43° C. 272.8 mg of a white foam are obtained, which foam is dissolved in 2 cm³ of dichloromethane and reacted with 1 cm³ of ethylenediamine for 72 hours at a temperature in the region of 24° C. The crude residue obtained is taken up in 50 cm³ of ethyl acetate and 10 cm³ of water. After decantation, the organic phase is washed with 10 cm³ of a 1 N aqueous hydrochloric acid solution, 10 cm³ of a saturated aqueous sodium hydrogen carbonate solution, 10 cm³ of water, 10 cm³ of a saturated aqueous sodium chloride solution, dried over magnesium sulfate, filtered on sintered glass and concentrated under reduced pressure (8 mbar) at a temperature in the region of 42° C. 263.4 mg of a pale yellow foam are obtained, which foam is purified by preparative thin-layer chromatography on silica [7 preparative Merck Kieselgel 60F254 plates; 20×20 cm; thickness 0.5 mm; deposition in solution in dichloromethane], eluting with a methanol-dichloromethane mixture (0.5-99.5 by volume). After elution of the zone corresponding to the desired product with a methanol-dichloromethane (15-85 by volume) mixture, filtration on sintered glass and then evaporation of the solvents under reduced pressure at a temperature in the region of 40° C., 191.4 mg of (RS)-1-[bis(4-chlorophenyl)methyl]-3-[([3,5-difluorophenyl)methylsulfonylmethyl]-3-methylazetidine are obtained in the form of a white foam [¹H NMR spectrum (300 MHz, CDCl₃, δ in ppm): 1.75 (s: 3H); 2.67 (s: 3H); 2.74 (broad d, J=7.5 Hz: 1H); 2.93 (d, J=7.5 Hz: 1H); 3.21 (broad d, J=7.5 Hz: 1H); 3.46 (d, J=7.5 Hz: 1H); 4.33 (broad s: 2H); 6.87 (tt, J=9 and 2.5 Hz: 1H); 7.12 (mt: 2H) from 7.15 to 7.35 (mt: 8H].

EXAMPLE 35

(RS)-1-(2-{1-[Bis(4-chlorophenyl)methyl]-3-[(3,5-difluorophenyl)methylsulfonylmethyl]azetidin-3-ylsulfanyl}ethyl)-4-methylpiperazine may be prepared in the following manner: 128 mg of 1-(ethanethiol-2-yl)-4-methylpiperazine are added to a solution of 99 mg of 1-[bis(4-chlorophenyl)methyl)]-3-[(3,5-difluorophenyl)-(methylsulfonyl)methylene]-azetidine in 2 cm³ of dichloromethane, at a temperature in the region of 20° C. After stirring overnight at a temperature in the region of 20° C., 706 mg of Merrifield resin (1.7 mMol/g) are added. After stirring overnight at a temperature in the region of 20° C., the suspension is filtered and the resin is rinsed with twice 1 cm³ of dichloromethane. The filtrate is concentrated under reduced pressure. 125 mg of a white oil are thus obtained, which oil is purified by chromatography on silica (13 cm³ of 0.06-0.2 mm silica), eluting with a methanol-dichloromethane (0-100 and then 5-95 by volume) mixture. The fractions containing only the desired product are combined and concentrated to dryness under reduced pressure. 62 mg of (RS)-1-(2-{1-[bis(4-chlorophenyl)methyl]-3-[(3,5-difluorophenyl)methylsulfonylmethyl]azetidin-3-ylsulfanyl}ethyl)-4-methylpiperazine are thus obtained in the form of white crystals [1H NMR spectrum (300 MHz, $(CD_3)_2SO$ d6, δ in ppm): 2.15 (s: 3H); 2.30 and 2.41 (2mfs: 8H); 2.55 (mt: 2H); 2.85 (s: 3H); 3.02 (mt 2H); 3.09 (d, J=8.5 Hz: 1H); 3.38 (d, J=8.5 Hz 1H); 3.42 (d, J=8.5 Hz: 1H); 3.79 (d, J=8.5 Hz 1H); 4.68 (s: 1H); 5.37 (s: 1H); from 7.30 to 7.50 (mt: 11H)].

EXAMPLE 36

(RS)-(2-{1-[Bis(4-chlorophenyl)methyl]-3-[(3,5-difluorophenyl)methylsulfonylmethyl]azetidin-3-ylsulfanyl}ethyl)dimethylamine may be prepared by carrying out the procedure as in Example 35, starting with 99 mg of 1-[bis(4-chlorophenyl)methyl)]-3-[(3,5-difluorophenyl)(methylsulfonyl)methylene]-azetidine, 2 cm³ of dichloromethane, 84 mg of 2-(dimethylamino)ethanethiol and 706 mg of Merrifield resin (1.7 mMol/g). 36 mg of (RS)-(2-{1-[bis(4-chlorophenyl)methyl]-3-[(3,5-difluorophenyl)-methylsulfonylmethyl]azetidin-3-ylsulfanyl}ethyl)-dimethylamine are thus obtained in the form of an off-white powder.

EXAMPLE 37

(RS)-{1-[[4-(Chloromethyl)phenyl]-(4-chloro-phenyl)methyl]-3-[(3,5-difluorophenyl)methylsulfonyl-methyl]azetidin-3-yl}ethylamine may be prepared in the following manner: A solution of 40 mg of (RS)-{1-[[4-(chloromethyl)phenyl]-(4-chlorophenyl)methyl]-3-[(3,5-difluorophenyl)methylsulfonylmethylene]azetidine in 0.1125 cm³ of ethylamine (2 M solution in tetrahydrofuran), containing a grain of sodium iodide, is stirred at a temperature in the region of 20° C. for 2 hours and then diluted with 20 cm³ of ethyl acetate and 5 cm³ of a saturated aqueous sodium hydrogen carbonate solution. The separated organic phase is washed with 5 cm³ of water, 5 cm³ of a saturated aqueous sodium chloride solution, dried over magnesium sulfate, filtered on sintered glass and concentrated under reduced pressure (15 mbar) at a temperature in the region of 40° C. The yellow oil obtained is purified by preparative thin-layer chromatography on silica [2 preparative Merck Kieselgel 60F254 plates; 20×20 cm; thickness 0.5 mm; deposition in solution in dichloromethane], eluting with a methanol-dichloromethane mixture (3-97 by volume). After elution of the zone corresponding to the desired product with a methanol-dichloromethane (15-85 by volume) mixture, filtration on sintered glass and then evaporation of the solvents under reduced pressure at a temperature in the region of 40° C., 17 mg of (RS)-{1-[[4-(chloromethyl)phenyl]-(4-chlorophenyl)methyl]-3-[(3,5-difluorophenyl)methylsulfonylmethyl]azetidin-3-yl}ethylamine are obtained in the form of a white solid [¹H NMR spectrum (400 MHz, $(CD_3)_2SO$ d6, δ in ppm): 1.11 (t, J=7 Hz: 3H); from 2.10 to 3.55 (mt: 8H); 2.95 (s: 3H); 4.44 (s: 1H); 5.09 (s: 1H); from 7.10 to 7.55 (mt: 11H)].

(RS)-{1-[[4-(Chloromethyl)phenyl]-(4-chloro-phenyl)methyl]-3-[(3,5-difluorophenyl)methylsulfonyl-methylene]azetidin may be prepared in the following manner: 0.525 cm³ of N,N-diisopropylethylamine is added, at a temperature in the region of 21° C., to a solution of 590 mg of (RS)-[4-((4-chlorophenyl)-{3-[(3,5-difluorophenyl)methylsulfonylmethylene]azetidin-1-yl}methyl)phenyl]methanol in 5 cm³ of anhydrous dichloromethane, followed by 0.19 cm³ of methanesulfonyl chloride. After 1 hour at a temperature in the region of 21° C., 2 cm³ of a methanol/dichloromethane (2.5/97.5 by volume) mixture are added and then after 5 minutes the reaction mixture is concentrated under reduced pressure (20 mbar) at a temperature in the region of 40° C. The yellow foam obtained is purified by chromatography on silica (50 g of 0.06-0.2 mm silica contained in a column 3 cm in diameter), eluting with a methanol/dichloromethane (0/100 and then 1/99 by volume) mixture, collecting 10-cm³ fractions. The fractions containing only the desired product are combined and concentrated to dryness under reduced pressure. 421.2 mg of (RS)-{1-[[4-(chloromethyl)-phenyl]-(4-chlorophenyl)methyl]-3-[(3,5-difluoro-phenyl)methylsulfonylmethylene]azetidine are thus obtained in the form of a yellow foam.

(RS)-[4-((4-Chlorophenyl)-{3-[(3,5-difluoro-phenyl)methylsulfonylmethylene]azetidin-1-yl}methyl)-phenyl]methanol may be prepared in the following manner: 49 mg of sodium tetraborohydride are added portionwise to a solution of 420 mg of (RS)-[4-((4-chlorophenyl)-{3-[(3,5-difluorophenyl)methyl-sulfonylmethylene]azetidin-1-yl}methyl)benzaldehyde in 7 cm³ of methanol, cooled to a temperature in the region of 0° C. (ice+water). After 2 hours at a temperature in the region of 0° C., the reaction medium is concentrated under reduced pressure (15 mbar) at a temperature in the region of 35° C. The residue obtained is purified by chromatography on silica (40 g of 0.06-0.2 mm silica contained in a column 3 cm in diameter), eluting with a methanol/dichloromethane (1/99 and then 2.5/97.5 by volume) mixture, collecting 10-cm³ fractions. The fractions containing only the desired product are combined and concentrated to dryness under reduced pressure. 418 mg of (RS)-[4-((4-chlorophenyl)-{3-[(3,5-difluorophenyl)methylsulfonylmethylene]azetidin-1-yl}methyl)phenyl]methanol are thus obtained in the form of a white foam.

EXAMPLE 38

(RS)-{1-[Bis(4-chlorophenyl)methyl]-3-[(3,5-bistrifluoromethylphenyl)methylsulfonylmethyl]azetidin-3-yl}isobutylamine may be prepared according to Example 29 starting with 50 mg of 1-[bis(4-chlorophenyl)methyl)]-3-[(3,5-bistrifluoromethylphenyl)(methylsulfonyl-methylene]azetidine, 0.5 cm³ of dichloromethane and 0.05 cm³ of isobutylamine. 57 mg of (RS)-{1-[bis(4-chlorophenyl)methyl]-3-[(3,5-bistrifluoromethylphenyl)methylsulfonylmethyl]azetidin-3-yl}isobutylamine are obtained in the form of a pale yellow foam [¹H NMR spectrum (300 MHz, CDCl₃, δ in ppm): 1.01 (d, J=7.5 Hz: 6H); 1.76 (mt: 1H); 2.47 (dd, J=10.5 and 7.5 Hz: 1H); from 2.75 to 2.85 (mt: 1H); 2.79 (s: 3H); 2.82 (dd, J=10.5 and 5.5 Hz: 1H); 3.00 (d, J=9 Hz: 1H); 3.10 (d, J=9 Hz: 1H); 3.31 (d, J=9 Hz: 1H); 3.40 (d, J=9 Hz: 1H); 4.30 (s: 1H); 4.74 (s: 1H); 7.13 (d, J=8.5 Hz: 2H); from 7.15 to 7.25 (mt: 6H); 7.96 (broad s: 1H); 8.31 (broad s: 2H)].

EXAMPLE 39

(RS)-1-[Bis(4-chlorophenyl)methyl]-3-cyano-3-[(3,5-difluorophenylmethylsulfonylmethyl]azetidine may be prepared in the following manner: 17 mg of potassium cyanide are added to a solution of 99 mg of 1-[bis(4-chlorophenyl)methyl)]-3-[(3,5-difluorophenyl)(methyl-sulfonyl)methylene]azetidine in 2.5 cm³ of dimethyl sulfoxide, at a temperature in the region of 20° C. The yellow and then brown solution obtained is heated for 15 minutes at a temperature in the region of 40° C. and then cooled to a temperature in the region of 20° C. The reaction medium is concentrated under reduced pressure and then taken up in 10 cm³ of dichloromethane, washed with three times 5 cm³ of water. The organic phase obtained is dried over magnesium sulfate, filtered and concentrated under reduced pressure. 100 mg of a yellow paste are thus obtained, which paste is purified by chromatography on silica (10 cm³ of 0.06-0.2 mm silica contained in a column 1 cm in diameter), eluting with dichloromethane. The fractions containing only the desired product are combined and concentrated to dryness under reduced pressure. 60 mg of (RS)-1-[bis(4-chlorophenyl)methyl]-3-cyano-3-[(3,5-difluorophenyl-methylsulfonylmethyl]azetidine are thus obtained in the form of a yellow paste [¹H NMR spectrum (300 MHz, (CD₃)₂SO, d6, δ in ppm): 2.94 (s: 3H); 3.07 (d, J=7.5 Hz: 1H); from 3.20 to 3.40 (mt: 1H); 3.61 (broad d, J=7.5 Hz: 1H); 3.68 (broad d, J=7.5 Hz 1H); 4.64 (s: 1H); 5.51 (s: 1H); from 7.25 to 7.50 (mt: 11H)].

EXAMPLE 40

(RS)-{1-[Bis(4-chlorophenyl)methyl]-3-[(3,5-difluorophenyl)methylsulfonylmethyl]azetidin-3-ylmethyl}-(1-cyclopropylethyl)amine may be prepared in the following manner: 0.03 cm³ of cyclopropyl methyl ketone, 0.006 cm³ of acetic acid and then 32 mg of sodium triacetoxyborohydride are successively added to a solution of 53 mg of (RS)-C-{1-[bis(4-chlorophenyl)-methyl]-3-[(3,5-difluorophenyl)methylsulfonylmethyl]-azetidin-3-yl}methylamine in 2 cm³ of 1,2-dichloroethane at a temperature in the region of 20° C. The solution obtained is stirred at a temperature in the region of 20° C. for 18 hours and then 2 cm³ of a saturated aqueous sodium hydrogen carbonate solution are added. After decantation, the organic phase is concentrated under reduced pressure. 60 mg of a viscous yellow oil are thus obtained, which oil is triturated with isopropyl ether and petroleum ether. After drying under 0.1 mbar, 55 mg of a residue are obtained which is purified by chromatography on silica (4 cm³ of 0.06-0.2 mm silica contained in a column 1.2 cm in diameter), eluting with a methanol/dichloromethane (0/100 and then 5/95 by volume) mixture. The fractions containing only the desired product are combined, concentrated to dryness under reduced pressure and repurified by chromatography on silica (4 cm³ of 0.04-0.063 mm silica contained in a column 1.2 cm in diameter), eluting with a methanol/dichloromethane (0/100 and then 1/99 by volume) mixture. The fractions containing only the desired product are combined and concentrated to dryness. 20 mg of (RS)-{1-[bis(4-chlorophenyl)methyl]-3-[(3,5-difluorophenyl)methylsulfonylmethyl]azetidin-3-ylmethyl}-(1-cyclopropylethyl)amine are thus obtained [¹H NMR spectrum (300 MHz, CDCl₃, δ in ppm): a mixture of diastereoisomers is observed, from 0.00 to 0.30 and from 0.40 to 0.80 (mts: 5H); 1.09 and 1.17 (2d, J=6.5 Hz: 3H in total); 1.87 (mt: 1H); from 2.55 to 2.75-from 2.75 to 2.95 and from 3.25 to 3.55 (mts: 4H); 2.68 (s: 3H); 3.12 (d, J=8.5 Hz: 1H); from 3.80 to 3.90 (mt: 1H); 4.42 and 4.43 (2s: 1H in total); 4.79 and 4.84 (2s: 1H in total); 6.89 (tt, J=9 and 2.5 Hz: 1H); 7.16 (mt: 2H); from 7.15 to 7.35 (mt: 8H]).

(RS)-C-{1-[Bis(4-chlorophenyl)methyl]-3-((3,5-difluorophenyl)methylsulfonylmethyl]azetidin-3-yl}methylamine may be prepared in the following manner: 1.27 cm³ of a 1.5 M solution of diisobutylaluminum hydride in tetrahydrofuran are added dropwise to a solution of 250 mg of (RS)-1-[bis(4-chlorophenyl)-methyl]-3-cyano-3-[(3,5-difluorophenyl)methylsulfonyl-methyl]azetidine in 10 cm³ of anhydrous tetrahydrofuran, cooled to a temperature in the region of 0° C. After 30 minutes at a temperature in the region of 0° C. and then 4 hours at a temperature in the region of 20° C., the solution is again cooled to a temperature of 0° C. 6.35 cm³ of water and then 1.06 cm³ of aqueous hydrochloric acid (12 N) are added successively. After decantation, the aqueous phase is extracted with three times 10 cm³ of ethyl acetate. The organic phases are combined, dried over magnesium sulfate, filtered and concentrated under reduced pressure. 0.42 g of a dark yellow oil is thus obtained which is purified by chromatography on silica (40 cm³ of 0.063-0.2 mm silica contained in a column 2.7 cm in diameter), eluting with a methanol/dichloromethane (0/100 and then 5/95 by volume) mixture. The fractions containing only the desired product are combined and concentrated to dryness under reduced pressure. 110 mg of (RS)-C-{1-[bis(4-chlorophenyl)methyl]-3-[(3,5-difluoro-phenyl)methylsulfonylmethyl]azetidin-3-yl}methylamine are thus obtained.

EXAMPLE 41

(RS)-N-{1-[Bis (4-chlorophenyl)methyl]-3-[(3,5-difluorophenyl)methylsulfonylmethyl]azetidin-3-ylmethyl}isobutyramide may be prepared in the following manner: 0.0187 cm³ of isobutyric acid, 0.032 cm³ of 1,3-diisopropylcarbodiimide and 2.5 mg of 4-dimethylaminopyridine are successively added to a solution of 53 mg of (RS)-C-{1-[bis(4-chlorophenyl)-methyl]-3-[(3,5-difluorophenyl)methylsulfonylmethyl]-azetidin-3-yl}methylamine in 2 cm³ of anhydrous dichloromethane at a temperature in the region of 20° C. After stirring for 72 hours at a temperature in the region of 20° C., 2 cm³ of water are added, the mixture is separated after settling and then the organic phase is dried over magnesium sulfate, filtered and concentrated to dryness under reduced pressure. The crude residue obtained is purified by preparative thin-layer chromatography on silica [1 preparative Merck Kieselgel 60F254 plate; 20×20 cm; thickness 1 mm], eluting with an ethyl acetate-dichloromethane (5-95 by volume) mixture. After elution of the zone corresponding to the desired product, filtration on sintered glass and then evaporation of the solvent under reduced pressure at a temperature in the region of 40° C., 16 mg of (RS)-N-{1-[bis(4-chlorophenyl)methyl]-3-[(3,5-difluorophenyl)-methylsulfonylmethyl]azetidin-3-ylmethyl}isobutyramide are obtained in the form of a pale yellow powder [¹H NMR spectrum (300 MHz, CDCl₃, δ in ppm): 1.22 (d, J=7 Hz: 6H); 2.46 (mt: 1H); 2.69 (s: 3H); 2.99 (d, J=8.5 Hz: 1H); 3.23 (AB, J=8.5 Hz: 2H); 3.40 (d, J=8.5 Hz: 1H); 3.57 (dd, J=14 and 4.5 Hz: 1H); 4.09 (dd, J=14 and 7.5 Hz: 1H); 4.34 (s: 1H); 4.35 (s: 1H); 6.71 (dd, J=7.5 and 4.5 Hz: 1H); 6.95 (tt, J=9 and 2.5 Hz: 1H); from 7.10 to 7.35 (mt: 10H)].

EXAMPLE 42

(RS)-N-{1-[Bis(4-chlorophenyl)methyl]-3-[(3,5-difluorophenyl)methylsulfonylmethyl]azetidin-3-ylmethyl}cyclopropanecarboxamide may be prepared in a manner similar to Example 39, starting with 53 mg of (RS)-C-{1-[bis(4-chlorophenyl)methyl]-3-[(3,5-difluoro-phenyl)methanesulfonylmethyl]azetidin-3-yl}methylamine, 2 cm³ of anhydrous dichloromethane, 0.0167 cm³ of cyclopropanecarboxylic acid, 0.032 cm³ of 1,3-diisopropylcarbodiimide and 2.5 mg of 4-dimethylaminopyridine. 28 mg of (RS)-N-{1-[bis(4-chlorophenyl)methyl]-3-[(3,5-difluorophenyl)-methylsulfonylmethyl]azetidin-3-ylmethyl}-cyclopropanecarboxamide are obtained in the form of a beige powder [¹H NMR spectrum (300 MHz, CDCl₃, δ in ppm): 0.81 (mt: 2H); 1.01 (mt: 2H); from 1.35 to 1.55 (mt: 1H); 2.70 (s: 3H); 3.02 (d, J=8.5 Hz: 1H); 3.21 (limiting AB, J=8 Hz: 2H); 3.45 (d, J=8.5 Hz: 1H); 3.62 (dd, J=14 and 4.5 Hz: 1H); 4.10 (dd, J=14 and 7.5 Hz); 4.31 (s: 1H); 4.36 (s: 1H); 6.75 (dd, J=7.5 and 4.5 Hz: 1H); 6.95 (tt, J=9 and 2 Hz: 1H); from 7.15 to 7.35 (mt: 10H)].

EXAMPLE 43

(RS)-{1-[Bis(4-chlorophenyl)methyl]-3-[(3,5-difluorophenyl)methylsulfonylmethyl]azetidin-3-ylmethyl}diethylamine may be prepared in a manner similar to Example 40, starting with 53 mg of (RS)-C-{1-[bis(4-chlorophenyl)methyl]-3-[(3,5-difluoro-phenyl)methylsulfonylmethyl]azetidin-3-yl}methylamine, 2 cm$^3$ of 1,2-dichloroethane, 0.017 cm$^3$ of acetaldehyde, 0.006 cm$^3$ of acetic acid and 32 mg of sodium triacetoxyborohydride. 12 mg of (RS)-{1-[bis(4-chloro-phenyl)methyl]-3-[(3,5-difluorophenyl)methylsulfonyl-methyl]azetidin-3-ylmethyl}diethylamine are thus obtained in the form of an off-white powder [$^1$H NMR spectrum (300 MHz, CDCl$_3$, δ in ppm): 1.00 (t, J=7 Hz 6H); 2.49 (q, J=7 Hz: 4H); 2.54 (d, J=13.5 Hz: 1H); 2.69 (s: 3H); 2.76 (broad d, J=7.5 Hz: 1H); 3.07 (broad d, J=7.5 Hz: 1H); 3.15 (d, J=13.5 Hz 1H); 3.24 (broad d, J=7.5 Hz: 1H); 4.06 (broad d, J=7.5 Hz: 1H): 4.35 (s: 1H); 5.02 (s: 1H); 6.91 (mt: 1H); from 7.15 to 7.40 (mt: 10H)].

EXAMPLE 44

(RS)-N-{1-[Bis(4-chlorophenyl)methyl]-3-[(3,5-difluorophenyl)methylsulfonylmethyl]azetidin-3-ylmethyl}methanesulfonamide may be prepared in the following manner: 150 mg of anhydrous IRA-68 resin are added to a solution of 53 mg of (RS)-C-{1-[bis(4-chlorophenyl)methyl]-3-[(3,5-difluorophenyl)-methylsulfonylmethyl]azetidin-3-yl}methylamine in 2 cm$^3$ of ethyl acetate, at a temperature in the region of 20° C., followed by 0.012 cm$^3$ of methylsulfonyl chloride. After stirring overnight at a temperature in the region of 20° C., 0.001 cm$^3$ of water and then 150 mg of anhydrous IRA-68 resin are added. After stirring for 1 hour at a temperature in the region of 20° C., the reaction mixture is filtered and the filtrate is concentrated under reduced pressure. 81 mg of a yellow paste are thus obtained, which paste is purified by preparative thin-layer chromatography on silica [1 preparative Merck Kieselgel 60F254 plate; 20×20 cm; thickness 1 mm], eluting with an ethyl acetate-dichloromethane (5-95 by volume) mixture. After elution of the zone corresponding to the desired product, filtration on sintered glass and evaporation of the solvents under reduced pressure at a temperature in the region of 40° C., 25 mg of (RS)-N-{1-[bis(4-chlorophenyl)methyl]-3-((3,5-difluorophenyl)methylsulfonylmethyl]azetidin-3-ylmethyl}methanesulfonamide are obtained in the form of a pale yellow powder [$^1$H NMR spectrum (300 MHz, CDCl$_3$, δ in ppm): 2.70 (s: 3H); from 2.95 to 3.10 (mt: 2H); 3.05 (s: 3H); 3.22 (broad d, J=8 Hz: 1H); 3.52 (d, J=8 Hz: 1H); 3.74 (dd, J=13.5 and 8 Hz: 1H); 3.90 (dd, J=13.5 and 5.5 Hz: 1H); 4.23 (s: 1H); 4.46 (s: 1H); 5.54 (mt: 1H); 7.00 (tt, J=9 and 2 Hz 1H); from 7.05 to 7.35 (mt: 10H)].

EXAMPLE 45

(RS) 1-{1-[Bis(4-chlorophenyl)methyl]-3-[(3,5-difluorophenyl)methylsulfonylmethyl]azetidin-3-ylmethyl}-3-isopropylurea may be prepared in the following manner: 0.0197 cm$^3$ of isopropyl isocyanate is added to a solution of 53 mg of (RS)-C-{1-[bis(4-chlorophenyl)methyl]-3-[(3,5-difluorophenyl)methylsulfonylmethyl]azetidin-3-yl}methylamine in 2 cm$^3$ of dichloromethane, at a temperature in the region of 20° C. After stirring overnight at a temperature in the region of 20° C., 0.05 cm$^3$ of water is added and then after stirring for 15 minutes at a temperature in the region of 20° C., the reaction mixture is dried over magnesium sulfate, filtered and concentrated under reduced pressure. The residue obtained (75 mg) is purified by preparative thin-layer chromatography on silica [1 preparative Merck Kieselgel 60F254 plate; 20×20 cm; thickness 1 mm], eluting with an ethyl acetate-dichloromethane (5-95 by volume) mixture. After elution of the zone corresponding to the desired product, filtration on sintered glass and then evaporation of the solvent under reduced pressure at a temperature in the region of 40° C., 16 mg of (RS)-1-{1-[bis(4-chlorophenyl)methyl]-3-[(3,5-difluorophenyl)methylsulfonylmethyl]-azetidin-3-ylmethyl}-3-isopropylurea are obtained in the form of a pale yellow powder [$^1$H NMR spectrum (300 MHz, CDCl$_3$, δ in ppm): 1.17 (d, J=7 Hz: 6H) 2.68 (s: 3H); 3.00 (broad d, J=8.5 Hz: 1H); 3.11 (d, J=8.5 Hz: 1H); 3.17 (d, J=8.5 Hz: 1H); 3.46 (broad d, J=8.5 Hz: 1H); 3.64 (dd, J=14 and 5 Hz: 1H); 3.86 (mt: 1H); 3.96 (dd, J=14 and 7.5 Hz: 1H); 4.15 (d, J=8 Hz: 1H); 4.29 (s: 1H); 4.43 (s: 1H); 5.11 (mt: 1H); 6.94 (tt, J=9 and 2 Hz: 1H); from 7.10 to 7.30 (mt: 10H)].

EXAMPLE 46

(RS)-{1-[Bis(4-chlorophenyl)methyl]-3-[(3,5-difluorophenyl)methylsulfonylmethyl]azetidin-3-ylmethyl}carbamic acid isobutyl ester may be prepared in the following manner: 0.016 cm$^3$ of isobutyl chloroformate is added to a solution of 53 mg of (RS)-C-{1-[bis(4-chlorophenyl)methyl]-3-[(3,5-difluoro-phenylmethylsulfonylmethyl]azetidin-3-yl}methylamine in 2 cm$^3$ of pyridine, at a temperature in the region of 20° C. After stirring overnight at a temperature in the region of 20° C., the reaction mixture is concentrated under reduced pressure. 68 mg of a yellow paste are obtained, which paste is purified by preparative thin-layer chromatography on silica gel [1 preparative Merck Kieselgel 60F254 plate; 20×20 cm; thickness 1 mm], eluting with an ethyl acetate-dichloromethane (5-95 by volume) mixture. After elution of the zone corresponding to the desired product, filtration on sintered glass and then evaporation of the solvents under reduced pressure at a temperature in the region of 40° C., 14 mg of (RS)-{1-[bis(4-chlorophenyl)methyl]-3-[(3,5-difluorophenyl)methylsulfonylmethyl]azetidin-3-ylmethyl}carbamic acid isobutyl ester are obtained in the form of an off-white powder [$^1$H NMR spectrum (300 MHz, CDCl$_3$, δ in ppm): 0.96 (d, J=7 Hz: 6H); 1.95 (mt: 1H); 2.68 (s: 3H); 3.04 (d, J=8.5 Hz 1H); 3.19 (s: 2H); 3.51 (d, J=8 Hz: 1H); 3.75 (dd, J=14 and 5 Hz: 1H); from 3.80 to 4.00 (mt: 3H); 4.30 (s: 1H); 4.34 (s: 1H); 5.63 (unresolved complex: 1H); 6.95 (tt, J=9 and 2 Hz: 1H); from 7.10 to 7.30 (mt: 10H)].

EXAMPLE 47

(RS)-{1-[Bis(4-chlorophenyl)methyl]-3-[(3,5-difluorophenyl)methylsulfonylmethyl]azetidin-3-ylmethyl}dimethylamine may be prepared in the following manner: 138 mg of potassium carbonate are added, at a temperature in the region of 20° C., to a solution of 52 mg of (RS)-C-{1-[bis(4-chlorophenyl)methyl]-3-[(3,5-difluorophenyl)methylsulfonylmethyl]azetidin-3-yl}methylamine in 2 cm$^3$ of acetonitrile, followed by 0.0075 cm$^3$ of methyl iodide. After stirring overnight at temperature in the region of 20° C., the reaction medium is filtered on sintered glass, the solid is rinsed with dichloromethane and the filtrate is concentrated under reduced pressure. The crude residue obtained (90 mg) is purified by preparative thin-layer chromatography on silica [1 preparative Merck Kieselgel 60F254 plate; 20×20 cm; thickness 1 mm], eluting with an ethyl acetate-dichloromethane (5-95 by volume) mixture. After elution of the zone corresponding to the desired product, filtration on sintered glass and then evaporation of the solvents under reduced pressure at a temperature in the region of 40° C., 11 mg of (RS)-{1-[bis(4-chlorophenyl)-methyl]-3-[(3,5-difluorophenyl)-methylsulfonylmethyl]azetidin-3-ylmethyl}dimethylamine are obtained [$^1$H NMR spectrum (300 MHz, CDCl$_3$, δ in ppm): 2.18 (s: 6H); 2.30 (d, J=13 Hz: 1H); from 4.65 to 4.78 (mt: 1H); 2.70 (s: 3H); 2.98 (d, J=13 Hz: 1H); 3.09 (d, J=8 Hz: 1H); 3.32 (d, J=7.5 Hz: 1H); 4.11 (d, J=8 Hz: 1H); 4.35 (s 1H); 4.94 (s: 1H); 6.92 (mt: 1H); from 7.10 to 7.40 (mt: 10H)].

EXAMPLE 48

(RS)-1-[Bis(4-chlorophenyl)methyl]-3-[(4-methoxyphenyl)methylsulfonylmethyl]azetidine may be prepared in the following manner: 25.5 mg of sodium tetraborohydride are added to a solution of 400 mg of 1-[bis(4-chlorophenyl)methyl]-3-[(4-methoxyphenyl)-methylsulfonylmethylene]azetidine in 4.5 cm$^3$ of ethanol, under an argon atmosphere, at a temperature in the region of 20° C. After stirring for 16 hours at a temperature in the region of 20° C., 26 mg of sodium tetraborohydride are added. The reaction medium is stirred at a temperature in the region of 20° C. for 4.5 hours and then at a temperature in the region of 50° C. for 3 hours. After cooling to a temperature in the region of 20° C., the reaction medium is concentrated under reduced pressure. The white deposit obtained is taken up in 2 cm$^3$ of water and 2 cm$^3$ of dichloromethane. After decantation, the organic phase is concentrated under reduced pressure and the yellow foam obtained is purified by preparative thin-layer chromatography on silica [2 preparative Merck Kieselgel 60F254 plates, 20×20 cm; thickness 0.5 mm], eluting with a methanol-dichloromethane (1-99 by volume) mixture. After elution of the zone corresponding to the desired product with a methanol-dichloromethane (10-90 by volume) mixture, filtration on sintered glass and then evaporation of the solvents under reduced pressure at a temperature in the region of 40° C., 14 mg of (RS)-1-[bis(4-chloro-phenyl)methyl]-3-[(4-methoxyphenyl)methylsulfonyl-methyl]azetidine are obtained in the form of a white foam [$^1$H NMR spectrum (300 MHz, CDCl$_3$, δ in ppm): 2.56 (mt: 1H); 2.58 (s: 3H); 3.20 (mt: 2H); from 3.35 to 3.55 (mt: 1H); 3.66 (broad t, J=7.5 Hz: 1H); 3.81 (s: 3H); 4.21 (d, J=4.5 Hz: 1H); 4.26 (broad s 1H); 6.90 (d, J=8.5 Hz: 2H); from 7.15 to 7.40 (mt 10H)].

1-[Bis(4-chlorophenyl)methyl]-3-[(4-methoxyphenyl)methylsulfonylmethylene]azetidine may be prepared by carrying out the procedure as described in Example 1, starting with 1 g of (RS)-1-[bis(4-chlorophenyl)methyl]-3-[methylsulfonyl-(4-methoxyphenyl)methyl]azetidin-3-ol, 20 cm$^3$ of dichloromethane, 0.229 cm$^3$ of methylsulfonyl chloride and 722 mg of 4-dimethylaminopyridine. After purification by chromatography on silica at atmospheric pressure (100 g of silica, particle size 0.063-0.2 mm contained in a column 3 cm in diameter), eluting with dichloromethane), the fractions containing only the desired product are combined and concentrated to dryness under reduced pressure. 650 mg of 1-[bis (4-chlorophenyl)methyl]-3-[(4-methoxyphenyl)methyl-sulfonylmethylene]azetidine are thus obtained in the form of a yellow gum.

(RS)-1-[Bis(4-chlorophenyl)methyl]-3-[methylsulfonyl-(4-methoxyphenyl)methyl]azetidin-3-ol may be prepared by carrying out the procedure as described in Example 1, starting with 19.6 cm$^3$ of 1.6 N n-butyllithium in solution in hexane, 5.7 g of 4-methoxybenzyl methyl sulfone and 8.71 g of 1-[bis (4-chlorophenyl)methyl]azetidin-3-one in 450 cm$^3$ of tetrahydrofuran. 8.3 g of (RS)-1-[bis(4-chloro-phenyl)methyl]-3-[methylsulfonyl-(4-methoxyphenyl)-methyl]azetidin-3-ol are thus obtained in the form of a beige solid.

4-Methoxybenzyl methyl sulfone may be prepared by carrying out the procedure as described in Example 27, starting with 13.6 cm$^3$ of 4-methoxybenzyl chloride, 30 mg of sodium iodide, 14.4 g of sodium methyl sulfinate in 125 cm$^3$ of ethanol. 5.75 g of 4-methoxybenzyl methyl sulfone are thus obtained in the form of a white powder.

EXAMPLE 49

(RS)-2-{1-[Bis(4-chlorophenyl)methyl]-azetidin-3-yl}-2-(3,5-difluorophenyl)-N-acetyl-morpholine may be prepared in the following manner: 252 mg of supported EDCI (2.3 equivalents, the supported EDCI reagent is commercially available, and may also be prepared according to the following reference: M. Desai, L. Stramiello, Tetrahedron Letters, 34, 48, 7685-7688 (1993)), 2 cm$^3$ of anhydrous dichloromethane, 0.006 cm$^3$ or morpholine and then 0.010 cm$^3$ of triethylamine are successively added, at a temperature in the region of 20° C., to 37 mg of (RS-{1-[bis(4-chlorophenyl) methyl]azetidin-3-yl}-(3,5-difluorophenyl)acetic acid hydrochloride. After stirring for 12 hours at a temperature in the region of 20° C., the reaction mixture is filtered on sintered glass. The filtrate is washed with 2 cm$^3$ of water, dried over magnesium sulfate, filtered and concentrated to dryness under reduced pressure (2.7 kPa) at a temperature in the region of 20° C. 15 mg of (RS)-2-{1-[bis(4-chlorophenyl) methyl]azetidin-3-yl}-2-(3,5-difluorophenyl)-N-acetylmorpholine are thus obtained in the form of a beige foam [$^1$H NMR spectrum (300 MHz, CDCl$_3$, δ in ppm): from 2.60 to 3.80 (mt: 13H); 3.93 (d, J=10 Hz: 1H); 4.27 (s: 1H) from 6.65 to 6.85 (mt 3H) from 7.20 to 7.40 (mt: 8H)].

EXAMPLE 50

(RS)-2-{1-[Bis(4-chlorophenyl)methyl]-azetidin-3-yl}-2-(3,5-difluorophenyl)-N-cyclohexyl-acetamide may be prepared in the following manner: 0.070 cm$^3$ of cyclohexylamine, 144 mg of 1-(3-dimethylaminopropyl)-3-ethylcarbodiimide hydrochloride, 0.141 cm$^3$ of triethylamine and then 4 mg of hydroxybenzotriazole hydrate are successively added to a solution of 250 mg of (RS)-{1-[bis(4-chlorophenyl)-methyl]azetidin-3-yl}-(3,5-difluorophenyl)acetic acid hydrochloride in 10 cm$^3$ of anhydrous dichloromethane, at a temperature in the region of 20° C. The solution obtained is stirred at a temperature in the region of 20° C. for about 12 hours. The reaction medium is deposited on a Varian cartridge (25 cm$^3$) filled with 12 g of fine silica (0.040-0.063 mm), conditioned and then eluted with a dichloromethane-petroleum ether (80-20 by volume) mixture with the aid of a Duramat pump, collecting 1.5-cm$^3$ fractions. Fractions 11 to 17 are combined and concentrated to dryness under reduced pressure (2.7 kPa) at 40° C. 169 mg of (RS)-2-{1-[bis(4-chlorophenyl)methyl]azetidin-3-yl}-2-(3,5-difluoro-phenyl)-N-cyclohexylacetamide are thus obtained in the form of a white foam [$^1$H NMR spectrum (300 MHz, CDCl$_3$, δ in ppm): from 0.90 to 1.45 (mt: 6H); from 1.50 to 1.90 (mt: 4H); 2.66 (mt: 1H); 2.90 (mt: 1H) from 3.00 to 3.15 (mt: 2H); 3.42 (broad t, J=7.5 Hz: 1H); 3.52 (d, J=10.5 Hz: 1H); from 3.60 to 3.80 (mt: 1H); 4.27 (s: 1H); 5.25 (broad d, J=8 Hz: 1H); 6.90 (tt, J=9 and 2.5 Hz: 1H); 6.82 (mt: 2H); from 7.20 to 7.35 (mt: 8H].

EXAMPLE 51

(RS)-2-{1-[Bis(4-chlorophenyl)methyl]-azetidin-3-yl}-2-(3,5-difluorophenyl)-N-acetyl-piperidine may be prepared in the following manner: 0.012 cm$^3$ of piperidine, 29 mg of 1-(3-dimethylamino-propyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)methyl]azetidin-3-yl}-3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), eluting with dichloromethane with the aid of a Duramat pump. The fractions between 8 and 15 cm$^3$ are combined and concentrated to dryness under reduced pressure (2.7 kPa) at 40° C. 14 mg of (RS)-2-{1-[bis(4-chloro-phenyl)methyl]azetidin-3-yl}-2-(3,5-difluorophenyl)-N-acetylpiperidine are thus obtained in the form of a white crystalline powder [$^1$H NMR spectrum (300 MHz, CDCl$_3$, δ in ppm): from 0.95 to 1.15 and from 1.30 to 1.50 (2mts: 6H in total); 2.74 (mt: 2H); from 3.00 to 3.15 (mt: 2H) from 3.30 to 3.45 (mt: 4H); from 3.55 to 3.70 (mt: 1H); 3.95 (d, J=10 Hz: 1H); 4.26 (s 1H); 6.68 (tt, J=9 and 2.5 Hz: 1H); 6.80 (mt: 2H); from 7.20 to 7.35 (mt: 8H)].

EXAMPLE 52

(RS)-2-{1-[Bis(4-chlorophenyl)methyl]-azetidin-3-yl}-2-(3,5-difluorophenyl)-N-acetyl-pyrrolidine may be prepared in the following manner: 0.010 cm$^3$ of pyrrolidine and 0.023 cm$^3$ of diisopropylcarbodiimide, 0.028 cm$^3$ of triethylamine and 1.5 mg of hydroxybenzotriazole hydrate are successively added to a solution of 50 mg of (RS)-{1-[bis(4-chloro-phenyl)methyl]azetidin-3-yl}-(3,5-difluorophenyl)acetic acid hydrochloride in 2 cm$^3$ of anhydrous dichloromethane at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), eluting with dichloromethane with the aid of a Duramat pump. The fractions between 11 and 19 cm$^3$ are combined and concentrated to dryness under reduced pressure (2.7 kPa) at 40° C. 29 mg of (RS)-2-{1-[bis(4-chloro-phenyl)methyl]azetidin-3-yl}-2-(3,5-difluorophenyl)-N-acetylpyrrolidine are thus obtained in the form of a white foam [$^1$H NMR spectrum (300 MHz, CDCl$_3$, δ in ppm): from 1.75 to 2.00 (mt: 4H); 2.74 (mt: 2H); from 3.00 to 3.30 (mt: 3H); from 3.35 to 3.60 (mt: 4H); 3.80 (d, J=10.5 Hz: 1H); 4.25 (s: 1H); 6.68 (tt, J=9 and 2.5 Hz: 1H); 6.84 (mt: 2H); from 7.20 to 7.40 (mt: 8H)].

EXAMPLE 53

(RS)-2-{1-[Bis(4-chlorophenyl)methyl]-azetidin-3-yl}-2-(3,5-difluorophenyl)-N-cyclopropyl-acetamide may be prepared in the following manner: 0.009 cm$^3$ of cyclopropylamine, 29 mg of 1-(3-dimethyl-aminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm$^3$ of anhydrous dichloromethane at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned and then eluted with dichloromethane with the aid of a Duramat pump, collecting 2-cm$^3$ fractions. Fractions 2 to 6 are combined and concentrated to dryness under reduced pressure (2.7 kPa) at 40° C. 29 mg of (RS)-2-{1-[bis(4-chlorophenyl)methyl]azetidin-3-yl}-2-(3,5-difluoro-phenyl)-N-cyclopropylacetamide are thus obtained in the form of a white foam [$^1$H NMR spectrum (300 MHz, CDCl$_3$, δ in ppm): 0.40 (mt: 2H); 0.74 (mt: 2H); 2.64 (mt: 2H); 2.89 (dd, J=7.5 and 5 Hz: 1H); 3.08 (mt: 2H); 3.42 (broad t, J=7.5 Hz: 1H); 3.51 (d, J=10.5 Hz 1H); 4.25 (s: 1H); 5.50 (unresolved complex: 1H); 6.70 (tt, J=9 and 2.5 Hz: 1H); 6.81 (mt: 2H) from 7.15 to 7.35 (mt: 8H)].

EXAMPLE 54

(RS)-2-{1-[Bis(4-chlorophenyl)methyl]-azetidin-3-yl}-2-(3,5-difluorophenyl)-N-cyclohexyl-N-methylacetamide may be prepared in the following manner: 0.016 cm$^3$ of N-methylcyclohexylamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned and eluted with dichloromethane with the aid of a Duramat pump, collecting 2-cm$^3$ fractions. Fractions 4 to 6 are combined and concentrated to dryness under reduced pressure (2.7 kPa) at 40° C. 17 mg of (RS)-2-{1-[bis(4-chlorophenyl)methyl]azetidin-3-yl}-2-(3,5-difluorophenyl)-N-cyclohexyl-N-methylacetamide are thus obtained in the form of a white foam [$^1$H NMR spectrum (250 MHz, (CD$_3$)$_2$SO d6, at a temperature of 373K, δ in ppm): from 0.98 to 1.85 (mt: 10H); from 2.60 to 3.05 (mt: 8H); (broad t, J=7.5 Hz: 1H); 4.25 (broad d, J=9 Hz: 1H); 4.45 (s: 1H); 7.00 (mt: 3H); from 7.25 to 7.45 (mt: 8H)].

EXAMPLE 55

(RS)-2-{1-[Bis(4-chlorophenyl)methyl]-azetidin-3-yl}-2-(3,5-difluorophenyl)-N-(tetrahydro-furan-2-ylmethyl)acetamide may be prepared in the following manner: 0.013 cm$^3$ of tetrahydrofurylamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-bis(4-chlorophenyl)-methyl]azetidin-3-yl]-(3,5-difluorophenyl) acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned and then eluted with dichloromethane with the aid of a Duramat pump, collecting 2-cm$^3$ fractions. Fractions 3 to 8 are combined and concentrated to dryness under reduced pressure (2.7 kPa) at 40° C. 27 mg of 2(RS)-2-{1-[bis(4-chlorophenyl)methyl]azetidin-3-yl}-2-(3,5-difluoro-phenyl)-N-(tetrahydrofuran-2-ylmethyl)acetamide are thus obtained in the form of a white solid [$^1$H NMR spectrum (300 MHz, CDC$_3$, δ in ppm): from 1.65 to 1.95 (mt:

4H); 2.64 (mt: 1H); 2.89 (dd, J=7.5 and 5.5 Hz: 1H); from 3.00 to 3.20 (mt: 3H); from 3.30 to 3.60 (mt: 2H); 3.58 (d, J=10.5 Hz: 1H); from 3.65 to 3.95 (mt: 3H); 4.25 (s: 1H); 5.81 (mt: 1H); 6.68 (tt, J=9 and 2.5 Hz: 1H); 6.82 (mt: 2H); from 7.15 to 7.35 (mt: 8H)].

EXAMPLE 56

(RS)-2-{1-[Bis(4-chlorophenyl)methyl]-azetidin-3-yl}-2-(3,5-difluorophenyl)-N-(2-morpholin-4-ylethyl)acetamide may be prepared in the following manner: 0.016 cm$^3$ of aminoethylmorpholine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned with dichloromethane with the aid of a Duramat pump, eluted successively with a dichloromethane-ethyl acetate (70-30 by volume) mixture, collecting 2-cm$^3$ fractions for fractions 1 to 12, and then with a dichloromethane-methanol (98-2 by volume) mixture, collecting 2-cm$^3$ fractions for fractions 12 to 27. Fractions 13 to 27 are combined and concentrated to dryness under reduced pressure (2.7 kPa) at 40° C. 34 mg of (RS)-2-{1-[bis(4-chlorophenyl)methyl]azetidin-3-yl]-2-(3,5-difluoro-phenyl)-N-(2-morpholin-4-ylethyl)acetamide are thus obtained in the form of a white foam [$^1$H NMR spectrum (300 MHz, CDCl$_3$, δ in ppm): 2.33 (broad t, J=5 Hz 4H); 2.38 (t, J=7 Hz: 2H); 2.65 (mt: 1H); from 2.85 to 3.20 (mt: 3H); 3.25 (broad q, J=7 Hz: 2H); 3.43 (mt: 1H); 3.57 (t, J=5 Hz: 4H); 3.61 (d, J=10.5 Hz: 1H); 4.26 (s: 1H); 5.98 (unresolved complex: 1H); 6.70 (tt, J=9 and 2.5 Hz: 1H); 6.83 (mt: 2H); from 7.15 to 7.35 (mt: 8H)].

EXAMPLE 57

(RS)-2-{1-[Bis(4-chlorophenyl)methyl]-azetidin-3-yl}-2-(3,5-difluorophenyl)-N-(1-ethyl-pyrrolidin-2-ylmethyl)acetamide may be prepared in the following manner: 0.018 cm$^3$ of aminomethylethyl-pyrrolidine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (of 12 mm in diameter) filled with 4 cm$^3$ of silica (0.060-0.200 mm), conditioned with dichloromethane with the aid of a vacuum apparatus, eluting with dichloromethane between 0 and 6 cm$^3$ and then with a dichloromethane-methanol (95-5 by volume) mixture. The fractions containing the desired product are combined and concentrated to dryness under reduced pressure (2.7 kPa) at 40° C. for 2 hours. The yellow paste thus obtained is taken up in 2 cm$^3$ of ethyl acetate and then with 2 cm$^3$ of distilled water. After stirring, the mixture is frozen, the organic phase is concentrated to dryness under reduced pressure (2.7 kPa) at 40° C. The residue obtained is taken up in 2 cm$^3$ of diisopropyl ether and is then concentrated to dryness under reduced pressure (2.7 kPa) at 40° C. 38 mg of (RS)-2-{1-[bis(4-chlorophenyl)methyl]azetidin-3-yl}-2-(3,5-difluorophenyl)-N-(1-ethylpyrrolidin-2-ylmethyl)acetamide are thus obtained in the form of a white foam [$^1$H NMR spectrum (300 MHz, CDCl$_3$ with addition of a few drops of CD$_3$COOD d4, δ in ppm): 0.96 and 1.17 (2t, J=7.5 Hz: 3H in total); from 1.60 to 2.00 (mt: 4H); from 2.50 to 2.95-from 3.10 to 3.85 (mts: 11H); from 3.95 to 4.10 (mt: 1H); 4.10 and 4.14 (2d, J=10.5 Hz: 1H in total); 5.18 and 5.25 (2 broad s: 1H in total); 6.66 (mt: 1H); from 6.80 to 7.00 (mt: 2H); from 7.15 to 7.45 (mt: 8H)].

EXAMPLE 58

(RS)-2-{1-[Bis(4-chlorophenyl)methyl]-azetidin-3-yl}-2-(3,5-difluorophenyl)-N-isobutyl-acetamide may be prepared in the following manner: 0.012 cm$^3$ of isobutylamine, 29 mg of 1-(3-dimethyl-aminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chloro-phenyl)methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (of 12 mm in diameter) filled with 5 cm$^3$ of silica (0.060-0.200 mm), conditioned in dichloromethane with the aid of a vacuum apparatus, eluting with dichloromethane between 0 and 6 cm$^3$ and then with a dichloromethane-ethyl acetate (95-5 by volume) mixture. The fractions containing only the desired product are combined and concentrated to dryness under reduced pressure (2.7 kPa) at 40° C. 40 mg of (RS)-2-{1-[bis(4-chlorophenyl)methyl]azetidin-3-yl}-2-(3,5-difluorophenyl)-N-isobutylacetamide are thus obtained in the form of a white foam [$^1$H NMR spectrum (300 MHz, (CD$_3$)$_2$SO d6 δ in ppm): 0.75 (d, J=7.5 Hz: 6H); 1.62 (mt: 1H); 2.61 (mt: 1H); from 2.70 to 2.95 (mt: 3H); 3.03 (mt: 2H); 3.22 (broad t, J=7 Hz: 1H); 3.83 (d, J=10.5 Hz: 1H); 4.45 (s: 1H); 7.00 (mt: 2H); 7.08 (tt, J=9 and 2.5 Hz: 1H); from 7.25 to 7.45 (mt: 8H); 8.11 (t, J=6 Hz: 1H)].

EXAMPLE 59

(RS)-2-{1-[Bis(4-chlorophenyl)-methyl]azetidin-3-yl}-2-(3,5-difluorophenyl)-N,N-dimethylacetamide may be prepared in the following manner: 0.06 cm$^3$ of dimethylamine in 2 M solution in tetrahydrofuran, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (of 12 mm in diameter) filled with 4.4 cm$^3$ of silica (0.060-0.200 mm), conditioned in dichloromethane with the aid of a vacuum apparatus, eluting with dichloromethane between 0 and 6 cm$^3$ and then with a dichloromethane-ethyl acetate (95-5 by volume) mixture. The fractions containing only the desired product are combined and concentrated to dryness under reduced pressure (2.7 kPa) at 40° C. 13 mg of (RS)-2-{1-[bis(4-chlorophenyl)methyl]azetidin-3-yl}-2-(3,5-difluoro-phenyl)-N,N-dimethylacetamide are thus obtained in the form of a white powder [$^1$H NMR spectrum (300 MHz, CDCl$_3$, δ in ppm): from 2.70 to 2.80 (mt: 2H); 2.92 (s: 3H); 2.95 (s: 3H); from 3.00 to 3.15 (mt: 2H); 3.38 (broad t, J=7.5 Hz: 1H); 3.96 (d, J=10 Hz: 1H); 4.26 (s: 1H); 6.69 (tt, J=9 and 2.5 Hz: 1H); 6.81 (mt 2H); from 7.20 to 7.35 (mt: 8H)].

EXAMPLE 60

(RS)-2-{1-[Bis(4-chlorophenyl)methyl]-azetidin-3-yl}-2-(3,5-difluorophenyl)-N-benzylacetamide may be prepared in the following manner: 0.013 cm³ of benzylamine, 29 mg of 1-(3-dimethylaminopropyl-3-ethylcarbodiimide hydrochloride, 0.028 cm³ of triethylamine and 1.5 mg of hydroxybenzotriazole hydrate are successively added to a solution of 50 mg of (RS)-{1-[bis(4-chlorophenyl)methyl]azetidin-3-yl}-(3,5-difluorophenyl)acetic acid hydrochloride in 2 cm³ of anhydrous dichloromethane, at a temperature in the region of 20° C. The solution obtained is stirred at a temperature in the region of 20° C. for about 12 hours. The reaction mixture is deposited on a Varian cartridge (of 12 mm in diameter) filled with 4.4 cm³ of silica (0.060-0.200 mm) conditioned in dichloromethane with the aid of a vacuum apparatus, eluting with dichloromethane between 0 and 6 cm³ and then with a dichloromethane-ethyl acetate (95-5 by volume) mixture. The fractions containing only the desired product are combined and concentrated to dryness under reduced pressure (2.7 kPa) at 40° C. 37 mg of (RS)-2-{1-[bis(4-chlorophenyl)methyl]azetidin-3-yl)-2-(3,5-difluorophenyl)-N-benzylacetamide are thus obtained in the form of white crystals [$^1$H NMR spectrum (300 MHz, CDCl$_3$, δ in ppm): 2.67 (mt: 1H); 2.93 (mt: 1H); 3.11 (mt: 2H); 3.43 (broad t, J=7.5 Hz: 1H); 3.62 (d, J=10.5 Hz: 1H); 4.26 (s: 1H); 4.38 (mt: 2H); 5.71 (mt: 1H); 6.71 (broad t, J=9 Hz: 1H); 6.83 (mt: 2H); from 7.10 to 7.40 (mt: 13H)].

EXAMPLE 61

(RS)-2-{1-[Bis(4-chlorophenyl)methyl]-azetidin-3-yl}-2-(3,5-difluorophenyl)-N-cyclohexyl-methylacetamide may be prepared in the following manner: 0.016 cm³ of aminomethylcyclohexane, 29 mg of 1-(3-dimethylaminopropyl)-3-ethylcarbodiimide hydrochloride, 0.028 cm³ of triethylamine and 1.5 mg of hydroxybenzotriazole hydrate are successively added to a solution of 50 mg of {1-[bis(4-chlorophenyl)methyl]-azetidin-3-yl}-(3,5-difluorophenyl)acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm), conditioned and then eluted with dichloromethane with the aid of a Duramat pump, collecting 2-cm³ fractions. Fractions 2 to 3 are combined and concentrated to dryness under reduced pressure (2.7 kPa) at 40° C. 49 mg of (RS)-2-{1-[bis(4-chlorophenyl)methyl]azetidin-3-yl}-2-(3,5-difluoro-phenyl)-N-cyclohexylmethylacetamide are thus obtained in the form of a white foam [$^1$H NMR spectrum (300 MHz, CDCl$_3$, δ in ppm): from 0.75 to 1.75 (mt: 11H); 2.65 (mt: 1H); from 2.85 to 3.15 (mt: 5H); 3.42 (broad t, J=7.5 Hz: 1H); 3.57 (d, J=10.5 Hz: 1H); 4.27 (s: 1H); 5.40 (mt: 1H); 6.71 (broad t, J=9 Hz: 1H); 6.83 (mt: 2H); from 7.15 to 7.40 (mt: 8H)].

EXAMPLE 62

(RS)-2-{1-[Bis(4-chlorophenyl)methyl]-azetidin-3-yl}-2-(3,5-difluorophenyl)-N-[3-(2-oxopyrrolidin-1-yl)propyl]acetamide may be prepared in the following manner: 0.017 cm³ of aminopropyl-pyrrolidinone, 29 mg of 1-(3-dimethylaminopropyl)-3-ethylcarbodiimide hydrochloride, 0.028 cm³ of triethylamine and 1.5 mg of hydroxybenzotriazole hydrate are successively added to a solution of 50 mg of (RS)-{1-[bis(4-chlorophenyl)methyl]azetidin-3-yl}-(3,5-difluorophenyl) acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm), conditioned and then eluted with dichloromethane with the aid of a Duramat pump, collecting 2-cm³ fractions. Fractions 4 to 12 are combined and concentrated to dryness under reduced pressure (2.7 kPa) at 40° C. 35 mg of (RS)-2-{1-[bis(4-chlorophenyl)methyl]azetidin-3-yl}-2-(3,5-difluorophenyl)-N-[3-(2-oxopyrrolidin-1-yl)propyl]acetamide are thus obtained in the form of a white foam [$^1$H NMR spectrum (300 MHz, CDCl$_3$, δ in ppm): from 1.50 to 1.65 (mt: 2H); 2.04 (mt: 2H); 2.43 (t, J=8 Hz: 2H); 2.64 (mt: 1H); 2.88 (dd, J=7.5 and 5.5 Hz: 1H); from 3.00 to 3.30 (mt: 6H); from 3.30 to 3.45 (mt: 3H); 3.64 (d, J=10.5 Hz: 1H); 4.27 (s 1H); 6.67 (tt, J=9 and 2.5 Hz: 1H); 6.90 (mt: 2H); 7.15 (t, J=6 Hz: 1H); from 7.20 to 7.35 (mt: 8H)].

EXAMPLE 63

(RS)-2-{1-[Bis(4-chlorophenyl)methyl]-azetidin-3-yl}-2-(3,5-difluorophenyl)-N-acetyl(4-methylpiperazine) may be prepared in the following manner: 0.013 cm³ of N-methylpiperazine, 29 mg of 1-(3-dimethylaminopropyl)-3-ethylcarbodiimide hydrochloride, 0.028 cm³ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm), conditioned with dichloromethane with the aid of a Duramat pump, eluted with a dichloromethane-ethanol (98-02 by volume) mixture, collecting 2-cm³ fractions. Fractions 10 to 24 are combined and concentrated to dryness under reduced pressure (2.7 kPa) at 40° C. 39 mg of (RS)-2-{1-[bis(4-chlorophenyl)methyl]azetidin-3-yl}-2-(3,5-difluorophenyl)-N-acetyl(4-methylpiperazine) are thus obtained in the form of a white foam [$^1$H NMR spectrum (300 MHz, CDCl$_3$, δ in ppm): 1.83 (mt: 1H); from 2.10 to 2.45 (mt: 3H); 2.21 (s: 3H); 2.74 (mt: 2H); from 2.95 to 3.15 (mt: 2H); from 3.30 to 3.55 (mt: 4H); 3.73 (mt: 1H); 3.93 (d, J=10 Hz: 1H); 4.25 (s: 1H); 6.69 (tt, J=9 and 2.5 Hz: 1H); 6.78 (mt: 2H); from 7.15 to 7.35 (mt: 8H)].

EXAMPLE 64

(RS)-2-{1-[Bis(4-chlorophenyl)methyl]-azetidin-3-yl}-2-(3,5-difluorophenyl)-N-(2,2-dimethyl-propyl)acetamide may be prepared in the following manner: 0.014 cm³ of neopentylamine, 29 mg of 1-(3-dimethylaminopropyl)-3-ethylcarbodiimide hydrochloride, 0.028 cm³ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm), conditioned with dichloromethane with the aid of a Duramat pump, eluted with a dichloromethane-petroleum ether (80-20 by volume) mixture, collecting 1.5-cm³ fractions. Fractions 4 to 8 are combined and concentrated to dryness under reduced pressure (2.7 kPa) at 40° C. 40 mg of (RS)-2-{1-[bis(4-chlorophenyl)methyl]azetidin-3-yl}-2-(3,5-difluorophenyl)-N-(2,2-dimethylpropyl)acetamide are thus obtained in the form of a white foam [$^1$H NMR spectrum (300 MHz, CDCl$_3$, δ in ppm): 0.81 (s: 9H); 2.66 (mt: 1H); from 2.90 to 3.20 (mt: 5H); 3.44 (broad t, J=7.5 Hz: 1H); 3.61 (d, J=10.5 Hz: 1H); 4.28 (s: 1H); 5.40 (mt: 1H); 6.72 (tt, J=9 and 2.5 Hz 1H); 6.85 (mt: 2H); from 7.20 to 7.35 (mt: 8H)].

EXAMPLE 65

(RS)-2-{1-[Bis(4-chlorophenyl)methyl]-azetidin-3-yl}-2-(3,5-difluorophenyl)-N-(2-pyrrolidin-1-ylethyl)acetamide may be prepared in the following manner: 0.015 cm$^3$ of aminoethylpyrrolidine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned with dichloromethane with the aid of a Duramat pump, eluted with a dichloromethane-ethanol (98-04 by volume) mixture, collecting 1.5-cm$^3$ fractions. Fractions 13 to 20 are combined and concentrated to dryness under reduced pressure (2.7 kPa) at 40° C. 33 mg of (RS)-2-{1-[bis(4-chlorophenyl)methyl]azetidin-3-yl}-2-(3,5-difluorophenyl)-N-(2-pyrrolidin-1-ylethyl)acetamide are thus obtained in the form of a white foam [$^1$H NMR spectrum (300 MHz, CDCl$_3$, δ in ppm): 1.78 (mt: 4H); from 2.50 to 2.70 (mt: 3H); 2.54 (mt 4H); 2.91 (dd, J=7.5 and 5 Hz: 1H); 3.10 (mt: 2H); from 3.20 to 3.45 (mt: 3H); 3.64 (d, J=10.5 Hz: 1H); 4.27 (s: 1H); 6.67 (tt, J=9 and 2.5 Hz: 1H); 6.86 (mt: 2H); from 7.15 to 7.35 (mt: 8H)].

EXAMPLE 66

(RS)-2-{1-[Bis(4-chlorophenyl)methyl]-azetidin-3-yl}-2-(3,5-difluorophenyl)-N-cyclopropylmethylacetamide may be prepared in the following manner: 0.011 cm$^3$ of cyclopropanemethylamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned and then eluted with a dichloromethane-petroleum ether (80-20 by volume) mixture with the aid of a Duramat pump, collecting 1.5-cm$^3$ fractions. Fractions 3 to 8 are combined and concentrated to dryness under reduced pressure (2.7 kPa) at 40° C. 37 mg of (RS)-2-{1-[bis(4-chlorophenyl)methyl]azetidin-3-yl}-2-(3,5-difluorophenyl)-N-cyclopropylmethylacetamide are thus obtained in the form of a white foam [$^1$H NMR spectrum (300 MHz, CDCl$_3$, δ in ppm): 0.13 (mt: 2H) 0.45 (mt: 2H); 0.86 (mt: 1H); 2.65 (mt: 1H); 2.91 (dd, J=7.5 and 5 Hz: 1H); from 3.00 to 3.15 (mt 4H); 3.41 (broad t, J=7.5 Hz: 1H); 3.57 (d, J=10.5 Hz: 1H); 4.25 (s: 1H); 5.50 (mt: 1H); 6.70 (tt, J=9 and 2.5 Hz: 1H); 6.84 (mt: 2H); from 7.15 to 7.35 (mt: 8H)].

EXAMPLE 67

(RS)-2-{1-[Bis(4-chlorophenyl)methyl]-azetidin-3-yl}-2-(3,5-difluorophenyl)-N-propylacetamide may be prepared in the following manner: 0.015 cm$^3$ of propylamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm), conditioned and eluted with dichloromethane with the aid of a Duramat pump. The fractions containing only the desired product are combined and concentrated to dryness under reduced pressure (2.7 kPa) at 40° C. 21 mg of (RS)-2-{1-[bis(4-chlorophenyl)methyl]azetidin-3-yl}-2-(3,5-difluorophenyl)-N-propylacetamide are thus obtained in the form of a white solid [$^1$H NMR spectrum (300 MHz, CDCl$_3$, δ in ppm): 0.84 (t, J=7.5 Hz: 3H); 1.45 (mt: 2H); 2.65 (mt: 1H); 2.92 (dd, J=7.5 and 5.5 Hz: 1H); from 3.00 to 3.20 (mt: 2H); 3.15 (q, J=7 Hz: 2H); 4.43 (broad t, J=7.5 Hz: 1H); 3.56 (d, J=10.5 Hz: 1H); 4.26 (s: 1H); 5.39 (mt: 1H); 6.70 (tt, J=9 and 2.5 Hz: 1H); 6.83 (mt: 2H); from 7.15 to 7.35 (mt: 8H].

EXAMPLE 68

(RS)-2-{1-[Bis(4-chlorophenyl)methyl]-azetidin-3-yl}-2-(3,5-difluorophenyl)-N-propylacetamide may be prepared in the following manner: 0.050 cm$^3$ of a 2 M solution of methylamine in tetrahydrofuran, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl) acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (6 cm$^3$) filled with 3 g of fine silica (0.040-0.063 mm) conditioned and eluted with dichloromethane with the aid of a Duramat pump. The fractions containing only the desired product are combined and concentrated to dryness under reduced pressure (2.7 kPa) at 40° C. 19 mg of (RS)-2-{1-(bis(4-chlorophenyl)methyl]azetidin-3-yl}-2-(3,5-difluorophenyl)-N-methylacetamide are thus obtained in the form of a white solid ($^1$H NMR spectrum (300 MHz, CDCl$_3$, δ in ppm): 2.66 (mt: 1H); 2.76 (d, J=5 Hz: 3H); 2.93 (mt: 1H); 3.10 (mt: 2H); 3.44 (broad t, J=7.5 Hz: 1H); 3.59 (d, J=10.5 Hz: 1H); 4.28 (s: 1H); 5.41 (unresolved complex: 1H); 6.71 (tt, J=9 and 2.5 Hz: 1H); 6.83 (mt: 2H); from 7.20 to 7.35 (mt: 8H)].

EXAMPLE 69

(RS)-2-{1-[Bis(4-chlorophenyl)methyl]-azetidin-3-yl}-2-(3,5-difluorophenyl)-N-isopropylacetamide may be prepared in the following manner: 0.011 cm$^3$ of isopropylamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)methyl]azetidin-3-yl}-(3,5-di-fluorophenyl)acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm) conditioned and then eluted with dichloromethane with the aid of a Duramat pump, collecting 1.5-cm³ fractions. Fractions 6 to 14 are combined and concentrated to dryness under reduced pressure (2.7 kPa) at 40° C. 21 mg of (RS)-2-{1-[bis(4-chlorophenyl)methyl]azetidin-3-yl}-2-(3,5-difluorophenyl)-N-isopropylacetamide are thus obtained in the form of a white foam [¹H NMR spectrum (300 MHz, CDCl₃, δ in ppm): 1.05 (d, J=7 Hz: 3H); 1.10 (d, J=7 Hz: 3H); 2.65 (mt: 1H); 2.90 (dd, J=7.5 and 5.5 Hz: 1H); from 3.00 to 3.15 (mt: 2H); 3.42 (broad t, J=7.5 Hz: 1H); 3.51 (d, J=10.5 Hz: 1H); 4.00 (mt: 1H); 4.26 (s: 1H); 5.19 (broad d, J=7.5 Hz: 1H); 6.70 (tt, J=9 and 2.5 Hz: 1H); 6.82 (mt: 2H): from 7.20 to 7.40 (mt: 8H)].

EXAMPLE 70

(RS)-2-{1-[Bis(4-chlorophenyl)methyl]-azetidin-3-yl}-2-(3,5-difluorophenyl)-N-piperidin-1-ylacetamide may be prepared in the following manner: 0.013 cm³ of aminopiperidine, 29 mg of 1-(3-dimethylaminopropyl)-3-ethylcarbodiimide hydrochloride, 0.028 cm³ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm) conditioned with dichloromethane with the aid of a Duramat pump, eluted with a dichloromethane-ethanol (98-02 by volume) mixture, collecting 2-cm³ fractions. Fractions 7 to 12 are combined and concentrated to dryness under reduced pressure (2.7 kPa) at 40° C. 33 mg of (RS)-2-{1-[bis(4-chlorophenyl)methyl]azetidin-3-yl}-2-(3,5-difluorophenyl)-N-piperidin-1-ylacetamide are thus obtained in the form of a white solid [¹H NMR spectrum (300 MHz, CDCl₃, δ in ppm): from 0.95 to 1.85-2.05 and 2.29 (mts: 10H); from 2.60 to 2.80 (mt 2H); from 3.00 to 3.20 (mt: 2H); 3.39 (broad t, J=7.5 Hz: 1H); 4.26 (s: 1H); 4.32 (d, J=10.5 Hz 1H); 6.00 (s: 1H); 6.65 (tt, J=9 and 2.5 Hz: 1H); 6.85 (mt: 2H); from 7.15 to 7.35 (mt: 8H)].

EXAMPLE 71

(RS)-2-{1-[Bis(4-chlorophenyl)methyl]-azetidin-3-yl}-2-(3,5-difluorophenyl)-N-cycloheptylacetamide may be prepared in the following manner: 0.015 cm³ of cycloheptylamine, 29 mg of 1-(3-dimethylaminopropyl)-3-ethylcarbodiimide hydrochloride, 0.028 cm³ of triethylamine and 1.5 mg of hydroxybenzotriazole hydrate are successively added to a solution of 50 mg of (RS)-{1-[bis(4-chlorophenyl) methyl]azetidin-3-yl}-(3,5-difluorophenyl)acetic acid hydrochloride in 2 cm³ of anhydrous dichloromethane, at a temperature in the region of 20° C. The solution obtained is stirred at a temperature in the region of 20° C. for about 12 hours. The reaction medium is deposited on a Varian cartridge (6 cm³) filled with 3 g of fine silica (0.040-0.063 mm) conditioned and then eluted with dichloromethane with the aid of a Duramat pump, collecting 2-cm³ fractions. Fractions 3 to 6 are combined and concentrated to dryness under reduced pressure (2.7 kPa) at 40° C. 24 mg of (RS)-2-{1-[bis(4-chlorophenyl)methyl]azetidin-3-yl}-2-(3,5-difluorophenyl)-N-cycloheptylacetamide are thus obtained in the form of a white foam [¹H NMR spectrum (300 MHz, CDCl₃, δ in ppm): from 1.20 to 1.95 (mt: 12H); 2.65 (mt: 1H); 2.90 (dd, J=7.5 and 5.5 Hz 1H); from 3.00 to 3.15 (mt: 2H); 3.42 (broad t, J=7.5 Hz: 1H); 3.52 (d, J=10.5 Hz: 1H); 3.86 (mt 1H); 4.26 (s: 1H); 5.31 (broad d, J=7.5 Hz: 1H); 6.70 (tt, J=9 and 2.5 Hz: 1H); 6.82 (mt: 2H); from 7.20 to 7.35 (mt: 8H)].

EXAMPLE 72

(RS)-2-{1-[Bis(4-chlorophenyl)methyl]-azetidin-3-yl}-2-(3,5-difluorophenyl)acetamide may be prepared in the following manner: 60 mg of 1-(3-dimethylaminopropyl)-3-ethylcarbodiimide hydrochloride and 3 mg of hydroxybenzotriazol hydrate are successively added to a solution of 98 mg of (RS)-{1-[bis(4-chlorophenyl)methyl] azetidin-3-yl}-(3,5-difluorophenyl)acetic acid hydrochloride in 4 cm³ of anhydrous dichloroethane, at a temperature in the region of 20° C., ammonia is bubbled through for 2 hours, with stirring at a temperature in the region of 20° C. The reaction medium is washed with water and is then deposited on a Varian cartridge (6 cm³) filled with 3 g of fine silica (0.040-0.063 mm) conditioned and eluted with a dichloromethane-ethyl acetate (9-1 by volume) mixture with the aid of a Duramat pump. The fractions between 36 and 80 ml are combined and concentrated to dryness under reduced pressure (2.7 kPa) at 40° C. 32 mg of (RS)-2-{1-[bis(4-chlorophenyl)methyl]azetidin-3-yl}-2-(3,5-difluorophenyl)acetamide are thus obtained in the form of an amorphous powder [¹H NMR spectrum (300 MHz, CDCl₃, δ in ppm): 2.66 (mt: 1H); 2.95 (dd, J=7 and 5 Hz: 1H); from 2.95 to 3.15 (mt: 2H); 3.45 (broad t, J=7 Hz: 1H); 3.67 (d, J=10.5 Hz: 1H); 4.27 (s: 1H); from 5.20 to 5.40 (unresolved complex 2H); 6.72 (tt, J=9 and 2.5 Hz: 1H); 6.84 (mt: 2H); from 7.20 to 7.35 (mt: 8H)].

EXAMPLE 73

Methyl (RS)-2-{1-[Bis(4-chlorophenyl)methyl]-azetidin-3-yl}-2-(3,5-difluorophenyl)-N-acetylamino acetate may be prepared in the following manner: 100 mg of glycine methyl ester hydrochloride, 115 mg of 1-(3-dimethylaminopropyl)-3-ethylcarbodiimide hydrochloride, and 6 mg of hydroxybenzotriazol hydrate are successively added to a solution of 200 mg of (RS)-{1-[bis(4-chlorophenyl)methyl]azetidin-3-yl}-(3,5-difluorophenyl)acetic acid hydrochloride in 8 cm³ of dichloroethane, at a temperature in the region of 20° C. The solution obtained is stirred at a temperature in the region of 20° C. for about 12 hours. The reaction medium is washed with water, dried, filtered and then concentrated to dryness under reduced pressure (2.7 kPa) at 40° C. The residue thus obtained is taken up in 1 cm³ of dichloromethane and then deposited on an IST FlashPack cartridge with the reference SIL-020-005 conditioned and eluted with a dichloromethane-ethyl acetate (95-05 by volume) mixture with the aid of a Duramat pump. The fractions between 18 and 42 ml are combined and concentrated to dryness under reduced pressure (2.7 kPa) at 40° C. 68 mg of methyl (RS)-2-{1-[bis(4-chlorophenyl)methyl]azetidin-3-yl}-2-(3,5-difluorophenyl)-N-acetylamino acetate are thus obtained in the form of white cottony crystals [¹H NMR spectrum (300 MHz, CDCl₃, δ in ppm): 2.67 (mt: 1H); 2.93 (broad dd, J=7.5 and 5 Hz: 1H); from 3.00 to 3.15 (mt: 2H); 3.41 (broad t, J=7.5 Hz: 1H); 3.68 (d, J=10.5 Hz: 1H); 3.74 (s: 3H); 3.93 (dd, J=18 and 5 Hz:

1H); 4.03 (dd, J=18 and 5 Hz: 1H); 4.27 (s: 1H); 5.9-6 (mt: 1H); 6.71 (tt, J=9 and 2-Hz: 1H); 6.85 (mt: 2H); from 7.20 to 7.35 (mt: 8H)].

EXAMPLE 74

(RS)-2-{1-[Bis(4-chlorophenyl)methyl]-azetidin-3-yl}-2-(3,5-difluorophenyl)-N-(3-dimethyl-aminopropyl)acetamide may be prepared in the following manner: 0.015 cm$^3$ of N,N-dimethylpropane-1,3-diamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. for about 12 hours. The reaction medium is deposited on a Varian cartridge (of 12 mm in diameter) filled with 4 cm$^3$ of silica (0.060-0.200 mm) conditioned with dichloromethane with the aid of a vacuum apparatus, eluting with dichloromethane between 0 and 6 cm$^3$ and then with a dichloromethane-methanol (95-5 by volume) mixture. The fractions containing only the desired product are combined and concentrated to dryness under reduced pressure (2.7 kPa) at 40° C. 33 mg [lacuna] (RS)-2-{1-[bis(4-chlorophenyl)methyl]azetidin-3-yl}-2-(3,5-difluorophenyl)-N-(3-dimethylamino-propyl)acetamide are thus obtained in the form of white crystals [$^1$H NMR spectrum (300 MHz, CDCl$_3$, with addition of a few drops of CD$_3$COOD d4, δ in ppm): 1.91 (mt: 2H); 2.71 (s: 6H); 2.95 (mt: 2H); from 3.15 to 3.40 (mt 2H); from 3.40 to 3.60 (mt: 1H); from 3.60 to 3.80 (mt: 2H); 4.00 (mt: 2H); 4.28 (d, J=10.5 Hz: 1H); 5.22 (s 1H); 6.68 (tt, J=9 and 2.5 Hz: 1H); 6.90 (mt: 2H); 7.33 (mt: 4H); 7.46 (d, J=8 Hz: 4H)].

EXAMPLE 75

(RS)-2-{1-[Bis(4-chlorophenyl)methyl]-azetidin-3-yl}-2-(3,5-difluorophenyl)-N-(2-hydroxyethyl)acetamide may be prepared in the following manner: 0.024 cm$^3$ of ethanolamine, 29 mg of 1-(3-dimethylaminopropyl)-3-ethylcarbodiimide hydrochloride, 0.028 cm$^3$ of triethylamine and 1.5 mg of hydroxybenzotriazole hydrate are successively added to a solution of 50 mg of (RS)-{1-[bis(4-chlorophenyl)-methyl]azetidin-3-yl}-(3,5-difluorophenyl)acetic acid hydrochloride in 2 cm$^3$ of anhydrous dichloromethane, at a temperature in the region of 20° C. The solution obtained is stirred at a temperature in the region of 20° C. The reaction medium is washed with 2 cm$^3$ of a saturated sodium bicarbonate solution, dried over magnesium sulfate and is then deposited on an IST FlashPack cartridge with the reference SIL-016-002 conditioned with dichloromethane and eluted with a dichloromethane-ethyl acetate (95-05 by volume) mixture with the aid of a Duramat pump. The fractions between 25 and 60 cm$^3$ are combined and concentrated to dryness under reduced pressure (2.7 kPa) at 40° C. The residue obtained is again chromatographed on an IST FlashPack cartridge with the reference SIL-016-002 conditioned with dichloromethane and eluted with a dichloromethane-ethyl acetate (95-05 by volume) mixture with the aid of a Duramat pump. The fractions between 25 and 35 cm$^3$ are combined and concentrated to dryness under reduced pressure (2.7 kPa) at 40° C. 14 mg of (RS)-2-{1-[bis(4-chlorophenyl)methyl]azetidin-3-yl}-2-(3,5-difluorophenyl)-N-(2-hydroxyethyl)acetamide are thus obtained in the form of a white solid [$^1$H NMR spectrum (300 MHz, CDCl$_3$, δ in ppm): 2.65 (mt: 1H); 2.91 (mt: 1H); from 3.00 to 3.15 (mt: 2H); from 3.30 to 3.50 (mt: 3H); 3.60 (d, J=10.5 Hz: 1H); 3.66 (t, J=5.5 Hz: 2H); 4.26 (s: 1H); 5.88 (mt: 1H); 6.71 (tt, J=9 and 2 Hz: 1H); 6.84 (mt: 2H); from 7.20 to 7.35 (mt: 8H)].

EXAMPLE 76

(RS)-1-[{1-[Bis(4-chlorophenyl)methyl]-azetidin-3-yl}-(3,5-difluorophenyl)methyl]-3-propylurea may be prepared in the following manner: 0.056 cm$^3$ of triethylamine and 0.064 cm$^3$ of diphenylphosphonoazide are successively added to a solution of 50 mg of (RS)-{1-[bis(4-chlorophenyl)methyl]azetidin-3-yl}-(3,5-difluorophenyl)acetic acid hydrochloride in 3 cm$^3$ of anhydrous toluene, under an inert argon atmosphere, at a temperature in the region of 20° C. The solution obtained is stirred at a temperature in the region of 50° C. for about 1 hour. 0.016 cm$^3$ of propylamine is added, the stirring is maintained at a temperature in the region of 20° C. for about 12 hours. The reaction medium is concentrated to dryness under reduced pressure (2.7 kPa) at a temperature in the region of 40° C. The residue is taken up in 1 cm$^3$ of dichloromethane and then deposited on a Varian cartridge (6 cm$^3$) filled with 3 g of fine silica (0.040-0.063 mm) conditioned and eluted with a dichloromethane-ethyl acetate (95-5 by volume) mixture with the aid of a Duramat pump. The fractions between 12 and 16 cm$^3$ are combined and concentrated to dryness under reduced pressure (2.7 kPa) at 40° C. 13 mg of (RS)-1-[{1-[bis(4-chlorophenyl)methyl]azetidin-3-yl}-2(3,5-difluorophenyl)methyl]-3-propylurea are thus obtained in the form of a beige solid [$^1$H NMR spectrum (400 MHz, CDCl$_3$, δ in ppm): 0.92 (t, J=7.5 Hz: 3H); 1.53 (mt: 2H); from 2.55 to 2.75 (mt: 1H); from 2.80 to 3.25 (mt: 6H); 4.26 (t, J=5.5 Hz: 1H); 4.29 (s 1H); 4.92 (t, J=7 Hz: 1H); 5.31 (d, J=5.5 Hz: 1H); 6.66 (tt, J=9 and 2.5 Hz: 1H); 6.79 (mt: 2H); from 7.15 to 7.40 (mt: 8H)].

EXAMPLE 77

(RS)-{1-[Bis(4-chlorophenyl)methyl]azetidin-3-yl}-(3,5-difluorophenyl)acetic acid hydrochloride may be prepared in the following manner: 3 cm$^3$ of 6 N hydrochloric acid are added to a solution of 0.44 g of (RS)-{1-[bis(4-chlorophenyl)methyl]azetidin-3-yl}-(3,5-difluorophenyl)acetic acid ethyl ester in 7 cm$^3$ of dioxane. The solution obtained is stirred under reflux for about 2 hours and then left at a temperature in the region of 20° C. for about 12 hours. The precipitate formed is filtered on No. 3 sintered glass, washed with 10 cm$^3$ of diisopropyl ether and then dried under reduced pressure (0.27 kPa) at a temperature in the region of 40° C. 0.185 g of (RS)-{1-[bis(4-chlorophenyl)methyl]-azetidin-3-yl}-(3,5-difluorophenyl)acetic acid hydrochloride is thus obtained in the form of a white powder [$^1$H NMR spectrum (400 MHz, (CD$_3$)$_2$SO d6, at a temperature of 363K, δ in ppm): 2.87 (dd, J=14 and 4 Hz: 1H); 2.95 (mt: 1H); 3.18 (mt: 1H); 3.96 (d, J=10.5 Hz: 1H); 4.18 (t, J=9 Hz: 1H); 4.72 (t, J=9 Hz: 1H); 5.26 (unresolved complex: 1H); 7.00 (mt: 2H); 7.06 (tt, J=9.5 and 2.5 Hz: 1H); from 7.30 to 7.60 (mt: 8H)].

EXAMPLE 78

(RS) {1-[Bis(4-chlorophenyl)methyl]azetidin-3-yl}-(3,5-difluorophenyl)acetic acid ethyl ester may be prepared in the following manner: 121 mg of sodium borohydride are added, at a temperature in the region of 0° C., to a suspension of 0.78 g of (RS)-{1-[bis(4-chlorophenyl)methyl]azetidin-3-ylidene]-(3,5-difluorophenyl)acetic acid ethyl ester in 20 cm$^3$ of ethanol. The suspension obtained is stirred at a temperature in the region of 20° C. for about 12 hours. The reaction medium is poured into 200 cm³ of distilled water and then extracted with three times 40 cm³ of ethyl acetate. The organic phase is successively washed with 3 times 40 cm³ of distilled water and then with 40 cm³ of a saturated sodium chloride solution. After decantation, the organic phase is dried over magnesium sulfate, filtered and concentrated to dryness under reduced pressure (2.7 kPa) at a temperature in the region of 40° C. The residue obtained is chromatographed on a column filled with 75 cm³ of fine silica (0.040-0.063 mm) under a pressure of 0.7 bar with a dichloromethane-ethyl acetate mixture (the percentage of ethyl acetate varying from 0 to 10%), collecting 15-cm³ fractions. Fractions 4 to 11 are combined and concentrated to dryness under reduced pressure (2.7 kPa) at 40° C. 0.46 g of (RS)-{1-[bis(4-chlorophenyl)methyl]azetidin-3-yl}-(3,5-difluorophenyl)acetic acid ethyl ester is thus obtained in the form of a yellow lacquer [$^1$H NMR spectrum (300 MHz, CDCl$_3$, δ in ppm): 1.19 (t, J=7 Hz: 3H); 2.62 (broad t, J=6 Hz: 1H); 2.87 (dd, J=7.5 and 6 Hz: 1H); from 2.95 to 3.15 (mt: 2H); 3.39 (broad t, J=7.5 Hz: 1H); 3.78 (d, J=10.5 Hz: 1H); 4.10 (mt: 2H); 4.25 (s: 1H); 6.69 (tt, J=9 and 2.5 Hz 1H); 6.80 (mt: 2H); from 7.20 to 7.35 (mt: 8H)].

Fractions 16 to 26 from the preceding chromatography are combined and concentrated to dryness under reduced pressure (2.7 kPa) at 40° C. 0.24 g of (RS)-2-{1-[bis(4-chlorophenyl)methyl]azetidin-3-yl}-2-(3,5-difluorophenyl)ethanol is thus obtained in the form of a yellow foam [$^1$H NMR spectrum (300 MHz, CDCl$_3$, δ in ppm): 1.98 (unresolved complex: 1H); 2.69 (mt: 1H); from 2.70 to 2.85 (mt: 1H); from 2.90 to 3.10 (mt: 2H); 3.18 (mt: 1H); 3.44 (mt: 1H); from 3.65 to 3.85 (mt: 2H); 4.28 (s: 1H); from 6.60 to 6.80 (mt: 3H); from 7.20 to 7.35 (mt: 8H)].

{1-[Bis(4-chlorophenyl)methyl]azetidin-3-ylidene}-(3,5-difluorophenyl)acetic acid ethyl ester may be prepared in the following manner: 6.6 g of 4-dimethylaminopyridine and 2.1 cm³ of methylsulfonyl chloride are added to a solution of 9.1 g of {1-[bis-4-chlorophenyl)methyl]-3-hydroxyazetidin-3-yl}-(3,5-difluorophenyl)acetic acid ethyl ester in 200 cm³ of dichloromethane. The solution obtained is stirred at a temperature in the region of 20° C. for about 12 hours. The reaction mixture is washed three times with 250 cm³ of distilled water and then dried with magnesium sulfate, filtered and concentrated to dryness under reduced pressure (2.7 kPa) at a temperature in the region of 40° C. The residue obtained is taken up hot with 50 cm³ of isopropyl ether and then left at a temperature in the region of 20° C. for about 12 hours. The white suspension obtained is filtered on sintered glass, washed with 20 cm³ of petroleum ether and then dried under vacuum under reduced pressure (0.27 kPa) at a temperature in the region of 40° C. for 2 hours. 7.9 g of {1-[bis(4-chlorophenyl)methyl]azetidin-3-ylidene}-(3,5-difluorophenyl)acetic acid ethyl ester are thus obtained in the form of a cream-colored powder [$^1$H NMR spectrum (300 MHz, CDCl$_3$, δ in ppm): 1.25 (t, J=7 Hz 3H); 3.85 (mt: 2H); 4.12 (AB, J=7.5 Hz: 2H); 4.23 (mt: 2H); 4.51 (s: 1H); from 6.65 to 6.80 (mt: 3H); from 7.20 to 7.40 (mt: 8H)].

{1-[Bis(4-chlorophenyl)methyl]-3-hydroxyazetidin-3-yl}-(3,5-difluorophenyl)acetic acid ethyl ester may be prepared in the following manner: 34.54 cm³ of a 1.6 M butyllithium solution in hexane are added dropwise over 15 minutes to a solution of 7.73 cm³ of diisopropylamine in 125 cm³ of anhydrous tetrahydrofuran under an inert nitrogen atmosphere at a temperature in the region of −70° C., the stirring is maintained at this temperature for 45 minutes, a solution of 11.01 g of ethyl 3,5-difluorophenylacetate in 85 cm³ of anhydrous tetrahydrofuran are added over 15 minutes, the stirring is continued for 1 hour at −78° C., 16.84 g of 1-[bis(4-chlorophenyl)methyl]-azetidin-3-one in 90 cm³ of anhydrous tetrahydrofuran are added, the stirring is continued for 1 hour at −70° C., 300 cm³ of a saturated ammonium chloride solution are added over 30 minutes at 0° C. with vigorous stirring, the reaction mixture is separated after settling after 12 hours, the organic phase is washed 3 times with a saturated sodium bicarbonate solution, dried over magnesium sulfate, filtered and then concentrated to dryness under reduced pressure (2.7 kPa). The residue obtained is chromatographed on a column 70 mn in diameter filled with 2000 cm³ of fine silica (0.040-0.063 mm) under a pressure of 0.7 bar with a dichloromethane-ethyl acetate (99-01 by volume) mixture. The fractions containing only the desired product are combined and concentrated to dryness under reduced pressure (2.7 kPa) at 40° C. for 2 hours. 9.1 g of {1-[bis(4-chlorophenyl)methyl]-3-hydroxyazetidin-3-yl}-(3,5-difluorophenyl)acetic acid ethyl ester are thus obtained in the form of a cream-colored solid [$^1$H NMR spectrum (300 MHz, CDCl$_3$, δ in ppm): 1.25 (t, J=7 Hz: 3H); 2.87 (d, J=8 Hz: 1H); 3.07 (d, J=8 Hz: 1H); (broad d, J=8 Hz: 1H); 3.28 (broad d, J=8 Hz: 1H); 4.12 (s: 2H); 4.21 (mt: 2H); 4.36 (s: 1H); 6.78 (tt, J=9 and 2.5 Hz: 1H); 6.98 (mt: 2H); from 7.20 to 7.40 (mt: 8H)].

Ethyl 3,5-difluorophenylacetate may be prepared in the following manner: 20.4 cm³ of triethylamine and then 27.6 g of 3,5-difluorophenylacetic acid chloride in solution in 60 cm³ of dichloromethane are successively added to a solution of 12 cm³ of ethanol in 300 cm³ of anhydrous dichloromethane at a temperature in the region of 20° C. The solution obtained is stirred at a temperature in the region of 20° C. for about 12 hours. The reaction mixture is successively washed with twice 150 cm³ of a decinormal solution of hydrochloric acid and then with twice 150 cm³ of a saturated sodium bicarbonate solution. The organic phase is dried with magnesium sulfate, filtered and concentrated to dryness under reduced pressure (2.7 kPa) at a temperature in the region of 40° C. 29 g of ethyl 3,5-difluorophenyl acetate are thus obtained in the form of a yellow oil.

3,5-Difluorophenylacetic acid chloride may be prepared in the following manner: 19.3 cm³ of oxalyl chloride and then a few drops of dimethylformamide are successively added to a solution of 25 g of 3,5-difluorophenylacetic acid in 350 cm³ of 1,2-dichloroethane at a temperature in the region of 20° C., after stirring for 3 hours at a temperature in the region of 20° C., 30 cm³ of oxalyl chloride and a then few drops of dimethylformamide are again successively added. The reaction medium is concentrated to dryness under reduced pressure (2.7 kPa) at a temperature in the region of 40° C. 27.6 g of 3,5-difluorophenylacetic acid chloride are thus obtained in the form of a yellow oil.

EXAMPLE 79

(RS)-1-[Bis(4-chlorophenyl)methyl]-3-[1-(3,5-difluorophenyl)-1-methylsulfonylethyl]azetidine is obtained in the following manner: 0.5 cm³ of a 2 M solution of lithium diisopropylamide is added to a solution of 0.5 g of (RS)-1-[bis(4-chlorophenyl)-methyl)]-3-[(3,5-difluorophenyl)(methylsulfonyl)-methyl]azetidine in 10 cm³ of tetrahydrofuran cooled to −78° C. and maintained under an inert atmosphere. The temperature is allowed to rise to −20° C. and then 0.06 cm³ of iodomethane is added. The temperature is allowed to rise to 0° C. over a period of 2 hours and then 20 cm³ of a saturated aqueous ammonium chloride solution are added. The reaction medium is separated after settling and the aqueous phases are extracted with twice 20 cm³ of ethyl acetate.

The organic extracts are combined, dried over magnesium sulfate and evaporated to dryness at 40° C. under 2.7 kPa, providing 550 mg of cream-colored residue. The residue is chromatographed on a silica column (Dynamax, reference 83-121-C, size 21.4 mm×250 mm, precolumn 21.4 mm×50 mm, reference R00083121G, 8μ silica, porosity 60 Angstroem; Rainin Instrument Co. Inc., Mac Road, Woburn, Mass. 01801, USA), eluting with a heptane: isopropanol (99:1 by volume) mixture at 15 cm$^3$ per minute (detection 254 nm, 10-cm$^3$ fractions). The fractions containing the compound with an Rf=32/77 (cyclohexane:ethyl acetate 70:30, 254 nm, silica plates reference 1.05719, Merck KGaA, 64271 Darmstadt, Germany) are combined and evaporated at 40° C. under 2.7 kPa, providing 80 mg of 1-[bis(4-chlorophenyl)-methyl]-3-[1-(3,5-difluorophenyl)-1-methylsulfonyl-ethyl] azetidine in the form of a white amorphous powder [$^1$H NMR spectrum (300 MHz, CDCl$_3$, δ in ppm): 2.05 (s: 3H); 2.54 (s: 3H); 2.63 (t, J=7.5 Hz: 1H); 3.17 (broad t, J=8 Hz: 1H); 3.32 (mt: 1H); 3.44 (broad t, J=8 Hz: 1H); 3.71 (mt: 1H); 4.27 (s: 1H); 6.83 (tt, J=9 and 2.5 Hz: 1H); 7.15 (mt: 2H); from 7.20 to 7.40 (mt: 8H)].

EXAMPLE 80

(RS)-1-[Bis(4-fluorophenyl)methyl]-3-[(3,5-difluorophenyl)methylsulfonylmethyl]azetidine may be prepared in the following manner: a few granules of potassium iodide are added to a suspension of 0.191 cm$^3$ of bis(4-fluorophenyl) chloromethane, 300 mg of (RS)-3-[(3,5-difluorophenyl)methylsulfonylmethyl]-azetidine and 167 mg of potassium carbonate in 5 cm$^3$ of acetonitrile, at a temperature in the region of 20° C. After 48 hours at a temperature in the region of 20° C., the reaction medium is filtered on sintered glass, the solid is rinsed with acetonitrile and the filtrate is purified by preparative thin-layer chromatography on silica [3 preparative Merck Kieselgel 60F254 plates, 20×20 cm; thickness 1 mm], eluting with a methanol-dichloromethane (1-99 by volume) mixture. After elution of the zone corresponding to the desired product with a methanol-dichloromethane (10-90 by volume) mixture, filtration on sintered glass and then evaporation of the solvents under reduced pressure at a temperature in the region of 40° C., 39 mg of (RS)-1-[bis(4-fluoro-phenyl) methyl]-3-[(3,5-difluorophenyl)methylsulfonyl-methyl]azetidine are obtained in the form of a yellow foam [$^1$H NMR spectrum (300 MHz, CDCl$_3$, δ in ppm): 2.54 (broad t, J=7 Hz: 1H); 2.66 (s: 3H); 3.18 (mt: 2H); from 3.20 to 3.45 (mt: 1H); 3.63 (broad t, J=7 Hz: 1H); 4.27 (s: 1H); 4.28 (d, J=11 Hz: 1H); 6.83 (tt, J=9 and 2 Hz: 1H); from 6.90 to 7.05 (mt: 6H); from 7.25 to 7.40 (mt: 4H)].

(RS)-3-[(3,5-Difluorophenyl)methylsulfonyl-methyl]azetidine hydrochloride may be prepared may be prepared in the following manner: a suspension of 8.5 g of 1-benzhydryl-3-[(3,5-difluorophenyl)(methylsulfonyl methylene]azetidine and 1.3 g of palladium hydroxide (20% by weight of palladium), in 600 cm$^3$ of methanol, 20 cm$^3$ of 1 N hydrochloric acid and 4 cm$^3$ of acetic acid, is stirred at a temperature in the region of 20° C. under a hydrogen atmosphere (1.5 bar) until complete absorption of a volume of 2.1 liters of hydrogen is obtained. The reaction medium is then filtered on sintered glass covered with charcoal. The filtrate is concentrated to dryness under reduced pressure and then the residue obtained is taken up in ethanol. The crystallized white product is filtered and dried. 5.4 g of (RS)-3-[(3,5-difluorophenyl)methylsulfonyl-methyl]azetidine hydrochloride are thus obtained in the form of white crystals.

1-Benzhydryl-3-[(3,5-difluorophenyl)(methyl-sulfonyl) methylene]azetidine may be prepared may be prepared in the following manner: a mixture of 18.8 g of 3-acetoxy-1-benzhydryl-3-[(3,5-difluorophenyl)-(methylsulfonyl)methyl] azetidine and 3.9 g of lithium hydroxide monohydrate in 120 cm$^3$ of acetonitrile is heated at a temperature in the region of 70° C. for 3 hours. After cooling to a temperature in the region of 2° C., 120 cm$^3$ of tert-butyl and methyl ether and 80 cm$^3$ of distilled water are successively added followed, slowly, by 5 cm$^3$ of acetic acid. After decantation, the organic phase is washed with 80 cm$^3$ of a saturated aqueous sodium hydrogen carbonate solution, 80 cm$^3$ of distilled water, 80 cm$^3$ of a saturated aqueous sodium chloride solution, dried over magnesium sulfate, filtered and concentrated to dryness under reduced pressure. The residue obtained is taken up in ethanol. After leaving overnight at a temperature in the region of 20° C., the mixture obtained is filtered on sintered glass, the white crystals obtained are rinsed with ethanol, diisopropyl ether and dried under reduced pressure at a temperature in the region of 45° C. 14.6 g of 1-benzhydryl-3-[(3,5-difluorophenyl)(methyl-sulfonyl)methylene]azetidine are thus obtained in the form of white crystals.

3-Acetoxy-1-benzhydryl-3-[(3,5-difluoro-phenyl)methylsulfonyl)methyl]azetidine may be prepared may be prepared in the following manner: 47.1 cm$^3$ of 1.6 N n-butyllithium in solution in hexane are added dropwise over approximately 25 minutes to a suspension of 12.37 g of 3,5-difluorobenzyl methyl sulfone in 200 cm$^3$ of tetrahydrofuran, under an inert nitrogen atmosphere at a temperature in the region of –30° C. The cloudy yellow solution is stirred at a temperature in the region of –30° C. for 2 hours and then a solution of 11.87 g of 1-benzhydrylazetidin-3-one in 75 cm$^3$ of dichloromethane is added dropwise. The reaction mixture is stirred for 1.5 hours at a temperature in the region of –30° C. and then 6.07 cm$^3$ of acetyl chloride are added and the temperature of the medium is allowed to return to a temperature in the region of –10° C. over about 30 minutes. 200 cm$^3$ of water and 100 cm$^3$ of dichloromethane are added. After stirring vigorously for 30 minutes and decantation, the organic phase is washed with 3 times 150 cm$^3$ of a saturated aqueous sodium hydrogen carbonate solution, 150 cm$^3$ of a saturated aqueous sodium chloride solution, dried over magnesium sulfate, filtered and concentrated to dryness under reduced pressure. The crystalline residue obtained is taken up in 50 cm$^3$ of boiling ethanol. The white suspension obtained is allowed to stand overnight at a temperature in the region of 20° C. and then the solid obtained is drained over sintered glass, rinsed with diisopropyl ether and dried under reduced pressure at a temperature in the region of 50° C. 19.5 g of 3-acetoxy-1-benzhydryl-3-[(3,5-difluorophenyl)(methyl-sulfonyl)methyl]azetidine are thus obtained in the form of white crystals.

1-Benzhydrylazetidin-3-one may be prepared according to the procedure described by KATRITZKY A. R. et al. in J. Heterocycl. Chem., 271 (1994).

3,5-Difluorobenzyl methyl sulfone may be prepared may be prepared in the following manner: a mixture of 66.69 cm$^3$ of 3,5-difluorobenzyl bromide, 71.97 g of the sodium salt of methanesulfinic acid and 150 mg of sodium iodide in 625 cm$^3$ of ethanol is heated under reflux, under an argon atmosphere, for about 16 hours. After cooling to a temperature in the region of 20° C., the reaction medium is diluted with 3 liters of ethyl acetate, washed with 500 cm$^3$ of water, 500 cm$^3$ of a saturated aqueous sodium chloride solution, dried over magnesium sulfate, filtered and evaporated under reduced pressure (50 mbar) at a temperature in the region of 40° C. The residue obtained is taken up in 300 cm$^3$ of ethyl ether, and the solid is filtered on sintered glass, rinsed with 200 cm$^3$ of ethyl ether, dried under reduced pressure at a temperature in the region of 20° C. 86 g of 3,5-difluorobenzyl methyl sulfone are thus obtained in the form of a white powder.

EXAMPLE 81

(RS)-{1-[(3-pyridyl)-(4-chlorophenyl)methyl]-3-[(3,5-difluorophenyl)methylsulfonylmethyl]azetidine may be prepared in the following manner: a mixture of 47 mg of 3-(pyridyl)-(4-chlorophenyl)bromomethane, 50 mg of (RS)-3-[(3,5-difluorophenyl)methylsulfonyl-methyl]azetidine hydrochloride and 58 mg of potassium carbonate in 2 cm$^3$ of acetonitrile, is stirred for about 3 hours at a temperature in the region of 20° C., for 2 hours at the reflux temperature of the solvent, for about 16 hours at a temperature in the region of 20° C. and then for 1.5 hours at the reflux temperature of the solvent. A few granules of potassium iodide are then added and the reaction mixture is maintained for about 2 hours at the reflux temperature of the solvent. After cooling to a temperature in the region of 20° C., the reaction medium is purified by preparative thin-layer chromatography on silica [2 preparative Merck Kieselgel 60F254 plates; 20×20 cm; thickness 0.5 mm], eluting with a methanol-dichloromethane (2.5-97.5 by volume) mixture. After elution of the zone corresponding to the desired product with a methanol-dichloromethane (10-90 by volume) mixture, filtration on sintered glass and then evaporation of the solvents under reduced pressure at a temperature in the region of 40° C., 11 mg of (RS)-{1-[(3-pyridyl)-(4-chlorophenyl)methyl]-3-[(3,5-difluorophenyl)methylsulfonylmethyl]azetidine are obtained in the form of a colorless lacquer [$^1$H NMR spectrum (300 MHz, CDCl$_3$, δ in ppm): 2.59 (mt: 1H); 2.66 (s: 3H); 3.21 (mt: 2H); from 3.30 to 3.50 (mt: 1H); 3.67 (mt: 1H); 4.28 (broad d, J=11 Hz: 1H); 4.32 (broad s: 1H); 6.84 (tt, J=9 and 2 Hz: 1H); 6.95 (mt: 2H); 7.19 (broad dd, J=8 and 5 Hz: 1H); from 7.20 to 7.40 (mt: 4H); 7.64 (broad d, J=8 Hz: 1H); 8.45 (mt: 1H); 8.59 (very broad s: 1H].

(3-Pyridyl)-(4-chlorophenyl)bromomethane may be prepared in the following manner: a mixture of 150 mg of (3-pyridyl)-(4-chlorophenyl)methanol in 0.356 cm$^3$ of hydrobromic acid (at 33% in acetic acid) and 0.101 cm$^3$ of acetyl bromide is heated under reflux for 1 hour and then left at a temperature in the region of 20° C. for 2 hours, before being concentrated under reduced pressure and coevaporated with a few cm$^3$ of toluene. 234 mg of (3-pyridyl)-(4-chlorophenyl)-bromomethane are thus obtained in the form of a gummy beige solid.

(3-Pyridyl)-(4-chlorophenyl)methanol may be prepared in the following manner: 0.5 cm$^3$ of 3-pyridinecarboxaldehyde is slowly added to a solution of 5.83 cm$^3$ of 4-chlorophenyl-magnesium bromide (1 M solution in ethyl ether) in 5 cm$^3$ of tetrahydrofuran, under an inert argon atmosphere. After about 3 hours, 3 cm$^3$ of a saturated aqueous ammonium chloride solution and 10 cm$^3$ of water are added to the reaction medium. After stirring for 5 minutes at a temperature in the region of 20° C., the reaction medium is acidified to a pH of about 2 with a 1 N aqueous hydrochloric acid solution. The aqueous phase is extracted with 3 times 15 cm$^3$ of dichloromethane. The remaining aqueous phase is treated with 10 cm$^3$ of a 1 N aqueous sodium hydroxide solution and reextracted with 3 times 15 cm$^3$ of ethyl acetate. The organic phases containing the ethyl acetate are combined, dried over magnesium sulfate, filtered and concentrated under reduced pressure. 466 mg of (3-pyridyl)-(4-chlorophenyl)methanol are thus obtained in the form of a bright yellow solid.

EXAMPLE 82

(RS)-{1-[(4-Pyridyl)-(4-chlorophenyl)methyl]-3-[(3,5-difluorophenyl)methylsulfonylmethyl]azetidine may be prepared in the following manner: a mixture of 160 mg of (4-(pyridyl)-(4-chlorophenyl)bromomethane, 169 mg of (RS)-3-[(3,5-difluorophenyl)methylsulfonyl-methyl]azetidine hydrochloride and 94 mg of potassium carbonate in 5 cm$^3$ of acetonitrile, is stirred for about 17 hours at a temperature in the region of 20° C. A few granules of sodium iodide are then added and after stirring for 2 hours at a temperature in the region of 20° C., the reaction mixture is maintained for about 1.5 hours at the reflux temperature of the solvent. After cooling to a temperature in the region of 20° C., the reaction medium is purified by preparative thin-layer chromatography on silica [4 preparative Merck Kieselgel 60F254 plates; 20×20 cm; thickness 0.5 mm], eluting with a methanol-dichloromethane (2.5-97.5 by volume) mixture. After elution of the zone corresponding to the desired products with a methanol-dichloromethane (10-90 by volume) mixture, filtration on sintered glass and then evaporation of the solvents under reduced pressure at a temperature in the region of 40° C., there are obtained a first mixture of diastereoisomers, that is to say 24 mg of (RS)-{1-[(4-pyridyl)-(4-chlorophenyl)methyl]-3-((3,5-difluorophenyl)methylsulfonylmethyl]azetidine in the form of a yellow lacquer, and a second mixture of diastereoisomers, that is to say 31 mg of (RS)-{1-[(4-pyridyl)-(4-chlorophenyl)methyl]-3-[(3,5-difluorophenyl)methylsulfonylmethyl]azetidine in the form of a yellow foam. The first mixture of diastereoisomers has the characteristics are the following [$^1$H NMR spectrum (300 MHz, CDCl$_3$, δ in ppm): 2.62 (t, J=7 Hz: 1H); 2.67 (s: 3H); 3.21 (broad t, J=7 Hz: 2H); 3.42 (mt: 1H); 3.70 (broad t, J=7 Hz: 1H); 4.28 (s: 1H); 4.28 (d, J=11 Hz 1H); 6.85 (tt, J=9 and 2.5 Hz: 1H); 6.97 (mt: 2H); from 7.20 to 7.35 (mt: 6H); 8.52 (dd, J=4.5 and 1.5 Hz: 2H).

The second mixture of diastereoisomers has the characteristics are the following [$^1$H NMR spectrum (300 MHz, CDCl$_3$, δ in ppm): 2.59 (t, J=7 Hz: 1H); 2.67 (s: 3H); 3.26 (mt: 2H); from 3.35 to 3.50 (mt 1H); 3.63 (broad t, J=7 Hz: 1H); 4.28 (s: 1H); 4.28 (d, J=11 Hz: 1H); 6.85 (tt, J=9 and 2 Hz: 1H); 6.97 (mt: 2H); from 7.20 to 7.40 (mt: 6H); 8.50 (dd, J=4.5 and 1.5 Hz: 2H).

(4-Pyridyl)-(4-chlorophenyl)bromomethane may be prepared in the following manner: a solution of 100 mg of (4-pyridyl)-(4-chlorophenyl)methanol in 0.24 cm$^3$ of hydrobromic acid (at 33% in acetic acid) is heated under reflux for 1 hour and then allowed to return to a temperature in the region of 20° C. 0.675 cm$^3$ of acetyl bromide is then added and the reaction mixture is heated under reflux for 1.5 hours and then allowed to return to a temperature in the region of 20° C. before being concentrated under reduced pressure. 163 mg of (4-pyridyl)-(4-chlorophenyl)bromomethane are thus obtained in the form of a beige foam-gum.

(4-Pyridyl)-(4-chlorophenyl)methanol may be prepared in the following manner: 348 mg of sodium tetraborohydride are added, at a temperature in the region of 20° C., to a solution of 2 g of 4-(4-chlorobenzoyl)pyridine in 160 cm$^3$ of ethanol. After stirring for 2 hours at a temperature in the region of 20° C., 90 mg of sodium tetraborohydride are added. After about 1.5 hours at the same temperature, the reaction medium is diluted with 200 cm$^3$ of dichloromethane and 200 cm$^3$ of water. The pH of the aqueous phase is adjusted to a value of about 5 by addition of about 13 cm$^3$ of an aqueous 1 N hydrochloric acid solution. After decantation, the aqueous phase is extracted with 3 times 100 cm³ of dichloromethane. The organic phases are combined, dried over magnesium sulfate, filtered and concentrated under reduced pressure. 2 g of (4-pyridyl)-(4-chlorophenyl)methanol are thus obtained in the form of a white powder.

EXAMPLE 83

(RS)-{1-((2-Chloropyrid-5-yl)-(4-chloro-phenyl)methyl]-3-[(3,5-difluorophenyl)methylsulfonyl-methyl]azetidine may be prepared in the following manner: a mixture of 300 mg of (2-chloropyrid-5-yl)-(4-chlorophenyl)bromomethane, 225 mg of (RS)-3-[(3,5-difluorophenyl)methylsulfonylmethyl]-azetidine hydrochloride, 125 mg of potassium iodide and 521 mg of potassium carbonate in 5 cm³ of acetonitrile, is heated for about 2 hours at the reflux temperature. of the solvent. After cooling to a temperature in the region of 20° C., the reaction medium is filtered on sintered glass. The solid residue is rinsed with dichloromethane and the filtrates are evaporated under reduced pressure. 402 mg of a chocolate foam are thus obtained, which foam is purified by preparative thin-layer chromatography on silica [4 preparative Merck Kieselgel 60F254 plates; 20×20 cm; thickness 0.5 mm], eluting with a methanol-dichloromethane (2.5-97.5 by volume) mixture. After elution of the zone corresponding to the desired product with a methanol-dichloromethane (10-90 by volume) mixture, filtration on sintered glass and then evaporation of the solvents under reduced pressure at a temperature in the region of 40° C., there are obtained a first mixture of diastereoisomers, that is to say 14 mg of (RS)-{1-[(2-chloropyrid-5-yl)-(4-chlorophenyl)methyl]-3-[(3,5-difluorophenyl)methylsulfonylmethyl]azetidine in the form of a brown foam, and a second mixture of diastereoisomers, that is to say 10 mg of (RS)-{1-[(2-chloropyrid-5-yl)-(4-chlorophenyl)methyl]-3-[(3,5-difluorophenyl)methylsulfonylmethyl]azetidine in the form of a beige foam.

The first mixture of diastereoisomers has the characteristics are the following: [¹H NMR spectrum (300 MHz, CDCl₃, δ in ppm): 2.57 (t, J=7.5 Hz: 1H); 2.65 (s: 3H); from 3.15 to 3.30 (mt: 2H); 3.40 (mt: 1H); 3.63 (broad t, J=7.5 Hz: 1H); 4.27 (d, J=11 Hz 1H); 4.31 (s: 1H); 6.84 (tt, J=9 and 2 Hz: 1H); 6.95 (mt: 2H); from 7.20 to 7.35 (mt: 5H); 7.63 (dd, J=8 and 2.5 Hz: 1H); 8.38 (d, J=2.5 Hz: 1H).

The second mixture of diastereoisomers has the characteristics are the following: [¹H NMR spectrum (300 MHz, CDCl₃, δ in ppm): 2.57 (t, J=7.5 Hz: 1H); 2.64 (s: 3H); 3.18 (broad t, J=7.5 Hz: 2H); 3.38 (mt: 1H); 3.63 (broad t, J=7.5 Hz: 1H); 4.24 (d, J=11.5 Hz: 1H); 4.29 (s: 1H); 6.83 (tt, J=9 and 2 Hz: 1H); 6.94 (mt: 2H); 7.20 (d, J=8 Hz: 1H); from 7.20 to 7.35 (mt: 4H); 7.59 (dd, J=8 and 2.5 Hz 1H); 8.34 (d, J=2.5 Hz: 1H).

2-(Chloropyrid-5-yl)-(4-chlorophenyl)bromo-methane may be prepared in the following manner: 0.153 cm³ of thionyl bromide is added to a solution of 100 mg of (2-chloropyrid-5-yl)-(4-chlorophenyl)methanol in 2 cm³ of carbontetrachloride, under an inert argon atmosphere, at a temperature in the region of 0° C. After 3.5 hours at a temperature in the region of 0° C., the reaction medium is concentrated under reduced pressure and coevaporated with a few cm³ of toluene. 1.3 g of a brown liquid are thus obtained, which liquid is taken up in dichloromethane and supplemented with water and sodium dithionite. After decantation, the organic phase is dried over magnesium sulfate, filtered and concentrated to dryness under reduced pressure. 0.33 g of 2-(chloropyrid-5-yl)-(4-chlorophenyl)bromo-methane is thus obtained in the form of a brown oil.

2-(Chloropyrid-5-yl)-(4-chlorophenyl)bromo-methane may be prepared by carrying out the procedure in a manner similar to Example 84, starting with 22.5 cm³ of 4-chlorophenylmagnesium bromide (1 M solution in ethyl ether) in 30 cm³ of tetrahydrofuran, under an inert argon atmosphere, and 2.9 g of 2-chloropyridine-5-carboxaldehyde in 30 cm³ of tetrahydrofuran. 3.42 g of 2-(chloropyrid-5-yl)-(4-chlorophenyl)methanol are thus obtained in the form of a pale green powder.

2-Chloropyridine-5-carboxaldehyde may be prepared according to the following reference: G. Pandey, T. D. Bagul, A. K. Sahoo, J. Org. Chem., 1998, 63, 760-768.

EXAMPLE 84

(RS)-5-((4-chlorophenyl)-{3-[(3,5-difluoro-phenyl)methylsulfonylmethyl]azetidin-1-yl}methyl)pyrimidine may be prepared in the following manner: a mixture of 50 mg of 5-[bromo-(4-chlorophenyl)methyl]pyrimidine, 52.6 mg of (RS)-3-[(3,5-difluorophenyl)methylsulfonylmethyl]-azetidine hydrochloride, 44 mg of potassium iodide and 73 mg of potassium carbonate in 2 cm³ of acetonitrile, is heated for about 5 hours at the reflux temperature of the solvent. After cooling to a temperature in the region of 20° C., the reaction medium is purified by direct deposition on preparative thin-layer chromatography on silica [2 preparative Merck Kieselgel 60F254 plates; 20×20 cm; thickness 0.5 mm], eluting with a methanol-dichloromethane (2.5-97.5 by volume) mixture. After elution of the zone corresponding to the desired product with a methanol-dichloromethane (10-90 by volume) mixture, filtration on sintered glass and then evaporation of the solvents under reduced pressure at a temperature in the region of 40° C., there are obtained a first mixture of diastereoisomers, that is to say 8 mg of (RS)-5-((4-chlorophenyl)-{3-[(3,5-difluorophenyl)methylsulfonylmethyl]azetidin-1-yl}methyl)pyrimidine in the form of a yellow foam, and a second mixture of diastereoisomers, that is to say 6 mg of (RS)-5-((4-chlorophenyl)-{3-[(3,5-difluoro-phenyl)methylsulfonylmethyl]azetidin-1-yl}methyl)-pyrimidine in the form of a yellow foam.

The first mixture of diastereoisomers has the characteristics are the following: [¹H NMR spectrum (300 MHz, CDCl₃, δ in ppm): 2.60 (broad t, J=7 Hz 1H); 2.66 (s: 3H); 3.24 (broad t, J=7 Hz: 2H); 3.41 (mt: 1H); 3.66 (broad t, J=7 Hz: 1H); 4.28 (d, J=11.5 Hz: 1H); 4.33 (broad s: 1H); 6.84 (broad t, J=9 Hz: 1H); 6.95 (mt: 2H); from 7.25 to 7.35 (mt 4H); 8.71 (broad s: 2H); 9.08 (broad s: 1H).

The second mixture of diastereoisomers has the characteristics are the following: [¹H NMR spectrum (300 MHz, CDCl₃, δ in ppm): 2.61 (t, J=7 Hz: 1H); 2.66 (s: 3H); 3.24 (broad t, J=7 Hz: 2H); 3.43 (mt: 1H); 3.65 (broad t, J=7 Hz: 1H); 4.28 (d, J=11.5 Hz: 1H); 4.33 (s: 1H); 6.85 (tt, J=9 and 2 Hz: 1H); 6.96 (mt: 2H); from 7.25 to 7.35 (mt 4H); 8.69 (s: 2H); 9.06 (s: 1H).

5-[Bromo-(4-chlorophenyl)methyl]pyrimidine may be prepared in the following manner: 0.36 cm³ of thionyl bromide is added to a solution of 205 mg of (4-chlorophenyl)pyrimidin-5-ylmethanol in 1 cm³ of carbontetrachloride, and 1 cm³ of dichloromethane, under an inert argon atmosphere, at a temperature in the region of 0° C. After 2.5 hours at a temperature in the region of 0° C., the reaction medium is brought to a temperature in the region of 20° C., concentrated under reduced pressure and coevaporated with a few cm³ of toluene. The brown liquid obtained is taken up in 10 cm³ of dichloromethane, washed with 5 cm³ of a saturated aqueous sodium dithionite solution and then with water. After decantation, the organic phase is dried over magnesium sulfate, filtered and concentrated to dryness under reduced pressure. 227 mg of a beige viscous liquid are thus obtained, which liquid is taken up in a minimum quantity of dichloromethane and purified by preparative thin-layer chromatography on silica [2 preparative Merck Kieselgel 60F254 plates; 20×20 cm, thickness 0.5 mm], eluting with a methanol-dichloromethane (2.5-97.5 by volume) mixture. After elution of the zone corresponding to the desired product with a methanol-dichloromethane (10-90 by volume) mixture, filtration on sintered glass and then evaporation of the solvents under reduced pressure at a temperature in the region of 40° C., 51 mg of 5-[bromo-(4-chlorophenyl)methyl]pyrimidine are obtained in the form of a yellow foam.

4-(Chlorophenyl)pyrimidin-5-ylmethanol may be prepared by carrying out the procedure in a manner similar to Example 83, 2.5 cm$^3$ of n-butyllithium (1.6 M solution in hexane) are added dropwise to a solution of 636 mg of 5-bromopyrimidine in 10 cm$^3$ of tetrahydrofuran, under an inert argon atmosphere, at a temperature in the region of −78° C. After 10 minutes at a temperature in the region of −78° C., a solution of 562 mg of 4-chlorobenzaldehyde in 1 cm$^3$ of tetrahydrofuran is added dropwise. After stirring for 30 minutes at a temperature in the region of −78° C., the temperature of the reaction medium is allowed to rise slowly to a temperature in the region of 20° C., and 15 cm$^3$ of a saturated aqueous ammonium chloride solution, 60 cm$^3$ of ethyl acetate and 10 cm$^3$ of water are added successively. The aqueous phase is extracted with 15 cm$^3$ of ethyl acetate, the organic phases are combined, dried over magnesium sulfate, filtered on sintered glass and concentrated under reduced pressure (20 mbar) at a temperature in the region of 44° C. The bulk of the orange-colored oil obtained (1.09 g) is purified by chromatography on a column 30 mm in diameter filled with 60 g of medium silica (0.063-0.200 mm) at atmospheric pressure, eluting with a methanol/dichloromethane (0/100 to 7/93 by volume) gradient. The fractions containing only the desired product are combined and concentrated to dryness under reduced pressure. 293 mg of 4-(chlorophenyl)pyrimidin-5-yl)methanol are thus obtained in the form of a yellow oil.

EXAMPLE 85

The phenolic ester of 4-({1-[bis(4-chloro-phenyl)methyl]azetidin-3-ylidene}methyl-sulfonylmethyl)-3,6-dihydro-2H-pyridine-1-carbothioic acid may be prepared in the following manner: 0.140 g of 4-dimethylaminopyridine and then 0.042 cm$^3$ of methanesulfonyl chloride are added to a solution of 0.23 g of the phenolic ester of 4-({1-bis(4-chloro-phenyl)methyl]-3-hydroxyazetidin-3-yl}methylsulfonyl-methyl)-3,6-dihydro-2H-pyridine-1-carbothioic acid in 5 cm$^3$ of dichloromethane. The reaction mixture is stirred for 20 hours at 20° C. and then diluted with 10 cm$^3$ of water. After decantation, the organic phase is successively washed with 100 cm$^3$ of water and 100 cm$^3$ of a saturated NaCl solution, dried over magnesium sulfate and then concentrated to dryness at 40° C. under 2.7 kPa. The oil obtained is triturated for 45 minutes in 50 cm$^3$ of diisopropyl ether. The solid formed is filtered, providing 120 mg of the phenolic ester of 4-({1-[bis(4-chlorophenyl)methyl]azetidin-3-ylidene}methylsulfonylmethyl)-3,6-dihydro-2H-pyridine-1-carbothioic acid in the form of a beige solid melting at 184° C. [$^1$H NMR spectrum (400 MHz, CDCl$_3$, δ in ppm): 2.53 (unresolved complex: 2H); 2.95 (s: 3H); 3.90 (unresolved complex: 2H); 4.04 (t, J=5.5 Hz: 1H); 4.24 (mt: 3H); 4.49 (unresolved complex: 2H); 4.60 (mt: 1H); 5.90 (unresolved complex: 1H); from 7.05 to 7.50 (mt: 13H)].

The phenolic ester of 4-({1-[bis(4-chloro-phenyl)methyl]-3-hydroxyazetidin-3-yl}methyl-sulfonylmethyl)-3,6-dihydro-2H-pyridine-1-carbothioic acid is prepared in the following manner: 0.52 g of potassium tert-butoxide is added to a mixture of 0.72 g of the phenolic ester of 4-methylsulfonyl-methyl-3,6-dihydro-2H-pyridine-1-carbothioic acid and 0.708 g of 1-[bis(4-chlorophenyl)methyl]azetidin-3-one in 15 cm$^3$ of dry tetrahydrofuran cooled under an inert atmosphere to −78° C. The reaction mixture is stirred at −78° C. for 4 hours and then 0.354 g of 1-[bis(4-chlorophenyl)-methyl] azetidin-3-one are added. After two hours at −78° C., the temperature is allowed to return to 20° C. The reaction mixture is diluted in 100 cm$^3$ of water and then the tetrahydrofuran is evaporated off under 2.7 kPa at 40° C. The aqueous phase is extracted with twice 100 cm$^3$ of ethyl acetate. The organic extracts are combined and dried over magnesium sulfate, concentrated under 2.7 kPa at 40° C. The residue obtained is chromatographed on silica (200 g of silica, Amicon, 20-45 μm, porosity 60 Angstroem, column 5 cm in diameter), eluting with a cyclohexane:ethyl acetate (6:4 by volume) mixture. The fractions with an Rf=11/64 (cyclohexane:ethyl acetate 6:4, silica plate, Merck reference 1.05719, Merck KGaA, 64721 Darmstatd, Germany) are combined and concentrated under 2.7 kPa at 40° C. to give 240 mg of the phenolic ester of 4-({1-[bis(4-chlorophenyl)methyl]-3-hydroxyazetidin-3-yl}methylsulfonylmethyl)-3,6-dihydro-2H-pyridine-1-carbothioic acid.

The phenolic ester of 4-methylsulfonylmethyl-3,6-dihydro-2H-pyridine-1-carbothioic acid may be prepared in the following manner: 0.778 cm$^3$ of phenyl thiochloroformate is added to a solution of 1 g of 1-benzyl-4-methylsulfonylm-ethyl-1,2,3,6-tetra-hydropyridine in 10 cm$^3$ of dichloromethane under an argon atmosphere. The solution instantly acquires a very dark amber color. The reaction mixture is stirred for 4 hours at 21° C. and then diluted in 100 cm$^3$ of dichloromethane. The organic medium is washed with twice 50 cm$^3$ of water, dried over magnesium sulfate and evaporated to dryness at 40° C. under 2.7 kPa. The residue obtained is purified by chromatography on a silica cartridge (reference SIL-020-005, FlashPack, Jones Chromatography Limited, New Road, Hengoed, Mid Glamorgan, CF82 8AU, Great Britain), eluting with a cyclohexane:ethyl acetate 6:4 mixture (10 cm$^3$/min, 5-cm$^3$ fractions). The fractions with an Rf=12/74 (cyclohexane:ethyl acetate 1:1, silica plate, Merck reference 1.05719, Merck KGaA, 64271 Darmstatd, Germany) are combined and concentrated under 2.7 kPa at 40° C. to give 700 mg of the phenolic ester of 4-methylsulfonylmethyl-3,6-dihydro-2H-pyridine-1-carbothioic acid.

1-Benzyl-4-methylsulfonylmethyl-1,2,3,6-tetrahydropyridine may be prepared in the following manner: a solution of 5.14 g of sodium borohydride and 25 g of sodium carbonate in 700 cm$^3$ of water is added dropwise over one hour, without exceeding a temperature of 5° C. in the reaction medium, to a solution of 17.6 g of 1-benzyl-4-methylsulfonylmethylpyridinium bromide in 700 cm$^3$ of water cooled to 5° C. The reaction medium is stirred for four hours at 0° C. and then the temperature is allowed to return to room temperature overnight. The yellow solid formed is isolated by filtration and dried under 2.7 kPa, giving 9.6 g of 1-benzyl-4-methylsulfo-nylmethyl-1,2,3,6-tetrahydropyridine having an Rf of 44/81 (dichloromethane:methanol, 95:5 by volume, silica plate, Merck reference 1.05719, Merck KGaA, 64271 Darmstatd, Germany).

1-Benzyl-4-methylsulfonylmethylpyridinium bromide may be prepared in the following manner: 14 cm$^3$ of benzyl bromide are added to a solution of 10 g of 4-methylsulfonyl-methylpyridine in 200 cm$^3$ of acetonitrile and then the mixture is heated under reflux for 3 hours and is then allowed to return to room temperature overnight. The solid formed is filtered, dried under vacuum at 2.7 kPa, giving 17.6 g of 1-benzyl-4-methylsulfonylmethylpyridinium bromide.

4-Methylsulfonylmethylpyridine may be prepared in the following manner: 14 g of sodium hydroxide pellets and then 35.7 g of sodium methanesulfinate are slowly added to a solution of 57.4 g of 4-chloromethylpyridine hydrochloride in 700 cm³ of ethanol. After addition, the temperature is 28° C. The reaction mixture is heated under reflux for two hours and then allowed to return to room temperature overnight. The reaction medium is heated to 50° C. and then filtered hot on paper. The filtrate is evaporated to dryness at 40° C. under 2.7 kPa. The residue is recrystallized from 300 cm³ of isopropanol, giving 29.6 g of 4-methylsulfonylmethylpyridine.

EXAMPLE 86

(RS)-1-[2-{1-[bis(4-chlorophenyl)methyl]-azetidin-3-yl}-2-(3,5-diflourophenyl)ethyl]-3-propyl-urea may be prepared by carrying out the procedure in the following manner: 0.052 cm³ of n-propyl isocynate is added to a solution of 90 mg of (RS)-2-{1-bis(4-chloro-phenyl)methyl]-azetidin-3-yl}-2-(3,5-diflourophenyl)ethylamine in 5 cm³ of tetrahydrofuran. After stirring for about 72 hours at a temperature in the region of 20° C., the reaction mixture is filtered, concentrated to dryness under reduced pressure and taken up in diisopropyl ether. The mixture obtained is filtered and concentrated to dryness under reduced pressure. 80 mg of a pale yellow solid are thus obtained, which solid is dissolved in 5 cm³ of tetrahydrofuran, and to which 80 mg of scavenger resin are added. After stirring for about 18 hours at a temperature in the region of 20° C., the reaction mixture is filtered and then concentrated to dryness under reduced pressure. 36 mg of a pasty solid are thus obtained, which solid is purified by chromatography under pressure on a silica cartridge, eluting with a mixture of cyclohexane and ethyl acetate (50/50 by volume). Fractions 16 to 20 are combined and concentrated to dryness under reduced pressure. 6 mg of (RS)-1-[2-{1-[bis(4-chloro-phenyl)methyl]azetidin-3-yl}-2-(3,5-diflourophenyl)ethyl]-3-propylurea are obtained in the form of an oil [$^1$H NMR spectrum (300 MHz, CDCl$_3$, δ in ppm): 0.88 (t, J=7.5 Hz: 3H); from 1.35 to 1.60 (mt: 2H); from 2.25 to 2.55 and from 2.65 to 3.05 (2 series of mts: 6H in total); 3.04 (mt: 2H); 3.22 (mt: 1H); 3.38 (mt: 1H); 4.07 (mt: 1H); from 4.10 to 4.20 (mt: 1H); 4.17 (s: 1H); 6.62 (tt, J=9 and 2.5 Hz: 1H); 6.82 (mt: 2H); from 7.20 to 7.45 (mt: 8H].

(RS)-2-{1-[bis-(4-chlorophenyl)methyl]-azetidin-3-yl}-2-(3,5-difluorophenyl)ethylamine may be prepared by carrying out the procedure in the following manner: 1.2 g of (RS)-2-{1-[bis-(4-chlorophenyl)-methyl]azetidin-3-yl}-2-(3,5-difluorophenyl)methane-sulfonic acid ethyl ester in solution in 10 cm³ of methanol, and then a solution of 30 cm³ of ammonia in 30 cm³ of methanol, are introduced into an autoclave, cooled by a bath of acetone and dry ice. The autoclave, closed, is stirred and heated at a temperature in the region of 60° C. for 24 hours. After cooling to a temperature in the region of 20° C., the ammonia is allowed to evaporate in air, at a temperature in the region of 20° C., and then the remaining solution is concentrated to dryness under reduced pressure. A gum is thus obtained which is triturated with ethyl ether, at a temperature in the region of 20° C. for about 16 hours. The insoluble matter obtained is filtered and dried in a desiccator for 3 hours. 830 mg of (RS)-2-{1-[bis-(4-chlorophenyl)-methyl]azetidin-3-yl}-2-(3,5-difluorophenyl) ethylamine are thus obtained in the form of a whitish solid.

(RS)-2-{1-[Bis-(4-chlorophenyl)methyl]-azetidin-3-yl}-2-(3,5-difluorophenyl)methanesulfonic acid ethyl ester may be prepared by carrying out the procedure in the following manner: 0.34 cm³ of methane-sulfonyl chloride is added to a solution of 1.9 g of (RS)-2-{1-[bis-(4-chlorophenyl)methyl]azetidin-3-yl}-2-(3,5-difluorophenyl)ethanol in 20 cm³ of dichloro-methane, at a temperature in the region of 20° C. After cooling of the reaction mixture to a temperature in the region of 10° C., 0.89 cm³ of triethylamine is added. After stirring the solution for 20 hours at a temperature in the region of 20° C., 100 cm³ of water and then 150 cm³ of dichloromethane are added dropwise. The decanted and separated organic phase is washed with twice 50 cm³ of water, 50 cm³ of a saturated aqueous sodium chloride solution, 50 cm³ of water and then dried over magnesium sulfate, filtered and evaporated to dryness under reduced pressure. The yellow foam thus obtained (2 g) is purified on a silica column (particle size 0.020-0.045 mm), under a pressure of 0.4 bar, eluting with a mixture of cyclohexane and ethyl acetate (80/20 by volume). Fractions 49 to 111 are combined and concentrated to dryness under reduced pressure. 1.2 g of the ethyl ester (RS)-2-{1-[bis(4-chlorophenyl)-methyl]azetidin-3-yl}-2-(3,5-difluoro-phenyl)methanesulfonic acid are obtained in the form of a white foam.

EXAMPLE 87

(RS)-N-[2-{1-[Bis(4-chlorophenyl)methyl]-azetidin-3-yl}-2-(3,5-difluorophenyl)ethyl]cyclo-propanecarboxamide may be prepared by carrying out the procedure in the following manner: 0.018 cm³ of diisopropylcarbodiimide, 10 mg of cyclopropanecarboxylic acid, 16 mg of hydroxybenzotriazole hydrate and then 0.4 g of morpholine supported on polystyrene are successively added to a solution of 90 mg of (RS)-2-{1-[bis(4-chlorophenyl)methyl]azetidin-3-yl}-2-(3,5-di-fluoromethyl)ethylamine in 5 cm³ of tetrahydrofuran, at a temperature in the region of 20° C. The suspension obtained is stirred at a temperature in the region of 20° C. for 20 hours. The reaction medium is filtered and concentrated to dryness under reduced pressure. 80 mg of a pasty product are thus obtained, which product is purified by passing over an SPE cartridge (SCX phase, 1 g of phase). 76 mg of a residue are thus obtained, which residue is purified by chromatography under pressure on a silica cartridge, eluting with a mixture of cyclohexane and ethyl acetate (70/30 by volume). Fractions 9 to 19 are combined and concentrated to dryness under reduced pressure. 12 mg of (RS)-N-[2-{1-[bis(4-chlorophenyl)methyl]-azetidin-3-yl}-2-(3,5-difluorophenyl)ethyl]cyclopropanecarboxamide are obtained in the form of a colorless oil [$^1$H NMR spectrum (300 MHz, CDCl$_3$, δ in ppm): 0.70 (mt: 1H); from 0.80 to 1.00 (mt: 2H); from 1.15 to 1.35 (mt: 1H); from 2.35 to 2.55 and from 2.70 to 3.10 (2 series of mts: 7H in total); 3.26 (mt: 1H); 3.47 (mt: 1H); 4.19 (s: 1H); 5.63 (mt: 1H); 6.62 (tt, J=9 and 2.5 Hz: 1H); 6.81 (mt: 2H); from 7.20 to 7.45 (mt: 8H)].

EXAMPLE 88

(RS)-N-[2-{1-Bis(4-chlorophenyl)methyl]-azetidin-3-yl}-2-(3,5,difluorophenyl)ethyl]-3-methyl-butyramide may be prepared by carrying out the procedure in the following manner: 114 mg of HATU, 30.6 mg of isovaleric acid and then 0.2 g of morpholine supported on polystyrene are added to a solution of 45 mg of (RS)-2-{1-[bis(4-chlorophenyl)methyl]-azetidin-3-yl}-2-(3,5-difluorophenyl)ethylamine in 5 cm³ of tetrahydrofuran, at a temperature in the region of 20° C. The suspension obtained is stirred at a temperature in the region of 20° C. for 20 hours. The reaction medium is filtered and concentrated to dryness under reduced pressure. 46 mg of an orange-colored oil are thus obtained, which oil is purified by chromatography under pressure on a cartridge of 5 g of silica, eluting with a mixture of cyclohexane and ethyl acetate (70/30 by volume). The fractions containing only the desired product are combined and concentrated to dryness under reduced pressure. 6 mg of (RS)-N-[2-{1-bis(4-chlorophenyl)methyl]-azetidin-3-yl}-2-(3,5,difluorophenyl)ethyl]-3-methylbutryramide are obtained in the form of a colorless oil [$^1$H NMR spectrum (400 MHz, CDCl$_3$, δ in ppm): 0.88 (d, J=6.5 Hz: 3H); 0.91 (d, J=6.5 Hz: 3H); from 1.85 to 2.10 (mt: 3H); from 2.30 to 2.55 and from 2.70 to 3.10 (2 series of mts: 6H in total); 3.37 (mt: 2H); 4.19 (s: 1H); 5.45 (mt: 1H); 6.65 (tt, J=9 and 2.5 Hz: 1H); 6.82 (mt: 2H); from 7.20 to 7.45 (mt: 8H)].

EXAMPLE 89

(RS)-N-[2-{1-[Bis(4-chlorophenyl)methyl]-azetidin-3-yl}-2-(3,5-difluorophenyl)ethyl]iso-butyramide may be prepared by carrying out the procedure in a manner similar to the preceding Example 3: starting with 45 mg of (RS)-2-{1-[bis(4-chloro-phenyl)methyl]azetidin-3-yl}-2-(3,5,difluorophenyl)-ethylamine, 5 cm$^3$ of tetrahydrofuran, 114 mg of HATU, 26 mg of isobutyric acid and 0.2 g of morpholine supported on polystyrene, there are obtained 10 mg of (RS)-N-[2-{1-[bis(4-chlorophenyl)methyl]azetidin-3-yl}-2-(3,5-difluorophenyl)ethyl]isobutyramide in the form of an opaque oil [$^1$H NMR spectrum (400 MHz, CD$_3$)$_2$SO-d$_6$, δ in ppm): 0.87 (d, J=7 Hz: 3H); 0.93 (d, J=7 Hz: 3H); from 2.15 to 2.85 (mt: 7H); from 3.00 to 3.25 (mt: 2H); 4.40 (s: 1H); from 7.00 to 7.20 (mt: 3H); 7.38 (mt: 4H); 7.52 (mt: 4H); 7.77 (mt: 1H)].

EXAMPLE 90

{1-[Bis(4-chlorophenyl)methyl]azetidin-3-yl}-(3,4-difluorophenyl)methanone may be prepared by carrying out the procedure in the following manner: 3 cm$^3$ of a 0.5 N solution of 3,4-difluorophenyl-magnesium bromide in tetrahydrofuran are added to a solution of 128 mg of N-methoxy-N-methyl amide of 1-[bis(4-chlorophenyl)methyl]azetidine-3-carboxylic acid in 3 cm$^3$ of tetrahydrofuran, cooled in a bath of acetone and dry ice. After stirring for 20 hours at a temperature in the region of 0° C., 10 cm$^3$ of water are added and then the reaction medium is stirred for 1 hour at a temperature in the region of 20° C. The decanted aqueous phase is extracted with 20 cm$^3$ of ethyl acetate. The combined organic phases are washed with twice 15 cm$^3$ of water, dried over magnesium sulfate and concentrated to dryness under reduced pressure. 123 mg of a residue are thus obtained, which residue is purified by chromatography under pressure on a cartridge of 20 g of silica, eluting with dichloromethane (stabilized over amylene). 47 mg of {1-{bis(4-chlorophenyl)methyl]azetidin-3-yl}-(3,4-difluorophenyl)methanone are thus obtained in the form of a white powder [$^1$H NMR spectrum (300 MHz, CDCl$_3$, δ in ppm): 3.34 (t, J=7.5 Hz: 2H); 3.56 (t, J=8 Hz: 2H); 4.05 (mt: 1H); 4.35 (s: 1H); from 7.15 to 7.40 (mt: 9H); 7.58 (dmt, J=9 Hz: 1H); 7.70 (ddd, J=9/7.5 and 2.5 Hz: 1H].

N-Methoxy-N-methyl amide of 1-[bis(4-chlorophenyl)methyl]azetidine-3-carboxylic acid may be prepared by carrying out the procedure in the following manner: 2.65 cm$^3$ of 1-methylpiperidine are added to a suspension of 2.03 g of N,O-dimethylhydroxyamine hydrochloride in 40 cm$^3$ of dichloromethane, cooled to a temperature in the region of 0° C. by an ice-cold water bath. The yellow solution obtained (solution A) is stored at a temperature in the region of 0° C.

2.65 cm$^3$ of 1-methyl-piperidine and then 1.6 cm$^3$ of methyl chloroformate are successively added to a suspension of 7 g of 1-[bis(4-chlorophenyl)methyl]azetidin-3-carboxylic acid in 300 cm$^3$ of dichloromethane and 40 cm$^3$ of tetrahydrofuran, cooled to a temperature in the region of −8° C. by a bath of ice and isopropanol. After stirring for about 5 minutes at a temperature in the region of −8° C., the previously prepared solution A is added dropwise. After stirring for 10 minutes at a temperature in the region of −8° C., the cooling bath is removed and the reaction mixture is stirred at a temperature in the region of 20° C. for about 20 hours, and then washed with 3 times 150 cm$^3$ of water, and concentrated to dryness under reduced pressure. 8.19 g of a residue are thus obtained, which residue is purified under pressure on 500 g of Amicon silica (particle diameter: 20-45 ?m), eluting with an ethyl acetate/dichloromethane (8-92 by volume) mixture. 6.6 g of N-methoxy-N-methyl amide of 1-[bis(4-chlorophenyl)methyl]azetidine-3-carboxylic acid are thus obtained in the form of a pale yellow oil.

1-[Bis(4-chlorophenyl)methyl]azetidine-3-carboxylic acid may be prepared in a manner similar to that described by ANDERSON A. G. and LOK R. *J. Org. Chem.*, 37, 3953-3955 (1972) from 1-benzhydrylazetidin-3-ol, using 1-[bis(4-chlorophenyl)methyl]azetidin-3-ol as raw material.

EXAMPLE 91

{1-[Bis(4-chlorophenyl)methyl]azetidin-3-yl}-(3,5-difluorophenyl)methanone may be prepared by carrying out the procedure as for {1-[bis(4-chloro-phenyl)methyl]azetidin-3-yl}-(3,4-difluoro-phenyl)methanone, starting with 1.1 g of N-methoxy-N-methyl amide of 1-[bis(4-chlorophenyl)methyl]-azetidine-3-carboxylic acid, 1.5 cm$^3$ of 1-bromo-3,5-difluorobenzene and 316 mg of magnesium turnings. 880 mg of {1-[bis(4-chlorophenyl)methyl]azetidin-3-yl}-(3,5-difluorophenyl)methanone are thus obtained in the form of a pale yellow viscous oil [$^1$H NMR spectrum (300 MHz, CDCl$_3$, δ in ppm): 3.34 (t, J=7.5 Hz: 2H); 3.55 (t, J=8 Hz: 2H); 4.03 (mt: 1H); 4.44 (s: 1H); 7.01 (tt, J=9 and 2.5 Hz: 1H); from 7.20 to 7.40 (mt 10H)].

EXAMPLE 92

{1-[Bis(4-chlorophenyl)methyl]azetidin-3-yl}-cyclohexylmethanone may be prepared by carrying out the procedure as for {1-[bis(4-chlorophenyl)methyl]-azetidin-3-yl}-(3,4-difluorophenyl)methanone, starting with 284 mg of N-methoxy-N-methyl amide of 1-[bis(4-chlorophenyl)methyl]azetidin-3-carboxylic acid and 1.68 cm$^3$ of 2 N cyclohexylmagnesium chloride in THF. 116 mg of {1-[bis(4-chlorophenyl)methyl]azetidin-3-yl}cyclohexylmethanhone are thus obtained in the form of a yellow viscous oil [$^1$H NMR spectrum (400 MHz, CDCl$_3$, δ in ppm): from 1.10 to 1.35 and from 1.55 to 1.85 (2 series of mt: 10H in total); 2.30 (mt: 1H); 3.14 (t, J=8 Hz: 2H); 3.36 (t, J=8Hz: 2H); 3.56 (mt: 1H); 4.31 (s: 1H); from 7.20 to 7.35 (mt: 8H)].

EXAMPLE 93

{1-[Bis(4-chlorophenyl)methyl]azetidin-3-yl}-phenylmethanone may be prepared by carrying out the procedure as for {1-[bis(4-chlorophenyl)methyl]-azetidin-3-yl}-(3,4-difluorophenyl)methanone, starting with 258 mg of N-methoxy-N-methyl amide of 1-[bis(4-chlorophenyl)methyl]azetidine-3-carboxylic acid and 1.02 cm$^3$ of 3 N phenylmagnesium bromide in THF. 208 mg of {1-[bis(4-chlorophenyl)methyl]azetidin-3-yl}-phenyl)methanone are thus obtained in the form of a yellow viscous oil [$^1$H NMR spectrum (300 MHz, CDCl$_3$, δ in ppm): 3.35 (t, J=8 Hz: 2H); 3.57 (t, J=8 Hz: 2H); 4.13 (mt: 1H); 4.35 (s: 1H); 7.25 (dmt, J=8 Hz: 4H); 7.34 (dmt, J=8 Hz: 4H); 7.45 (broad t, J=8 Hz: 2H); 7.56 (tt, J=8 and 1.5 Hz: 1H); 7.84 (dmt, J=8 Hz: 2H)].

EXAMPLE 94

(RS)-1-{1-[Bis(4-chlorophenyl)methyl]-azetidin-3-yl}-1-(3,5-difluorophenyl)ethanol may be prepared by carrying out the procedure in the following manner: 0.167 cm$^3$ of a 3 N solution of methylmagnesium bromide is added to a solution of 100 mg of {1-[bis(4-chlorophenyl)methyl]azetidin-3-yl}-(3,5-difluorophenyl)-methanone in 4 cm$^3$ of tetrahydrofuran, cooled to a temperature of less than −40° C. After stirring for 20 hours at a temperature in the region of 0° C., 5 cm$^3$ of water are added and then the decanted aqueous phase is extracted with 5 cm$^3$ of ethyl acetate. The combined organic phases are dried over magnesium sulfate and concentrated to dryness under reduced pressure. 91 mg of a residue are thus obtained, which residue is purified by chromatography under pressure on a cartridge of 10 g of silica, eluting with an ethyl acetate/cyclohexane (1/9 by volume) mixture. 74 mg of (RS)-1-{1-[bis(4-chlorophenyl)methyl]-azetidin-3-yl}-1-(3,5-difluorophenyl)ethanol are thus obtained in the form of a colorless oil [$^1$H NMR spectrum (300 MHz, CDCl$_3$, δ in ppm): 1.46 (s: 3H); 2.71 (mt: 1H); 2.82 (mt: 1H); 2.98 (t, J=7.5 Hz: 1H); 3.24 (t, J=7.5 Hz: 1H); 3.34 (mt: 1H); 4.31 (s: 1H); 4.33 (unresolved complex: 1H); 6.67 (tt, J=9 and 2.5 Hz: 1H); 6.98 (mt: 2H); from 7.25 to 7.35 (mt: 8H)].

EXAMPLE 95

The O-allyloxime of {1-[bis(4-chlorophenyl)-methyl]azetidin-3-yl}-(3,5-difluorophenyl)methanone may be prepared by carrying out the procedure in the following manner: a solution of 100 mg of {1-[bis(4-chlorophenyl)methyl]azetidin-3-yl}-(3,5-difluoro-phenyl)methanone and 101 mg of O-allylhydroxyamine hydrochloride in 5 cm$^3$ of pyridine is stirred at a temperature in the region of 20° C. for 20 hours. 5 cm$^3$ of water are then added and the reaction mixture is extracted with twice 5 cm$^3$ of ethyl acetate. The combined organic phases are dried over magnesium sulfate and concentrated to dryness under reduced pressure. 111 mg of a yellow oil are thus obtained, which oil is purified by chromatography under pressure on a cartridge of 20 g of silica (diameter of the particles from 0.04 to 0.063 mm), eluting with an ethyl acetate/cyclohexane (2/98 by volume) mixture. 68 mg of O-allyloxime of {1-[bis(4-chlorophenyl)-methyl]azetidin-3-yl}-(3,5-difluorophenyl)methanone are thus obtained in the form of a colorless viscous oil [$^1$H NMR spectrum (300 MHz, CDCl$_3$, δ in ppm). A mixture of the 2 Z and E isomers is observed in the approximate proportions 65/35 or conversely; 2.84 and 3.11 (2 broad t, respectively J=8 Hz and J=7.5 Hz 2H in total); 3.44 and 3.66 (2 broad t, respectively J=7.5 Hz and J=8 Hz: 2H in total); 3.58 and 3.81 (2 mts: 1H in total); 4.16 and 4.30 (2 s: 1H in total); 4.59 (mt: 2H); 5.22 (dmt, J=11 Hz: 1H); 5.27 (dmt, J=18 Hz: 1H); 5.96 (mt: 1H); 6.80 (tt, J=9 and 2.5 Hz: 1H); 6.91 (mt: 2H); from 7.20 to 7.35 (mt: 8H].

EXAMPLE 96

The O-ethyloxime of {1-[bis(4-chlorophenyl)-methyl]azetidin-3-yl}-(3,5-difluorophenyl)methanone may be prepared by carrying out the procedure as described for the preparation of O-allyloxime of {1-[bis(4-chlorophenyl)me-thyl]azetidin-3-yl}-(3,5-difluorophenyl)methanone: starting with 100 mg of {1-[bis(4-chlorophenyl)methyl]azetidin-3-yl}-(3,5-difluorophenyl)methanone and 90 mg of O-ethylhydroxylamine hydrochloride there are thus obtained 83 mg of O-ethyloxime {1-[bis(4-chlorophenyl)-methyl]azetidin-3-yl}-(3,5-difluorophenyl)methanone in the form of a colorless viscous oil [$^1$H NMR spectrum (300 MHz, CDCl$_3$, δ in ppm). A mixture of the 2 Z and E isomers is observed in the approximate proportions 65/35 or conversely; 1.25 and 1.27 (2 t, J=7 Hz and J=8 Hz: 3H in total); 2.82 and 3.12 (2 broad t, respectively J=8 Hz and J=7.5 Hz: 2H in total); 3.45 and 3.66 (2 broad t, respectively J=7.5 Hz and J=8 Hz: 2H in total); 3.58 and 3.78 (2 mts: 1H in total); from 4.05 to 4.20 (mt: 2H); 4.16 and 4.30 (2 s: 1H in total); 6.80 (tt, J=9 and 2.5 Hz: 1H); 6.91 (mt: 2H); from 7.20 to 7.35 (mt: 8H)].

EXAMPLE 97

(RS)-1-[{1-[bis(4-chlorophenyl)-methyl]azetidin-3-yl}-(3,5-difluorophenyl)methyl]-3-methylurea may be prepared in the following manner: 0.336-cm$^3$ of triethylamine and 0.384 cm$^3$ of diphenylphosphonazide are successively added to a solution of 300 mg of {1-[bis(4-chlorophenyl)-methyl]azetidin-3-yl}-(3,5-difluorophenyl)acetic acid hydrochloride in 15 cm$^3$ of anhydrous toluene, under an inert nitrogen atmosphere, at a temperature in the region of 20° C. The solution obtained is stirred at a temperature in the region of 60° C. for about 90 minutes. 2.6 cm$^3$ of a 2M solution of methylamine in tetrahydrofuran are added, the stirring is maintained at a temperature in the region of 20° C. for about 12 hours, the reaction mixture is concentrated to dryness under reduced pressure (2.7 kPa) at a temperature in the region of 40° C. The residue is taken up in 1 cm$^3$ of methanol and then deposited on a BOND-ELUT SCX VARIAN cartridge, 5 g, with the reference 1225-6027, conditioned in methanol. The cartridge is washed in methanol and then eluted with 2 N ammoniacal methanol. The ammoniacal fractions are combined and concentrated to dryness under reduced pressure (2.7 kPa) at a temperature in the region of 40° C. 250 mg of a clear oil are thus obtained, which oil is taken up in 1 cm$^3$ of dichloromethane and then deposited on a cartridge with a diameter of 16 mm, filled with 5 g of silica having a particle size of 0.015-0.035 mm, conditioned and eluted with dichloromethane between 0 and 40 cm$^3$ and then eluted with a dichloromethane-ethyl acetate (80-20 by volume) mixture with the aid of a pumping system. The fractions between 50 and 80 cm$^3$ are combined and concentrated to dryness under reduced pressure (2.7 kPa) at 40° C. 140 mg of (RS)-1-[{1-[bis(4-chlorophenyl)methyl]azetidin-3-yl}-(3,5-difluorophenyl)methyl]-3-methylurea are thus obtained in the form of a foam [$^1$H NMR spectrum (400 MHz, CDCl$_3$, δ in ppm): 2.66 (mt: 1H); 2.82 (d, J=5 Hz: 3H); 2.95 (mt: 1H); 3.03 (mt: 1H); 3.18 (mt: 2H); 4.24 (mt: 1H); 4.30 (s: 1H); 4.92 (t, J=7 Hz: 1H); 5.36 (broad d, J=7 Hz: 1H); 6.67 (tt, J=9 and 2.5 Hz: 1H); 6.80 (mt: 2H) from 7.20 to 7.30 (mt: 8H)].

The preparation of {1-[bis(4-chlorophenyl)-methyl]azetidin-3-yl}-(3,5-difluorophenyl)-acetic acid hydrochloride has been described in the patent "carbon-containing derivatives", Example 77.

EXAMPLE 98

(RS)-1-[{1-[bis(4-chlorophenyl)methyl]-azetidin-3-yl}-(3,5-difluorophenyl)methyl]-3-isopropylurea may be prepared in the following manner: 3 cm$^3$, that is 0.1 mM of a freshly prepared solution of (RS)-1-[{1-[bis(4-chlorophenyl)me-thyl]-3-[(3,5-difluoro-phenyl)-isocyanatomethyl]azetidine are added to a solution of 17 μl of isopropylamine in 1 cm³ of anhydrous toluene, under an inert nitrogen atmosphere, at a temperature in the region of 20° C. The solution obtained is stirred at a temperature in the region of 20° C. for about 12 hours. The reaction medium is concentrated to dryness under reduced pressure (2.7 kPa) at a temperature in the region of 40° C. The solid residue is taken up in 1 cm³ of methanol and then deposited on a BOND-ELUT SCX VARIAN cartridge, 500 mg, with the reference 1210-2040, conditioned in methanol. The cartridge is washed with methanol and then eluted with 2 N ammoniacal methanol. The ammoniacal fractions are combined and concentrated to dryness under reduced pressure (2.7 kPa) at a temperature in the region of 40° C. The solid residue thus obtained is combined with 1 cm³ of dichloromethane and then deposited on an IST FlashPack cartridge with the reference SIL 016-002, filled with 2 g of silica (0.065-0.090 mm) conditioned in dichloromethane and eluted with a dichloromethane-ethyl acetate (90-10 by volume) mixture with the aid of a pumping system. The fractions between 20 and 38 cm³ are combined and concentrated to dryness under reduced pressure (2.7 kPa) at 40° C. 14 mg of (RS)-1-[{1-[bis(4-chlorophenyl)methyl]azetidin-3-yl}-(3,5-difluorophenyl)methyl]-3-isopropylurea are thus obtained in the form of a white foam [$^1$H NMR spectrum (400 MHz, CDCl$_3$, δ in ppm): 1.14 (d, J=6.5 Hz: 3H); 1.15 (d, J=6.5 Hz: 3H); 2.66 (mt: 1H); 2.92 (broad dd, J=8 and 5.5 Hz: 1H), 3.01 (broad dd, J=8 and 5.5 Hz: 1H); 3.16 (t, J=8 Hz: 1H); 3.20 (t, J=8 Hz: 1H); 3.85 (mt: 1H); 4.06 (d, J=8 Hz: 1H); 4.29 (s: 1H); 4.91 (t, J=7 Hz: 1H); 5.17 (d, J=6.5 Hz: 1H); 6.66 (tt, J=9 and 2 Hz: 1H); 6.78 (mt: 2H); from 7.20 to 7.35 (mt: 8H)].

(RS)-1-[bis(4-chlorophenyl)methyl]-3-[(3,5-difluorophenyl)-isocyanatomethyl]azetidine may be prepared in the following manner: 0.126 cm³ of triethylamine and 0.195 cm³ of diphenylphosphonazide are successively added to a solution of 150 mg of {1-[bis-(4-chlorophenyl)methyl]azetidin-3-yl}-(3,5-difluorophenyl)acetic acid hydrochloride in 9 cm³ of anhydrous toluene, under an inert nitrogen atmosphere, at a temperature in the region of 20° C. The solution obtained is stirred at a temperature in the region of 50° C. for about 1 hour. The mixture is allowed to cool and (RS)-1-[bis(4-chlorophenyl)methyl]-3-[(3,5-difluorophenyl)isocyanatomethyl]azetidine is thus obtained in solution in toluene which will be subsequently used in this form.

EXAMPLE 99

(RS)-1-[{1-[bis(4-chlorophenyl)methyl]-azetidin-3-yl}-(3,5-difluorophenyl)methyl]-3-isobutylurea may be prepared in the following manner: 3 cm³, that is 0.1 mM of a freshly prepared solution of (RS)-1-[bis(4-chlorophenyl)methyl]-3-[(3,5-difluorophenyl)isocyanatomethyl]azetidine are added to a solution of 20 μl of isobutylamine in 1 cm³ of anhydrous toluene, under an inert nitrogen atmosphere, at a temperature in the region of 20° C. The solution obtained is stirred at a temperature in the region of 20° C. for about 12 hours. The reaction medium is concentrated to dryness under reduced pressure (2.7 kPa) at a temperature in the region of 40° C. The solid residue is taken up in 1 cm³ of methanol and then deposited on a BOND-ELUT SCX VARIAN cartridge, 500 mg, with the reference 1210-2040 conditioned in methanol. The cartridge is washed with methanol and then eluted with 2 N ammoniacal methanol. The ammoniacal fractions are combined and concentrated to dryness under reduced pressure (2.7 kPa) at a temperature in the region of 40° C. The residue thus obtained is taken up in 1 cm³ of dichloromethane and then deposited on an IST FlashPack cartridge with the reference SIL 016-002 filled with 2 g of silica (0.065-0.090 mm) conditioned in dichloromethane and eluted with a dichloromethane-ethyl acetate (90-10 by volume) mixture with the aid of a pumping system. The fractions between 0 and 15 cm³ are combined and concentrated to dryness under reduced pressure (2.7 kPa) at 40° C. 14 mg of (RS)-1-[{1-[bis(4-chlorophenyl)methyl]azetidin-3-yl}-(3,5-difluorophenyl)methyl]-3-isobutylurea are thus obtained in the form of a white foam [$^1$H NMR spectrum (400 MHz, CDCl$_3$, δ in ppm): 0.89 (d, J=6.5 Hz: 3H); 0.90 (d, J=6.5 Hz: 3H); 1.74 (mt: 1H); 2.66 (mt: 1H); from 2.90 to 3.25 (mt: 6H); 4.29 (s and mt: 2H in total); 4.90 (t, J=7 Hz: 1H); 5.34 (broad d, J=6.5 Hz: 1H); 6.66 (tt, J=9 and 2 Hz: 1H); 6.80 (mt: 2H); from 7.20 to 7.35 (mt: 8H)]).

EXAMPLE 100

N-Methyl-N-phenyl-1-[bis(4-chlorophenyl)-methyl]azetidine-3-carboxamide may be prepared in the following manner: 0.039 cm³ of N-methylaniline, 87 mg of 1-(3-dimethylaminopropyl)-3-ethylcarbodiimide hydrochloride, 0.063 cm³ of triethyalmine and then 4 mg of hydroxybenzotriazole hydrate are successively added to a solution of 100 mg of 1-[bis(4-chlorophenyl)-methyl]azetidine-3-carboxylic acid in 2 cm³ of anhydrous dichloromethane, at a temperature in the region of 20° C. The solution obtained is stirred at a temperature in the region of 20° C. for about 12 hours. The reaction medium is deposited on an IST FlashPack cartridge with the reference SIL 016-005 filled with 5 g of silica (0.065-0.090 mm) conditioned in dichloromethane and eluted with a gradient of a dichloromethane-ethyl acetate mixture (the percentage of ethyl acetate varying from 0 to 5 by volume) with the aid of a pumping system, collecting 1.5-cm³ fractions. Fractions 3 to 15 are combined and concentrated to dryness under reduced pressure (2.7 kPa) at 50° C. 95 mg of 1-[bis(4-chlorophenyl)methyl]azetidine-N-methyl-N-phenyl-3-carboxamide are thus obtained in the form of a cream-colored foam [$^1$H NMR spectrum (400 MHz, CDCl$_3$, δ in ppm): 3.08 (mt: 2H); 3.21 (mt: 3H); 3.27 (s: 3H); 4.35 (s: 1H); 7.06 (d, J=7.5 Hz: 2H); from 7.15 to 7.45 (mt: 11H)].

EXAMPLE 101

1-[Bis(4-chlorophenyl)methyl]azetidine-N-benzyl-N-methyl-3-carboxamide may be prepared in the following manner: 0.0213 cm³ of N-benzylmethylamine is added to a suspension of 150 mg of 1-[bis(4-chlorophenyl)methyl]azetidine-3-carboxylic acid activated on TFP resin (165 μM) in 2 cm³ of dichloromethane. The suspension is stirred at a temperature in the region of 20° C. for 22 hours, and then filtered on sintered glass. The solid residue is washed again with twice 1 cm³ of dichloromethane. The filtrates are combined and concentrated to dryness under reduced pressure (2.7 kPa) at a temperature in the region of 40° C. 38 mg of 1-[bis(4-chlorophenyl)methyl]azetidine-N-benzyl-N-methyl-3-carboxamide are thus obtained in the form of a colorless gum [$^1$H NMR spectrum (300 MHz, CDCl$_3$, δ in ppm): 2.78 (s: 3H); from 3.25 to 3.55 (mt: 5H); 4.38 (mt: 2H); 4.57 (s: 1H); from 7.15 to 7.40 (mt: 13H)].

1-[Bis(4-chlorophenyl)methyl]azetidine-3-carboxylic acid activated on TFP resin may be prepared in the following manner: 2 g of 1-[bis(4-chlorophenyl)-methyl]azetidine-3-carboxylic acid, 73 mg of 4-dimethylaminopyridine and 0.927 cm³ of 1,3-diisopropylcarbodiimide are added to a suspension of 2.7 g of TFP resin (free phenol function, 1.1 mmol/g, that is 2.975 mM) in 40 cm³ of anhydrous dimethylformamide. After stirring for 19 hours at a temperature in the region of 20° C., the suspension is filtered, the resin is washed with 40 cm³ of dimethylformamide, 40 cm³ of tetrahydrofuran, 40 cm³ of dichloromethane and then dried under vacuum to constant weight. 3.6 g of 1-[bis(4-chlorophenyl)methyl]-azetidine-3-carboxylic acid activated on TFP resin are thus obtained.

1-[Bis(chlorophenyl)methyl]azetidine-3-carboxylic acid may be prepared in a manner similar to that described by ANDERSON A. G. and LOK R. *J. Org. Chem.*, 37, (1972), 3953-3955 (from 1-benzhydrylazetidin-3-ol, using 1-[bis(4-chlorophenyl)methyl]azetidin-3-ol as raw material.

The TFP resin (free phenol function) may be prepared according to the procedure described in patent WO9967228.

EXAMPLE 102

(RS)-[{1-[bis(4-chlorophenyl)methyl]azetidin-3-yl}-(3,5-difluorophenyl)methyl]methylamine may be prepared in the following manner: 0.099 cm³ of methylamine, and then successively 84 mg of sodium triacetoxyborohydride and 0.014 cm³ of acetic acid are added to a solution of 108 mg of {1-[bis(4-chloro-phenyl)methyl]azetidin-3-yl}-(3,5-difluorophenyl)-methanone in 2 cm³ of anhydrous 1,2-dichloroethane. After stirring for 12 hours at a temperature in the region of 20° C., 0.992 cm³ of methylamine, 85 mg of sodium triacetoxyborohydride and then 0.143 cm³ of acetic acid are again successively added. The solution obtained is stirred at a temperature in the region of 20° C. for about 24 hours and then washed with 4 cm³ of a saturated sodium bicarbonate solution. The organic phase is decanted off and then dried over magnesium sulfate, filtered and then concentrated under reduced pressure (2.7 kPa). The residue thus obtained is purified on an IST FlashPack cartridge with the reference SIL 016-002 filled with 2 g of silica (0.065-0.090 mm) conditioned in dichloromethane and eluted with a gradient of dichloromethane-methanol mixture (the percentage of methanol varying from 0 to 6 by volume) with the aid of a pumping system, collecting 1-cm³ fractions. Fractions 8 to 18 are combined and concentrated to dryness under reduced pressure (2.7 kPa) at 50° C. 66 mg of [{1-[bis(4-chlorophenyl)-methyl]azetidin-3-yl}-(3,5-difluorophenyl)methyl]-methylamine are thus obtained in the form of a colorless honey [$^1$H NMR spectrum (300 MHz, CDCl$_3$, δ in ppm): 2.25 (s: 3H); 2.60 (mt: 1H); 2.68 (t, J=7 Hz: 1H); 2.94 (t, J=7 Hz: 1H); 3.02 (broad t, J=7 Hz: 1H); 3.34 (broad t, J=7 Hz: 1H); 3.58 (d, J=9 Hz: 1H); 4.25 (s: 1H); 6.67 (tt, J=9 and 2.5 Hz: 1H); 6.80 (mt: 2H); from 7.20 to 7.35 (mt: 8H)].

EXAMPLE 103

(RS) [{1-[bis(4-chlorophenyl)methyl]azetidin-3-yl}-(3,5-difluorophenyl)methyl]isobutylamine may be prepared in the following manner: 0.028 cm³ of isobutylamine, and then successively 85 mg of sodium triacetoxyborohydride and 0.015 cm³ of acetic acid are added to a solution of 109 mg of {1-[bis(4-chloro-phenyl)methyl]azetidin-3-yl}-(3,5-difluoro-phenyl)methanone in 2 cm³ of anhydrous 1,2-dichloroethane. The solution obtained is stirred at a temperature in the region of 20° C. for about 12 hours. The reaction medium is deposited on a cartridge filled with 5 g of silica, conditioned in dichloromethane and eluted with a gradient of dichloromethane-ethyl acetate mixture (the percentage of ethyl acetate varying from 0 to 10 by volume) with the aid of a pumping system. The fractions containing the desired product are combined and concentrated to dryness under reduced pressure (2.7 kPa) at 40° C. 8 mg of (RS)-[{1-[bis(4-chlorophenyl)methyl]azetidin-3-yl}-(3,5-difluorophenyl)-methyl] isobutylamine are thus obtained [$^1$H NMR spectrum (300 MHz, CDCl$_3$, δ in ppm): 0.85 (d, J=7 Hz: 3H); 0.87 (d, J=7 Hz: 3H); 1.63 (mt: 1H); 2.15 (dd, J=11 and 7.5 Hz: 1H); 2.25 (dd, J=11 and 7 Hz: 1H); 2.57 (mt: 1H); 2.70 (t, J=7 Hz: 1H); 2.92 (t, J=7 Hz: 1H); 3.01 (broad t, J=7.5 Hz: 1H); 3.33 (broad t, J=7.5 Hz: 1H); 3.66 (d, J=9 Hz: 1H); 4.25 (s: 1H); 6.66 (tt, J=9 and 2.5 Hz: 1H); 6.81 (mt: 2H); from 7.20 to 7.35 (mt: 8H)].

EXAMPLE 104

(RS)-[{1-[bis(4-chlorophenyl)methyl]azetidin-3-yl}-(3,5-difluorophenyl)methyl]butylamine may be prepared in the following manner: 0.0265 cm³ of n-butylamine, and then successively 95 mg of sodium triacetoxyborohydride and 0.0.143 cm³ of acetic acid are added to a solution of 108 mg of {1-[bis(4-chloro-phenyl)methyl]azetidin-3-yl}-(3,5-difluorophenyl)-methanone in 2 cm³ of anhydrous 1,2-dichloroethane. After stirring for about 16 hours at a temperature in the region of 20° C., 0.0265 cm³ of n-butylamine, 85 mg of sodium triacetoxyborohydride and then 0.143 cm³ of acetic acid are again successively added. The solution obtained is stirred at a temperature in the region of 20° C. for about 24 hours and then washed with 4 cm3 of a saturated sodium bicarbonate solution. The organic phase is decanted off and then dried over magnesium sulfate, filtered and then concentrated under reduced pressure (2.7 kPa). The residue thus obtained is purified on an IST FlashPack cartridge with the reference SIL 016-002 filled with 2 g of silica (0.065-0.090 mm) conditioned in dichloromethane and eluted with a gradient of dichloromethane-methanol mixture (the percentage of methanol varying from 0 to 6 by volume) with the aid of a pumping system, collecting 1-cm³ fractions. Fractions 25 to 30 are combined and concentrated to dryness under reduced pressure (2.7 kPa) at 50° C. 37 mg of (RS)-[{1-[bis(4-chlorophenyl)methyl]azetidin-3-yl}-(3,5-difluorophenyl)-methyl] butylamine are thus obtained in the form of a colorless honey [$^1$H NMR spectrum (300 MHz, CDCl$_3$, δ in ppm): 0.85 (t, J=7.5 Hz: 3H); from 1.20 to 1.50 (mt: 4H); 2.37 (broad t, J=7 Hz: 2H); 2.56 (mt: 1H); 2.67 (t, J=7 Hz: 1H); 2.89 (t, J=7 Hz: 1H); 2.99 (broad t, J=7 Hz: 1H); 3.32 (broad t, J=7 Hz: 1H); 3.67 (d, J=9 Hz: 1H)

EXAMPLE 105

(RS)-N-[{1-[bis(4-chlorophenyl)methyl]-azetidin-3-yl}-(3,5-difluorophenyl)methyl]-3-methylbutyramide may be prepared in the following manner: 0.025 cm³ of N,N'-diisopropylcarbodiimide, 10 mg of hydroxybenzotriazole hydrate and 30 mg of (RS)-C-1-[bis(4-chlorophenyl)methyl]azetidin-3-yl]-C-(3,5-difluorophenyl)methylamine are successively added to a solution of 0.017 cm³ of isovaleric acid in 2 cm³ of anhydrous dichloromethane, at a temperature in the region of 20° C. The solution obtained is stirred at a temperature in the region of 20° C. for about 12 hours. The reaction medium is deposited on a BOND-ELUT SCX VARIAN cartridge, 500 mg, with the reference 1210-2040 conditioned in methanol. The cartridge is washed with methanol and then eluted with 2 N ammoniacal methanol. The ammoniacal fractions are combined and concentrated to dryness under reduced pressure (2.7 kPa) at a temperature in the region of 40° C. 35 mg of (RS)-N-[{1-[bis(4-chlorophenyl)methyl] azetidin-3-yl}-(3,5-difluorophenyl)methyl]-3-methylbutyramide are thus obtained in the form of a yellow honey [$^1$H NMR spectrum (300 MHz, CDCl$_3$, δ in ppm): 0.98 (d, J=5 Hz: 6H); from 2.05 to 2.25 (mt: 3H); 2.71 (mt: 1H); 2.90 (mt: 1H); 3.00 (mt: 1H); 3.20 (mt: 2H); 4.30 (s: 1H); 5.14 (t, J=7.5 Hz: 1H); 6.48 (broad d, J=7.5 Hz: 1H); 6.67 (tt, J=9 and 2.5 Hz: 1H); 6.75 (mt: 2H); from 7.20 to 7.40 (mt: 8H)].

(RS)-C-{1-[bis(4-chlorophenyl)methyl]-azetidin-3-yl}-C-(3,5-difluorophenyl)methylamine may be prepared in the following manner: [lacuna], and then successively 385 mg of ammonium acetate and 29 mg of sodium cyanoborohydride to a solution of 216 mg of (RS)-{1-[bis(4-chlorphenyl)methyl]azetidin-3-yl}-(3,5-difluorophenyl)methanone in 10 cm³ of methanol. The solution obtained is stirred at a temperature in the region of 20° C. for about 12 hours and then kept warm at 45° C. for 6 h. 29 mg of sodium cyanoborohydride are added to this solution. The stirring is continued at a temperature in the region of 20° C. for 72 hours. The reaction medium is poured into a mixture of 30 cm³ of ice-cold water with 5 cm³ of a 4 N aqueous sodium hydroxide solution, and then extracted with twice 30 cm³ of ethyl acetate, the organic phase is extracted with twice 30 cm³ of N hydrochloric acid, the aqueous phase thus obtained is alkalizined with a normal aqueous sodium hydroxide solution and then extracted with three times 20 cm³ of ethyl acetate. The combined organic phases are dried over magnesium sulfate, filtered and then concentrated to dryness under reduced pressure (2.7 kPa) at 40° C. 35 mg of (RS)-C-{1-[bis(4-chlorophenyl)methyl]azetidin-3-yl}-C-(3,5-difluorophenyl)methylamine are thus obtained in the form of a yellow honey.

The medicaments according to the invention consist of a compound of formula (I) or an isomer or a salt of such a compound, in the pure state or in the form of a composition in which it is combined with any other pharmaceutically compatible product which may be inert or physiologically active. The medicaments according to the invention may be used orally, parenterally, rectally or topically.

As solid compositions for oral administration, tablets, pills, powders (gelatine capsules, sachets) or granules may be used. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugar-coated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil. These compositions may comprise substances other than diluents, for example wetting, sweetening, thickening, flavoring or stabilizing products.

Sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. Sterilization may be carried out in several ways, for example by asepticizing filtration, by incorporating sterilizing agents into the composition, by irradiation or by heating. They may also be prepared in the form of sterile solid compositions which may be dissolved at the time of use in sterile water or any other injectable sterile medium.

Compositions for rectal administration are suppositories or rectal capsules which contain, in addition to the active product, excipients such as cocoa butter, semisynthetic glycerides or polyethylene glycols.

Compositions for topical administration may be, for example, creams, lotions, collyria, collutoria, nasal drops or aerosols.

In human therapy, the compounds according to the invention are particularly useful for the treatment and/or prevention of psychoses including schizophrenia, anxiety disorders, depression, epilepsy, neurodegeneration, cerebellar and spinocerebellar disorders, cognitive disorders, cranial trauma, panic attacks, peripheral neuropathies, glaucomas, migraine, Parkinson's disease, Alzheimer's disease, Huntington's chorea, Raynaud's syndrome, tremor, obsessive-compulsive disorder, senile dementia, thymic disorders, Tourette's syndrome, tardive dyskinesia, bipolar disorders, cancers, movement disorders induced by medicaments, dystonia, endotoxemic shocks, hemorrhagic shocks, hypotension, insomnia, immunological diseases, multiple sclerosis, vomiting, asthma, appetite disorders (bulimia, anorexia), obesity, memory disorders, intestinal transit disorders, in weaning from chronic treatments and alcohol or drug abuse (opioids, barbiturates, cannabis, cocaine, amphetamine, phencyclide, hallucinogens, benzodiazepines for example), as analgesics or potentiators of the analgesic activity of the narcotic and nonnarcotic drugs.

The doses depend on the desired effect, the duration of the treatment and the route of administration used; they are generally between 5 mg and 1000 mg per day orally for an adult with unit doses ranging from 1 mg to 250 mg of active substance.

In general, the doctor will determine the appropriate dosage depending on the age, weight and any other factors specific to the subject to be treated.

The following examples illustrate the compositions according to the invention:

EXAMPLE A

Gelatin capsules containing a dose of 50 mg of active product and having the following composition are prepared according to the usual technique:

| | |
|---|---|
| Compound of formula (I) | 50 mg |
| Cellulose | 18 mg |
| Lactose | 55 mg |
| Colloidal silica | 1 mg |
| Sodium carboxymethylstarch | 10 mg |
| Talc | 10 mg |
| Magnesium stearate | 1 mg |

EXAMPLE B

Tablets containing a dose of 50 mg of active product and having the following composition are prepared according to the usual technique:

| | |
|---|---|
| Compound of formula (I) | 50 mg |
| Lactose | 104 mg |
| Cellulose | 40 mg |
| Polyvidone | 10 mg |
| Sodium carboxymethylstarch | 22 mg |
| Talc | 10 mg |
| Magnesium stearate | 2 mg |
| Colloidal silica | 2 mg |
| Mixture of hydroxymethylcellulose, glycerin, titanium oxide (72-3.5-24.5) qs 1 finished film-coated tablet containing 245 mg | |

EXAMPLE C

An injectable solution containing 10 mg of active product having the following composition is prepared:

| | |
|---|---|
| Compound of formula (I) | 10 mg |
| Benzoic acid | 80 mg |
| Benzyl alcohol | 0.06 ml |
| Sodium benzoate | 80 mg |
| Ethanol, 95% | 0.4 ml |
| Sodium hydroxide | 24 mg |
| Propylene glycol | 1.6 ml |
| Water | qs 4 ml |

The invention claimed is:

1. A method of antagonizing the cannabinoid (CB1) receptor wherein a disease treatable by said antagonizing activity is selected from the group consisting of Alzheimer's Disease, Parkinson's Disease, and schizophrenia, this method comprising administering to a patient in need of said antagonization an effective amount of a compound of formula

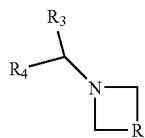

(I)

in which

R represents a radical selected from $CR_1R_2$, $C=C(R_5)SO_2R_6$ and $C=C(R_7)SO_2alk$, either $R_1$ represents a hydrogen atom and $R_2$ represents a radical selected from —$C(R_8)(R_9)(R_{10})$, —$C(R_8)(R_{11})(R_{12})$, —CO—$NR_{13}R_{14}$, —$CH_2$—CO—$NR_{13}R_{14}$, —$CH_2$—CO—$R_6$, —CO—$R_6$, —CO-cycloalkyl, —SO—$R_6$, —$SO_2$—$R_6$, —$C(OH)(R_{12})(R_6)$, —$C(OH)(R_6)(alkyl)$, —$C(=NOalk)R_6$, —$C(=NO-CH_2-CHCH_2)R_6$, —$CH_2$—$CH(R_6)NR_{31}R_{32}$, —$CH_2$—$C(=NOalk)R_6$, —$CH(R_6)NR_{31}R_{32}$, —$CH(R_6)NHSO_2alk$, —$CH(R_6)NHCONHalk$ and —$CH(R_6)NHCOalk$, or $R_1$ represents an alkyl, NH—$R_{15}$, cyano, —S-alk-$NR_{16}R_{17}$, —$CH_2$—$NR_{18}R_{19}$, or —$NR_2OR_{21}$ radical and $R_2$ represents a —$C(R_8)(R_{11})(R_{12})$ radical, $R_3$ and $R_4$, which may be identical or different, represent either an alkyl or cycloalkyl radical, or an aromatic radical selected from phenyl, naphthyl and indenyl, these aromatic radicals being unsubstituted or substituted with one or more radicals selected from halogen, alkyl, alkoxy, formyl, hydroxyl, trifluoromethyl, trifluoromethoxy, —CO-alk, cyano, —COGH, —COGalk, —$CONR_{22}R_{23}$, —CO—NH—$NR_{24}R_{25}$, alkylsulfanyl, alkylsulfinyl, alkylsulfonyl, alkylsulfanylalkyl, alkylsulfinylalkyl, alkylsulfonylalkyl, hydroxyalkyl and -alk-$NR_{24}R_{25}$ radicals; or a heteroaromatic radical selected from the benzofuryl, benzothiazolyl, benzothienyl, benzoxazolyl, chromanyl, 2,3-dihydrobenzofuryl, 2,3-dihydrobenzothienyl, furyl, imidazolyl, isochromanyl, isoquinolyl, pyrrolyl, pyridyl, pyrimidinyl, quinolyl, 1,2,3,4-tetrahydroisoquinolyl, thiazolyl and thienyl rings, these heteroaromatic radicals being unsubstituted or substituted with one or more radicals selected from halogen, alkyl, alkoxy, hydroxyl, trifluoromethyl, trifluoromethoxy, cyano, —COGH, —COGalk, —CO—NH—$NR_{24}R_{25}$, —$CONR_{22}R_{23}$, -alk-$NR_{24}R_{25}$, alkylsulfanyl, alkylsulfinyl, alkylsulfonyl, alkylsulfanylalkyl, alkylsulfinylalkyl, alkylsulfonylalkyl and hydroxyalkyl radicals, $R_5$ represents a hydrogen or alkyl radical, $R_6$ represents an Ar or Het radical, $R_7$ represents a cycloalkyl, heterocycloalkyl or heterocyclenyl radical, optionally substituted by a —CSO-phenyl radical, $R_8$ represents a hydrogen or alkyl radical, $R_9$ represents a radical selected from —CO—$NR_{26}R_{27}$, —COGH, —COGalk, —$CH_2OH$, —NH—CO—NH-alk, —$CH_2$—$NHR_{28}$ and —NHCOalk, $R_{10}$ represents an Ar or Het radical, $R_{11}$ represents a radical selected from —$SO_2$-alk, —$SO_2$—Ar and —$SO_2$-Het, $R_{12}$ represents a hydrogen, Ar or Het radical, $R_{13}$ represents a hydrogen or alkyl radical, $R_{14}$ represents an Ar, Het, -alk-Ar or -alk-Het radical, $R_{15}$ represents an alkyl, cycloalkyl or -alk-$NR_{29}R_{30}$ radical, $R_{16}$ and $R_{17}$, which may be identical or different, represent a hydrogen or alkyl radical or, alternatively, $R_{16}$ and $R_{17}$, taken together with the nitrogen atom to which they are attached, form a 3- to 10-membered unsaturated or saturated mono- or bicyclic heterocycle ring, optionally containing one or more other heteroatoms selected from oxygen, sulfur and nitrogen and optionally substituted with one or more alkyl radicals, $R_{18}$ represents a hydrogen or alkyl radical, $R_{19}$ represents a hydrogen, alkyl, cycloalkyl, cycloalkylalkyl, cycloalkylcarbonyl, —$SO_2$alk, —CO—NHalk or —COGalk radical, or, alternatively, $R_{18}$ and $R_{19}$, taken together with the nitrogen atom to which they are attached, form a 3- to 10-membered unsaturated or saturated mono- or bicyclic heterocycle ring, optionally containing one or more heteroatoms selected from oxygen, sulfur and nitrogen and optionally substituted with one or more alkyl radicals, —$NR_{20}R_{21}$ represents a 3- to 8-membered saturated or unsaturated monocyclic heterocycle ring, optionally containing another heteroatom selected from oxygen, nitrogen and sulfur, $R_{22}$ and $R_{23}$, which may be identical or different, represent a hydrogen or alkyl radical or, alternatively, $R_{22}$ and $R_{23}$, taken together with the nitrogen atom to which they are attached, form a 3- to 10-membered saturated mono- or bicyclic heterocycle, optionally containing another heteroatom selected from oxygen, sulfur and nitrogen and being optionally substituted with one or more alkyl radicals, $R_{24}$ and $R_{25}$, which may be identical or different, represent a hydrogen, alkyl, —COOalk, cycloalkyl, alkylcycloalkyl, -alk-O-alk or hydroxyalkyl radical or, alternatively, $R_{24}$ and $R_{25}$, taken together with the nitrogen atom to which they are attached, form a 3- to 10-membered saturated or unsaturated mono- or bicyclic heterocycle, optionally containing another heteroatom selected from oxygen, sulfur and nitrogen and being optionally substituted with one or more alkyl, —COalk, —COOalk, —CO—NHalk, —CS—NHalk, oxo, hydroxyalkyl, -alk-O-alk or —CO—$NH_2$ radicals, $R_{26}$ and $R_{27}$, which may be identical or different, represent a hydrogen, alkyl, hydroxyalkyl, cycloalkyl, cycloalkylalkyl, -alk-COOalk, -alk-Ar, -alk-Het, Het or -alk-N(alk)$_2$ radical, or, alternatively, $R_{26}$ and $R_{27}$, taken together with the nitrogen atom to which they are attached, may form a 3- to 10-membered unsaturated or saturated mono- or bicyclic heterocycle, optionally containing one or more other heteroatoms selected from oxygen, sulfur and nitrogen, and optionally substituted with one or more halogen, alkyl or alkoxy radicals, $R_{28}$ represents a —CH$_2$-alk, benzyl, —SO$_2$alk, —CONHalk, —COalk, cycloalkylalkylcarbonyl, cycloalkylcarbonyl or —CO—(CH$_2$)$_n$OH radical, n is equal to 1, 2 or 3, $R_{29}$ and $R_{30}$, which may be identical or different, represent a hydrogen or alkyl radical or, alternatively, $R_{29}$ and $R_{30}$, taken together with the nitrogen atom to which they are attached, form a 3- to 10-membered saturated mono- or bicyclic heterocycle, optionally containing another heteroatom selected from oxygen, sulfur and nitrogen, and being optionally substituted with one or more alkyl radicals, $R_{31}$ and $R_{32}$, which may be identical or different, represent a hydrogen, alkyl, Ar or -alk-Ar radical or, alternatively, $R_{31}$ and $R_{32}$, taken together with the nitrogen atom to which they are attached, form a heterocycle selected from aziridinyl, azetidinyl, pyrrolidinyl and piperidinyl, alk represents an alkyl or alkylene radical, Ar represents a phenyl or naphthyl radical optionally substituted with one or more substituents selected from halogen, alkyl, alkoxy, —CO-alk, cyano, —COOH, —COOalk, —CONR$_{22}$R$_{23}$, —CO—NH—NR$_{24}$R$_{25}$, alkylsulfanyl, alkylsulfinyl, alkylsulfonyl, alkylsulfanylalkyl, alkylsulfinylalkyl, alkylsulfonylalkyl, hydroxyalkyl, -alk-NR$_{24}$R$_{25}$, —NR$_{24}$R$_{25}$, alkylthioalkyl, formyl, hydroxyl, CF$_3$, OCF$_3$, Het, —O-alk-NH-cycloalkyl and SO$_2$NH$_2$ radicals, Het represents a 3- to 10-membered unsaturated or saturated mono- or bicyclic heterocycle containing one or more heteroatoms selected from oxygen, sulfur and nitrogen and optionally substituted with one or more halogen, alkyl, alkoxy, alkoxycarbonyl, —CONR$_{22}$R$_{23}$, hydroxyl, hydroxyalkyl, oxo or SO$_2$NH$_2$ radicals, the alkyl, alkylene and alkoxy radicals are in the form of a straight or branched chain and contain 1 to 6 carbon atoms, the cycloalkyl radicals contain 3 to 10 carbon atoms and the heterocycloalkyl and heterocyclenyl radicals contain 3 to 10 carbon atoms, their optical isomers and their salts with an inorganic or organic acid.

2. The method according to claim 1, wherein, in formula (I),

Het is selected from benzofuryl, benzothiazolyl, benzothienyl, benzoxazolyl, chromanyl, 2,3-dihydrobenzofuryl, 2,3-dihydrobenzothienyl, furyl, indolinyl, indolyl, isochromanyl, isoquinolyl, piperidyl, pyrrolyl, pyridyl, pyrimidinyl, quinolyl, 1,2,3,4-tetrahydroisoquinolyl, 1,2,3,4-tetrahydroquinolyl, thiazolyl and thienyl.

3. The method according to claim 1, wherein $R_{16}$ and $R_{17}$ of formula (I), together with the nitrogen atom to which they are attached, form a heterocycle selected from azetidinyl, pyrrolidinyl, piperidinyl, morpholinyl, thiamorpholinyl and piperazinyl rings.

4. The method according to claim 1, wherein $R_{18}$ and $R_{19}$ of formula (I), together with the nitrogen atom to which they are attached, form a heterocycle selected from azetidinyl, pyrrolidinyl, piperidinyl, morpholinyl, thiamorpholinyl and piperazinyl rings.

5. The method according to claim 1, wherein, in the compound of formula (I), the heterocycle formed by NR$_{20}$R$_{21}$ is selected from azetidinyl, pyrrolidinyl, piperidinyl, morpholinyl, thiamorpholinyl, piperazinyl and imidazolyl rings.

6. The method according to claim 1, wherein $R_{22}$ and $R_{23}$ of formula (I), together with the nitrogen atom to which they are attached, form a heterocycle selected from azetidinyl, pyrrolidinyl, piperidinyl, morpholinyl, thiamorpholinyl and piperazinyl rings.

7. The method according to claim 1, wherein $R_{24}$ and $R_{25}$ of formula (I), together with the nitrogen atom to which they are attached, form a heterocycle selected from azetidinyl, pyrrolidinyl, piperidinyl, morpholinyl, thiamorpholinyl and piperazinyl rings.

8. The method according to claim 1, wherein $R_{26}$ and $R_{27}$ of formula (I), together with the nitrogen atom to which they are attached, form a heterocycle selected from azetidinyl, pyrrolidinyl, piperidinyl, morpholinyl, thiamorpholinyl and piperazinyl rings.

9. The method according to claim 1, wherein $R_{29}$ and $R_{30}$ of formula (I), together with the nitrogen atom to which they are attached, form a heterocycle selected from azetidinyl, pyrrolidinyl, piperidinyl, morpholinyl, thiamorpholinyl and piperazinyl rings.

10. The method according to claim 1, wherein, in the compound of formula (I),

R represents a CR$_1$R$_2$ radical, either R$_1$ represents a hydrogen atom and R$_2$ represents a —C(R$_8$)(R$_{11}$)(R$_{12}$) or C(R$_8$)(R$_9$)(R$_{10}$) radical, or R$_1$ represents an alkyl radical and R$_2$ represents a —C(R$_8$)(R$_{11}$)(R$_{12}$) radical, R$_3$ and R$_4$, which may be identical or different, represent either a phenyl which is unsubstituted or substituted with one or more halogen, alkyl, alkoxy, trifluoromethyl, trifluoromethoxy, cyano, —CONR$_{22}$R$_{23}$, hydroxyalkyl or -alk-NR$_{24}$R$_{25}$ radicals; or a heteroaromatic ring selected from the pyridyl, pyrimidinyl, thiazolyl and thienyl rings, said heteroaromatic ring being unsubstituted or substituted with one or more halogen, alkyl, alkoxy, hydroxyl, trifluoromethyl, trifluoromethoxy, cyano, —CONR$_{22}$R$_{23}$, -alk-NR$_{24}$R$_{25}$ or hydroxyalkyl radicals, R$_8$ represents a hydrogen atom, R$_9$ represents a —CO—NR$_{26}$R$_{27}$, —COOalk, —CH$_2$OH, —NH—CO—NH-alk, —CH$_2$—NHR$_{28}$ or —NH-COOalk radical, R$_{10}$ represents an Ar or Het radical, R$_{11}$ represents an —SO$_2$-alk, —SO$_2$—Ar or —SO$_2$-Het radical, R$_{12}$ represents a hydrogen, Ar or Het radical, R$_{22}$ and R$_{23}$, which may be identical or different, represent a hydrogen or alkyl radical or, alternatively, R$_{22}$ and R$_{23}$, together with the nitrogen atom to which they are attached, form a 3- to 10-membered saturated mono- or bicyclic heterocycle, said heterocycle optionally containing another heteroatom selected from oxygen, sulfur and nitrogen, said heterocycle further being optionally substituted with one or more alkyl radicals, R$_{24}$ and R$_{25}$, which are identical or different, represent a hydrogen, alkyl, cycloalkyl, alkylcycloalkyl or hydroxyalkyl radical or, alternatively, R$_{24}$ and R$_{25}$, together with the nitrogen atom to which they are attached, form a 3- to 10-membered saturated or unsaturated mono- or bicyclic heterocycle, said heterocycle optionally containing another heteroatom selected from oxygen, sulfur and nitrogen, said heterocycle further being optionally substituted with one or more alkyl, —COalk, —COOalk, —CO—NHalk, —CS—NHalk, oxo or —CO—NH$_2$ radicals, Ar represents a phenyl or naphthyl radical optionally substituted with 1 or 2 substituents selected from halogen, alkyl, alkoxy, —CO-alk, cyano, —COGalk, —CONR$_{22}$R$_{23}$, alkylsulfonyl, hydroxyalkyl, -alk-NR$_{24}$R$_{25}$, —NR$_{24}$R$_{25}$, hydroxyl, CF$_3$, OCF$_3$, —O-alk-NH-cycloalkyl and SO$_2$NH$_2$ radicals, and Het represents a benzofuryl, benzothiazolyl, benzothienyl, benzoxazolyl, furyl, isoquinolyl, pyrrolyl, pyridyl, quinolyl, 1,2,3,4-tetrahydroisoquinolyl, 1,2,3,4-tetrahydroquinolyl, thiazolyl or thienyl ring.

11. The method of claim 1 wherein said compound is selected from the group consisting of:
(RS)-1-[bis(4-chlorophenyl)methyl)]-3-[(3,5-difluorophenyl)(methylsulfonyl)methyl]azetidine,
(R)-1-[bis(4-chlorophenyl)methyl)]-3-[(3,5-difluorophenyl)(methylsulfonyl)methyl]azetidine,
(S)-1-[bis(4-chlorophenyl)methyl)]-3-[(3,5-difluorophenyl)(methylsulfonyl)methyl]azetidine,
(RS)-1-[bis(4-chlorophenyl)methyl)]-3-[(pyrid-3-yl)(methylsulfonyl)methyl]azetidine,
(R)-1-[bis(4-chlorophenyl)methyl)]-3-[(pyrid-3-yl) (methylsulfonyl)methyl]azetidine,
(S)-1-[bis(4-chlorophenyl)methyl)]-3-[(pyrid-3-yl) (methylsulfonyl)methyl]azetidine,
(RS)-1-[bis(3-fluorophenyl)methyl]-3-[(3,5-difluorophenyl)methylsulfonylmethyl]azetidine,
(R)-1-[bis(3-fluorophenyl)methyl]-3-[(3,5-difluorophenyl)methylsulfonylmethyl]azetidine,
(S)-1-[bis(3-fluorophenyl)methyl]-3-[(3,5-difluorophenyl)methylsulfonylmethyl]azetidine,
1-[bis(4-chlorophenyl)methyl]-3-(RS)-{[3-azetidin-1-yl-phenyl]methylsulfonylmethyl}azetidine,
1-[bis(4-chlorophenyl)methyl]-3-(R)-{[3-azetidin-1-ylphenyl]methylsulfonylmethyl}azetidine,
1-[bis(4-chlorophenyl)methyl]-3-(S)-{[3-azetidin-1-ylphenyl]methylsulfonylmethyl}azetidine,
(RS)-1-[3 ({1-[bis(4-chlorophenyl)methyl]azetidin-3-yl}-methylsulfonylmethyl)phenyl]pyrrolidine,
(R)-1-[3-({1-[bis(4-chlorophenyl)methyl]azetidin-3-yl}-methylsulfonylmethyl)phenyl]pyrrolidine,
(S)-1-[3-({1-[bis(4-chlorophenyl)methyl]azetidin-3-yl}methylsulfonylmethyl)phenyl]pyrrolidine,
(RS)—N-[3-({1-[bis(4-chlorophenyl)methyl]azetidin-3-yl}methylsulfonylmethyl)-phenyl]-N-methylamine,
(R)—N-[3-({1-[bis(4-chlorophenyl)methyl]azetidin-3-yl}methylsulfonylmethyl)phenyl]-N-methylamine, and
(S)—N-[3-({1-[bis(4-chlorophenyl)methyl]azetidin-3-yl}methylsulfonylmethyl)phenyl]-N-methylamine,
as well as their optical isomers and their pharmaceutically acceptable salts with an inorganic or organic acid.

12. The method of claim 1 wherein said compound is selected from the group consisting of:
(RS)-1-[bis(4-chlorophenyl)methyl]-3-[(3,5-bistrifluoromethylphenyl)methylsulfonylmethyl]-azetidine,
(R)-1-[bis(4-chlorophenyl)methyl]-3[(3,5-bistrifluoromethylphenyl)methylsulfonylmethyl]azetidine,
(S)-1-[bis(4-chlorophenyl)methyl]-3-[(3,5-bistrifluoromethylphenyl)methylsulfonylmethyl]-azetidine,
1-[bis(4-chlorophenyl)methyl]-3-(phenylsulfonylmethyl) azetidine,
(RS)-1-[bis(4-chlorophenyl)methyl]-3-[(3,5-difluorophenyl)methylsulfonylmethyl]-3-methyl-azetidine,
(R)-1-[bis(4-chlorophenyl)methyl]-3-[(3,5-difluorophenyl)methylsulfonylmethyl]-3-methylazetidine,
(S)-1-[bis(4-chlorophenyl)methyl]-3-[(3,5-difluorophenyl)methylsulfonylmethyl]-3-methylazetidine,
(RS)-2-{1-[bis(4-chlorophenyl)methyl]azetidin3-yl}-2-(3,5-difluorophenyl)-N-cyclohexylacetamide,
(R)-2-{1-[bis(4-chlorophenyl)methyl]azeditin-3-yl}-2-(3,5-difluorophenyl)-N-cyclohexylacetamide,
(S)-2-{1-[bis(4-chlorophenyl)methyl]azetidin-3-yl}-2-(3,5-difluorophenyl)-N-cyclohexylacetamide,
(RS)-2-{1-[bis(4-chlorophenyl)methyl]azetidin-3-yl}-2-(3,5-difluorophenyl)-N-isobutylacetamide,
(R)-2-{1-[bis(4-chlorophenyl)methyl]azetidin-3-yl}-2-(3,5-difluorophenyl)-N-isobutylacetamide,
(S)-2-{1-[bis(4-chlorophenyl)methyl]azetidin-3-yl}-2-(3,5-difluorophenyl)-N-isobutylacetamide,
(RS)-2-{1-[bis(4-chlorophenyl)methyl]azetidin-3-yl}2-(3,5-difluorophenyl)-N-cyclopropylmethyl-acetamide,
(R)-2-{1-[bis(4-chlorophenyl)methyl]azetidin-3-yl}2-(3,5-difluorophenyl)-N-cyclopropylmethyl-acetamide,
(S)-2-{1-bis(4-chlorophenyl)methyl]azetidin-3-yl}2-(3,5-difluorophenyl)-N-cyclo propylmethyl-acetamide,
(RS)-2-{1-[bis(4-chlorophenyl)methyl]azetidin-3-yl}-2-(3,5-difluorophenyl)-N-isopropylacetamide, and
(R)-2-{1-[bis(4-chlorophenyl)methyl]azetidin-3-yl}-2-(3,5-difluorophenyl)-N-isopropylacetamide,
as well as their optical isomers and their pharmaceutically acceptable salts with an inorganic or organic acid.

13. The method of claim 1 wherein said compound is selected from the group consisting of:
(S)-2-{1-[bis(4-chlorophenyl)methyl]azetidin-3-yl}-2-(3,5-difluorophenyl)-N-isopropylacetamide,
(RS)-1-[bis(4-chlorophenyl)methyl]-3-[1-(3,5-difluorophenyl)-1-methylsulfonylethyl]azetidine,
(R)-1-[bis(4-chlorophenyl)methyl]-3-[1-(3,5-difluorophenyl)-1-methylsulfonylethyl]azetidine,
(S)-1-[bis(4-chlorophenyl)methyl]-3-[1-(3,5-difluorophenyl)-1-methylsulfonylethyl]azetidine,
(RS)-1-[bis(4-fluorophenyl)methyl]-3-[(3,5-difluorophenyl)methylsulfonylmethyl]azetidine,
(R)-1-[bis(4-fluorophenyl)methyl]-3-[(3,5-difluorophenyl)methylsulfonylmethyl]azetidine,
(S)-1-[bis(4-fluorophenyl)methyl]-3-[(3,5-difluorophenyl)methylsulfonylmethyl]azetidine,
(RS)-{1-[(3-pyridyl)-(4-chlorophenyl)methyl]-3-[(3,5-difluorophenyl)methylsulfonylmethyl]azetidine,
(SS)-{1-[(3-pyridyl)-(4-chlorophenyl)methyl]-3-[(3,5-difluorophenyl)methylsulfonylmethyl]-azetidine,
(RR)-{1-[(3-pyridyl)-(4-chlorophenyl)methyl]-3-[(3,5-difluorophenyl)methylsulfonylmethyl]-azetidine, (SR)-{1-[(3-pyridyl)-(4-chlorophenyl)methyl]-3-[(3,5 difluorophenyl)methylsulfonylmethyl]-azetidine,
(RS)-{1-[(4-pyridyl)-(4-chlorophenyl)methyl]-3-[(3,5-difluorophenyl)methylsulfonylmethyl]-azetidine,
(SS)-{1-[(4-pyridyl)-(4-chlorophenyl)methyl]-3-[(3,5-difluorophenyl)methylsulfonylmethyl]-azetidine,
(RR)-{1-[(4-pyridyl)-(4-chlorophenyl)methyl]-3-[(3,5-difluorophenyl)methylsulfonylmethyl]-azetidine,
(SR)-{1-[(4-pyridyl)-(4-chlorophenyl)methyl]-3-[(3,5-difluorophenyl)methylsulfonylmethyl]-azetidine,
(RS)-5-((4-chlorophenyl)-{3-[(3,5-difluorophenyl)methylsulfonylmethyl]azetidin-1-yl}methyl)-pyrimidine,
(SR)-5-((4-chlorophenyl)-{3-[(3,5-difluorophenyl)methylsulfonylmethyl]azetidin-1-yl}methyl)-pyrimidine, (RR)-5-((4-chlorophenyl)-{3-[(3,5-difluorophenyl)methylsulfonylmethyl]azetidin-1-yl}methyl)-pyrimidine, (SS)-5-((4-chlorophenyl)-{3-[(3,5-difluorophenyl)methylsulfonylmethyl]azetidin-1-yl}methyl)-pyrimidine, (SS)-{1-[(2-chloropyrid-5-yl)-(4-chlorophenyl)methyl]3-[(3,5-difluorophenyl)methylsulfonylmethyl]-azetidine, (RR)-{1-[(2-chloropyrid-5-yl)-(4-chlorophenyl)methyl]3-[(3,5-difluorophenyl)methylsulfonyl-methyl]azetidine, (RS)-{1-[(2-chloropyrid-5-yl)-(4-chlorophenyl)methyl]3-[(3,5-difluorophenyl)methylsulfonyl-methyl]azetidine, and (SR)-{1-[(2-chloropyrid-5-yl)-(4-chlorophenyl)methyl]-3-[(3,5-difluorophenyl)methylsulfonylmethyl]azetidine, as well as their optical isomers and their pharmaceutically acceptable salts with an inorganic or organic acid.

\* \* \* \* \*

UNITED STATES PATENT AND TRADEMARK OFFICE
CERTIFICATE OF CORRECTION

PATENT NO.       : 7,741,316 B2
APPLICATION NO.  : 10/988337
DATED            : June 22, 2010
INVENTOR(S)      : Daniel Achard et al.

It is certified that error appears in the above-identified patent and that said Letters Patent is hereby corrected as shown below:

On the Title Pg, Item (56) on page 2, under "Other Publications", line 3, delete "cortax:" and insert -- cortex: --, therefor.

On the Title Pg, Item (56) on page 2, under "Other Publications", line 43, delete "Chemicl" and insert -- Chemical --, therefor.

In column 1, line 7, after "of" delete "copending".

In column 5, line 16, after "represents" delete "represents".

In column 15, line 1, delete "NHCONRf" and insert -- NHCONHRf --, therefor.

In column 15-16, line 50, delete " 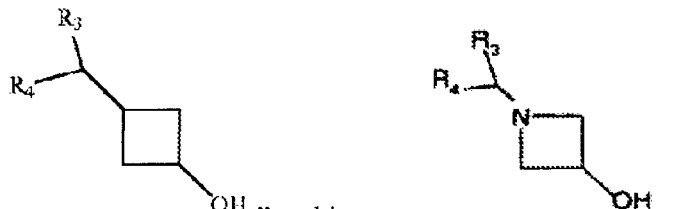 " and insert -- --, therefor.

In column 17, line 34, after "molecule" delete "molecule".

In column 17, line 36, after "molecule" delete "molecule".

In column 19, line 1, delete " 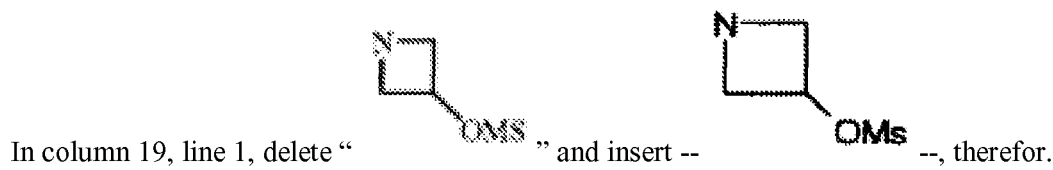 " and insert -- --, therefor.

Signed and Sealed this
Thirtieth Day of August, 2011

David J. Kappos
*Director of the United States Patent and Trademark Office*

CERTIFICATE OF CORRECTION (continued)

U.S. Pat. No. 7,741,316 B2

In column 19, line 56, after "molecule" delete "molecule".

In column 26, line 49, delete "m'yhodes" and insert -- methods --, therefor.

In column 35, line 51, after "ppm)" insert -- : --.

In column 36, line 36, delete "+5.80" and insert -- +5.8° --, therefor.

In column 37, line 30, delete "-22.50" and insert -- -22.5° --, therefor.

In column 38, line 1, delete "-3.-[(R)" and insert -- -3-[(R) --, therefor.

In column 39, line 29, delete "4-methoxycarbonyl)" and insert -- 4-(methoxycarbonyl) --, therefor.

In column 42, line 61, delete "difluoro-phenyl)" and insert -- difluorophenyl) --, therefor.

In column 46, line 15, delete "brown-oil" and insert -- brown oil --, therefor.

In column 46, line 40, delete "(s 3H);" and insert -- (s: 3H); --, therefor.

In column 47, line 3, delete "3-((" and insert -- 3-[( --, therefor.

In column 47, line 56, delete "liters" and insert -- litres --, therefor.

In column 48, line 12, after "ppm)" insert -- : --.

In column 49, line 1, delete "KATRITSKY" and insert -- KATRITZKY --, therefor.

In column 49, line 48, delete "Hz 4H);" and insert -- Hz: 4H); --, therefor.

In column 50, line 35, after "is" delete "is".

In column 51, line 19, delete "diastoero-isomers" and insert -- diastereoisomers --, therefor.

In column 53, line 1, delete "1-liter" and insert -- 1-litre --, therefor.

In column 53, line 33, delete "(mt" and insert -- (mt: --, therefor.

In column 54, line 29, delete "(s" and insert -- (s: --, therefor.

In column 54, line 31, delete "(mt" and insert -- (mt: --, therefor.

In column 57, line 47, delete "dietheyl" and insert -- diethyl --, therefor.

CERTIFICATE OF CORRECTION (continued)

In column 61, line 38, delete "under-reduced" and insert -- under reduced --, therefor.

In column 62, line 12, delete "Hz 2H);" and insert -- Hz: 2H); --, therefor.

In column 63, line 22-23, delete "added-successively." and insert -- added successively. --, therefor.

In column 64, line 2, delete "Hz 1H);" and insert -- Hz: 1H); --, therefor.

In column 64, line 39, delete "(mt 8H);" and insert -- (mt: 8H); --, therefor.

In column 65, line 13, delete "Hz 2H);" and insert -- Hz: 2H); --, therefor.

In column 69, line 7, after "ppm)" insert -- : --.

In column 69, line 8, delete "Hz 1H);" and insert -- Hz: 1H); --, therefor.

In column 70, line 38, delete "Hz 2H);" and insert -- Hz: 2H); --, therefor.

In column 70, line 62, delete "Hz 1H);" and insert -- Hz: 1H); --, therefor.

In column 71, line 67, delete "(s" and insert -- (s: --, therefor.

In column 72, line 15, delete "solution-obtained" and insert -- solution obtained --, therefor.

In column 73, line 17, delete "complex 1H);" and insert -- complex: 1H); --, therefor.

In column 73, line 35, delete "Hz 2H);" and insert -- Hz: 2H); --, therefor.

In column 75, line 7, delete "[1H" and insert -- [$^1$H --, therefor.

In column 75, line 9, delete "(mt 2H);" and insert -- (mt: 2H); --, therefor.

In column 75, line 10, delete "Hz 1H);" and insert -- Hz: 1H); --, therefor.

In column 75, line 11, delete "Hz 1H);" and insert -- Hz: 1H); --, therefor.

In column 77, line 15, delete "Hz 1H);" and insert -- Hz: 1H); --, therefor.

In column 77, line 57, delete "3-((3,5" and insert -- 3-[(3,5 --, therefor.

In column 79, line 18, after "Hz" insert -- : --.

In column 79, line 21, delete "Hz 1H);" and insert -- Hz: 1H); --, therefor.

CERTIFICATE OF CORRECTION (continued)
U.S. Pat. No. 7,741,316 B2

In column 79, line 48, delete "3-((3,5" and insert -- 3-[(3,5 --, therefor.

In column 79, line 55, after "Hz" insert -- : --.

In column 80, line 47, after "Hz" insert -- : --.

In column 81, line 12, delete "(s 1H);" and insert -- (s: 1H); --, therefor.

In column 81, line 46, delete "s 1H);" and insert -- s: 1H); --, therefor.

In column 81, line 47, after "mt" insert -- : --.

In column 82, line 38, after "mt" insert -- : --.

In column 83, line 29, after "(s" insert -- : --.

In column 84, line 14, after "Hz" insert -- : --.

In column 84, line 67, delete "$CDC_3$," and insert -- $CDCl_3$, --, therefor.

In column 85, line 33, after "Hz" insert -- : --.

In column 86, line 66, delete "(mt 2H);" and insert -- (mt:2H); --, therefor.

In column 87, line 22, delete "yl)-" and insert -- yl}- --, therefor.

In column 88, line 15, after "(s" insert -- : --.

In column 89, line 6, after "Hz" insert -- : --.

In column 89, line 35, after "mt" insert -- : --.

In column 89, line 67, after "mt" insert -- : --.

In column 90, line 52, delete "-(bis" and insert -- -[bis --, therefor.

In column 91, line 46, after "mt" insert -- : --.

In column 91, line 47, after "Hz" insert -- : --.

In column 92, line 7, after "Hz" insert -- : --.

In column 92, line 8, after "mt" insert -- : --.

In column 92, line 37, after "complex" insert -- : --.

In column 93, line 1, delete "5.9-6" and insert -- 5.96 --, therefor.

In column 93, line 2, delete "2-Hz:" and insert -- 2 Hz: --, therefor.

In column 93, line 31, after "mt" insert -- : --.

In column 93, line 33, after "(s" insert -- : --.

In column 94, line 33, after "(s" insert -- : --.

In column 94, line 66, delete "ylidene]" and insert -- ylidene} --, therefor.

In column 95, line 22, after "Hz" insert -- : --.

In column 95, line 55, after "Hz" insert -- : --.

In column 95, line 55, after "Hz" insert -- : --.

In column 100, line 37, after "Hz" insert -- : --.

In column 100, line 43, after "(mt" insert -- : --.

In column 101, line 42, after "Hz" insert -- : --.

In column 101, line 51, after "Hz" insert -- : --.

In column 102, line 43, after "Hz" insert -- : --.

In column 102, line 46, after "(mt" insert -- : --.

In column 102, line 53, after "(mt" insert -- : --.

In column 103, line 34, delete "mm" and insert -- mn --, therefor.

In column 104, line 23, delete "Darmstatd," and insert -- Darmstadt, --, therefor.

In column 104, line 45, delete "Darmstatd," and insert -- Darmstadt, --, therefor.

In column 104, line 62, delete "Darmstatd," and insert -- Darmstadt, --, therefor.

In column 105, line 21, delete "-diflourophenyl)" and insert -- -difluorophenyl) --, therefor.

CERTIFICATE OF CORRECTION (continued)
U.S. Pat. No. 7,741,316 B2

In column 105, line 25, delete "-diflourophenyl)" and insert -- -difluorophenyl) --, therefor.

In column 105, line 41-42, delete "-diflourophenyl)" and insert -- -difluorophenyl) --, therefor.

In column 108, line 40, after "(mt" insert -- : --.

In column 108, line 51, delete "cyclohexylmethanhone" and insert -- cyclohexylmethanone --, therefor.

In column 109, line 55, after "Hz" insert -- : --.

In column 112, line 21, delete "triethyalmine" and insert -- triethylamine --, therefor.

In column 115, line 16, delete "alkalizined" and insert -- alkalinized --, therefor.

In column 117, line 54, in claim 1, delete "—COGH, —COGalk," and insert -- —COOH, —COOalk, --, therefor.

In column 117, line 67, in claim 1, delete "—COGH, —COGalk," and insert -- —COOH, —COOalk, --, therefor.

In column 118, line 12, in claim 1, delete "—COGH, —COGalk," and insert -- —COOH, —COOalk, --, therefor.

In column 118, line 36, in claim 1, delete "—COGalk" and insert -- —COOalk --, therefor.

In column 121, line 7, in claim 10, delete "—COGalk" and insert -- —COOalk --, therefor.